(12) United States Patent
Ero et al.

(10) Patent No.: US 10,155,983 B2
(45) Date of Patent: Dec. 18, 2018

(54) METHOD OF DIAGNOSIS OF COMPLEMENT-MEDIATED THROMBOTIC MICROANGIOPATHIES

(71) Applicant: MACHAON DIAGNOSTICS, INC., Oakland, CA (US)

(72) Inventors: Michael P. Ero, Oakland, CA (US); James S. Kain, Oakland, CA (US)

(73) Assignee: Machaon Diagnostics, Inc., Oakland, CA (US)

(*) Notice: Subject to any disclaimer, the term of this patent is extended or adjusted under 35 U.S.C. 154(b) by 623 days.

(21) Appl. No.: 14/675,726

(22) Filed: Mar. 31, 2015

(65) Prior Publication Data

US 2015/0337377 A1     Nov. 26, 2015

Related U.S. Application Data

(60) Provisional application No. 61/972,568, filed on Mar. 31, 2014.

(51) Int. Cl.
    *C12Q 1/68*      (2018.01)
    *C12Q 1/6883*    (2018.01)

(52) U.S. Cl.
    CPC ...... *C12Q 1/6883* (2013.01); *C12Q 2600/118* (2013.01); *C12Q 2600/156* (2013.01)

(58) Field of Classification Search
    None
    See application file for complete search history.

(56) References Cited

U.S. PATENT DOCUMENTS

| | | | |
|---|---|---|---|
| 7,919,103 B2 | 4/2011 | Beliveau et al. | |
| 8,497,350 B2 | 7/2013 | Hageman | |
| 8,569,225 B2 | 10/2013 | Gilkeson et al. | |
| 2005/0158300 A1 | 7/2005 | Cines et al. | |
| 2007/0037183 A1 | 2/2007 | Edwards et al. | |
| 2007/0281300 A1 | 12/2007 | Russell et al. | |
| 2008/0193414 A1 | 8/2008 | Proudfoot et al. | |
| 2009/0220953 A1 | 9/2009 | Dawkins et al. | |
| 2010/0120665 A1 | 5/2010 | Kaleko et al. | |
| 2011/0190221 A1 | 8/2011 | Francois et al. | |
| 2011/0212900 A1 | 9/2011 | Ikezoe et al. | |
| 2011/0229497 A1 | 9/2011 | Thurman et al. | |
| 2011/0236455 A1 | 9/2011 | Zipfel et al. | |
| 2012/0040884 A1 | 2/2012 | Hageman | |
| 2012/0135000 A1 | 5/2012 | Hoh et al. | |
| 2012/0202708 A1 | 8/2012 | Perlee et al. | |
| 2012/0204276 A1 | 8/2012 | Gale et al. | |
| 2012/0225056 A1 | 9/2012 | Rother et al. | |
| 2013/0129728 A1 | 5/2013 | Holers et al. | |
| 2013/0149373 A1 | 6/2013 | Kumar-Singh et al. | |
| 2013/0203971 A1 | 8/2013 | Brandstaetter et al. | |
| 2013/0246083 A1 | 9/2013 | Bell | |
| 2013/0266560 A1 | 10/2013 | Demopulos et al. | |
| 2013/0323751 A1 | 12/2013 | Singbartl et al. | |
| 2013/0344073 A1 | 12/2013 | Schwaeble et al. | |

FOREIGN PATENT DOCUMENTS

| | | |
|---|---|---|
| WO | 2009015087 A2 | 1/2009 |
| WO | 2010103291 A2 | 9/2010 |
| WO | 2012095519 A1 | 7/2012 |
| WO | 2012149329 A2 | 11/2012 |
| WO | 2013082563 A1 | 6/2013 |
| WO | 2014035876 A1 | 3/2014 |

OTHER PUBLICATIONS

Abarrategui-Garrido C, Martinez-Barricarte R, Lopez-Trascasa M, de Cordoba SR, Sanchez-Corral P, Characterization of complement factor H-related (CFHR) proteins in plasma reveals novel genetic variations of CFHR1 associated with atypical hemolytic uremic syndrome. Blood 114: 4261-4271, 2009.*

Bu F, Maga T, Meyer NC, Wang K, Thomas CP, Nester CM, Smith RJ. Comprehensive genetic analysis of complement and coagulation genes in atypical hemolytic uremic syndrome. J Am Soc Nephrol. Jan. 2014; 25(1):55-64. Epub Sep. 12, 2013.*

Bu et al. Supplementary Data. J Am Soc Nephrol. Jan. 2014; 25(1):55-64. pp. 1-6.*

Lemaire M et al. Recessive mutations in DGKE cause atypical hemolytic-uremic syndrome. Nat Genet. May 2013; 45(5):531-6. Epub Mar. 31, 2013.*

Lemaire M et al. 2013, supplemetary Information. Nat Genet. May 2013; 45(5):531-6. pp. 1-17.*

Maga TK, Nishimura CJ, Weaver AE, Frees KL, Smith RJ. Mutations in alternative pathway complement proteins in American patients with atypical hemolytic uremic syndrome. Hum Mutat. Jun. 2010; 31(6):E1445-60.*

Moore et al. Association of factor H autoantibodies with deletions of CFHR1, CFHR3, CFHR4, and with mutations in CFH, CFI, CD46, and C3 in patients with atypical hemolytic uremic syndrome. Blood. Jan. 14, 2010; 115(2):379-87. Epub Oct. 27, 2009.*

Sullivan M, Erlic Z, Hoffmann MM, Arbeiter K, Patzer L, Budde K, Hoppe B, Zeier M, Lhotta K, Rybicki LA, Bock A, Berisha G, Neumann HP. Epidemiological approach to identifying genetic predispositions for atypical hemolytic uremic syndrome. Ann Hum Genet. Jan. 2010; 74(1):17-26.*

(Continued)

*Primary Examiner* — Aaron A Priest
*Assistant Examiner* — Olayinka A Oyeyemi
(74) *Attorney, Agent, or Firm* — Laura M. Lloyd

(57) ABSTRACT

A method for identifying a patient's risk for developing complement-mediated thrombic microangiopathy is described. A sample of genetic material is obtained from a patient. The genetic material is amplified using primers specific for complement-mediated thrombic microangiopathy. After amplification, the genetic sequence of the amplicon is determined. The genetic sequence of the amplicon is compared to a reference sequence, and variations are identified between the sample amplicon and the reference sequence. A variation between the sample amplicon and the reference sequence is indicative of a risk for the patient for developing complement-mediated thrombic microangiopathy.

6 Claims, No Drawings
Specification includes a Sequence Listing.

(56) References Cited

OTHER PUBLICATIONS

Westra D, Vernon KA, Volokhina EB, Pickering MC, van de Kar NC, van den Heuvel LP. Atypical hemolytic uremic syndrome and genetic aberrations in the complement factor H-related 5 gene. J Hum Genet. Jul. 2012; 57(7):459-64. Epub May 24, 2012.*

Yang Y, Muzny DM, Reid JG, Bainbridge MN, Willis A, Ward PA, Braxton A, Beuten J, Xia F, Niu Z, Hardison M, Person R, Bekheirnia MR, Leduc MS, Kirby A, Pham P, Scull J, Wang M, Ding Y, Plon SE, Lupski JR, Beaudet AL, Gibbs RA, Eng CM. Clinical whole-exome sequencing for the diagnosis of mendelian disorders. N Engl J Med. Oct. 17, 2013; 369(16):1502.*

Zipfel PF, Edey M, Heinen S, Józsi M, Richter H, Misselwitz J, Hoppe B, Routledge D, Strain L, Hughes AE, Goodship JA, Licht C, Goodship TH, Skerka C. Deletion of complement factor H-related genes CFHR1 and CFHR3 is associated with atypical hemolytic uremic syndrome. PLoS Genet. Mar. 16, 2007; 3(3):e41. Epub Feb. 1, 2007.*

Joseph C, Gattineni J. Complement disorders and hemolytic uremic syndrome. Current opinion in pediatrics. 2013; 25(2):209-215.*

* cited by examiner

SEQUENCE LISTING

<160> NUMBER OF SEQ ID NOS: 1014

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ctccaagaag aaatacagaa attctgacag         30

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
ccatgttcac aaccacctca ga         22

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3
tctcatggtg ttgtagctca catg         24

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
cataaggtac agatgtagag gaaaagaagg         30

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
gcaatggaac cagatcggga at         22

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
atttgtaact gttatcagtt gatttgctac t         31

<210> SEQ ID NO 7
<211> LENGTH: 28
<212> TYPE: DNA
<213> ORGANISM: Artificial Sequence

```
<220> FEATURE:
<223> OTHER INFORMATION: Primer

<400> SEQUENCE: 7
ctatggagat tcagtggaat tcaattgc                                28

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
atgctaagga caaataaata acacccact                               29

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
gtaccgttgc cagtccttct at                                      22

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
cgtctgtccc tccctatcaa ca                                      22

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
caaactagga tatgtaacag cagatggt                                28

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gcccaatctt tgcaaaggga at                                      22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gtaggaaagg ctcccaccct t                                       21
```

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gtctgctccg atctctgctt t                                              21

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
tttttaacat cttgcattcc attccttgt                                      29

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
agaggaagaa gattaatgtt ctagagaacg                                     30

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
tttttaaaat ttttattgca agtgaaacct tgt                                 33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
aggaaaatgt tattttcctt atttggaaaa tgg                                 33

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
gggacattac ttcattcccg ttgt                                           24

<210> SEQ ID NO 20
<211> LENGTH: 25
<212> TYPE: DNA
<213> ORGANISM: Artificial Sequence
<220> FEATURE:
<223> OTHER INFORMATION: Primer

```
<400> SEQUENCE: 20
agagaaagat gggagagggt atacc                                              25

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ctcctcctct taccgtactc ctt                                                23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
gcttgtggtt gacggtgaag at                                                 22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
ttctcactgg acagcactag ttttt                                              25

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
cctcagaacc tcagaacctc aac                                                23

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
gggttgcact gtgattccag a                                                  21

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
cccacatgag gtagtgtttc ttct                                               24

<210> SEQ ID NO 27
```

```
<211> LENGTH: 22
<212> TYPE: DNA
<213> ORGANISM: Artificial Sequence
<220> FEATURE:
<223> OTHER INFORMATION: Primer

<400> SEQUENCE: 27
cctgaacttc agccatgcat ct                                              22

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
cttccagggt gaccttgtca tc                                              22

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
ccacgcagga gtccttgac                                                  19

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
catgaggtca aagggcattc ct                                              22

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
tccaggtaga tgatgagggt gtt                                             23

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
cccgagccat cctcaatct                                                  19

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
```
caaggcttgg aacaccatga ag                                                22

<210> SEQ ID NO 34
<211> LENGTH: 24
<212> TYPE: DNA
<213> ORGANISM: Artificial Sequence
<220> FEATURE:
<223> OTHER INFORMATION: Primer

<400> SEQUENCE: 34
gaacaggtga ggtttcaagt agga                                              24

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
tctttagcgg cacgatgaca tat                                               23

<210> SEQ ID NO 36
<211> LENGTH: 19
<212> TYPE: DNA
<213> ORGANISM: Artificial Sequence
<220> FEATURE:
<223> OTHER INFORMATION: Primer

<400> SEQUENCE: 36
ggttgtctga aggccagct                                                    19

<210> SEQ ID NO 37
<211> LENGTH: 22
<212> TYPE: DNA
<213> ORGANISM: Artificial Sequence
<220> FEATURE:
<223> OTHER INFORMATION: Primer

<400> SEQUENCE: 37
ggaagagaaa ggtgcgggtt aa                                                22

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
gcaggaggaa gttgacgttg ag                                                22

<210> SEQ ID NO 39
<211> LENGTH: 28
<212> TYPE: DNA
<213> ORGANISM: Artificial Sequence
<220> FEATURE:
<223> OTHER INFORMATION: Primer

<400> SEQUENCE: 39
ccctcaaact actgtagtgt agaaaaga                                          28

<210> SEQ ID NO 40
<211> LENGTH: 28
<212> TYPE: DNA

```
<213> ORGANISM: Artificial Sequence
<220> FEATURE:
<223> OTHER INFORMATION: Primer

<400> SEQUENCE: 40
attttatccc acttgttatg ctactcgt                                          28

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
tttttcctag gatatcctaa acctgagga                                         29

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
gtcattcagg tttagtagct tcttcct                                           27

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
gccaagggcc tttctgtttt t                                                 21

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
gctccagctg cttttgcata tg                                                22

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45
gacagaatct atattattgc ctctgtgact                                        30

<210> SEQ ID NO 46
<211> LENGTH: 28
<212> TYPE: DNA
<213> ORGANISM: Artificial Sequence
<220> FEATURE:
<223> OTHER INFORMATION: Primer

<400> SEQUENCE: 46
tagcggatga aaatatgagg agatgaac                                          28
```

```
<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
gtgctaggaa attagctcct atacatttct                                    30

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
tttaggctgt tctgggcag tt                                             22

<210> SEQ ID NO 49
<211> LENGTH: 26
<212> TYPE: DNA
<213> ORGANISM: Artificial Sequence
<220> FEATURE:
<223> OTHER INFORMATION: Primer

<400> SEQUENCE: 49
atttgttgct gactatagag tggcat                                        26

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
ccgttttatt tccattaaat ggaactctt                                     29

<210> SEQ ID NO 51
<211> LENGTH: 28
<212> TYPE: DNA
<213> ORGANISM: Artificial Sequence
<220> FEATURE:
<223> OTHER INFORMATION: Primer

<400> SEQUENCE: 51
ggaatgtgtt cctttccttt tgtgaaaa                                      28

<210> SEQ ID NO 52
<211> LENGTH: 27
<212> TYPE: DNA
<213> ORGANISM: Artificial Sequence
<220> FEATURE:
<223> OTHER INFORMATION: Primer

<400> SEQUENCE: 52
tttttaagtt gatggtccaa ctgtgtt                                       27

<210> SEQ ID NO 53
<211> LENGTH: 30
<212> TYPE: DNA
<213> ORGANISM: Artificial Sequence
<220> FEATURE:
```

<223> OTHER INFORMATION: Primer

<400> SEQUENCE: 53
cttttcatca gcatctagtc taccataagg                                              30

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
ctagggacaa gaaaagtaca ttccaca                                                 27

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
agggtgcctg gcatattgtt aaa                                                     23

<210> SEQ ID NO 56
<211> LENGTH: 31
<212> TYPE: DNA
<213> ORGANISM: Artificial Sequence
<220> FEATURE:
<223> OTHER INFORMATION: Primer

<400> SEQUENCE: 56
tgcatatatt ttatttgcca aatgttatgg t                                            31

<210> SEQ ID NO 57
<211> LENGTH: 22
<212> TYPE: DNA
<213> ORGANISM: Artificial Sequence
<220> FEATURE:
<223> OTHER INFORMATION: Primer

<400> SEQUENCE: 57
accaggtcta ggtctggagt tt                                                      22

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
aaatggccat aagagatggt ggtt                                                    24

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
tatcaggtga gagcgtccag at                                                      22

<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
gaggagtgag tccctatgct ga                                          22

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
gttttcgcac tcgtcgatgt                                             20

<210> SEQ ID NO 62
<211> LENGTH: 19
<212> TYPE: DNA
<213> ORGANISM: Artificial Sequence
<220> FEATURE:
<223> OTHER INFORMATION: Primer

<400> SEQUENCE: 62
gggttgggaa cgcagaagt                                              19

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
gaagtggaac tcgcagagga a                                           21

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
agagtccaat ccaccgaact ct                                          22

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
aatctgtctg ctaatacaga aaagagaaca                                  30

<210> SEQ ID NO 66
<211> LENGTH: 28
<212> TYPE: DNA
<213> ORGANISM: Artificial Sequence
<220> FEATURE:
<223> OTHER INFORMATION: Primer

```
<400> SEQUENCE: 66
ctcaatgttt gctcttgaaa aagagtct                                    28

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67
gtcatgacaa ttagacattg acattgattt                                  30

<210> SEQ ID NO 68
<211> LENGTH: 22
<212> TYPE: DNA
<213> ORGANISM: Artificial Sequence
<220> FEATURE:
<223> OTHER INFORMATION: Primer

<400> SEQUENCE: 68
gactatgctg tgcagacctt ca                                          22

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
atggcacaga ggttacctga ag                                          22

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
tgtaaaccag gatatgcaac agca                                        24

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
gtgcaccgcc tgtttcttt                                              19

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
gtatccctgc ctttagccag ttta                                        24

<210> SEQ ID NO 73
<211> LENGTH: 22
```

```
<212> TYPE: DNA
<213> ORGANISM: Artificial Sequence
<220> FEATURE:
<223> OTHER INFORMATION: Primer

<400> SEQUENCE: 73
ggaatgcgct gtttctcagt ga                                              22

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
cccaggaaaa tctccaggtc cta                                             23

<210> SEQ ID NO 75
<211> LENGTH: 22
<212> TYPE: DNA
<213> ORGANISM: Artificial Sequence
<220> FEATURE:
<223> OTHER INFORMATION: Primer

<400> SEQUENCE: 75
gcttcagtgc ttacctcgat gt                                              22

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
ccctagcttc atggtagtgc a                                               21

<210> SEQ ID NO 77
<211> LENGTH: 29
<212> TYPE: DNA
<213> ORGANISM: Artificial Sequence
<220> FEATURE:
<223> OTHER INFORMATION: Primer

<400> SEQUENCE: 77
ggatgcattt tatttgctca tgaaagaga                                       29

<210> SEQ ID NO 78
<211> LENGTH: 30
<212> TYPE: DNA
<213> ORGANISM: Artificial Sequence
<220> FEATURE:
<223> OTHER INFORMATION: Primer

<400> SEQUENCE: 78
gtacattatt tttggatgtt tatgcgatct                                      30

<210> SEQ ID NO 79
<211> LENGTH: 27
<212> TYPE: DNA
<213> ORGANISM: Artificial Sequence
<220> FEATURE:
<223> OTHER INFORMATION: Primer

<400> SEQUENCE: 79
```
aaagtgctgt gtttgtattt gccttat                                           27

<210> SEQ ID NO 80
<211> LENGTH: 33
<212> TYPE: DNA
<213> ORGANISM: Artificial Sequence
<220> FEATURE:
<223> OTHER INFORMATION: Primer

<400> SEQUENCE: 80
gtaattcttc agttttatgt tattttccca gca                                    33

<210> SEQ ID NO 81
<211> LENGTH: 28
<212> TYPE: DNA
<213> ORGANISM: Artificial Sequence
<220> FEATURE:
<223> OTHER INFORMATION: Primer

<400> SEQUENCE: 81
gatccgtgtg taatatcccg agaaatta                                          28

<210> SEQ ID NO 82
<211> LENGTH: 28
<212> TYPE: DNA
<213> ORGANISM: Artificial Sequence
<220> FEATURE:
<223> OTHER INFORMATION: Primer

<400> SEQUENCE: 82
gactgtgttt ctttcctttt gtggaaaa                                          28

<210> SEQ ID NO 83
<211> LENGTH: 22
<212> TYPE: DNA
<213> ORGANISM: Artificial Sequence
<220> FEATURE:
<223> OTHER INFORMATION: Primer

<400> SEQUENCE: 83
caagagtaat ggcatgcggt tt                                                22

<210> SEQ ID NO 84
<211> LENGTH: 26
<212> TYPE: DNA
<213> ORGANISM: Artificial Sequence
<220> FEATURE:
<223> OTHER INFORMATION: Primer

<400> SEQUENCE: 84
gcattttatt tgctcatgaa aggcaa                                            26

<210> SEQ ID NO 85
<211> LENGTH: 31
<212> TYPE: DNA
<213> ORGANISM: Artificial Sequence
<220> FEATURE:
<223> OTHER INFORMATION: Primer

<400> SEQUENCE: 85
aattcattaa caaatgtttc attgttttgc c                                      31

<210> SEQ ID NO 86
<211> LENGTH: 30
<212> TYPE: DNA
<213> ORGANISM: Artificial Sequence

```
<220> FEATURE:
<223> OTHER INFORMATION: Primer

<400> SEQUENCE: 86
tttattccta caatgggact ttcttagtcg                                          30

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
gccagctaag gtgctttggt a                                                   21

<210> SEQ ID NO 88
<211> LENGTH: 31
<212> TYPE: DNA
<213> ORGANISM: Artificial Sequence
<220> FEATURE:
<223> OTHER INFORMATION: Primer

<400> SEQUENCE: 88
tcaattcatt aacagatgtt tcattgtttc a                                        31

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
ggtgctgatt gtgaaaacat tgc                                                 23

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
gtgggagtac tgcaacctga aaa                                                 23

<210> SEQ ID NO 91
<211> LENGTH: 22
<212> TYPE: DNA
<213> ORGANISM: Artificial Sequence
<220> FEATURE:
<223> OTHER INFORMATION: Primer

<400> SEQUENCE: 91
tggtgctaca cgacaaatcc aa                                                  22

<210> SEQ ID NO 92
<211> LENGTH: 26
<212> TYPE: DNA
<213> ORGANISM: Artificial Sequence
<220> FEATURE:
<223> OTHER INFORMATION: Primer

<400> SEQUENCE: 92
tagagagaca tagtgtgtgt gtgtca                                              26
```

<210> SEQ ID NO 93
<211> LENGTH: 33
<212> TYPE: DNA
<213> ORGANISM: Artificial Sequence
<220> FEATURE:
<223> OTHER INFORMATION: Primer

<400> SEQUENCE: 93
gctgaatgaa aacaaaact ataaatgaga tga                33

<210> SEQ ID NO 94
<211> LENGTH: 29
<212> TYPE: DNA
<213> ORGANISM: Artificial Sequence
<220> FEATURE:
<223> OTHER INFORMATION: Primer

<400> SEQUENCE: 94
ccaaaaatag aagtgcaata taaaggcaa                    29

<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
cttcccgcaa aaagtgtatc tgc                          23

<210> SEQ ID NO 96
<211> LENGTH: 27
<212> TYPE: DNA
<213> ORGANISM: Artificial Sequence
<220> FEATURE:
<223> OTHER INFORMATION: Primer

<400> SEQUENCE: 96
acaccattct tgattgttta ggatgct                      27

<210> SEQ ID NO 97
<211> LENGTH: 27
<212> TYPE: DNA
<213> ORGANISM: Artificial Sequence
<220> FEATURE:
<223> OTHER INFORMATION: Primer

<400> SEQUENCE: 97
tgacttcaca tggtttaagc tgaatga                      27

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
actcagggaa ctcttcttgt ttgg                         24

<210> SEQ ID NO 99
<211> LENGTH: 28
<212> TYPE: DNA
<213> ORGANISM: Artificial Sequence
<220> FEATURE:
<223> OTHER INFORMATION: Primer

<400> SEQUENCE: 99 ttttagtgg cacaaataca attatgcc                                    28

<210> SEQ ID NO 100
<211> LENGTH: 25
<212> TYPE: DNA
<213> ORGANISM: Artificial Sequence
<220> FEATURE:
<223> OTHER INFORMATION: Primer

<400> SEQUENCE: 100
caattcttgg aagaggagaa ctgga                                      25

<210> SEQ ID NO 101
<211> LENGTH: 27
<212> TYPE: DNA
<213> ORGANISM: Artificial Sequence
<220> FEATURE:
<223> OTHER INFORMATION: Primer

<400> SEQUENCE: 101
caaatggtga ctactcacct ttaagga                                    27

<210> SEQ ID NO 102
<211> LENGTH: 27
<212> TYPE: DNA
<213> ORGANISM: Artificial Sequence
<220> FEATURE:
<223> OTHER INFORMATION: Primer

<400> SEQUENCE: 102
accatttctt ctttcagatc catgtgt                                    27

<210> SEQ ID NO 103
<211> LENGTH: 28
<212> TYPE: DNA
<213> ORGANISM: Artificial Sequence
<220> FEATURE:
<223> OTHER INFORMATION: Primer

<400> SEQUENCE: 103
agttttgtga tgttgcttaa aagcatca                                   28

<210> SEQ ID NO 104
<211> LENGTH: 30
<212> TYPE: DNA
<213> ORGANISM: Artificial Sequence
<220> FEATURE:
<223> OTHER INFORMATION: Primer

<400> SEQUENCE: 104
cccttgcatc ttatttttat atagcacaca                                 30

<210> SEQ ID NO 105
<211> LENGTH: 29
<212> TYPE: DNA
<213> ORGANISM: Artificial Sequence
<220> FEATURE:
<223> OTHER INFORMATION: Primer

<400> SEQUENCE: 105
ccaaaaatac accatggatt tctgtatga                                  29

<210> SEQ ID NO 106

```
<211> LENGTH: 22
<212> TYPE: DNA
<213> ORGANISM: Artificial Sequence
<220> FEATURE:
<223> OTHER INFORMATION: Primer

<400> SEQUENCE: 106
accgccacct cagataccta at                                                  22

<210> SEQ ID NO 107
<211> LENGTH: 32
<212> TYPE: DNA
<213> ORGANISM: Artificial Sequence
<220> FEATURE:
<223> OTHER INFORMATION: Primer

<400> SEQUENCE: 107
atcgctattt tagaatccat tacatgtatt gt                                       32

<210> SEQ ID NO 108
<211> LENGTH: 25
<212> TYPE: DNA
<213> ORGANISM: Artificial Sequence
<220> FEATURE:
<223> OTHER INFORMATION: Primer

<400> SEQUENCE: 108
ctcaagaacc tgacatactt gacga                                               25

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
cacggtcacg aacttgttgc                                                     20

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110
agcaaagcca gtcatcatgg at                                                  22

<210> SEQ ID NO 111
<211> LENGTH: 29
<212> TYPE: DNA
<213> ORGANISM: Artificial Sequence
<220> FEATURE:
<223> OTHER INFORMATION: Primer

<400> SEQUENCE: 111
tttttggttt tcaggtatca attgctagg                                           29

<210> SEQ ID NO 112
<211> LENGTH: 30
<212> TYPE: DNA
<213> ORGANISM: Artificial Sequence
<220> FEATURE:
<223> OTHER INFORMATION: Primer

<400> SEQUENCE: 112
```
cccactccta cataaaatat attccttgct                                           30

<210> SEQ ID NO 113
<211> LENGTH: 22
<212> TYPE: DNA
<213> ORGANISM: Artificial Sequence
<220> FEATURE:
<223> OTHER INFORMATION: Primer

<400> SEQUENCE: 113
cgtcaggaag ttactgggat ca                                                   22

<210> SEQ ID NO 114
<211> LENGTH: 25
<212> TYPE: DNA
<213> ORGANISM: Artificial Sequence
<220> FEATURE:
<223> OTHER INFORMATION: Primer

<400> SEQUENCE: 114
ccctctgtat gacccaatat caacc                                                25

<210> SEQ ID NO 115
<211> LENGTH: 31
<212> TYPE: DNA
<213> ORGANISM: Artificial Sequence
<220> FEATURE:
<223> OTHER INFORMATION: Primer

<400> SEQUENCE: 115
aatcaataaa gcttttctt cttagaatgg g                                          31

<210> SEQ ID NO 116
<211> LENGTH: 29
<212> TYPE: DNA
<213> ORGANISM: Artificial Sequence
<220> FEATURE:
<223> OTHER INFORMATION: Primer

<400> SEQUENCE: 116
agacagatga gtaaatatcc atctggtga                                            29

<210> SEQ ID NO 117
<211> LENGTH: 25
<212> TYPE: DNA
<213> ORGANISM: Artificial Sequence
<220> FEATURE:
<223> OTHER INFORMATION: Primer

<400> SEQUENCE: 117
tcttgagatg aggtgggatc ttagg                                                25

<210> SEQ ID NO 118
<211> LENGTH: 22
<212> TYPE: DNA
<213> ORGANISM: Artificial Sequence
<220> FEATURE:
<223> OTHER INFORMATION: Primer

<400> SEQUENCE: 118
gcgcaggaga gaacctctct at                                                   22

<210> SEQ ID NO 119
<211> LENGTH: 24
<212> TYPE: DNA

```
<213> ORGANISM: Artificial Sequence
<220> FEATURE:
<223> OTHER INFORMATION: Primer

<400> SEQUENCE: 119
tccaggctgg ataagctcta catt                                          24

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
gggtgttcct gctcccattt                                               20

<210> SEQ ID NO 121
<211> LENGTH: 22
<212> TYPE: DNA
<213> ORGANISM: Artificial Sequence
<220> FEATURE:
<223> OTHER INFORMATION: Primer

<400> SEQUENCE: 121
tgggagagga gacacaatgt ca                                            22

<210> SEQ ID NO 122
<211> LENGTH: 23
<212> TYPE: DNA
<213> ORGANISM: Artificial Sequence
<220> FEATURE:
<223> OTHER INFORMATION: Primer

<400> SEQUENCE: 122
tctgctcaat ggccatgatg tac                                           23

<210> SEQ ID NO 123
<211> LENGTH: 21
<212> TYPE: DNA
<213> ORGANISM: Artificial Sequence
<220> FEATURE:
<223> OTHER INFORMATION: Primer

<400> SEQUENCE: 123
cactctgagc ctccctcctt a                                             21

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
gggatgaagt cggtggtgat                                               20

<210> SEQ ID NO 125
<211> LENGTH: 24
<212> TYPE: DNA
<213> ORGANISM: Artificial Sequence
<220> FEATURE:
<223> OTHER INFORMATION: Primer

<400> SEQUENCE: 125
ccctaaatcc cagcctctta caat                                          24
```

```
<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
acacccaaat gcaccctgaa t                                                 21

<210> SEQ ID NO 127
<211> LENGTH: 22
<212> TYPE: DNA
<213> ORGANISM: Artificial Sequence
<220> FEATURE:
<223> OTHER INFORMATION: Primer

<400> SEQUENCE: 127
ggcctcagtg tcttctctag ga                                                22

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
ccctcacctg gctcttacct                                                   20

<210> SEQ ID NO 129
<211> LENGTH: 29
<212> TYPE: DNA
<213> ORGANISM: Artificial Sequence
<220> FEATURE:
<223> OTHER INFORMATION: Primer

<400> SEQUENCE: 129
gatgagttaa gtgctcaaaa gatgttagc                                         29

<210> SEQ ID NO 130
<211> LENGTH: 22
<212> TYPE: DNA
<213> ORGANISM: Artificial Sequence
<220> FEATURE:
<223> OTHER INFORMATION: Primer

<400> SEQUENCE: 130
ttctcttcgt cttggcattc gt                                                22

<210> SEQ ID NO 131
<211> LENGTH: 22
<212> TYPE: DNA
<213> ORGANISM: Artificial Sequence
<220> FEATURE:
<223> OTHER INFORMATION: Primer

<400> SEQUENCE: 131
cagggtctaa gtcccactcc tt                                                22

<210> SEQ ID NO 132
<211> LENGTH: 22
<212> TYPE: DNA
<213> ORGANISM: Artificial Sequence
<220> FEATURE:
```

<223> OTHER INFORMATION: Primer

<400> SEQUENCE: 132
gctcttggtt ctgccggtaa tt                                        22

<210> SEQ ID NO 133
<211> LENGTH: 23
<212> TYPE: DNA
<213> ORGANISM: Artificial Sequence
<220> FEATURE:
<223> OTHER INFORMATION: Primer

<400> SEQUENCE: 133
cgccctatcc tacctcacta aac                                       23

<210> SEQ ID NO 134
<211> LENGTH: 22
<212> TYPE: DNA
<213> ORGANISM: Artificial Sequence
<220> FEATURE:
<223> OTHER INFORMATION: Primer

<400> SEQUENCE: 134
cactggccct taccttactc tg                                        22

<210> SEQ ID NO 135
<211> LENGTH: 28
<212> TYPE: DNA
<213> ORGANISM: Artificial Sequence
<220> FEATURE:
<223> OTHER INFORMATION: Primer

<400> SEQUENCE: 135
tgttcatttt ctgaataggc ttctggaa                                  28

<210> SEQ ID NO 136
<211> LENGTH: 28
<212> TYPE: DNA
<213> ORGANISM: Artificial Sequence
<220> FEATURE:
<223> OTHER INFORMATION: Primer

<400> SEQUENCE: 136
gaggtttctc taattttcca gtggtcaa                                  28

<210> SEQ ID NO 137
<211> LENGTH: 31
<212> TYPE: DNA
<213> ORGANISM: Artificial Sequence
<220> FEATURE:
<223> OTHER INFORMATION: Primer

<400> SEQUENCE: 137
aaattctaag atgtggaatt gcaaagtttg t                              31

<210> SEQ ID NO 138
<211> LENGTH: 28
<212> TYPE: DNA
<213> ORGANISM: Artificial Sequence
<220> FEATURE:
<223> OTHER INFORMATION: Primer

<400> SEQUENCE: 138
acagccaaac catatcaagt gtttagat                                  28

```
<210> SEQ ID NO 139
<211> LENGTH: 31
<212> TYPE: DNA
<213> ORGANISM: Artificial Sequence
<220> FEATURE:
<223> OTHER INFORMATION: Primer

<400> SEQUENCE: 139
tgaagacaca gaaattttac taatgctgtc t                              31

<210> SEQ ID NO 140
<211> LENGTH: 30
<212> TYPE: DNA
<213> ORGANISM: Artificial Sequence
<220> FEATURE:
<223> OTHER INFORMATION: Primer

<400> SEQUENCE: 140
cctactatga gattggtgaa cgagtagatt                                30

<210> SEQ ID NO 141
<211> LENGTH: 22
<212> TYPE: DNA
<213> ORGANISM: Artificial Sequence
<220> FEATURE:
<223> OTHER INFORMATION: Primer

<400> SEQUENCE: 141
gtaatgcagt ccacctcacc at                                        22

<210> SEQ ID NO 142
<211> LENGTH: 30
<212> TYPE: DNA
<213> ORGANISM: Artificial Sequence
<220> FEATURE:
<223> OTHER INFORMATION: Primer

<400> SEQUENCE: 142
ctgatagaaa gtatggcata caaataccct                                30

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
gcaaatactc caccaacctg ctt                                       23

<210> SEQ ID NO 144
<211> LENGTH: 27
<212> TYPE: DNA
<213> ORGANISM: Artificial Sequence
<220> FEATURE:
<223> OTHER INFORMATION: Primer

<400> SEQUENCE: 144
tttttcattt caatcaaagc gatgtca                                   27

<210> SEQ ID NO 145
<211> LENGTH: 29
<212> TYPE: DNA
<213> ORGANISM: Artificial Sequence
<220> FEATURE:
<223> OTHER INFORMATION: Primer
```

```
<400> SEQUENCE: 145
ttgataccaa aactacttgt tgcttgaat                                        29

<210> SEQ ID NO 146
<211> LENGTH: 27
<212> TYPE: DNA
<213> ORGANISM: Artificial Sequence
<220> FEATURE:
<223> OTHER INFORMATION: Primer

<400> SEQUENCE: 146
tcctacatgg tagctaatcc agtcaaa                                          27

<210> SEQ ID NO 147
<211> LENGTH: 26
<212> TYPE: DNA
<213> ORGANISM: Artificial Sequence
<220> FEATURE:
<223> OTHER INFORMATION: Primer

<400> SEQUENCE: 147
ctgaagagat agaaagggc agatga                                            26

<210> SEQ ID NO 148
<211> LENGTH: 33
<212> TYPE: DNA
<213> ORGANISM: Artificial Sequence
<220> FEATURE:
<223> OTHER INFORMATION: Primer

<400> SEQUENCE: 148
tgtttctagg tttttgatgt aactaaaact cct                                   33

<210> SEQ ID NO 149
<211> LENGTH: 30
<212> TYPE: DNA
<213> ORGANISM: Artificial Sequence
<220> FEATURE:
<223> OTHER INFORMATION: Primer

<400> SEQUENCE: 149
aaaacagtac atgatgagtg catgaaaaat                                       30

<210> SEQ ID NO 150
<211> LENGTH: 24
<212> TYPE: DNA
<213> ORGANISM: Artificial Sequence
<220> FEATURE:
<223> OTHER INFORMATION: Primer

<400> SEQUENCE: 150
ggtgttcatc accttctggt gtag                                             24

<210> SEQ ID NO 151
<211> LENGTH: 28
<212> TYPE: DNA
<213> ORGANISM: Artificial Sequence
<220> FEATURE:
<223> OTHER INFORMATION: Primer

<400> SEQUENCE: 151
acgtgtggtt acttttgtag atggtatt                                         28

<210> SEQ ID NO 152
<211> LENGTH: 19
```

<212> TYPE: DNA
<213> ORGANISM: Artificial Sequence
<220> FEATURE:
<223> OTHER INFORMATION: Primer

<400> SEQUENCE: 152
cgtgcccacc tgctatagc                                                  19

<210> SEQ ID NO 153
<211> LENGTH: 22
<212> TYPE: DNA
<213> ORGANISM: Artificial Sequence
<220> FEATURE:
<223> OTHER INFORMATION: Primer

<400> SEQUENCE: 153
gccatgcttc caggattagg aa                                              22

<210> SEQ ID NO 154
<211> LENGTH: 25
<212> TYPE: DNA
<213> ORGANISM: Artificial Sequence
<220> FEATURE:
<223> OTHER INFORMATION: Primer

<400> SEQUENCE: 154
ccttttatac cctggaaacc catga                                           25

<210> SEQ ID NO 155
<211> LENGTH: 24
<212> TYPE: DNA
<213> ORGANISM: Artificial Sequence
<220> FEATURE:
<223> OTHER INFORMATION: Primer

<400> SEQUENCE: 155
gggaagacgt gaagttagga atga                                            24

<210> SEQ ID NO 156
<211> LENGTH: 22
<212> TYPE: DNA
<213> ORGANISM: Artificial Sequence
<220> FEATURE:
<223> OTHER INFORMATION: Primer

<400> SEQUENCE: 156
ggcccagaac ctagctctag aa                                              22

<210> SEQ ID NO 157
<211> LENGTH: 22
<212> TYPE: DNA
<213> ORGANISM: Artificial Sequence
<220> FEATURE:
<223> OTHER INFORMATION: Primer

<400> SEQUENCE: 157
tgcctgatgc cctttatctt gg                                              22

<210> SEQ ID NO 158
<211> LENGTH: 18
<212> TYPE: DNA
<213> ORGANISM: Artificial Sequence
<220> FEATURE:
<223> OTHER INFORMATION: Primer

<400> SEQUENCE: 158
caggctcgcg atggagat						18

<210> SEQ ID NO 159
<211> LENGTH: 24
<212> TYPE: DNA
<213> ORGANISM: Artificial Sequence
<220> FEATURE:
<223> OTHER INFORMATION: Primer

<400> SEQUENCE: 159
gcagaggtag ctagtttggt tcag					24

<210> SEQ ID NO 160
<211> LENGTH: 18
<212> TYPE: DNA
<213> ORGANISM: Artificial Sequence
<220> FEATURE:
<223> OTHER INFORMATION: Primer

<400> SEQUENCE: 160
cccagggatc gcattgca						18

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
aatttcagca ccacctgagc taa					23

<210> SEQ ID NO 162
<211> LENGTH: 22
<212> TYPE: DNA
<213> ORGANISM: Artificial Sequence
<220> FEATURE:
<223> OTHER INFORMATION: Primer

<400> SEQUENCE: 162
ctcaagacag ggatgactgg tt					22

<210> SEQ ID NO 163
<211> LENGTH: 26
<212> TYPE: DNA
<213> ORGANISM: Artificial Sequence
<220> FEATURE:
<223> OTHER INFORMATION: Primer

<400> SEQUENCE: 163
tgtctcgaat tacaccacaa aattgc					26

<210> SEQ ID NO 164
<211> LENGTH: 24
<212> TYPE: DNA
<213> ORGANISM: Artificial Sequence
<220> FEATURE:
<223> OTHER INFORMATION: Primer

<400> SEQUENCE: 164
ttccatatca tcctgggtct ctgt					24

<210> SEQ ID NO 165
<211> LENGTH: 22
<212> TYPE: DNA
<213> ORGANISM: Artificial Sequence

```
<220> FEATURE:
<223> OTHER INFORMATION: Primer

<400> SEQUENCE: 165
gcatctcctt ctgccttgct aa                                            22

<210> SEQ ID NO 166
<211> LENGTH: 33
<212> TYPE: DNA
<213> ORGANISM: Artificial Sequence
<220> FEATURE:
<223> OTHER INFORMATION: Primer

<400> SEQUENCE: 166
atgtgtaaat tgggatataa tgcaaataca tca                                33

<210> SEQ ID NO 167
<211> LENGTH: 23
<212> TYPE: DNA
<213> ORGANISM: Artificial Sequence
<220> FEATURE:
<223> OTHER INFORMATION: Primer

<400> SEQUENCE: 167
ggctagagtg ggatgaggaa gaa                                           23

<210> SEQ ID NO 168
<211> LENGTH: 23
<212> TYPE: DNA
<213> ORGANISM: Artificial Sequence
<220> FEATURE:
<223> OTHER INFORMATION: Primer

<400> SEQUENCE: 168
cttggaccct catccttcct ttt                                           23

<210> SEQ ID NO 169
<211> LENGTH: 22
<212> TYPE: DNA
<213> ORGANISM: Artificial Sequence
<220> FEATURE:
<223> OTHER INFORMATION: Primer

<400> SEQUENCE: 169
cccggtctcc ctactacaat gt                                            22

<210> SEQ ID NO 170
<211> LENGTH: 22
<212> TYPE: DNA
<213> ORGANISM: Artificial Sequence
<220> FEATURE:
<223> OTHER INFORMATION: Primer

<400> SEQUENCE: 170
acaggtggca agttatggtg tg                                            22

<210> SEQ ID NO 171
<211> LENGTH: 33
<212> TYPE: DNA
<213> ORGANISM: Artificial Sequence
<220> FEATURE:
<223> OTHER INFORMATION: Primer

<400> SEQUENCE: 171
cagatgtctt cctaagaaat caaataagat aca                                33
```

<210> SEQ ID NO 172
<211> LENGTH: 27
<212> TYPE: DNA
<213> ORGANISM: Artificial Sequence
<220> FEATURE:
<223> OTHER INFORMATION: Primer

<400> SEQUENCE: 172
tccacaagaa aatgtttgag agaaggt                                27

<210> SEQ ID NO 173
<211> LENGTH: 24
<212> TYPE: DNA
<213> ORGANISM: Artificial Sequence
<220> FEATURE:
<223> OTHER INFORMATION: Primer

<400> SEQUENCE: 173
agggtaactc tacagaagtt gcct                                   24

<210> SEQ ID NO 174
<211> LENGTH: 24
<212> TYPE: DNA
<213> ORGANISM: Artificial Sequence
<220> FEATURE:
<223> OTHER INFORMATION: Primer

<400> SEQUENCE: 174
gggacattac ttcattcccg ttgt                                   24

<210> SEQ ID NO 175
<211> LENGTH: 31
<212> TYPE: DNA
<213> ORGANISM: Artificial Sequence
<220> FEATURE:
<223> OTHER INFORMATION: Primer

<400> SEQUENCE: 175
gtattagttg atttgctact caaaatgaac a                           31

<210> SEQ ID NO 176
<211> LENGTH: 32
<212> TYPE: DNA
<213> ORGANISM: Artificial Sequence
<220> FEATURE:
<223> OTHER INFORMATION: Primer

<400> SEQUENCE: 176
gggaagtttt ctattactcc tgtgaatata at                          32

<210> SEQ ID NO 177
<211> LENGTH: 31
<212> TYPE: DNA
<213> ORGANISM: Artificial Sequence
<220> FEATURE:
<223> OTHER INFORMATION: Primer

<400> SEQUENCE: 177
ttggaaggta acataatcaa aacagtcatc t                           31

<210> SEQ ID NO 178
<211> LENGTH: 24
<212> TYPE: DNA
<213> ORGANISM: Artificial Sequence
<220> FEATURE:
<223> OTHER INFORMATION: Primer -continued

```
<400> SEQUENCE: 178
tgtaaaccag gatatgcaac agca                                              24

<210> SEQ ID NO 179
<211> LENGTH: 33
<212> TYPE: DNA
<213> ORGANISM: Artificial Sequence
<220> FEATURE:
<223> OTHER INFORMATION: Primer

<400> SEQUENCE: 179
ctattttagg aacatgctca aaatcagatg tag                                    33

<210> SEQ ID NO 180
<211> LENGTH: 31
<212> TYPE: DNA
<213> ORGANISM: Artificial Sequence
<220> FEATURE:
<223> OTHER INFORMATION: Primer

<400> SEQUENCE: 180
cgaatacatc agttctatca tttcaagcag t                                      31

<210> SEQ ID NO 181
<211> LENGTH: 26
<212> TYPE: DNA
<213> ORGANISM: Artificial Sequence
<220> FEATURE:
<223> OTHER INFORMATION: Primer

<400> SEQUENCE: 181
ctaagtgacc ttaaagccct agcttt                                            26

<210> SEQ ID NO 182
<211> LENGTH: 32
<212> TYPE: DNA
<213> ORGANISM: Artificial Sequence
<220> FEATURE:
<223> OTHER INFORMATION: Primer

<400> SEQUENCE: 182
atgtacatat atatgtagtc ctcctatgag tg                                     32

<210> SEQ ID NO 183
<211> LENGTH: 31
<212> TYPE: DNA
<213> ORGANISM: Artificial Sequence
<220> FEATURE:
<223> OTHER INFORMATION: Primer

<400> SEQUENCE: 183
tccctcaaga tattcaatga tctttagcat g                                      31

<210> SEQ ID NO 184
<211> LENGTH: 29
<212> TYPE: DNA
<213> ORGANISM: Artificial Sequence
<220> FEATURE:
<223> OTHER INFORMATION: Primer

<400> SEQUENCE: 184
attcattgta acttattttg cccattcaa                                         29

<210> SEQ ID NO 185
```

```
<211> LENGTH: 30
<212> TYPE: DNA
<213> ORGANISM: Artificial Sequence
<220> FEATURE:
<223> OTHER INFORMATION: Primer

<400> SEQUENCE: 185
ggaatatgga cacaatgaag tagtggaata                                    30

<210> SEQ ID NO 186
<211> LENGTH: 30
<212> TYPE: DNA
<213> ORGANISM: Artificial Sequence
<220> FEATURE:
<223> OTHER INFORMATION: Primer

<400> SEQUENCE: 186
cacattggac tatgaatgct atgatggata                                    30

<210> SEQ ID NO 187
<211> LENGTH: 30
<212> TYPE: DNA
<213> ORGANISM: Artificial Sequence
<220> FEATURE:
<223> OTHER INFORMATION: Primer

<400> SEQUENCE: 187
gtgttttgag aaataattcc tgaaccatca                                    30

<210> SEQ ID NO 188
<211> LENGTH: 30
<212> TYPE: DNA
<213> ORGANISM: Artificial Sequence
<220> FEATURE:
<223> OTHER INFORMATION: Primer

<400> SEQUENCE: 188
aggatatctg aagaaaatga aacaacatgc                                    30

<210> SEQ ID NO 189
<211> LENGTH: 28
<212> TYPE: DNA
<213> ORGANISM: Artificial Sequence
<220> FEATURE:
<223> OTHER INFORMATION: Primer

<400> SEQUENCE: 189
aaacgaaaga agaatatgga cacagtga                                      28

<210> SEQ ID NO 190
<211> LENGTH: 29
<212> TYPE: DNA
<213> ORGANISM: Artificial Sequence
<220> FEATURE:
<223> OTHER INFORMATION: Primer

<400> SEQUENCE: 190
gaacttttgt ttggttgact gatttacct                                     29

<210> SEQ ID NO 191
<211> LENGTH: 30
<212> TYPE: DNA
<213> ORGANISM: Artificial Sequence
<220> FEATURE:
<223> OTHER INFORMATION: Primer

<400> SEQUENCE: 191
```
cttgagtaat atgctcataa gttcctttct                                    30

<210> SEQ ID NO 192
<211> LENGTH: 29
<212> TYPE: DNA
<213> ORGANISM: Artificial Sequence
<220> FEATURE:
<223> OTHER INFORMATION: Primer

<400> SEQUENCE: 192
gatcaggaat aacttggttg gtgaaattt                                     29

<210> SEQ ID NO 193
<211> LENGTH: 21
<212> TYPE: DNA
<213> ORGANISM: Artificial Sequence
<220> FEATURE:
<223> OTHER INFORMATION: Primer

<400> SEQUENCE: 193
ggtttcctcc ctcctcagac a                                             21

<210> SEQ ID NO 194
<211> LENGTH: 24
<212> TYPE: DNA
<213> ORGANISM: Artificial Sequence
<220> FEATURE:
<223> OTHER INFORMATION: Primer

<400> SEQUENCE: 194
atagacctgt gactgtctag gcat                                          24

<210> SEQ ID NO 195
<211> LENGTH: 25
<212> TYPE: DNA
<213> ORGANISM: Artificial Sequence
<220> FEATURE:
<223> OTHER INFORMATION: Primer

<400> SEQUENCE: 195
tcaagaaaga gaatgcgaac ttcct                                         25

<210> SEQ ID NO 196
<211> LENGTH: 31
<212> TYPE: DNA
<213> ORGANISM: Artificial Sequence
<220> FEATURE:
<223> OTHER INFORMATION: Primer

<400> SEQUENCE: 196
agttggtttg attcctatca tttgaatttt c                                  31

<210> SEQ ID NO 197
<211> LENGTH: 26
<212> TYPE: DNA
<213> ORGANISM: Artificial Sequence
<220> FEATURE:
<223> OTHER INFORMATION: Primer

<400> SEQUENCE: 197
ttcctccaat cttatcctga ggatga                                        26

<210> SEQ ID NO 198
<211> LENGTH: 25
<212> TYPE: DNA

```
<213> ORGANISM: Artificial Sequence
<220> FEATURE:
<223> OTHER INFORMATION: Primer

<400> SEQUENCE: 198
ttgatggaga gtggacaact ttacc                                          25

<210> SEQ ID NO 199
<211> LENGTH: 30
<212> TYPE: DNA
<213> ORGANISM: Artificial Sequence
<220> FEATURE:
<223> OTHER INFORMATION: Primer

<400> SEQUENCE: 199
tacacatgat gtcagttttc aaagttttcc                                     30

<210> SEQ ID NO 200
<211> LENGTH: 30
<212> TYPE: DNA
<213> ORGANISM: Artificial Sequence
<220> FEATURE:
<223> OTHER INFORMATION: Primer

<400> SEQUENCE: 200
acataatgtc tcaacaaata aatgctgttt                                     30

<210> SEQ ID NO 201
<211> LENGTH: 29
<212> TYPE: DNA
<213> ORGANISM: Artificial Sequence
<220> FEATURE:
<223> OTHER INFORMATION: Primer

<400> SEQUENCE: 201
aagaggtgca aaatagcagg agttaatat                                      29

<210> SEQ ID NO 202
<211> LENGTH: 28
<212> TYPE: DNA
<213> ORGANISM: Artificial Sequence
<220> FEATURE:
<223> OTHER INFORMATION: Primer

<400> SEQUENCE: 202
gaaaatacaa tgtgtggatg gagaatgg                                       28

<210> SEQ ID NO 203
<211> LENGTH: 30
<212> TYPE: DNA
<213> ORGANISM: Artificial Sequence
<220> FEATURE:
<223> OTHER INFORMATION: Primer

<400> SEQUENCE: 203
tcttataaga gttggatcag actcagttca                                     30

<210> SEQ ID NO 204
<211> LENGTH: 30
<212> TYPE: DNA
<213> ORGANISM: Artificial Sequence
<220> FEATURE:
<223> OTHER INFORMATION: Primer

<400> SEQUENCE: 204
cccttagtac attgaaattc aaagtcatgc                                     30
```

<210> SEQ ID NO 205
<211> LENGTH: 18
<212> TYPE: DNA
<213> ORGANISM: Artificial Sequence
<220> FEATURE:
<223> OTHER INFORMATION: Primer

<400> SEQUENCE: 205
cctgcgtcgg agaagaca                                                 18

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
ccgtgagggc catgtctttc                                               20

<210> SEQ ID NO 207
<211> LENGTH: 21
<212> TYPE: DNA
<213> ORGANISM: Artificial Sequence
<220> FEATURE:
<223> OTHER INFORMATION: Primer

<400> SEQUENCE: 207
ctttgcctct cctaagcctg t                                             21

<210> SEQ ID NO 208
<211> LENGTH: 21
<212> TYPE: DNA
<213> ORGANISM: Artificial Sequence
<220> FEATURE:
<223> OTHER INFORMATION: Primer

<400> SEQUENCE: 208
gagccctctc tgaaggacaa g                                             21

<210> SEQ ID NO 209
<211> LENGTH: 24
<212> TYPE: DNA
<213> ORGANISM: Artificial Sequence
<220> FEATURE:
<223> OTHER INFORMATION: Primer

<400> SEQUENCE: 209
gagagcaata actcccaagt ggtt                                          24

<210> SEQ ID NO 210
<211> LENGTH: 26
<212> TYPE: DNA
<213> ORGANISM: Artificial Sequence
<220> FEATURE:
<223> OTHER INFORMATION: Primer

<400> SEQUENCE: 210
ttctctgtga tgtcatagta gctcct                                        26

<210> SEQ ID NO 211
<211> LENGTH: 27
<212> TYPE: DNA
<213> ORGANISM: Artificial Sequence
<220> FEATURE:

<223> OTHER INFORMATION: Primer

<400> SEQUENCE: 211
ttttggtact tttaccctta caggagg                                    27

<210> SEQ ID NO 212
<211> LENGTH: 27
<212> TYPE: DNA
<213> ORGANISM: Artificial Sequence
<220> FEATURE:
<223> OTHER INFORMATION: Primer

<400> SEQUENCE: 212
ctcagtttac ctagctttga aaatgcc                                    27

<210> SEQ ID NO 213
<211> LENGTH: 30
<212> TYPE: DNA
<213> ORGANISM: Artificial Sequence
<220> FEATURE:
<223> OTHER INFORMATION: Primer

<400> SEQUENCE: 213
ttatccaggt tttcagttac aaatgactca                                 30

<210> SEQ ID NO 214
<211> LENGTH: 31
<212> TYPE: DNA
<213> ORGANISM: Artificial Sequence
<220> FEATURE:
<223> OTHER INFORMATION: Primer

<400> SEQUENCE: 214
aaaactgttg atattatata cagtgctgtg t                               31

<210> SEQ ID NO 215
<211> LENGTH: 21
<212> TYPE: DNA
<213> ORGANISM: Artificial Sequence
<220> FEATURE:
<223> OTHER INFORMATION: Primer

<400> SEQUENCE: 215
ccactgctcc gtttcatcca g                                          21

<210> SEQ ID NO 216
<211> LENGTH: 29
<212> TYPE: DNA
<213> ORGANISM: Artificial Sequence
<220> FEATURE:
<223> OTHER INFORMATION: Primer

<400> SEQUENCE: 216
agggttgatt gagtttggat aaaatgaga                                  29

<210> SEQ ID NO 217
<211> LENGTH: 18
<212> TYPE: DNA
<213> ORGANISM: Artificial Sequence
<220> FEATURE:
<223> OTHER INFORMATION: Primer

<400> SEQUENCE: 217
gggcgtgaca atggtgtg                                              18

```
<210> SEQ ID NO 218
<211> LENGTH: 23
<212> TYPE: DNA
<213> ORGANISM: Artificial Sequence
<220> FEATURE:
<223> OTHER INFORMATION: Primer

<400> SEQUENCE: 218
agggcttaga aagggagaag aca                                              23

<210> SEQ ID NO 219
<211> LENGTH: 22
<212> TYPE: DNA
<213> ORGANISM: Artificial Sequence
<220> FEATURE:
<223> OTHER INFORMATION: Primer

<400> SEQUENCE: 219
gcagacacgt acaaagactt cc                                               22

<210> SEQ ID NO 220
<211> LENGTH: 22
<212> TYPE: DNA
<213> ORGANISM: Artificial Sequence
<220> FEATURE:
<223> OTHER INFORMATION: Primer

<400> SEQUENCE: 220
tacctaggcc actcacagtc at                                               22

<210> SEQ ID NO 221
<211> LENGTH: 22
<212> TYPE: DNA
<213> ORGANISM: Artificial Sequence
<220> FEATURE:
<223> OTHER INFORMATION: Primer

<400> SEQUENCE: 221
gggtgtgtgt tgatgctgag tt                                               22

<210> SEQ ID NO 222
<211> LENGTH: 29
<212> TYPE: DNA
<213> ORGANISM: Artificial Sequence
<220> FEATURE:
<223> OTHER INFORMATION: Primer

<400> SEQUENCE: 222
ctgaaaggaa aagaaagacc agccagata                                        29

<210> SEQ ID NO 223
<211> LENGTH: 23
<212> TYPE: DNA
<213> ORGANISM: Artificial Sequence
<220> FEATURE:
<223> OTHER INFORMATION: Primer

<400> SEQUENCE: 223
gtagggccaa gagggcatag gat                                              23

<210> SEQ ID NO 224
<211> LENGTH: 22
<212> TYPE: DNA
<213> ORGANISM: Artificial Sequence
<220> FEATURE:
<223> OTHER INFORMATION: Primer
```

<400> SEQUENCE: 224
ctccctcttg cttcccagta aa					22

<210> SEQ ID NO 225
<211> LENGTH: 22
<212> TYPE: DNA
<213> ORGANISM: Artificial Sequence
<220> FEATURE:
<223> OTHER INFORMATION: Primer

<400> SEQUENCE: 225
cctccaggcc cttctcgtta ta					22

<210> SEQ ID NO 226
<211> LENGTH: 28
<212> TYPE: DNA
<213> ORGANISM: Artificial Sequence
<220> FEATURE:
<223> OTHER INFORMATION: Primer

<400> SEQUENCE: 226
acagtatcag atacacagtg tacttgga					28

<210> SEQ ID NO 227
<211> LENGTH: 22
<212> TYPE: DNA
<213> ORGANISM: Artificial Sequence
<220> FEATURE:
<223> OTHER INFORMATION: Primer

<400> SEQUENCE: 227
gcagagcttg ttcagctttc ca					22

<210> SEQ ID NO 228
<211> LENGTH: 22
<212> TYPE: DNA
<213> ORGANISM: Artificial Sequence
<220> FEATURE:
<223> OTHER INFORMATION: Primer

<400> SEQUENCE: 228
ggtccgtgct taaggatgct ta					22

<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229
gctggcacga gaacctcatg					20

<210> SEQ ID NO 230
<211> LENGTH: 21
<212> TYPE: DNA
<213> ORGANISM: Artificial Sequence
<220> FEATURE:
<223> OTHER INFORMATION: Primer

<400> SEQUENCE: 230
agcctgccct tgttcatgat c					21

<210> SEQ ID NO 231
<211> LENGTH: 22

<212> TYPE: DNA
<213> ORGANISM: Artificial Sequence
<220> FEATURE:
<223> OTHER INFORMATION: Primer

<400> SEQUENCE: 231
gggattgttg cgtcccatat ct                                         22

<210> SEQ ID NO 232
<211> LENGTH: 23
<212> TYPE: DNA
<213> ORGANISM: Artificial Sequence
<220> FEATURE:
<223> OTHER INFORMATION: Primer

<400> SEQUENCE: 232
ccattcaaaa gagcactgca gaa                                        23

<210> SEQ ID NO 233
<211> LENGTH: 27
<212> TYPE: DNA
<213> ORGANISM: Artificial Sequence
<220> FEATURE:
<223> OTHER INFORMATION: Primer

<400> SEQUENCE: 233
gggaggaaga agaaagatta tgacatt                                    27

<210> SEQ ID NO 234
<211> LENGTH: 27
<212> TYPE: DNA
<213> ORGANISM: Artificial Sequence
<220> FEATURE:
<223> OTHER INFORMATION: Primer

<400> SEQUENCE: 234
aacatttgac cactgaaatg taaccaa                                    27

<210> SEQ ID NO 235
<211> LENGTH: 30
<212> TYPE: DNA
<213> ORGANISM: Artificial Sequence
<220> FEATURE:
<223> OTHER INFORMATION: Primer

<400> SEQUENCE: 235
cttgatgcag taacttatag ttgtgatcct                                 30

<210> SEQ ID NO 236
<211> LENGTH: 29
<212> TYPE: DNA
<213> ORGANISM: Artificial Sequence
<220> FEATURE:
<223> OTHER INFORMATION: Primer

<400> SEQUENCE: 236
atgttcaggc tgggttatta ctaaaatgt                                  29

<210> SEQ ID NO 237
<211> LENGTH: 30
<212> TYPE: DNA
<213> ORGANISM: Artificial Sequence
<220> FEATURE:
<223> OTHER INFORMATION: Primer

<400> SEQUENCE: 237
agaggctaga tttatgtcta cctttacaac                                        30

<210> SEQ ID NO 238
<211> LENGTH: 28
<212> TYPE: DNA
<213> ORGANISM: Artificial Sequence
<220> FEATURE:
<223> OTHER INFORMATION: Primer

<400> SEQUENCE: 238
ccaaactctt ttgttgacag tatgttgg                                          28

<210> SEQ ID NO 239
<211> LENGTH: 27
<212> TYPE: DNA
<213> ORGANISM: Artificial Sequence
<220> FEATURE:
<223> OTHER INFORMATION: Primer

<400> SEQUENCE: 239
tcatcctcat aacaatgcta tgatgca                                           27

<210> SEQ ID NO 240
<211> LENGTH: 24
<212> TYPE: DNA
<213> ORGANISM: Artificial Sequence
<220> FEATURE:
<223> OTHER INFORMATION: Primer

<400> SEQUENCE: 240
gtggtgggag gagatgtttg atag                                              24

<210> SEQ ID NO 241
<211> LENGTH: 28
<212> TYPE: DNA
<213> ORGANISM: Artificial Sequence
<220> FEATURE:
<223> OTHER INFORMATION: Primer

<400> SEQUENCE: 241
tcagatatgc tttatcatct gccacaat                                          28

<210> SEQ ID NO 242
<211> LENGTH: 25
<212> TYPE: DNA
<213> ORGANISM: Artificial Sequence
<220> FEATURE:
<223> OTHER INFORMATION: Primer

<400> SEQUENCE: 242
gcatctccat tgtcaaaaga acaca                                             25

<210> SEQ ID NO 243
<211> LENGTH: 27
<212> TYPE: DNA
<213> ORGANISM: Artificial Sequence
<220> FEATURE:
<223> OTHER INFORMATION: Primer

<400> SEQUENCE: 243
caattagcac aagctttagc aaaacaa                                           27

<210> SEQ ID NO 244
<211> LENGTH: 22
<212> TYPE: DNA
<213> ORGANISM: Artificial Sequence

```
<220> FEATURE:
<223> OTHER INFORMATION: Primer

<400> SEQUENCE: 244
cgcttccagt gcaaggagat ta                                          22

<210> SEQ ID NO 245
<211> LENGTH: 18
<212> TYPE: DNA
<213> ORGANISM: Artificial Sequence
<220> FEATURE:
<223> OTHER INFORMATION: Primer

<400> SEQUENCE: 245
cgtcgccgtt cagtagca                                               18

<210> SEQ ID NO 246
<211> LENGTH: 29
<212> TYPE: DNA
<213> ORGANISM: Artificial Sequence
<220> FEATURE:
<223> OTHER INFORMATION: Primer

<400> SEQUENCE: 246
tgcaaacctt tgttagtaac tttagttcg                                   29

<210> SEQ ID NO 247
<211> LENGTH: 25
<212> TYPE: DNA
<213> ORGANISM: Artificial Sequence
<220> FEATURE:
<223> OTHER INFORMATION: Primer

<400> SEQUENCE: 247
gtctttctgg ctttctgtac aatgg                                       25

<210> SEQ ID NO 248
<211> LENGTH: 23
<212> TYPE: DNA
<213> ORGANISM: Artificial Sequence
<220> FEATURE:
<223> OTHER INFORMATION: Primer

<400> SEQUENCE: 248
ctgcccagct tggaaggtat tat                                         23

<210> SEQ ID NO 249
<211> LENGTH: 29
<212> TYPE: DNA
<213> ORGANISM: Artificial Sequence
<220> FEATURE:
<223> OTHER INFORMATION: Primer

<400> SEQUENCE: 249
gcatggaaaa tgtgcttttc atctttaag                                   29

<210> SEQ ID NO 250
<211> LENGTH: 27
<212> TYPE: DNA
<213> ORGANISM: Artificial Sequence
<220> FEATURE:
<223> OTHER INFORMATION: Primer

<400> SEQUENCE: 250
attttatgac tatgacgttg ccctgat                                     27
```

```
<210> SEQ ID NO 251
<211> LENGTH: 22
<212> TYPE: DNA
<213> ORGANISM: Artificial Sequence
<220> FEATURE:
<223> OTHER INFORMATION: Primer

<400> SEQUENCE: 251
cccaatcctt cctaagccac tt                                              22

<210> SEQ ID NO 252
<211> LENGTH: 24
<212> TYPE: DNA
<213> ORGANISM: Artificial Sequence
<220> FEATURE:
<223> OTHER INFORMATION: Primer

<400> SEQUENCE: 252
ccatagactc ctacccaaaa ggct                                            24

<210> SEQ ID NO 253
<211> LENGTH: 25
<212> TYPE: DNA
<213> ORGANISM: Artificial Sequence
<220> FEATURE:
<223> OTHER INFORMATION: Primer

<400> SEQUENCE: 253
ggttaaaaga tggcttggaa gacca                                           25

<210> SEQ ID NO 254
<211> LENGTH: 22
<212> TYPE: DNA
<213> ORGANISM: Artificial Sequence
<220> FEATURE:
<223> OTHER INFORMATION: Primer

<400> SEQUENCE: 254
ctccttccga cttctccaag ag                                              22

<210> SEQ ID NO 255
<211> LENGTH: 25
<212> TYPE: DNA
<213> ORGANISM: Artificial Sequence
<220> FEATURE:
<223> OTHER INFORMATION: Primer

<400> SEQUENCE: 255
ggaaaatgga gaagggacag aactg                                           25

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
gagtcacagt cggtgccaat                                                 20

<210> SEQ ID NO 257
<211> LENGTH: 18
<212> TYPE: DNA
<213> ORGANISM: Artificial Sequence
<220> FEATURE:
<223> OTHER INFORMATION: Primer
```

<400> SEQUENCE: 257
cactcgaagc caccctgt                                                        18

<210> SEQ ID NO 258
<211> LENGTH: 18
<212> TYPE: DNA
<213> ORGANISM: Artificial Sequence
<220> FEATURE:
<223> OTHER INFORMATION: Primer

<400> SEQUENCE: 258
cgcggtgcac attagctg                                                        18

<210> SEQ ID NO 259
<211> LENGTH: 23
<212> TYPE: DNA
<213> ORGANISM: Artificial Sequence
<220> FEATURE:
<223> OTHER INFORMATION: Primer

<400> SEQUENCE: 259
ccctgaatat tctcccacct ctt                                                  23

<210> SEQ ID NO 260
<211> LENGTH: 23
<212> TYPE: DNA
<213> ORGANISM: Artificial Sequence
<220> FEATURE:
<223> OTHER INFORMATION: Primer

<400> SEQUENCE: 260
aagcgtggtt ccctagactt ttt                                                  23

<210> SEQ ID NO 261
<211> LENGTH: 22
<212> TYPE: DNA
<213> ORGANISM: Artificial Sequence
<220> FEATURE:
<223> OTHER INFORMATION: Primer

<400> SEQUENCE: 261
ccgctgctct gttctggaat at                                                   22

<210> SEQ ID NO 262
<211> LENGTH: 29
<212> TYPE: DNA
<213> ORGANISM: Artificial Sequence
<220> FEATURE:
<223> OTHER INFORMATION: Primer

<400> SEQUENCE: 262
actctctatt ttgcttcatc catttcagt                                            29

<210> SEQ ID NO 263
<211> LENGTH: 33
<212> TYPE: DNA
<213> ORGANISM: Artificial Sequence
<220> FEATURE:
<223> OTHER INFORMATION: Primer

<400> SEQUENCE: 263
tcattaactt aatttgacta tctggtttgt gga                                       33

<210> SEQ ID NO 264

```
<211> LENGTH: 22
<212> TYPE: DNA
<213> ORGANISM: Artificial Sequence
<220> FEATURE:
<223> OTHER INFORMATION: Primer

<400> SEQUENCE: 264
ctctggtttg cttcgagaag ga                                              22

<210> SEQ ID NO 265
<211> LENGTH: 30
<212> TYPE: DNA
<213> ORGANISM: Artificial Sequence
<220> FEATURE:
<223> OTHER INFORMATION: Primer

<400> SEQUENCE: 265
gggactgact tttaaacatt atttgttccc                                      30

<210> SEQ ID NO 266
<211> LENGTH: 22
<212> TYPE: DNA
<213> ORGANISM: Artificial Sequence
<220> FEATURE:
<223> OTHER INFORMATION: Primer

<400> SEQUENCE: 266
gtgacaacgg aggtgagaag ca                                              22

<210> SEQ ID NO 267
<211> LENGTH: 28
<212> TYPE: DNA
<213> ORGANISM: Artificial Sequence
<220> FEATURE:
<223> OTHER INFORMATION: Primer

<400> SEQUENCE: 267
catattgcca tgttttact tgttccct                                         28

<210> SEQ ID NO 268
<211> LENGTH: 23
<212> TYPE: DNA
<213> ORGANISM: Artificial Sequence
<220> FEATURE:
<223> OTHER INFORMATION: Primer

<400> SEQUENCE: 268
gcctcctcca cctattagca atg                                             23

<210> SEQ ID NO 269
<211> LENGTH: 25
<212> TYPE: DNA
<213> ORGANISM: Artificial Sequence
<220> FEATURE:
<223> OTHER INFORMATION: Primer

<400> SEQUENCE: 269
tgagactcct tcaggaagtt actgg                                           25

<210> SEQ ID NO 270
<211> LENGTH: 30
<212> TYPE: DNA
<213> ORGANISM: Artificial Sequence
<220> FEATURE:
<223> OTHER INFORMATION: Primer

<400> SEQUENCE: 270
```
tcctgaacca tcatataaca ttctacttga                                     30

<210> SEQ ID NO 271
<211> LENGTH: 30
<212> TYPE: DNA
<213> ORGANISM: Artificial Sequence
<220> FEATURE:
<223> OTHER INFORMATION: Primer

<400> SEQUENCE: 271
aggactttac taaactagct tccagttagt                                     30

<210> SEQ ID NO 272
<211> LENGTH: 29
<212> TYPE: DNA
<213> ORGANISM: Artificial Sequence
<220> FEATURE:
<223> OTHER INFORMATION: Primer

<400> SEQUENCE: 272
aatatccatc tggtgagaga gtacgttat                                      29

<210> SEQ ID NO 273
<211> LENGTH: 23
<212> TYPE: DNA
<213> ORGANISM: Artificial Sequence
<220> FEATURE:
<223> OTHER INFORMATION: Primer

<400> SEQUENCE: 273
agccacttca cccggtttat taa                                            23

<210> SEQ ID NO 274
<211> LENGTH: 33
<212> TYPE: DNA
<213> ORGANISM: Artificial Sequence
<220> FEATURE:
<223> OTHER INFORMATION: Primer

<400> SEQUENCE: 274
cacaatataa ttgtaaacca ggatatgcaa cag                                 33

<210> SEQ ID NO 275
<211> LENGTH: 29
<212> TYPE: DNA
<213> ORGANISM: Artificial Sequence
<220> FEATURE:
<223> OTHER INFORMATION: Primer

<400> SEQUENCE: 275
ggaagtcctc cataatcatt aggatgaga                                      29

<210> SEQ ID NO 276
<211> LENGTH: 27
<212> TYPE: DNA
<213> ORGANISM: Artificial Sequence
<220> FEATURE:
<223> OTHER INFORMATION: Primer

<400> SEQUENCE: 276
agaaggaagg aaaaagaaac actcctt                                        27

<210> SEQ ID NO 277
<211> LENGTH: 23
<212> TYPE: DNA

```
<213> ORGANISM: Artificial Sequence
<220> FEATURE:
<223> OTHER INFORMATION: Primer

<400> SEQUENCE: 277
gcctcctcca cctattagca atg                                      23

<210> SEQ ID NO 278
<211> LENGTH: 30
<212> TYPE: DNA
<213> ORGANISM: Artificial Sequence
<220> FEATURE:
<223> OTHER INFORMATION: Primer

<400> SEQUENCE: 278
ttcagaaagt ttccaataaa actgttgatt                               30

<210> SEQ ID NO 279
<211> LENGTH: 30
<212> TYPE: DNA
<213> ORGANISM: Artificial Sequence
<220> FEATURE:
<223> OTHER INFORMATION: Primer

<400> SEQUENCE: 279
aatagtactc aatttattag cacacactga                               30

<210> SEQ ID NO 280
<211> LENGTH: 33
<212> TYPE: DNA
<213> ORGANISM: Artificial Sequence
<220> FEATURE:
<223> OTHER INFORMATION: Primer

<400> SEQUENCE: 280
tttattacaa gaagtgaaac cttgtgattt tcc                           33

<210> SEQ ID NO 281
<211> LENGTH: 27
<212> TYPE: DNA
<213> ORGANISM: Artificial Sequence
<220> FEATURE:
<223> OTHER INFORMATION: Primer

<400> SEQUENCE: 281
tgagtttcca gaaattcaac atggaca                                  27

<210> SEQ ID NO 282
<211> LENGTH: 29
<212> TYPE: DNA
<213> ORGANISM: Artificial Sequence
<220> FEATURE:
<223> OTHER INFORMATION: Primer

<400> SEQUENCE: 282
tatgcactag aatcttgtga tatcccagt                                29

<210> SEQ ID NO 283
<211> LENGTH: 26
<212> TYPE: DNA
<213> ORGANISM: Artificial Sequence
<220> FEATURE:
<223> OTHER INFORMATION: Primer

<400> SEQUENCE: 283
attcgagaac aggtgaatca gttgaa                                   26
```

```
<210> SEQ ID NO 284
<211> LENGTH: 22
<212> TYPE: DNA
<213> ORGANISM: Artificial Sequence
<220> FEATURE:
<223> OTHER INFORMATION: Primer

<400> SEQUENCE: 284
acgcatcatg tgatccacaa ga                                           22

<210> SEQ ID NO 285
<211> LENGTH: 25
<212> TYPE: DNA
<213> ORGANISM: Artificial Sequence
<220> FEATURE:
<223> OTHER INFORMATION: Primer

<400> SEQUENCE: 285
ggtggaggaa tatatctttg cgagt                                        25

<210> SEQ ID NO 286
<211> LENGTH: 28
<212> TYPE: DNA
<213> ORGANISM: Artificial Sequence
<220> FEATURE:
<223> OTHER INFORMATION: Primer

<400> SEQUENCE: 286
catgggttat gaatacagtg aaagagga                                     28

<210> SEQ ID NO 287
<211> LENGTH: 30
<212> TYPE: DNA
<213> ORGANISM: Artificial Sequence
<220> FEATURE:
<223> OTHER INFORMATION: Primer

<400> SEQUENCE: 287
agataaaaag agagacagtt gagagacaga                                   30

<210> SEQ ID NO 288
<211> LENGTH: 22
<212> TYPE: DNA
<213> ORGANISM: Artificial Sequence
<220> FEATURE:
<223> OTHER INFORMATION: Primer

<400> SEQUENCE: 288
ggtccgtgct taaggatgct ta                                           22

<210> SEQ ID NO 289
<211> LENGTH: 24
<212> TYPE: DNA
<213> ORGANISM: Artificial Sequence
<220> FEATURE:
<223> OTHER INFORMATION: Primer

<400> SEQUENCE: 289
gtggacttcc cttcagtgta tctc                                         24

<210> SEQ ID NO 290
<211> LENGTH: 23
<212> TYPE: DNA
<213> ORGANISM: Artificial Sequence
<220> FEATURE:
```

<223> OTHER INFORMATION: Primer

<400> SEQUENCE: 290
cgccctatcc tacctcacta aac                                              23

<210> SEQ ID NO 291
<211> LENGTH: 30
<212> TYPE: DNA
<213> ORGANISM: Artificial Sequence
<220> FEATURE:
<223> OTHER INFORMATION: Primer

<400> SEQUENCE: 291
atttagttcg gcctttaaga tgtcaaaaac                                       30

<210> SEQ ID NO 292
<211> LENGTH: 30
<212> TYPE: DNA
<213> ORGANISM: Artificial Sequence
<220> FEATURE:
<223> OTHER INFORMATION: Primer

<400> SEQUENCE: 292
cctactatga gattggtgaa cgagtagatt                                       30

<210> SEQ ID NO 293
<211> LENGTH: 31
<212> TYPE: DNA
<213> ORGANISM: Artificial Sequence
<220> FEATURE:
<223> OTHER INFORMATION: Primer

<400> SEQUENCE: 293
tccctcaaga tattcaatga tctttagcat g                                     31

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
gttttcgcac tcgtcgatgt                                                  20

<210> SEQ ID NO 295
<211> LENGTH: 25
<212> TYPE: DNA
<213> ORGANISM: Artificial Sequence
<220> FEATURE:
<223> OTHER INFORMATION: Primer

<400> SEQUENCE: 295
cctgaataaa ctgcagaaca gagct                                            25

<210> SEQ ID NO 296
<211> LENGTH: 25
<212> TYPE: DNA
<213> ORGANISM: Artificial Sequence
<220> FEATURE:
<223> OTHER INFORMATION: Primer

<400> SEQUENCE: 296
gggtgtatcc agtctactac tgttg                                            25

```
<210> SEQ ID NO 297
<211> LENGTH: 26
<212> TYPE: DNA
<213> ORGANISM: Artificial Sequence
<220> FEATURE:
<223> OTHER INFORMATION: Primer

<400> SEQUENCE: 297
ccctgattct gtcatcctag agaaac                                          26

<210> SEQ ID NO 298
<211> LENGTH: 28
<212> TYPE: DNA
<213> ORGANISM: Artificial Sequence
<220> FEATURE:
<223> OTHER INFORMATION: Primer

<400> SEQUENCE: 298
ccctccttat tactatggag attcagtg                                        28

<210> SEQ ID NO 299
<211> LENGTH: 22
<212> TYPE: DNA
<213> ORGANISM: Artificial Sequence
<220> FEATURE:
<223> OTHER INFORMATION: Primer

<400> SEQUENCE: 299
tgcaggaatc cagacaacga tc                                              22

<210> SEQ ID NO 300
<211> LENGTH: 25
<212> TYPE: DNA
<213> ORGANISM: Artificial Sequence
<220> FEATURE:
<223> OTHER INFORMATION: Primer

<400> SEQUENCE: 300
gggagacaga gcgaaatttc atcta                                           25

<210> SEQ ID NO 301
<211> LENGTH: 30
<212> TYPE: DNA
<213> ORGANISM: Artificial Sequence
<220> FEATURE:
<223> OTHER INFORMATION: Primer

<400> SEQUENCE: 301
aacatgttgt aaggactctt tattcaaggt                                      30

<210> SEQ ID NO 302
<211> LENGTH: 26
<212> TYPE: DNA
<213> ORGANISM: Artificial Sequence
<220> FEATURE:
<223> OTHER INFORMATION: Primer

<400> SEQUENCE: 302
tgtagattgc aatgaacttc ctccaa                                          26

<210> SEQ ID NO 303
<211> LENGTH: 30
<212> TYPE: DNA
<213> ORGANISM: Artificial Sequence
<220> FEATURE:
<223> OTHER INFORMATION: Primer
```

```
<400> SEQUENCE: 303
cctttctgat ttcaattact gggaaaatgt                              30

<210> SEQ ID NO 304
<211> LENGTH: 23
<212> TYPE: DNA
<213> ORGANISM: Artificial Sequence
<220> FEATURE:
<223> OTHER INFORMATION: Primer

<400> SEQUENCE: 304
ttttagaaag gccctgtgga cat                                    23

<210> SEQ ID NO 305
<211> LENGTH: 23
<212> TYPE: DNA
<213> ORGANISM: Artificial Sequence
<220> FEATURE:
<223> OTHER INFORMATION: Primer

<400> SEQUENCE: 305
ctacagccag aaggccaaat gga                                    23

<210> SEQ ID NO 306
<211> LENGTH: 30
<212> TYPE: DNA
<213> ORGANISM: Artificial Sequence
<220> FEATURE:
<223> OTHER INFORMATION: Primer

<400> SEQUENCE: 306
caaagacctt cttgttacat atctcagtca                             30

<210> SEQ ID NO 307
<211> LENGTH: 26
<212> TYPE: DNA
<213> ORGANISM: Artificial Sequence
<220> FEATURE:
<223> OTHER INFORMATION: Primer

<400> SEQUENCE: 307
tagtggcaca aatacaatta tgccca                                 26

<210> SEQ ID NO 308
<211> LENGTH: 27
<212> TYPE: DNA
<213> ORGANISM: Artificial Sequence
<220> FEATURE:
<223> OTHER INFORMATION: Primer

<400> SEQUENCE: 308
ctgtatgacc caatatcaac ctcactt                                27

<210> SEQ ID NO 309
<211> LENGTH: 28
<212> TYPE: DNA
<213> ORGANISM: Artificial Sequence
<220> FEATURE:
<223> OTHER INFORMATION: Primer

<400> SEQUENCE: 309
tcattgtcca ctcccataga aaagaatc                               28

<210> SEQ ID NO 310
<211> LENGTH: 30
```

```
<212> TYPE: DNA
<213> ORGANISM: Artificial Sequence
<220> FEATURE:
<223> OTHER INFORMATION: Primer

<400> SEQUENCE: 310
caaacctttg ttagtaactt tagttcgtct                                      30

<210> SEQ ID NO 311
<211> LENGTH: 28
<212> TYPE: DNA
<213> ORGANISM: Artificial Sequence
<220> FEATURE:
<223> OTHER INFORMATION: Primer

<400> SEQUENCE: 311
ggtcaagtca aaacagaact tttgtttg                                        28

<210> SEQ ID NO 312
<211> LENGTH: 30
<212> TYPE: DNA
<213> ORGANISM: Artificial Sequence
<220> FEATURE:
<223> OTHER INFORMATION: Primer

<400> SEQUENCE: 312
ataaggtaca gatgtagagg aaaagaagga                                      30

<210> SEQ ID NO 313
<211> LENGTH: 25
<212> TYPE: DNA
<213> ORGANISM: Artificial Sequence
<220> FEATURE:
<223> OTHER INFORMATION: Primer

<400> SEQUENCE: 313
accacagtta catgtacgga gaaag                                           25

<210> SEQ ID NO 314
<211> LENGTH: 28
<212> TYPE: DNA
<213> ORGANISM: Artificial Sequence
<220> FEATURE:
<223> OTHER INFORMATION: Primer

<400> SEQUENCE: 314
ccattaattc atccaggtct tcacaaga                                        28

<210> SEQ ID NO 315
<211> LENGTH: 27
<212> TYPE: DNA
<213> ORGANISM: Artificial Sequence
<220> FEATURE:
<223> OTHER INFORMATION: Primer

<400> SEQUENCE: 315
gctactcaaa atgaacacta ggtggaa                                         27

<210> SEQ ID NO 316
<211> LENGTH: 30
<212> TYPE: DNA
<213> ORGANISM: Artificial Sequence
<220> FEATURE:
<223> OTHER INFORMATION: Primer

<400> SEQUENCE: 316
```
ctgtaatggc ctgttttatt actagcattg         30

<210> SEQ ID NO 317
<211> LENGTH: 28
<212> TYPE: DNA
<213> ORGANISM: Artificial Sequence
<220> FEATURE:
<223> OTHER INFORMATION: Primer

<400> SEQUENCE: 317
attgtaactt attttgccca ttcaagca         28

<210> SEQ ID NO 318
<211> LENGTH: 24
<212> TYPE: DNA
<213> ORGANISM: Artificial Sequence
<220> FEATURE:
<223> OTHER INFORMATION: Primer

<400> SEQUENCE: 318
agtttctgat aggcggagca tcta         24

<210> SEQ ID NO 319
<211> LENGTH: 30
<212> TYPE: DNA
<213> ORGANISM: Artificial Sequence
<220> FEATURE:
<223> OTHER INFORMATION: Primer

<400> SEQUENCE: 319
gtgttttgag aaataattcc tgaaccatca         30

<210> SEQ ID NO 320
<211> LENGTH: 30
<212> TYPE: DNA
<213> ORGANISM: Artificial Sequence
<220> FEATURE:
<223> OTHER INFORMATION: Primer

<400> SEQUENCE: 320
tctactatag agcaagtaca atcatgtggt         30

<210> SEQ ID NO 321
<211> LENGTH: 26
<212> TYPE: DNA
<213> ORGANISM: Artificial Sequence
<220> FEATURE:
<223> OTHER INFORMATION: Primer

<400> SEQUENCE: 321
tgctacggct accaatattt cttcag         26

<210> SEQ ID NO 322
<211> LENGTH: 22
<212> TYPE: DNA
<213> ORGANISM: Artificial Sequence
<220> FEATURE:
<223> OTHER INFORMATION: Primer

<400> SEQUENCE: 322
atgtctttgg caactctgag ct         22

<210> SEQ ID NO 323
<211> LENGTH: 31
<212> TYPE: DNA
<213> ORGANISM: Artificial Sequence
<220> FEATURE:
<223> OTHER INFORMATION: Primer

<400> SEQUENCE: 323
ttgtaactgt tatcagttga tttgctactc a                                    31

<210> SEQ ID NO 324
<211> LENGTH: 29
<212> TYPE: DNA
<213> ORGANISM: Artificial Sequence
<220> FEATURE:
<223> OTHER INFORMATION: Primer

<400> SEQUENCE: 324
tgaagttata tgtgatgaga acattgcca                                       29

<210> SEQ ID NO 325
<211> LENGTH: 22
<212> TYPE: DNA
<213> ORGANISM: Artificial Sequence
<220> FEATURE:
<223> OTHER INFORMATION: Primer

<400> SEQUENCE: 325
ctccgagacc aggagggata ca                                              22

<210> SEQ ID NO 326
<211> LENGTH: 27
<212> TYPE: DNA
<213> ORGANISM: Artificial Sequence
<220> FEATURE:
<223> OTHER INFORMATION: Primer

<400> SEQUENCE: 326
tgctctttcc tcactttgtt taaacct                                         27

<210> SEQ ID NO 327
<211> LENGTH: 25
<212> TYPE: DNA
<213> ORGANISM: Artificial Sequence
<220> FEATURE:
<223> OTHER INFORMATION: Primer

<400> SEQUENCE: 327
aggctatgac aaagtcaagg acatc                                           25

<210> SEQ ID NO 328
<211> LENGTH: 24
<212> TYPE: DNA
<213> ORGANISM: Artificial Sequence
<220> FEATURE:
<223> OTHER INFORMATION: Primer

<400> SEQUENCE: 328
gggaagacgt gaagttagga atga                                            24

<210> SEQ ID NO 329
<211> LENGTH: 22
<212> TYPE: DNA
<213> ORGANISM: Artificial Sequence
<220> FEATURE:
<223> OTHER INFORMATION: Primer

<400> SEQUENCE: 329
tgagagggag gtgcaatagg aa                                              22

<210> SEQ ID NO 330
<211> LENGTH: 24
<212> TYPE: DNA
<213> ORGANISM: Artificial Sequence
<220> FEATURE:
<223> OTHER INFORMATION: Primer

<400> SEQUENCE: 330
ggaattcttc ctaagccctg tgat                                        24

<210> SEQ ID NO 331
<211> LENGTH: 24
<212> TYPE: DNA
<213> ORGANISM: Artificial Sequence
<220> FEATURE:
<223> OTHER INFORMATION: Primer

<400> SEQUENCE: 331
gactggtaat tcctccatga acct                                        24

<210> SEQ ID NO 332
<211> LENGTH: 27
<212> TYPE: DNA
<213> ORGANISM: Artificial Sequence
<220> FEATURE:
<223> OTHER INFORMATION: Primer

<400> SEQUENCE: 332
ttctcctaac acgaggaaac aaatacc                                     27

<210> SEQ ID NO 333
<211> LENGTH: 23
<212> TYPE: DNA
<213> ORGANISM: Artificial Sequence
<220> FEATURE:
<223> OTHER INFORMATION: Primer

<400> SEQUENCE: 333
ttggacactg agccaagcag aca                                         23

<210> SEQ ID NO 334
<211> LENGTH: 30
<212> TYPE: DNA
<213> ORGANISM: Artificial Sequence
<220> FEATURE:
<223> OTHER INFORMATION: Primer

<400> SEQUENCE: 334
agagtgaaag tttatcacac tgagaaaagg                                  30

<210> SEQ ID NO 335
<211> LENGTH: 22
<212> TYPE: DNA
<213> ORGANISM: Artificial Sequence
<220> FEATURE:
<223> OTHER INFORMATION: Primer

<400> SEQUENCE: 335
cttggcatgc tgtgcaaaca ta                                          22

<210> SEQ ID NO 336
<211> LENGTH: 30
<212> TYPE: DNA
<213> ORGANISM: Artificial Sequence
<220> FEATURE:
<223> OTHER INFORMATION: Primer

```
<400> SEQUENCE: 336
agaatgactt gaaaactagt ctcttgctac                                              30

<210> SEQ ID NO 337
<211> LENGTH: 30
<212> TYPE: DNA
<213> ORGANISM: Artificial Sequence
<220> FEATURE:
<223> OTHER INFORMATION: Primer

<400> SEQUENCE: 337
tacacagaaa ggttaggtaa tcaaaaagca                                              30

<210> SEQ ID NO 338
<211> LENGTH: 29
<212> TYPE: DNA
<213> ORGANISM: Artificial Sequence
<220> FEATURE:
<223> OTHER INFORMATION: Primer

<400> SEQUENCE: 338
tagcgataca aacagcccta agatatttc                                               29

<210> SEQ ID NO 339
<211> LENGTH: 26
<212> TYPE: DNA
<213> ORGANISM: Artificial Sequence
<220> FEATURE:
<223> OTHER INFORMATION: Primer

<400> SEQUENCE: 339
aaaaacaacg ttgaaaatgc agatgt                                                  26

<210> SEQ ID NO 340
<211> LENGTH: 27
<212> TYPE: DNA
<213> ORGANISM: Artificial Sequence
<220> FEATURE:
<223> OTHER INFORMATION: Primer

<400> SEQUENCE: 340
cacaagaaaa tgtttgagag aaggtga                                                 27

<210> SEQ ID NO 341
<211> LENGTH: 31
<212> TYPE: DNA
<213> ORGANISM: Artificial Sequence
<220> FEATURE:
<223> OTHER INFORMATION: Primer

<400> SEQUENCE: 341
tgatgtttac cacaaaggac tttactaaac t                                            31

<210> SEQ ID NO 342
<211> LENGTH: 31
<212> TYPE: DNA
<213> ORGANISM: Artificial Sequence
<220> FEATURE:
<223> OTHER INFORMATION: Primer

<400> SEQUENCE: 342
ttcttcagtt ttatgttatt ttcccagcaa c                                            31

<210> SEQ ID NO 343
```

```
<211> LENGTH: 24
<212> TYPE: DNA
<213> ORGANISM: Artificial Sequence
<220> FEATURE:
<223> OTHER INFORMATION: Primer

<400> SEQUENCE: 343
acatagtcgg tttggacagt gttt                                          24

<210> SEQ ID NO 344
<211> LENGTH: 25
<212> TYPE: DNA
<213> ORGANISM: Artificial Sequence
<220> FEATURE:
<223> OTHER INFORMATION: Primer

<400> SEQUENCE: 344
tcagtcaata aatcactccc gcatt                                         25

<210> SEQ ID NO 345
<211> LENGTH: 28
<212> TYPE: DNA
<213> ORGANISM: Artificial Sequence
<220> FEATURE:
<223> OTHER INFORMATION: Primer

<400> SEQUENCE: 345
gctcttggcc aatatatatt caaatggg                                      28

<210> SEQ ID NO 346
<211> LENGTH: 22
<212> TYPE: DNA
<213> ORGANISM: Artificial Sequence
<220> FEATURE:
<223> OTHER INFORMATION: Primer

<400> SEQUENCE: 346
ccaggttggt ggctcattac ta                                            22

<210> SEQ ID NO 347
<211> LENGTH: 27
<212> TYPE: DNA
<213> ORGANISM: Artificial Sequence
<220> FEATURE:
<223> OTHER INFORMATION: Primer

<400> SEQUENCE: 347
cagaatgttg tcacagaaaa tgtgagt                                       27

<210> SEQ ID NO 348
<211> LENGTH: 22
<212> TYPE: DNA
<213> ORGANISM: Artificial Sequence
<220> FEATURE:
<223> OTHER INFORMATION: Primer

<400> SEQUENCE: 348
agcactggat gctttgtgag tt                                            22

<210> SEQ ID NO 349
<211> LENGTH: 30
<212> TYPE: DNA
<213> ORGANISM: Artificial Sequence
<220> FEATURE:
<223> OTHER INFORMATION: Primer

<400> SEQUENCE: 349
```
tgtttttaac atcttgcatt ccattccttg                                              30

<210> SEQ ID NO 350
<211> LENGTH: 28
<212> TYPE: DNA
<213> ORGANISM: Artificial Sequence
<220> FEATURE:
<223> OTHER INFORMATION: Primer

<400> SEQUENCE: 350
gatttagata gcaaagagtc tggatgga                                                28

<210> SEQ ID NO 351
<211> LENGTH: 22
<212> TYPE: DNA
<213> ORGANISM: Artificial Sequence
<220> FEATURE:
<223> OTHER INFORMATION: Primer

<400> SEQUENCE: 351
tcctagtgct gcctccatct ag                                                     22

<210> SEQ ID NO 352
<211> LENGTH: 26
<212> TYPE: DNA
<213> ORGANISM: Artificial Sequence
<220> FEATURE:
<223> OTHER INFORMATION: Primer

<400> SEQUENCE: 352
ctgaatggta aaataagcgc cttcat                                                 26

<210> SEQ ID NO 353
<211> LENGTH: 31
<212> TYPE: DNA
<213> ORGANISM: Artificial Sequence
<220> FEATURE:
<223> OTHER INFORMATION: Primer

<400> SEQUENCE: 353
aattcattaa caaatgtttc attgttttgc c                                           31

<210> SEQ ID NO 354
<211> LENGTH: 26
<212> TYPE: DNA
<213> ORGANISM: Artificial Sequence
<220> FEATURE:
<223> OTHER INFORMATION: Primer

<400> SEQUENCE: 354
aaaaacaacg ttgaaaatgc agatgt                                                 26

<210> SEQ ID NO 355
<211> LENGTH: 28
<212> TYPE: DNA
<213> ORGANISM: Artificial Sequence
<220> FEATURE:
<223> OTHER INFORMATION: Primer

<400> SEQUENCE: 355
acatgtagtc ctcatttgag tgtgaatt                                               28

<210> SEQ ID NO 356
<211> LENGTH: 26
<212> TYPE: DNA

```
<213> ORGANISM: Artificial Sequence
<220> FEATURE:
<223> OTHER INFORMATION: Primer

<400> SEQUENCE: 356
gtttcattgt ttcaccatac tgccat                                        26

<210> SEQ ID NO 357
<211> LENGTH: 30
<212> TYPE: DNA
<213> ORGANISM: Artificial Sequence
<220> FEATURE:
<223> OTHER INFORMATION: Primer

<400> SEQUENCE: 357
gagaattcaa aaacctaatc attccaccaa                                    30

<210> SEQ ID NO 358
<211> LENGTH: 24
<212> TYPE: DNA
<213> ORGANISM: Artificial Sequence
<220> FEATURE:
<223> OTHER INFORMATION: Primer

<400> SEQUENCE: 358
cagttactgt atggtttgca agca                                          24

<210> SEQ ID NO 359
<211> LENGTH: 20
<212> TYPE: DNA
<213> ORGANISM: Artificial Sequence
<220> FEATURE:
<223> OTHER INFORMATION: Primer

<400> SEQUENCE: 359
gcgtggtctt gagatgaggt                                               20

<210> SEQ ID NO 360
<211> LENGTH: 23
<212> TYPE: DNA
<213> ORGANISM: Artificial Sequence
<220> FEATURE:
<223> OTHER INFORMATION: Primer

<400> SEQUENCE: 360
agggcttaga aagggagaag aca                                           23

<210> SEQ ID NO 361
<211> LENGTH: 21
<212> TYPE: DNA
<213> ORGANISM: Artificial Sequence
<220> FEATURE:
<223> OTHER INFORMATION: Primer

<400> SEQUENCE: 361
gggagggatt tactaggtgg t                                             21

<210> SEQ ID NO 362
<211> LENGTH: 22
<212> TYPE: DNA
<213> ORGANISM: Artificial Sequence
<220> FEATURE:
<223> OTHER INFORMATION: Primer

<400> SEQUENCE: 362
cctccatgta ggtcacccaa tt                                            22
```

<210> SEQ ID NO 363
<211> LENGTH: 22
<212> TYPE: DNA
<213> ORGANISM: Artificial Sequence
<220> FEATURE:
<223> OTHER INFORMATION: Primer

<400> SEQUENCE: 363
ggtacattgt caccacctgg ta                                              22

<210> SEQ ID NO 364
<211> LENGTH: 24
<212> TYPE: DNA
<213> ORGANISM: Artificial Sequence
<220> FEATURE:
<223> OTHER INFORMATION: Primer

<400> SEQUENCE: 364
gtagtgtttc ttctcctcca gctt                                            24

<210> SEQ ID NO 365
<211> LENGTH: 21
<212> TYPE: DNA
<213> ORGANISM: Artificial Sequence
<220> FEATURE:
<223> OTHER INFORMATION: Primer

<400> SEQUENCE: 365
gcaccgatca gcgtgtagta c                                               21

<210> SEQ ID NO 366
<211> LENGTH: 22
<212> TYPE: DNA
<213> ORGANISM: Artificial Sequence
<220> FEATURE:
<223> OTHER INFORMATION: Primer

<400> SEQUENCE: 366
ccatctccct gggttagaga ct                                              22

<210> SEQ ID NO 367
<211> LENGTH: 22
<212> TYPE: DNA
<213> ORGANISM: Artificial Sequence
<220> FEATURE:
<223> OTHER INFORMATION: Primer

<400> SEQUENCE: 367
gggttagtct gacccagaga ca                                              22

<210> SEQ ID NO 368
<211> LENGTH: 20
<212> TYPE: DNA
<213> ORGANISM: Artificial Sequence
<220> FEATURE:
<223> OTHER INFORMATION: Primer

<400> SEQUENCE: 368
gcctcacctg agtgcaagat                                                 20

<210> SEQ ID NO 369
<211> LENGTH: 22
<212> TYPE: DNA
<213> ORGANISM: Artificial Sequence
<220> FEATURE:

<223> OTHER INFORMATION: Primer

<400> SEQUENCE: 369
ggcctcagtg tcttctctag ga                                            22

<210> SEQ ID NO 370
<211> LENGTH: 22
<212> TYPE: DNA
<213> ORGANISM: Artificial Sequence
<220> FEATURE:
<223> OTHER INFORMATION: Primer

<400> SEQUENCE: 370
ggagagctgc aaattccctg aa                                            22

<210> SEQ ID NO 371
<211> LENGTH: 22
<212> TYPE: DNA
<213> ORGANISM: Artificial Sequence
<220> FEATURE:
<223> OTHER INFORMATION: Primer

<400> SEQUENCE: 371
cctccaggcc cttctcgtta ta                                            22

<210> SEQ ID NO 372
<211> LENGTH: 22
<212> TYPE: DNA
<213> ORGANISM: Artificial Sequence
<220> FEATURE:
<223> OTHER INFORMATION: Primer

<400> SEQUENCE: 372
agcaaggact gtctgtgttg tc                                            22

<210> SEQ ID NO 373
<211> LENGTH: 22
<212> TYPE: DNA
<213> ORGANISM: Artificial Sequence
<220> FEATURE:
<223> OTHER INFORMATION: Primer

<400> SEQUENCE: 373
ggtccatgct ccttggctaa ag                                            22

<210> SEQ ID NO 374
<211> LENGTH: 23
<212> TYPE: DNA
<213> ORGANISM: Artificial Sequence
<220> FEATURE:
<223> OTHER INFORMATION: Primer

<400> SEQUENCE: 374
gggtgtgtgt ctgcatatct ctt                                           23

<210> SEQ ID NO 375
<211> LENGTH: 22
<212> TYPE: DNA
<213> ORGANISM: Artificial Sequence
<220> FEATURE:
<223> OTHER INFORMATION: Primer

<400> SEQUENCE: 375
ggtgaccttg tcatccgact tt                                            22

```
<210> SEQ ID NO 376
<211> LENGTH: 22
<212> TYPE: DNA
<213> ORGANISM: Artificial Sequence
<220> FEATURE:
<223> OTHER INFORMATION: Primer

<400> SEQUENCE: 376
cagaaggctg gattgtggag ta                                              22

<210> SEQ ID NO 377
<211> LENGTH: 21
<212> TYPE: DNA
<213> ORGANISM: Artificial Sequence
<220> FEATURE:
<223> OTHER INFORMATION: Primer

<400> SEQUENCE: 377
gcagctctgt gatgtagttg c                                               21

<210> SEQ ID NO 378
<211> LENGTH: 22
<212> TYPE: DNA
<213> ORGANISM: Artificial Sequence
<220> FEATURE:
<223> OTHER INFORMATION: Primer

<400> SEQUENCE: 378
tctgagctct gtacgtagca ct                                              22

<210> SEQ ID NO 379
<211> LENGTH: 22
<212> TYPE: DNA
<213> ORGANISM: Artificial Sequence
<220> FEATURE:
<223> OTHER INFORMATION: Primer

<400> SEQUENCE: 379
ggtcactggc ccttacctta ct                                              22

<210> SEQ ID NO 380
<211> LENGTH: 26
<212> TYPE: DNA
<213> ORGANISM: Artificial Sequence
<220> FEATURE:
<223> OTHER INFORMATION: Primer

<400> SEQUENCE: 380
tgttccttag gaatgtgttc ctttcc                                          26

<210> SEQ ID NO 381
<211> LENGTH: 23
<212> TYPE: DNA
<213> ORGANISM: Artificial Sequence
<220> FEATURE:
<223> OTHER INFORMATION: Primer

<400> SEQUENCE: 381
gtggaggagg aacctagacc aga                                             23

<210> SEQ ID NO 382
<211> LENGTH: 27
<212> TYPE: DNA
<213> ORGANISM: Artificial Sequence
<220> FEATURE:
<223> OTHER INFORMATION: Primer
```

<400> SEQUENCE: 382
gttttccaca aagggcttta ctaaact                                              27

<210> SEQ ID NO 383
<211> LENGTH: 28
<212> TYPE: DNA
<213> ORGANISM: Artificial Sequence
<220> FEATURE:
<223> OTHER INFORMATION: Primer

<400> SEQUENCE: 383
gtatagcaat taagagctca ggttctga                                             28

<210> SEQ ID NO 384
<211> LENGTH: 29
<212> TYPE: DNA
<213> ORGANISM: Artificial Sequence
<220> FEATURE:
<223> OTHER INFORMATION: Primer

<400> SEQUENCE: 384
cttcagtttt gtgttatttt tcccaggaa                                            29

<210> SEQ ID NO 385
<211> LENGTH: 30
<212> TYPE: DNA
<213> ORGANISM: Artificial Sequence
<220> FEATURE:
<223> OTHER INFORMATION: Primer

<400> SEQUENCE: 385
cattttctta gaacaagtga aaacatgtgg                                           30

<210> SEQ ID NO 386
<211> LENGTH: 26
<212> TYPE: DNA
<213> ORGANISM: Artificial Sequence
<220> FEATURE:
<223> OTHER INFORMATION: Primer

<400> SEQUENCE: 386
accaacttaa gaggtgcaaa atagca                                               26

<210> SEQ ID NO 387
<211> LENGTH: 29
<212> TYPE: DNA
<213> ORGANISM: Artificial Sequence
<220> FEATURE:
<223> OTHER INFORMATION: Primer

<400> SEQUENCE: 387
cccaaaaata gaagtgcaat ataaaggca                                            29

<210> SEQ ID NO 388
<211> LENGTH: 22
<212> TYPE: DNA
<213> ORGANISM: Artificial Sequence
<220> FEATURE:
<223> OTHER INFORMATION: Primer

<400> SEQUENCE: 388
gaggctcatt ctcctccctc ta                                                   22

<210> SEQ ID NO 389
<211> LENGTH: 19

```
<212> TYPE: DNA
<213> ORGANISM: Artificial Sequence
<220> FEATURE:
<223> OTHER INFORMATION: Primer

<400> SEQUENCE: 389
cgcacatgca cgagtagga                                            19

<210> SEQ ID NO 390
<211> LENGTH: 19
<212> TYPE: DNA
<213> ORGANISM: Artificial Sequence
<220> FEATURE:
<223> OTHER INFORMATION: Primer

<400> SEQUENCE: 390
cgtgcccacc tgctatagc                                            19

<210> SEQ ID NO 391
<211> LENGTH: 27
<212> TYPE: DNA
<213> ORGANISM: Artificial Sequence
<220> FEATURE:
<223> OTHER INFORMATION: Primer

<400> SEQUENCE: 391
gagccgaagt aataagttac actgagt                                   27

<210> SEQ ID NO 392
<211> LENGTH: 29
<212> TYPE: DNA
<213> ORGANISM: Artificial Sequence
<220> FEATURE:
<223> OTHER INFORMATION: Primer

<400> SEQUENCE: 392
gggatgagct acaatgaata taaagagtc                                 29

<210> SEQ ID NO 393
<211> LENGTH: 23
<212> TYPE: DNA
<213> ORGANISM: Artificial Sequence
<220> FEATURE:
<223> OTHER INFORMATION: Primer

<400> SEQUENCE: 393
cctttggttg cccttctttt cat                                       23

<210> SEQ ID NO 394
<211> LENGTH: 28
<212> TYPE: DNA
<213> ORGANISM: Artificial Sequence
<220> FEATURE:
<223> OTHER INFORMATION: Primer

<400> SEQUENCE: 394
gtttcttttc tggttaggta tcgtcctt                                  28

<210> SEQ ID NO 395
<211> LENGTH: 27
<212> TYPE: DNA
<213> ORGANISM: Artificial Sequence
<220> FEATURE:
<223> OTHER INFORMATION: Primer

<400> SEQUENCE: 395
```
tttttaagtt gatggtccaa ctgtgtt                                        27

<210> SEQ ID NO 396
<211> LENGTH: 26
<212> TYPE: DNA
<213> ORGANISM: Artificial Sequence
<220> FEATURE:
<223> OTHER INFORMATION: Primer

<400> SEQUENCE: 396
agtcataatt ctcagaggct accgta                                         26

<210> SEQ ID NO 397
<211> LENGTH: 22
<212> TYPE: DNA
<213> ORGANISM: Artificial Sequence
<220> FEATURE:
<223> OTHER INFORMATION: Primer

<400> SEQUENCE: 397
ctcaagacag ggatgactgg tt                                             22

<210> SEQ ID NO 398
<211> LENGTH: 25
<212> TYPE: DNA
<213> ORGANISM: Artificial Sequence
<220> FEATURE:
<223> OTHER INFORMATION: Primer

<400> SEQUENCE: 398
gccttcatct gattacctcc tccat                                          25

<210> SEQ ID NO 399
<211> LENGTH: 20
<212> TYPE: DNA
<213> ORGANISM: Artificial Sequence
<220> FEATURE:
<223> OTHER INFORMATION: Primer

<400> SEQUENCE: 399
ccctcacctg gctcttacct                                                20

<210> SEQ ID NO 400
<211> LENGTH: 28
<212> TYPE: DNA
<213> ORGANISM: Artificial Sequence
<220> FEATURE:
<223> OTHER INFORMATION: Primer

<400> SEQUENCE: 400
aaatattttg gctctctaag acttggct                                       28

<210> SEQ ID NO 401
<211> LENGTH: 28
<212> TYPE: DNA
<213> ORGANISM: Artificial Sequence
<220> FEATURE:
<223> OTHER INFORMATION: Primer

<400> SEQUENCE: 401
acagccaaac catatcaagt gtttagat                                       28

<210> SEQ ID NO 402
<211> LENGTH: 24
<212> TYPE: DNA
<213> ORGANISM: Artificial Sequence

```
<220> FEATURE:
<223> OTHER INFORMATION: Primer

<400> SEQUENCE: 402
aattattcat tgtagggctg ggca                                         24

<210> SEQ ID NO 403
<211> LENGTH: 22
<212> TYPE: DNA
<213> ORGANISM: Artificial Sequence
<220> FEATURE:
<223> OTHER INFORMATION: Primer

<400> SEQUENCE: 403
ctccttccga cttctccaag ag                                           22

<210> SEQ ID NO 404
<211> LENGTH: 23
<212> TYPE: DNA
<213> ORGANISM: Artificial Sequence
<220> FEATURE:
<223> OTHER INFORMATION: Primer

<400> SEQUENCE: 404
ctggtaacaa cacctctgtg gta                                          23

<210> SEQ ID NO 405
<211> LENGTH: 26
<212> TYPE: DNA
<213> ORGANISM: Artificial Sequence
<220> FEATURE:
<223> OTHER INFORMATION: Primer

<400> SEQUENCE: 405
gtgacagcac cagagaatgg aaaaat                                       26

<210> SEQ ID NO 406
<211> LENGTH: 22
<212> TYPE: DNA
<213> ORGANISM: Artificial Sequence
<220> FEATURE:
<223> OTHER INFORMATION: Primer

<400> SEQUENCE: 406
gctttgtcca gctcatactt gg                                           22

<210> SEQ ID NO 407
<211> LENGTH: 25
<212> TYPE: DNA
<213> ORGANISM: Artificial Sequence
<220> FEATURE:
<223> OTHER INFORMATION: Primer

<400> SEQUENCE: 407
ggagatgctg tatgcactga atctg                                        25

<210> SEQ ID NO 408
<211> LENGTH: 22
<212> TYPE: DNA
<213> ORGANISM: Artificial Sequence
<220> FEATURE:
<223> OTHER INFORMATION: Primer

<400> SEQUENCE: 408
ctccctcttg cttcccagta aa                                           22
```

```
<210> SEQ ID NO 409
<211> LENGTH: 30
<212> TYPE: DNA
<213> ORGANISM: Artificial Sequence
<220> FEATURE:
<223> OTHER INFORMATION: Primer

<400> SEQUENCE: 409
cattgtactg agaaataaaa ggccttccta                                         30

<210> SEQ ID NO 410
<211> LENGTH: 18
<212> TYPE: DNA
<213> ORGANISM: Artificial Sequence
<220> FEATURE:
<223> OTHER INFORMATION: Primer

<400> SEQUENCE: 410
ggtgcccgtt tcacgaag                                                      18

<210> SEQ ID NO 411
<211> LENGTH: 28
<212> TYPE: DNA
<213> ORGANISM: Artificial Sequence
<220> FEATURE:
<223> OTHER INFORMATION: Primer

<400> SEQUENCE: 411
gttacaagca atgaaacctt gtgagttt                                           28

<210> SEQ ID NO 412
<211> LENGTH: 23
<212> TYPE: DNA
<213> ORGANISM: Artificial Sequence
<220> FEATURE:
<223> OTHER INFORMATION: Primer

<400> SEQUENCE: 412
gaatgagagg caagtcgcac tta                                                23

<210> SEQ ID NO 413
<211> LENGTH: 29
<212> TYPE: DNA
<213> ORGANISM: Artificial Sequence
<220> FEATURE:
<223> OTHER INFORMATION: Primer

<400> SEQUENCE: 413
ttgtgatttt ccagaaattc aacatggag                                          29

<210> SEQ ID NO 414
<211> LENGTH: 22
<212> TYPE: DNA
<213> ORGANISM: Artificial Sequence
<220> FEATURE:
<223> OTHER INFORMATION: Primer

<400> SEQUENCE: 414
gcccaggttt gaagacagag aa                                                 22

<210> SEQ ID NO 415
<211> LENGTH: 29
<212> TYPE: DNA
<213> ORGANISM: Artificial Sequence
<220> FEATURE:
<223> OTHER INFORMATION: Primer
```

```
<400> SEQUENCE: 415
gaaaggtctt tgtttgtct ttgtcttgt                                29

<210> SEQ ID NO 416
<211> LENGTH: 27
<212> TYPE: DNA
<213> ORGANISM: Artificial Sequence
<220> FEATURE:
<223> OTHER INFORMATION: Primer

<400> SEQUENCE: 416
tgacatttcc tcttgtacaa cctttgt                                 27

<210> SEQ ID NO 417
<211> LENGTH: 27
<212> TYPE: DNA
<213> ORGANISM: Artificial Sequence
<220> FEATURE:
<223> OTHER INFORMATION: Primer

<400> SEQUENCE: 417
gtagaatgct ctccagcaat taagagt                                 27

<210> SEQ ID NO 418
<211> LENGTH: 27
<212> TYPE: DNA
<213> ORGANISM: Artificial Sequence
<220> FEATURE:
<223> OTHER INFORMATION: Primer

<400> SEQUENCE: 418
gccatattgc catgttttta cttgttc                                 27

<210> SEQ ID NO 419
<211> LENGTH: 29
<212> TYPE: DNA
<213> ORGANISM: Artificial Sequence
<220> FEATURE:
<223> OTHER INFORMATION: Primer

<400> SEQUENCE: 419
gtgttacttc tctgtgatgt catagtagc                               29

<210> SEQ ID NO 420
<211> LENGTH: 27
<212> TYPE: DNA
<213> ORGANISM: Artificial Sequence
<220> FEATURE:
<223> OTHER INFORMATION: Primer

<400> SEQUENCE: 420
aaaaagtgct gttagattaa actgcca                                 27

<210> SEQ ID NO 421
<211> LENGTH: 30
<212> TYPE: DNA
<213> ORGANISM: Artificial Sequence
<220> FEATURE:
<223> OTHER INFORMATION: Primer

<400> SEQUENCE: 421
ctacaagaaa gtctatgaga atacaagcca                              30

<210> SEQ ID NO 422
```

```
<211> LENGTH: 31
<212> TYPE: DNA
<213> ORGANISM: Artificial Sequence
<220> FEATURE:
<223> OTHER INFORMATION: Primer

<400> SEQUENCE: 422
tgaagacaca gaaattttac taatgctgtc t                              31

<210> SEQ ID NO 423
<211> LENGTH: 30
<212> TYPE: DNA
<213> ORGANISM: Artificial Sequence
<220> FEATURE:
<223> OTHER INFORMATION: Primer

<400> SEQUENCE: 423
agaaacaaga aacaagaaaa tgcatatgct                               30

<210> SEQ ID NO 424
<211> LENGTH: 25
<212> TYPE: DNA
<213> ORGANISM: Artificial Sequence
<220> FEATURE:
<223> OTHER INFORMATION: Primer

<400> SEQUENCE: 424
ctatgagcac tcaggtaaaa gcatg                                    25

<210> SEQ ID NO 425
<211> LENGTH: 22
<212> TYPE: DNA
<213> ORGANISM: Artificial Sequence
<220> FEATURE:
<223> OTHER INFORMATION: Primer

<400> SEQUENCE: 425
tgcccagcca atacatcatc at                                       22

<210> SEQ ID NO 426
<211> LENGTH: 33
<212> TYPE: DNA
<213> ORGANISM: Artificial Sequence
<220> FEATURE:
<223> OTHER INFORMATION: Primer

<400> SEQUENCE: 426
tttttaaaat ttttattgca agtgaaacct tgt                           33

<210> SEQ ID NO 427
<211> LENGTH: 30
<212> TYPE: DNA
<213> ORGANISM: Artificial Sequence
<220> FEATURE:
<223> OTHER INFORMATION: Primer

<400> SEQUENCE: 427
acataatagc attttgatgc aatgtgatca                               30

<210> SEQ ID NO 428
<211> LENGTH: 28
<212> TYPE: DNA
<213> ORGANISM: Artificial Sequence
<220> FEATURE:
<223> OTHER INFORMATION: Primer

<400> SEQUENCE: 428
```
aatccttgtg atgaacaaga catgaatg                                28

<210> SEQ ID NO 429
<211> LENGTH: 30
<212> TYPE: DNA
<213> ORGANISM: Artificial Sequence
<220> FEATURE:
<223> OTHER INFORMATION: Primer

<400> SEQUENCE: 429
tcttgtgata tcccagtatt tatgaatgcc                              30

<210> SEQ ID NO 430
<211> LENGTH: 26
<212> TYPE: DNA
<213> ORGANISM: Artificial Sequence
<220> FEATURE:
<223> OTHER INFORMATION: Primer

<400> SEQUENCE: 430
ccacatttgc taattggttt tcttgc                                  26

<210> SEQ ID NO 431
<211> LENGTH: 23
<212> TYPE: DNA
<213> ORGANISM: Artificial Sequence
<220> FEATURE:
<223> OTHER INFORMATION: Primer

<400> SEQUENCE: 431
gggtgagcaa gtgacttaca ctt                                     23

<210> SEQ ID NO 432
<211> LENGTH: 29
<212> TYPE: DNA
<213> ORGANISM: Artificial Sequence
<220> FEATURE:
<223> OTHER INFORMATION: Primer

<400> SEQUENCE: 432
catcaggatc aattacatgt gggaaagat                               29

<210> SEQ ID NO 433
<211> LENGTH: 28
<212> TYPE: DNA
<213> ORGANISM: Artificial Sequence
<220> FEATURE:
<223> OTHER INFORMATION: Primer

<400> SEQUENCE: 433
aaacgaaaga agaatatgga cacagtga                                28

<210> SEQ ID NO 434
<211> LENGTH: 29
<212> TYPE: DNA
<213> ORGANISM: Artificial Sequence
<220> FEATURE:
<223> OTHER INFORMATION: Primer

<400> SEQUENCE: 434
tgatattata tacagtgctg tgtttgcgt                               29

<210> SEQ ID NO 435
<211> LENGTH: 29
<212> TYPE: DNA

```
<213> ORGANISM: Artificial Sequence
<220> FEATURE:
<223> OTHER INFORMATION: Primer

<400> SEQUENCE: 435
cttatattcc aaatggtgac tactcacct                                29

<210> SEQ ID NO 436
<211> LENGTH: 22
<212> TYPE: DNA
<213> ORGANISM: Artificial Sequence
<220> FEATURE:
<223> OTHER INFORMATION: Primer

<400> SEQUENCE: 436
agctgggtcc ctagtctgat tc                                       22

<210> SEQ ID NO 437
<211> LENGTH: 22
<212> TYPE: DNA
<213> ORGANISM: Artificial Sequence
<220> FEATURE:
<223> OTHER INFORMATION: Primer

<400> SEQUENCE: 437
gcaggccaag atctcagtca tt                                       22

<210> SEQ ID NO 438
<211> LENGTH: 24
<212> TYPE: DNA
<213> ORGANISM: Artificial Sequence
<220> FEATURE:
<223> OTHER INFORMATION: Primer

<400> SEQUENCE: 438
tacattggca aggatcgcaa aaac                                     24

<210> SEQ ID NO 439
<211> LENGTH: 30
<212> TYPE: DNA
<213> ORGANISM: Artificial Sequence
<220> FEATURE:
<223> OTHER INFORMATION: Primer

<400> SEQUENCE: 439
gcaggaattc ctgaatttta tgactatgac                               30

<210> SEQ ID NO 440
<211> LENGTH: 22
<212> TYPE: DNA
<213> ORGANISM: Artificial Sequence
<220> FEATURE:
<223> OTHER INFORMATION: Primer

<400> SEQUENCE: 440
ggtgagaaac gggcatccta ag                                       22

<210> SEQ ID NO 441
<211> LENGTH: 22
<212> TYPE: DNA
<213> ORGANISM: Artificial Sequence
<220> FEATURE:
<223> OTHER INFORMATION: Primer

<400> SEQUENCE: 441
gccactttgt ggtcaaaggg aa                                       22
```

```
<210> SEQ ID NO 442
<211> LENGTH: 22
<212> TYPE: DNA
<213> ORGANISM: Artificial Sequence
<220> FEATURE:
<223> OTHER INFORMATION: Primer

<400> SEQUENCE: 442
gctccggaca ctgtaactct tg                                              22

<210> SEQ ID NO 443
<211> LENGTH: 23
<212> TYPE: DNA
<213> ORGANISM: Artificial Sequence
<220> FEATURE:
<223> OTHER INFORMATION: Primer

<400> SEQUENCE: 443
tgggttctga accaactcaa tgg                                             23

<210> SEQ ID NO 444
<211> LENGTH: 22
<212> TYPE: DNA
<213> ORGANISM: Artificial Sequence
<220> FEATURE:
<223> OTHER INFORMATION: Primer

<400> SEQUENCE: 444
ggcaacgagg catcaatcat tt                                              22

<210> SEQ ID NO 445
<211> LENGTH: 29
<212> TYPE: DNA
<213> ORGANISM: Artificial Sequence
<220> FEATURE:
<223> OTHER INFORMATION: Primer

<400> SEQUENCE: 445
cctaaagaaa agtttcagaa tccctggat                                       29

<210> SEQ ID NO 446
<211> LENGTH: 30
<212> TYPE: DNA
<213> ORGANISM: Artificial Sequence
<220> FEATURE:
<223> OTHER INFORMATION: Primer

<400> SEQUENCE: 446
gtgctaggaa attagctcct atacatttct                                      30

<210> SEQ ID NO 447
<211> LENGTH: 22
<212> TYPE: DNA
<213> ORGANISM: Artificial Sequence
<220> FEATURE:
<223> OTHER INFORMATION: Primer

<400> SEQUENCE: 447
ggaattccag tcgcgaatac ca                                              22

<210> SEQ ID NO 448
<211> LENGTH: 29
<212> TYPE: DNA
<213> ORGANISM: Artificial Sequence
<220> FEATURE:
```

```
<223> OTHER INFORMATION: Primer

<400> SEQUENCE: 448
agcaattctc aagaatcatt taagcttgc                                29

<210> SEQ ID NO 449
<211> LENGTH: 30
<212> TYPE: DNA
<213> ORGANISM: Artificial Sequence
<220> FEATURE:
<223> OTHER INFORMATION: Primer

<400> SEQUENCE: 449
caaacagtgc aactgaaact tttgtattag                               30

<210> SEQ ID NO 450
<211> LENGTH: 29
<212> TYPE: DNA
<213> ORGANISM: Artificial Sequence
<220> FEATURE:
<223> OTHER INFORMATION: Primer

<400> SEQUENCE: 450
ggatgcattt tatttgctca tgaaagaga                                29

<210> SEQ ID NO 451
<211> LENGTH: 27
<212> TYPE: DNA
<213> ORGANISM: Artificial Sequence
<220> FEATURE:
<223> OTHER INFORMATION: Primer

<400> SEQUENCE: 451
aaagtgctgt gtttgtattt gccttat                                  27

<210> SEQ ID NO 452
<211> LENGTH: 30
<212> TYPE: DNA
<213> ORGANISM: Artificial Sequence
<220> FEATURE:
<223> OTHER INFORMATION: Primer

<400> SEQUENCE: 452
actatgtaga tcaggaagat ttgctactct                               30

<210> SEQ ID NO 453
<211> LENGTH: 28
<212> TYPE: DNA
<213> ORGANISM: Artificial Sequence
<220> FEATURE:
<223> OTHER INFORMATION: Primer

<400> SEQUENCE: 453
tgctacttcc atcttgtaca ttaatccg                                 28

<210> SEQ ID NO 454
<211> LENGTH: 26
<212> TYPE: DNA
<213> ORGANISM: Artificial Sequence
<220> FEATURE:
<223> OTHER INFORMATION: Primer

<400> SEQUENCE: 454
atttgttgct gactatagag tggcat                                   26
```

```
<210> SEQ ID NO 455
<211> LENGTH: 28
<212> TYPE: DNA
<213> ORGANISM: Artificial Sequence
<220> FEATURE:
<223> OTHER INFORMATION: Primer

<400> SEQUENCE: 455
attatattcc cacccattca aaagagca                                        28

<210> SEQ ID NO 456
<211> LENGTH: 28
<212> TYPE: DNA
<213> ORGANISM: Artificial Sequence
<220> FEATURE:
<223> OTHER INFORMATION: Primer

<400> SEQUENCE: 456
cttctagcac aaaattcatg tttccagt                                        28

<210> SEQ ID NO 457
<211> LENGTH: 29
<212> TYPE: DNA
<213> ORGANISM: Artificial Sequence
<220> FEATURE:
<223> OTHER INFORMATION: Primer

<400> SEQUENCE: 457
ccattataaa atacagagtg tggtgagca                                       29

<210> SEQ ID NO 458
<211> LENGTH: 29
<212> TYPE: DNA
<213> ORGANISM: Artificial Sequence
<220> FEATURE:
<223> OTHER INFORMATION: Primer

<400> SEQUENCE: 458
gttatgtaca ttgcatgggt atatgcttt                                       29

<210> SEQ ID NO 459
<211> LENGTH: 27
<212> TYPE: DNA
<213> ORGANISM: Artificial Sequence
<220> FEATURE:
<223> OTHER INFORMATION: Primer

<400> SEQUENCE: 459
acaatgggac tttcttagtt gagttgt                                         27

<210> SEQ ID NO 460
<211> LENGTH: 26
<212> TYPE: DNA
<213> ORGANISM: Artificial Sequence
<220> FEATURE:
<223> OTHER INFORMATION: Primer

<400> SEQUENCE: 460
gcattttatt tgctcatgaa aggcaa                                          26

<210> SEQ ID NO 461
<211> LENGTH: 26
<212> TYPE: DNA
<213> ORGANISM: Artificial Sequence
<220> FEATURE:
<223> OTHER INFORMATION: Primer
```

<400> SEQUENCE: 461
ctaagtgacc ttaaagccct agcttt                                        26

<210> SEQ ID NO 462
<211> LENGTH: 22
<212> TYPE: DNA
<213> ORGANISM: Artificial Sequence
<220> FEATURE:
<223> OTHER INFORMATION: Primer

<400> SEQUENCE: 462
gcaatggaga taccacgtcc tt                                            22

<210> SEQ ID NO 463
<211> LENGTH: 27
<212> TYPE: DNA
<213> ORGANISM: Artificial Sequence
<220> FEATURE:
<223> OTHER INFORMATION: Primer

<400> SEQUENCE: 463
aatgggactt tcttagtcga gttgtac                                       27

<210> SEQ ID NO 464
<211> LENGTH: 21
<212> TYPE: DNA
<213> ORGANISM: Artificial Sequence
<220> FEATURE:
<223> OTHER INFORMATION: Primer

<400> SEQUENCE: 464
gtaggaaagg ctcccacctt t                                             21

<210> SEQ ID NO 465
<211> LENGTH: 27
<212> TYPE: DNA
<213> ORGANISM: Artificial Sequence
<220> FEATURE:
<223> OTHER INFORMATION: Primer

<400> SEQUENCE: 465
atccatgtgt ggtatctgaa gaaaaca                                       27

<210> SEQ ID NO 466
<211> LENGTH: 25
<212> TYPE: DNA
<213> ORGANISM: Artificial Sequence
<220> FEATURE:
<223> OTHER INFORMATION: Primer

<400> SEQUENCE: 466
ccgcatgttc aggaaataga agtgt                                         25

<210> SEQ ID NO 467
<211> LENGTH: 22
<212> TYPE: DNA
<213> ORGANISM: Artificial Sequence
<220> FEATURE:
<223> OTHER INFORMATION: Primer

<400> SEQUENCE: 467
ctgtaccgtc ttcccagtga tg                                            22

<210> SEQ ID NO 468
<211> LENGTH: 23

<212> TYPE: DNA
<213> ORGANISM: Artificial Sequence
<220> FEATURE:
<223> OTHER INFORMATION: Primer

<400> SEQUENCE: 468
gcatcctgag gcctcttttc tag                                            23

<210> SEQ ID NO 469
<211> LENGTH: 26
<212> TYPE: DNA
<213> ORGANISM: Artificial Sequence
<220> FEATURE:
<223> OTHER INFORMATION: Primer

<400> SEQUENCE: 469
gagttttcat agtaggctcg gatctt                                         26

<210> SEQ ID NO 470
<211> LENGTH: 22
<212> TYPE: DNA
<213> ORGANISM: Artificial Sequence
<220> FEATURE:
<223> OTHER INFORMATION: Primer

<400> SEQUENCE: 470
ggcacctcaa tgttgaccat ga                                             22

<210> SEQ ID NO 471
<211> LENGTH: 22
<212> TYPE: DNA
<213> ORGANISM: Artificial Sequence
<220> FEATURE:
<223> OTHER INFORMATION: Primer

<400> SEQUENCE: 471
ttctcttcgt cttggcattc gt                                             22

<210> SEQ ID NO 472
<211> LENGTH: 23
<212> TYPE: DNA
<213> ORGANISM: Artificial Sequence
<220> FEATURE:
<223> OTHER INFORMATION: Primer

<400> SEQUENCE: 472
tgggaccttc atactacgaa tgc                                            23

<210> SEQ ID NO 473
<211> LENGTH: 22
<212> TYPE: DNA
<213> ORGANISM: Artificial Sequence
<220> FEATURE:
<223> OTHER INFORMATION: Primer

<400> SEQUENCE: 473
ctgagcctcc ctccttagac ta                                             22

<210> SEQ ID NO 474
<211> LENGTH: 22
<212> TYPE: DNA
<213> ORGANISM: Artificial Sequence
<220> FEATURE:
<223> OTHER INFORMATION: Primer

<400> SEQUENCE: 474
ctcagcttgg cttagggtca tc                                          22

<210> SEQ ID NO 475
<211> LENGTH: 23
<212> TYPE: DNA
<213> ORGANISM: Artificial Sequence
<220> FEATURE:
<223> OTHER INFORMATION: Primer

<400> SEQUENCE: 475
ctgaagccac accatgacaa cca                                         23

<210> SEQ ID NO 476
<211> LENGTH: 28
<212> TYPE: DNA
<213> ORGANISM: Artificial Sequence
<220> FEATURE:
<223> OTHER INFORMATION: Primer

<400> SEQUENCE: 476
aaagagagag ggaaagagag atgtagag                                    28

<210> SEQ ID NO 477
<211> LENGTH: 22
<212> TYPE: DNA
<213> ORGANISM: Artificial Sequence
<220> FEATURE:
<223> OTHER INFORMATION: Primer

<400> SEQUENCE: 477
gcccaatctt tgcaaaggga at                                          22

<210> SEQ ID NO 478
<211> LENGTH: 23
<212> TYPE: DNA
<213> ORGANISM: Artificial Sequence
<220> FEATURE:
<223> OTHER INFORMATION: Primer

<400> SEQUENCE: 478
tgaatccaca acacccaaa tgc                                          23

<210> SEQ ID NO 479
<211> LENGTH: 22
<212> TYPE: DNA
<213> ORGANISM: Artificial Sequence
<220> FEATURE:
<223> OTHER INFORMATION: Primer

<400> SEQUENCE: 479
ggaagagaaa ggtgcgggtt aa                                          22

<210> SEQ ID NO 480
<211> LENGTH: 23
<212> TYPE: DNA
<213> ORGANISM: Artificial Sequence
<220> FEATURE:
<223> OTHER INFORMATION: Primer

<400> SEQUENCE: 480
ctctctgaag gacaagggtt tgt                                         23

<210> SEQ ID NO 481
<211> LENGTH: 21
<212> TYPE: DNA
<213> ORGANISM: Artificial Sequence

```
<220> FEATURE:
<223> OTHER INFORMATION: Primer

<400> SEQUENCE: 481
agcctgccct tgttcatgat c                                        21

<210> SEQ ID NO 482
<211> LENGTH: 20
<212> TYPE: DNA
<213> ORGANISM: Artificial Sequence
<220> FEATURE:
<223> OTHER INFORMATION: Primer

<400> SEQUENCE: 482
ccctcctcag acggaggttt                                          20

<210> SEQ ID NO 483
<211> LENGTH: 22
<212> TYPE: DNA
<213> ORGANISM: Artificial Sequence
<220> FEATURE:
<223> OTHER INFORMATION: Primer

<400> SEQUENCE: 483
cccaattgga acccatgtcc aa                                       22

<210> SEQ ID NO 484
<211> LENGTH: 30
<212> TYPE: DNA
<213> ORGANISM: Artificial Sequence
<220> FEATURE:
<223> OTHER INFORMATION: Primer

<400> SEQUENCE: 484
tagcacacat taaatttgtt tctgcaatga                               30

<210> SEQ ID NO 485
<211> LENGTH: 30
<212> TYPE: DNA
<213> ORGANISM: Artificial Sequence
<220> FEATURE:
<223> OTHER INFORMATION: Primer

<400> SEQUENCE: 485
tgaagatatt gttttggtgc tagaagagtt                               30

<210> SEQ ID NO 486
<211> LENGTH: 28
<212> TYPE: DNA
<213> ORGANISM: Artificial Sequence
<220> FEATURE:
<223> OTHER INFORMATION: Primer

<400> SEQUENCE: 486
gaatcttcca ttttcctgaa acactacc                                 28

<210> SEQ ID NO 487
<211> LENGTH: 25
<212> TYPE: DNA
<213> ORGANISM: Artificial Sequence
<220> FEATURE:
<223> OTHER INFORMATION: Primer

<400> SEQUENCE: 487
gctgttttcc agagtctact gcata                                    25
```

<210> SEQ ID NO 488
<211> LENGTH: 22
<212> TYPE: DNA
<213> ORGANISM: Artificial Sequence
<220> FEATURE:
<223> OTHER INFORMATION: Primer

<400> SEQUENCE: 488
agtgagccaa gatttgcgtg at                                           22

<210> SEQ ID NO 489
<211> LENGTH: 22
<212> TYPE: DNA
<213> ORGANISM: Artificial Sequence
<220> FEATURE:
<223> OTHER INFORMATION: Primer

<400> SEQUENCE: 489
acctcctcaa ctctccaatg gt                                           22

<210> SEQ ID NO 490
<211> LENGTH: 30
<212> TYPE: DNA
<213> ORGANISM: Artificial Sequence
<220> FEATURE:
<223> OTHER INFORMATION: Primer

<400> SEQUENCE: 490
tgtagcttcc taagaactat ctttcagtca                                   30

<210> SEQ ID NO 491
<211> LENGTH: 21
<212> TYPE: DNA
<213> ORGANISM: Artificial Sequence
<220> FEATURE:
<223> OTHER INFORMATION: Primer

<400> SEQUENCE: 491
gcgcacttgt actccatctt g                                            21

<210> SEQ ID NO 492
<211> LENGTH: 24
<212> TYPE: DNA
<213> ORGANISM: Artificial Sequence
<220> FEATURE:
<223> OTHER INFORMATION: Primer

<400> SEQUENCE: 492
gcagaggtag ctagtttggt tcag                                         24

<210> SEQ ID NO 493
<211> LENGTH: 18
<212> TYPE: DNA
<213> ORGANISM: Artificial Sequence
<220> FEATURE:
<223> OTHER INFORMATION: Primer

<400> SEQUENCE: 493
cgcggtgcac attagctg                                                18

<210> SEQ ID NO 494
<211> LENGTH: 20
<212> TYPE: DNA
<213> ORGANISM: Artificial Sequence
<220> FEATURE:
<223> OTHER INFORMATION: Primer

<400> SEQUENCE: 494
gagcgcactg tcattaggtg                                              20

<210> SEQ ID NO 495
<211> LENGTH: 27
<212> TYPE: DNA
<213> ORGANISM: Artificial Sequence
<220> FEATURE:
<223> OTHER INFORMATION: Primer

<400> SEQUENCE: 495
gaaaagtaaa tgcagaaagc atctcca                                      27

<210> SEQ ID NO 496
<211> LENGTH: 27
<212> TYPE: DNA
<213> ORGANISM: Artificial Sequence
<220> FEATURE:
<223> OTHER INFORMATION: Primer

<400> SEQUENCE: 496
tgtgaattct aaatggatgt gtgtgga                                      27

<210> SEQ ID NO 497
<211> LENGTH: 28
<212> TYPE: DNA
<213> ORGANISM: Artificial Sequence
<220> FEATURE:
<223> OTHER INFORMATION: Primer

<400> SEQUENCE: 497
aagctttagc aaaacaacat acagttgt                                     28

<210> SEQ ID NO 498
<211> LENGTH: 30
<212> TYPE: DNA
<213> ORGANISM: Artificial Sequence
<220> FEATURE:
<223> OTHER INFORMATION: Primer

<400> SEQUENCE: 498
aaaatgaaat gcataagggt taagggattg                                   30

<210> SEQ ID NO 499
<211> LENGTH: 22
<212> TYPE: DNA
<213> ORGANISM: Artificial Sequence
<220> FEATURE:
<223> OTHER INFORMATION: Primer

<400> SEQUENCE: 499
ggtgttcatc accttctggt gt                                           22

<210> SEQ ID NO 500
<211> LENGTH: 30
<212> TYPE: DNA
<213> ORGANISM: Artificial Sequence
<220> FEATURE:
<223> OTHER INFORMATION: Primer

<400> SEQUENCE: 500
atttcagcaa attatagcac cattgttctc                                   30

<210> SEQ ID NO 501

```
<211> LENGTH: 29
<212> TYPE: DNA
<213> ORGANISM: Artificial Sequence
<220> FEATURE:
<223> OTHER INFORMATION: Primer

<400> SEQUENCE: 501
ttcaaagcca cttgttaaca ctttgttag                                  29

<210> SEQ ID NO 502
<211> LENGTH: 32
<212> TYPE: DNA
<213> ORGANISM: Artificial Sequence
<220> FEATURE:
<223> OTHER INFORMATION: Primer

<400> SEQUENCE: 502
ttggttaatg ctaaccaaat agattaaaag ga                              32

<210> SEQ ID NO 503
<211> LENGTH: 30
<212> TYPE: DNA
<213> ORGANISM: Artificial Sequence
<220> FEATURE:
<223> OTHER INFORMATION: Primer

<400> SEQUENCE: 503
gcatttgaat acatgaatca aagaatggct                                 30

<210> SEQ ID NO 504
<211> LENGTH: 22
<212> TYPE: DNA
<213> ORGANISM: Artificial Sequence
<220> FEATURE:
<223> OTHER INFORMATION: Primer

<400> SEQUENCE: 504
ttgcagtcct ttcctttggg aa                                         22

<210> SEQ ID NO 505
<211> LENGTH: 27
<212> TYPE: DNA
<213> ORGANISM: Artificial Sequence
<220> FEATURE:
<223> OTHER INFORMATION: Primer

<400> SEQUENCE: 505
agaaggaagg aaaaagaaac actcctt                                    27

<210> SEQ ID NO 506
<211> LENGTH: 23
<212> TYPE: DNA
<213> ORGANISM: Artificial Sequence
<220> FEATURE:
<223> OTHER INFORMATION: Primer

<400> SEQUENCE: 506
tttttcccgt aacggttgtt ctc                                        23

<210> SEQ ID NO 507
<211> LENGTH: 22
<212> TYPE: DNA
<213> ORGANISM: Artificial Sequence
<220> FEATURE:
<223> OTHER INFORMATION: Primer

<400> SEQUENCE: 507
```

```
ccgctgctct gttctggaat at                                          22

<210> SEQ ID NO 508
<211> LENGTH: 30
<212> TYPE: DNA
<213> ORGANISM: Artificial Sequence
<220> FEATURE:
<223> OTHER INFORMATION: Primer

<400> SEQUENCE: 508
gactggcaat agtgatataa ttcaggcata                                  30

<210> SEQ ID NO 509
<211> LENGTH: 24
<212> TYPE: DNA
<213> ORGANISM: Artificial Sequence
<220> FEATURE:
<223> OTHER INFORMATION: Primer

<400> SEQUENCE: 509
taaccttcac actgaggtgg agaa                                        24

<210> SEQ ID NO 510
<211> LENGTH: 29
<212> TYPE: DNA
<213> ORGANISM: Artificial Sequence
<220> FEATURE:
<223> OTHER INFORMATION: Primer

<400> SEQUENCE: 510
ttggtaccac ttacactttg aatgaagaa                                   29

<210> SEQ ID NO 511
<211> LENGTH: 30
<212> TYPE: DNA
<213> ORGANISM: Artificial Sequence
<220> FEATURE:
<223> OTHER INFORMATION: Primer

<400> SEQUENCE: 511
acctgcctta ttcagtagca tttgtaataa                                  30

<210> SEQ ID NO 512
<211> LENGTH: 30
<212> TYPE: DNA
<213> ORGANISM: Artificial Sequence
<220> FEATURE:
<223> OTHER INFORMATION: Primer

<400> SEQUENCE: 512
tgctgatatt ccttagaatg aacgatgttt                                  30

<210> SEQ ID NO 513
<211> LENGTH: 26
<212> TYPE: DNA
<213> ORGANISM: Artificial Sequence
<220> FEATURE:
<223> OTHER INFORMATION: Primer

<400> SEQUENCE: 513
ggctcctaca ttgataacgt actctc                                      26

<210> SEQ ID NO 514
<211> LENGTH: 30
<212> TYPE: DNA
```

<213> ORGANISM: Artificial Sequence
<220> FEATURE:
<223> OTHER INFORMATION: Primer

<400> SEQUENCE: 514
ctggaaatgt tgaggcatat ctgtaaattt                              30

<210> SEQ ID NO 515
<211> LENGTH: 29
<212> TYPE: DNA
<213> ORGANISM: Artificial Sequence
<220> FEATURE:
<223> OTHER INFORMATION: Primer

<400> SEQUENCE: 515
cgtgatttca tctccagttc tgtgtttaa                               29

<210> SEQ ID NO 516
<211> LENGTH: 30
<212> TYPE: DNA
<213> ORGANISM: Artificial Sequence
<220> FEATURE:
<223> OTHER INFORMATION: Primer

<400> SEQUENCE: 516
gacaggaaag attttgactg aatgaaactt                              30

<210> SEQ ID NO 517
<211> LENGTH: 30
<212> TYPE: DNA
<213> ORGANISM: Artificial Sequence
<220> FEATURE:
<223> OTHER INFORMATION: Primer

<400> SEQUENCE: 517
cttgtggaag gaagagtcag tatcaataaa                              30

<210> SEQ ID NO 518
<211> LENGTH: 31
<212> TYPE: DNA
<213> ORGANISM: Artificial Sequence
<220> FEATURE:
<223> OTHER INFORMATION: Primer

<400> SEQUENCE: 518
cccacaaaaa gactaaagtt agtaaacttt t                            31

<210> SEQ ID NO 519
<211> LENGTH: 22
<212> TYPE: DNA
<213> ORGANISM: Artificial Sequence
<220> FEATURE:
<223> OTHER INFORMATION: Primer

<400> SEQUENCE: 519
gcccgtgata caccaagaaa tg                                      22

<210> SEQ ID NO 520
<211> LENGTH: 22
<212> TYPE: DNA
<213> ORGANISM: Artificial Sequence
<220> FEATURE:
<223> OTHER INFORMATION: Primer

<400> SEQUENCE: 520
gaaccgagga cacctagtag gt                                      22

<210> SEQ ID NO 521
<211> LENGTH: 27
<212> TYPE: DNA
<213> ORGANISM: Artificial Sequence
<220> FEATURE:
<223> OTHER INFORMATION: Primer

<400> SEQUENCE: 521
tcgtgctgaa taagaagaac aaactga                                27

<210> SEQ ID NO 522
<211> LENGTH: 27
<212> TYPE: DNA
<213> ORGANISM: Artificial Sequence
<220> FEATURE:
<223> OTHER INFORMATION: Primer

<400> SEQUENCE: 522
ccattttcga ctactggaaa tcgacat                                27

<210> SEQ ID NO 523
<211> LENGTH: 28
<212> TYPE: DNA
<213> ORGANISM: Artificial Sequence
<220> FEATURE:
<223> OTHER INFORMATION: Primer

<400> SEQUENCE: 523
tgtgtcacat tcacggtaat taatctca                               28

<210> SEQ ID NO 524
<211> LENGTH: 25
<212> TYPE: DNA
<213> ORGANISM: Artificial Sequence
<220> FEATURE:
<223> OTHER INFORMATION: Primer

<400> SEQUENCE: 524
ccatccatct tgtgtgcaat gaatg                                  25

<210> SEQ ID NO 525
<211> LENGTH: 33
<212> TYPE: DNA
<213> ORGANISM: Artificial Sequence
<220> FEATURE:
<223> OTHER INFORMATION: Primer

<400> SEQUENCE: 525
tcatctatgt tacttagaaa gacatgaaca tgc                         33

<210> SEQ ID NO 526
<211> LENGTH: 31
<212> TYPE: DNA
<213> ORGANISM: Artificial Sequence
<220> FEATURE:
<223> OTHER INFORMATION: Primer

<400> SEQUENCE: 526
aaatatcaga ctcatcacag agatttttcc a                           31

<210> SEQ ID NO 527
<211> LENGTH: 22
<212> TYPE: DNA
<213> ORGANISM: Artificial Sequence
<220> FEATURE:

<223> OTHER INFORMATION: Primer

<400> SEQUENCE: 527
agagggacca tctcctcttg tc                                              22

<210> SEQ ID NO 528
<211> LENGTH: 22
<212> TYPE: DNA
<213> ORGANISM: Artificial Sequence
<220> FEATURE:
<223> OTHER INFORMATION: Primer

<400> SEQUENCE: 528
cttgtcttgg gacattccgg aa                                              22

<210> SEQ ID NO 529
<211> LENGTH: 24
<212> TYPE: DNA
<213> ORGANISM: Artificial Sequence
<220> FEATURE:
<223> OTHER INFORMATION: Primer

<400> SEQUENCE: 529
acagggagtt caagtcagaa aagg                                            24

<210> SEQ ID NO 530
<211> LENGTH: 23
<212> TYPE: DNA
<213> ORGANISM: Artificial Sequence
<220> FEATURE:
<223> OTHER INFORMATION: Primer

<400> SEQUENCE: 530
tctcacatcc gtggaatgac aag                                             23

<210> SEQ ID NO 531
<211> LENGTH: 30
<212> TYPE: DNA
<213> ORGANISM: Artificial Sequence
<220> FEATURE:
<223> OTHER INFORMATION: Primer

<400> SEQUENCE: 531
tgtctagctt tcaaagttca ccaatacttt                                      30

<210> SEQ ID NO 532
<211> LENGTH: 21
<212> TYPE: DNA
<213> ORGANISM: Artificial Sequence
<220> FEATURE:
<223> OTHER INFORMATION: Primer

<400> SEQUENCE: 532
caactggcct gctctgttct a                                               21

<210> SEQ ID NO 533
<211> LENGTH: 22
<212> TYPE: DNA
<213> ORGANISM: Artificial Sequence
<220> FEATURE:
<223> OTHER INFORMATION: Primer

<400> SEQUENCE: 533
agctgtccaa tgactttgac ga                                              22

```
<210> SEQ ID NO 534
<211> LENGTH: 26
<212> TYPE: DNA
<213> ORGANISM: Artificial Sequence
<220> FEATURE:
<223> OTHER INFORMATION: Primer

<400> SEQUENCE: 534
tgatccttac taacgtgaca gcaatg                                          26

<210> SEQ ID NO 535
<211> LENGTH: 22
<212> TYPE: DNA
<213> ORGANISM: Artificial Sequence
<220> FEATURE:
<223> OTHER INFORMATION: Primer

<400> SEQUENCE: 535
ggtctgagca agccacactt ac                                              22

<210> SEQ ID NO 536
<211> LENGTH: 21
<212> TYPE: DNA
<213> ORGANISM: Artificial Sequence
<220> FEATURE:
<223> OTHER INFORMATION: Primer

<400> SEQUENCE: 536
cccagatcat gaacaagggc a                                               21

<210> SEQ ID NO 537
<211> LENGTH: 23
<212> TYPE: DNA
<213> ORGANISM: Artificial Sequence
<220> FEATURE:
<223> OTHER INFORMATION: Primer

<400> SEQUENCE: 537
gagggaggag gtctaatcct gag                                             23

<210> SEQ ID NO 538
<211> LENGTH: 28
<212> TYPE: DNA
<213> ORGANISM: Artificial Sequence
<220> FEATURE:
<223> OTHER INFORMATION: Primer

<400> SEQUENCE: 538
aggatgccac tatgtctata ttggacat                                        28

<210> SEQ ID NO 539
<211> LENGTH: 20
<212> TYPE: DNA
<213> ORGANISM: Artificial Sequence
<220> FEATURE:
<223> OTHER INFORMATION: Primer

<400> SEQUENCE: 539
gggagatccc attctccagg                                                 20

<210> SEQ ID NO 540
<211> LENGTH: 27
<212> TYPE: DNA
<213> ORGANISM: Artificial Sequence
<220> FEATURE:
<223> OTHER INFORMATION: Primer
```

<400> SEQUENCE: 540
ctctagtagg ttctaggcca cattttg                                      27

<210> SEQ ID NO 541
<211> LENGTH: 22
<212> TYPE: DNA
<213> ORGANISM: Artificial Sequence
<220> FEATURE:
<223> OTHER INFORMATION: Primer

<400> SEQUENCE: 541
acatcatcgg gaaggacact tg                                           22

<210> SEQ ID NO 542
<211> LENGTH: 22
<212> TYPE: DNA
<213> ORGANISM: Artificial Sequence
<220> FEATURE:
<223> OTHER INFORMATION: Primer

<400> SEQUENCE: 542
ggaaatccga gccgttctct ac                                           22

<210> SEQ ID NO 543
<211> LENGTH: 20
<212> TYPE: DNA
<213> ORGANISM: Artificial Sequence
<220> FEATURE:
<223> OTHER INFORMATION: Primer

<400> SEQUENCE: 543
cacctcctcg ttctgatccc                                              20

<210> SEQ ID NO 544
<211> LENGTH: 24
<212> TYPE: DNA
<213> ORGANISM: Artificial Sequence
<220> FEATURE:
<223> OTHER INFORMATION: Primer

<400> SEQUENCE: 544
gggtaaatga cctgggttta gtga                                         24

<210> SEQ ID NO 545
<211> LENGTH: 23
<212> TYPE: DNA
<213> ORGANISM: Artificial Sequence
<220> FEATURE:
<223> OTHER INFORMATION: Primer

<400> SEQUENCE: 545
caattcccag gtctcaggga ttc                                          23

<210> SEQ ID NO 546
<211> LENGTH: 24
<212> TYPE: DNA
<213> ORGANISM: Artificial Sequence
<220> FEATURE:
<223> OTHER INFORMATION: Primer

<400> SEQUENCE: 546
gtgtaaaggg tgtaaaggag gcaa                                         24

<210> SEQ ID NO 547
<211> LENGTH: 30

<212> TYPE: DNA
<213> ORGANISM: Artificial Sequence
<220> FEATURE:
<223> OTHER INFORMATION: Primer

<400> SEQUENCE: 547
gccaatatct ctttgctcag gttattgata                                    30

<210> SEQ ID NO 548
<211> LENGTH: 24
<212> TYPE: DNA
<213> ORGANISM: Artificial Sequence
<220> FEATURE:
<223> OTHER INFORMATION: Primer

<400> SEQUENCE: 548
ccctaccaag gatcctatgt ttgg                                          24

<210> SEQ ID NO 549
<211> LENGTH: 29
<212> TYPE: DNA
<213> ORGANISM: Artificial Sequence
<220> FEATURE:
<223> OTHER INFORMATION: Primer

<400> SEQUENCE: 549
taagtgaaca tcaccagaaa tttgaagga                                     29

<210> SEQ ID NO 550
<211> LENGTH: 30
<212> TYPE: DNA
<213> ORGANISM: Artificial Sequence
<220> FEATURE:
<223> OTHER INFORMATION: Primer

<400> SEQUENCE: 550
ggcaagagga ggtatataga agtatccttt                                    30

<210> SEQ ID NO 551
<211> LENGTH: 30
<212> TYPE: DNA
<213> ORGANISM: Artificial Sequence
<220> FEATURE:
<223> OTHER INFORMATION: Primer

<400> SEQUENCE: 551
gttcaaagct cacttgacat taagtacatt                                    30

<210> SEQ ID NO 552
<211> LENGTH: 26
<212> TYPE: DNA
<213> ORGANISM: Artificial Sequence
<220> FEATURE:
<223> OTHER INFORMATION: Primer

<400> SEQUENCE: 552
cgctgatgtg gtttgttata cacaga                                        26

<210> SEQ ID NO 553
<211> LENGTH: 23
<212> TYPE: DNA
<213> ORGANISM: Artificial Sequence
<220> FEATURE:
<223> OTHER INFORMATION: Primer

<400> SEQUENCE: 553

```
cattccaagc cagtatcaat gca                                           23

<210> SEQ ID NO 554
<211> LENGTH: 25
<212> TYPE: DNA
<213> ORGANISM: Artificial Sequence
<220> FEATURE:
<223> OTHER INFORMATION: Primer

<400> SEQUENCE: 554
actacaatgc aggcacttac caaaa                                         25

<210> SEQ ID NO 555
<211> LENGTH: 28
<212> TYPE: DNA
<213> ORGANISM: Artificial Sequence
<220> FEATURE:
<223> OTHER INFORMATION: Primer

<400> SEQUENCE: 555
tgtggcatag ataatcaaga agtgtgtt                                      28

<210> SEQ ID NO 556
<211> LENGTH: 29
<212> TYPE: DNA
<213> ORGANISM: Artificial Sequence
<220> FEATURE:
<223> OTHER INFORMATION: Primer

<400> SEQUENCE: 556
tttcaaaaga atacctggag tggaaaaga                                     29

<210> SEQ ID NO 557
<211> LENGTH: 26
<212> TYPE: DNA
<213> ORGANISM: Artificial Sequence
<220> FEATURE:
<223> OTHER INFORMATION: Primer

<400> SEQUENCE: 557
gtgtttacac caaagtggcc aattat                                        26

<210> SEQ ID NO 558
<211> LENGTH: 33
<212> TYPE: DNA
<213> ORGANISM: Artificial Sequence
<220> FEATURE:
<223> OTHER INFORMATION: Primer

<400> SEQUENCE: 558
tctttaaata attagcaaaa ctgagagagt ggt                                33

<210> SEQ ID NO 559
<211> LENGTH: 26
<212> TYPE: DNA
<213> ORGANISM: Artificial Sequence
<220> FEATURE:
<223> OTHER INFORMATION: Primer

<400> SEQUENCE: 559
atcaacagct tagaattgga ttggga                                        26

<210> SEQ ID NO 560
<211> LENGTH: 27
<212> TYPE: DNA
<213> ORGANISM: Artificial Sequence
```

<220> FEATURE:
<223> OTHER INFORMATION: Primer

<400> SEQUENCE: 560
aagtcttcat aatccagaga ccaccta                                       27

<210> SEQ ID NO 561
<211> LENGTH: 30
<212> TYPE: DNA
<213> ORGANISM: Artificial Sequence
<220> FEATURE:
<223> OTHER INFORMATION: Primer

<400> SEQUENCE: 561
agtcttcact tgttaaccaa ttatggctaa                                    30

<210> SEQ ID NO 562
<211> LENGTH: 26
<212> TYPE: DNA
<213> ORGANISM: Artificial Sequence
<220> FEATURE:
<223> OTHER INFORMATION: Primer

<400> SEQUENCE: 562
gtacagagtt gtagggcttt gatagg                                        26

<210> SEQ ID NO 563
<211> LENGTH: 33
<212> TYPE: DNA
<213> ORGANISM: Artificial Sequence
<220> FEATURE:
<223> OTHER INFORMATION: Primer

<400> SEQUENCE: 563
ttctccaaaa tcacattttt cattctttaa act                                33

<210> SEQ ID NO 564
<211> LENGTH: 22
<212> TYPE: DNA
<213> ORGANISM: Artificial Sequence
<220> FEATURE:
<223> OTHER INFORMATION: Primer

<400> SEQUENCE: 564
ggtggtcaca cctgaagaga aa                                            22

<210> SEQ ID NO 565
<211> LENGTH: 24
<212> TYPE: DNA
<213> ORGANISM: Artificial Sequence
<220> FEATURE:
<223> OTHER INFORMATION: Primer

<400> SEQUENCE: 565
gatctgtaga aagtgggagg tgtt                                          24

<210> SEQ ID NO 566
<211> LENGTH: 23
<212> TYPE: DNA
<213> ORGANISM: Artificial Sequence
<220> FEATURE:
<223> OTHER INFORMATION: Primer

<400> SEQUENCE: 566
gccaggcatc atctcttcct att                                           23

<210> SEQ ID NO 567
<211> LENGTH: 22
<212> TYPE: DNA
<213> ORGANISM: Artificial Sequence
<220> FEATURE:
<223> OTHER INFORMATION: Primer

<400> SEQUENCE: 567
aggctctgcc tacctcgaat ta                                    22

<210> SEQ ID NO 568
<211> LENGTH: 21
<212> TYPE: DNA
<213> ORGANISM: Artificial Sequence
<220> FEATURE:
<223> OTHER INFORMATION: Primer

<400> SEQUENCE: 568
cttcagagcc aactgcgagt a                                     21

<210> SEQ ID NO 569
<211> LENGTH: 21
<212> TYPE: DNA
<213> ORGANISM: Artificial Sequence
<220> FEATURE:
<223> OTHER INFORMATION: Primer

<400> SEQUENCE: 569
tcggcttaca gctaatgtgc a                                     21

<210> SEQ ID NO 570
<211> LENGTH: 22
<212> TYPE: DNA
<213> ORGANISM: Artificial Sequence
<220> FEATURE:
<223> OTHER INFORMATION: Primer

<400> SEQUENCE: 570
gttacgggag acaacaacac ca                                    22

<210> SEQ ID NO 571
<211> LENGTH: 25
<212> TYPE: DNA
<213> ORGANISM: Artificial Sequence
<220> FEATURE:
<223> OTHER INFORMATION: Primer

<400> SEQUENCE: 571
cggttgaaaa tccttgaatt tgcca                                 25

<210> SEQ ID NO 572
<211> LENGTH: 22
<212> TYPE: DNA
<213> ORGANISM: Artificial Sequence
<220> FEATURE:
<223> OTHER INFORMATION: Primer

<400> SEQUENCE: 572
ggtagctctg tccatcacca tg                                    22

<210> SEQ ID NO 573
<211> LENGTH: 30
<212> TYPE: DNA
<213> ORGANISM: Artificial Sequence
<220> FEATURE:
<223> OTHER INFORMATION: Primer

```
<400> SEQUENCE: 573
actgacacat gttttctttt gatttcaaga                                    30

<210> SEQ ID NO 574
<211> LENGTH: 33
<212> TYPE: DNA
<213> ORGANISM: Artificial Sequence
<220> FEATURE:
<223> OTHER INFORMATION: Primer

<400> SEQUENCE: 574
aaatttgtga gtaaattact tgccatctga att                                33

<210> SEQ ID NO 575
<211> LENGTH: 24
<212> TYPE: DNA
<213> ORGANISM: Artificial Sequence
<220> FEATURE:
<223> OTHER INFORMATION: Primer

<400> SEQUENCE: 575
ctcacagaca cagagggaca actt                                          24

<210> SEQ ID NO 576
<211> LENGTH: 26
<212> TYPE: DNA
<213> ORGANISM: Artificial Sequence
<220> FEATURE:
<223> OTHER INFORMATION: Primer

<400> SEQUENCE: 576
cccataaaac ccagacataa agcaaa                                        26

<210> SEQ ID NO 577
<211> LENGTH: 26
<212> TYPE: DNA
<213> ORGANISM: Artificial Sequence
<220> FEATURE:
<223> OTHER INFORMATION: Primer

<400> SEQUENCE: 577
catctcaaag agaggaacga agttga                                        26

<210> SEQ ID NO 578
<211> LENGTH: 21
<212> TYPE: DNA
<213> ORGANISM: Artificial Sequence
<220> FEATURE:
<223> OTHER INFORMATION: Primer

<400> SEQUENCE: 578
cttgctcttg cggaagatgt c                                             21

<210> SEQ ID NO 579
<211> LENGTH: 26
<212> TYPE: DNA
<213> ORGANISM: Artificial Sequence
<220> FEATURE:
<223> OTHER INFORMATION: Primer

<400> SEQUENCE: 579
ccaaacacat agacatctga gggata                                        26

<210> SEQ ID NO 580
```

```
<211> LENGTH: 25
<212> TYPE: DNA
<213> ORGANISM: Artificial Sequence
<220> FEATURE:
<223> OTHER INFORMATION: Primer

<400> SEQUENCE: 580
gcagtggaaa gagatctcat cactc                                        25

<210> SEQ ID NO 581
<211> LENGTH: 28
<212> TYPE: DNA
<213> ORGANISM: Artificial Sequence
<220> FEATURE:
<223> OTHER INFORMATION: Primer

<400> SEQUENCE: 581
catatgtcac tagaccatat cttggctt                                     28

<210> SEQ ID NO 582
<211> LENGTH: 24
<212> TYPE: DNA
<213> ORGANISM: Artificial Sequence
<220> FEATURE:
<223> OTHER INFORMATION: Primer

<400> SEQUENCE: 582
gtaggatgga agaccaggat ctga                                         24

<210> SEQ ID NO 583
<211> LENGTH: 33
<212> TYPE: DNA
<213> ORGANISM: Artificial Sequence
<220> FEATURE:
<223> OTHER INFORMATION: Primer

<400> SEQUENCE: 583
agacatacaa agctagatat tacatgaagt tac                               33

<210> SEQ ID NO 584
<211> LENGTH: 27
<212> TYPE: DNA
<213> ORGANISM: Artificial Sequence
<220> FEATURE:
<223> OTHER INFORMATION: Primer

<400> SEQUENCE: 584
ccgacacact gcttgaaatg atagaat                                      27

<210> SEQ ID NO 585
<211> LENGTH: 25
<212> TYPE: DNA
<213> ORGANISM: Artificial Sequence
<220> FEATURE:
<223> OTHER INFORMATION: Primer

<400> SEQUENCE: 585
ctttctccgt acatgtaact gtggt                                        25

<210> SEQ ID NO 586
<211> LENGTH: 26
<212> TYPE: DNA
<213> ORGANISM: Artificial Sequence
<220> FEATURE:
<223> OTHER INFORMATION: Primer

<400> SEQUENCE: 586
```
aactgatgaa gctggagcat atactg                                        26

<210> SEQ ID NO 587
<211> LENGTH: 29
<212> TYPE: DNA
<213> ORGANISM: Artificial Sequence
<220> FEATURE:
<223> OTHER INFORMATION: Primer

<400> SEQUENCE: 587
gtccaaaatg attttgaagg agacacaaa                                     29

<210> SEQ ID NO 588
<211> LENGTH: 33
<212> TYPE: DNA
<213> ORGANISM: Artificial Sequence
<220> FEATURE:
<223> OTHER INFORMATION: Primer

<400> SEQUENCE: 588
ctaaagttct gaataaaggt gtgcatttta tga                                33

<210> SEQ ID NO 589
<211> LENGTH: 33
<212> TYPE: DNA
<213> ORGANISM: Artificial Sequence
<220> FEATURE:
<223> OTHER INFORMATION: Primer

<400> SEQUENCE: 589
agtatgtggc aaaacctata tttaacctgt aaa                                33

<210> SEQ ID NO 590
<211> LENGTH: 33
<212> TYPE: DNA
<213> ORGANISM: Artificial Sequence
<220> FEATURE:
<223> OTHER INFORMATION: Primer

<400> SEQUENCE: 590
cacactcata ggaggactac atatatatgt aca                                33

<210> SEQ ID NO 591
<211> LENGTH: 25
<212> TYPE: DNA
<213> ORGANISM: Artificial Sequence
<220> FEATURE:
<223> OTHER INFORMATION: Primer

<400> SEQUENCE: 591
ggtattccac tatgccttcc ctaca                                         25

<210> SEQ ID NO 592
<211> LENGTH: 32
<212> TYPE: DNA
<213> ORGANISM: Artificial Sequence
<220> FEATURE:
<223> OTHER INFORMATION: Primer

<400> SEQUENCE: 592
aaacatgtaa ttgaacctga agaatttcca tc                                 32

<210> SEQ ID NO 593
<211> LENGTH: 25
<212> TYPE: DNA

```
<213> ORGANISM: Artificial Sequence
<220> FEATURE:
<223> OTHER INFORMATION: Primer

<400> SEQUENCE: 593
tctgtggtgt ttccataact gcttt                                   25

<210> SEQ ID NO 594
<211> LENGTH: 20
<212> TYPE: DNA
<213> ORGANISM: Artificial Sequence
<220> FEATURE:
<223> OTHER INFORMATION: Primer

<400> SEQUENCE: 594
cattcgggct tgctcatagg                                         20

<210> SEQ ID NO 595
<211> LENGTH: 33
<212> TYPE: DNA
<213> ORGANISM: Artificial Sequence
<220> FEATURE:
<223> OTHER INFORMATION: Primer

<400> SEQUENCE: 595
gaggaagatt cagaaatgaa tccattttca att                          33

<210> SEQ ID NO 596
<211> LENGTH: 23
<212> TYPE: DNA
<213> ORGANISM: Artificial Sequence
<220> FEATURE:
<223> OTHER INFORMATION: Primer

<400> SEQUENCE: 596
caattctcac tgcactccca cta                                     23

<210> SEQ ID NO 597
<211> LENGTH: 27
<212> TYPE: DNA
<213> ORGANISM: Artificial Sequence
<220> FEATURE:
<223> OTHER INFORMATION: Primer

<400> SEQUENCE: 597
gtttctgcat cagtgagatt ttccatg                                 27

<210> SEQ ID NO 598
<211> LENGTH: 22
<212> TYPE: DNA
<213> ORGANISM: Artificial Sequence
<220> FEATURE:
<223> OTHER INFORMATION: Primer

<400> SEQUENCE: 598
ccagaagcag tctgctcaga ag                                      22

<210> SEQ ID NO 599
<211> LENGTH: 25
<212> TYPE: DNA
<213> ORGANISM: Artificial Sequence
<220> FEATURE:
<223> OTHER INFORMATION: Primer

<400> SEQUENCE: 599
tcactgtggt tgtcatattc tgagc                                   25
```

<210> SEQ ID NO 600
<211> LENGTH: 31
<212> TYPE: DNA
<213> ORGANISM: Artificial Sequence
<220> FEATURE:
<223> OTHER INFORMATION: Primer

<400> SEQUENCE: 600
aacttgggaa aaagggttat aatcttcttc a                                31

<210> SEQ ID NO 601
<211> LENGTH: 30
<212> TYPE: DNA
<213> ORGANISM: Artificial Sequence
<220> FEATURE:
<223> OTHER INFORMATION: Primer

<400> SEQUENCE: 601
gcccgtttat tataaaatta ggattgcaat                                  30

<210> SEQ ID NO 602
<211> LENGTH: 33
<212> TYPE: DNA
<213> ORGANISM: Artificial Sequence
<220> FEATURE:
<223> OTHER INFORMATION: Primer

<400> SEQUENCE: 602
aacacagttc tagggtaata acccataaaa att                              33

<210> SEQ ID NO 603
<211> LENGTH: 28
<212> TYPE: DNA
<213> ORGANISM: Artificial Sequence
<220> FEATURE:
<223> OTHER INFORMATION: Primer

<400> SEQUENCE: 603
gtcccttcat tagaaatcta ggattgca                                    28

<210> SEQ ID NO 604
<211> LENGTH: 30
<212> TYPE: DNA
<213> ORGANISM: Artificial Sequence
<220> FEATURE:
<223> OTHER INFORMATION: Primer

<400> SEQUENCE: 604
cccagtttat gtcaaatcag gagatatctt                                  30

<210> SEQ ID NO 605
<211> LENGTH: 29
<212> TYPE: DNA
<213> ORGANISM: Artificial Sequence
<220> FEATURE:
<223> OTHER INFORMATION: Primer

<400> SEQUENCE: 605
aaaacagata ctagtcacca tactcagga                                   29

<210> SEQ ID NO 606
<211> LENGTH: 33
<212> TYPE: DNA
<213> ORGANISM: Artificial Sequence
<220> FEATURE:

<223> OTHER INFORMATION: Primer

<400> SEQUENCE: 606
gcacaagaga atattaacct catttgaaag aat                                    33

<210> SEQ ID NO 607
<211> LENGTH: 30
<212> TYPE: DNA
<213> ORGANISM: Artificial Sequence
<220> FEATURE:
<223> OTHER INFORMATION: Primer

<400> SEQUENCE: 607
gccactcaat tgtcaagtta cagaatactt                                        30

<210> SEQ ID NO 608
<211> LENGTH: 30
<212> TYPE: DNA
<213> ORGANISM: Artificial Sequence
<220> FEATURE:
<223> OTHER INFORMATION: Primer

<400> SEQUENCE: 608
gcttccaaca gccttacttt gtatatacaa                                        30

<210> SEQ ID NO 609
<211> LENGTH: 30
<212> TYPE: DNA
<213> ORGANISM: Artificial Sequence
<220> FEATURE:
<223> OTHER INFORMATION: Primer

<400> SEQUENCE: 609
gctactttta gcatagatgg atgtttgaag                                        30

<210> SEQ ID NO 610
<211> LENGTH: 30
<212> TYPE: DNA
<213> ORGANISM: Artificial Sequence
<220> FEATURE:
<223> OTHER INFORMATION: Primer

<400> SEQUENCE: 610
tctttcccag atagcttgag taatgttttt                                        30

<210> SEQ ID NO 611
<211> LENGTH: 24
<212> TYPE: DNA
<213> ORGANISM: Artificial Sequence
<220> FEATURE:
<223> OTHER INFORMATION: Primer

<400> SEQUENCE: 611
ggtgaccacc caaattggta acat                                              24

<210> SEQ ID NO 612
<211> LENGTH: 30
<212> TYPE: DNA
<213> ORGANISM: Artificial Sequence
<220> FEATURE:
<223> OTHER INFORMATION: Primer

<400> SEQUENCE: 612
cccttgtgat tatcaagacc ttatgatctt                                        30

```
<210> SEQ ID NO 613
<211> LENGTH: 30
<212> TYPE: DNA
<213> ORGANISM: Artificial Sequence
<220> FEATURE:
<223> OTHER INFORMATION: Primer

<400> SEQUENCE: 613
gtgcaacaga ttagtcataa gttcttgttt                                    30

<210> SEQ ID NO 614
<211> LENGTH: 24
<212> TYPE: DNA
<213> ORGANISM: Artificial Sequence
<220> FEATURE:
<223> OTHER INFORMATION: Primer

<400> SEQUENCE: 614
atccttcttc tctcccatgg gtat                                          24

<210> SEQ ID NO 615
<211> LENGTH: 23
<212> TYPE: DNA
<213> ORGANISM: Artificial Sequence
<220> FEATURE:
<223> OTHER INFORMATION: Primer

<400> SEQUENCE: 615
ctccgaagag ccactttatc ctc                                           23

<210> SEQ ID NO 616
<211> LENGTH: 22
<212> TYPE: DNA
<213> ORGANISM: Artificial Sequence
<220> FEATURE:
<223> OTHER INFORMATION: Primer

<400> SEQUENCE: 616
ataatgggca ggcaaggagg ga                                            22

<210> SEQ ID NO 617
<211> LENGTH: 23
<212> TYPE: DNA
<213> ORGANISM: Artificial Sequence
<220> FEATURE:
<223> OTHER INFORMATION: Primer

<400> SEQUENCE: 617
agaagtctca gtgcctgatc aga                                           23

<210> SEQ ID NO 618
<211> LENGTH: 30
<212> TYPE: DNA
<213> ORGANISM: Artificial Sequence
<220> FEATURE:
<223> OTHER INFORMATION: Primer

<400> SEQUENCE: 618
actagattcc cactctacat tgtatgagaa                                    30

<210> SEQ ID NO 619
<211> LENGTH: 30
<212> TYPE: DNA
<213> ORGANISM: Artificial Sequence
<220> FEATURE:
<223> OTHER INFORMATION: Primer
```

<400> SEQUENCE: 619
acagctttta caccatattc aaacacattt                              30

<210> SEQ ID NO 620
<211> LENGTH: 26
<212> TYPE: DNA
<213> ORGANISM: Artificial Sequence
<220> FEATURE:
<223> OTHER INFORMATION: Primer

<400> SEQUENCE: 620
ggtgtaatca cttatgtgct ctcctt                                  26

<210> SEQ ID NO 621
<211> LENGTH: 30
<212> TYPE: DNA
<213> ORGANISM: Artificial Sequence
<220> FEATURE:
<223> OTHER INFORMATION: Primer

<400> SEQUENCE: 621
gcgatcagga actaagtgta catctatttt                              30

<210> SEQ ID NO 622
<211> LENGTH: 31
<212> TYPE: DNA
<213> ORGANISM: Artificial Sequence
<220> FEATURE:
<223> OTHER INFORMATION: Primer

<400> SEQUENCE: 622
gcttaaacca tgtgaagtca tttttagttc t                            31

<210> SEQ ID NO 623
<211> LENGTH: 33
<212> TYPE: DNA
<213> ORGANISM: Artificial Sequence
<220> FEATURE:
<223> OTHER INFORMATION: Primer

<400> SEQUENCE: 623
ccatcagtca ttttatttgc atttgaaaaa tct                          33

<210> SEQ ID NO 624
<211> LENGTH: 20
<212> TYPE: DNA
<213> ORGANISM: Artificial Sequence
<220> FEATURE:
<223> OTHER INFORMATION: Primer

<400> SEQUENCE: 624
cggtcatcgc tgtgcattac                                         20

<210> SEQ ID NO 625
<211> LENGTH: 22
<212> TYPE: DNA
<213> ORGANISM: Artificial Sequence
<220> FEATURE:
<223> OTHER INFORMATION: Primer

<400> SEQUENCE: 625
gcagtctcta acccagggag at                                      22

<210> SEQ ID NO 626
<211> LENGTH: 24

```
<212> TYPE: DNA
<213> ORGANISM: Artificial Sequence
<220> FEATURE:
<223> OTHER INFORMATION: Primer

<400> SEQUENCE: 626
ctccttgatc cttcagtttc tcca                                        24

<210> SEQ ID NO 627
<211> LENGTH: 20
<212> TYPE: DNA
<213> ORGANISM: Artificial Sequence
<220> FEATURE:
<223> OTHER INFORMATION: Primer

<400> SEQUENCE: 627
gggcagtggg aaggattacg                                             20

<210> SEQ ID NO 628
<211> LENGTH: 22
<212> TYPE: DNA
<213> ORGANISM: Artificial Sequence
<220> FEATURE:
<223> OTHER INFORMATION: Primer

<400> SEQUENCE: 628
cagggtttac tgggaagcaa ga                                          22

<210> SEQ ID NO 629
<211> LENGTH: 23
<212> TYPE: DNA
<213> ORGANISM: Artificial Sequence
<220> FEATURE:
<223> OTHER INFORMATION: Primer

<400> SEQUENCE: 629
caactttctg cttgggagag aga                                         23

<210> SEQ ID NO 630
<211> LENGTH: 19
<212> TYPE: DNA
<213> ORGANISM: Artificial Sequence
<220> FEATURE:
<223> OTHER INFORMATION: Primer

<400> SEQUENCE: 630
ccgagcagaa gacctggtg                                              19

<210> SEQ ID NO 631
<211> LENGTH: 23
<212> TYPE: DNA
<213> ORGANISM: Artificial Sequence
<220> FEATURE:
<223> OTHER INFORMATION: Primer

<400> SEQUENCE: 631
aagatccgct actacaccta cct                                         23

<210> SEQ ID NO 632
<211> LENGTH: 22
<212> TYPE: DNA
<213> ORGANISM: Artificial Sequence
<220> FEATURE:
<223> OTHER INFORMATION: Primer

<400> SEQUENCE: 632
```

```
tctctggatc tcagagccga tt                                              22
```

<210> SEQ ID NO 633
<211> LENGTH: 22
<212> TYPE: DNA
<213> ORGANISM: Artificial Sequence
<220> FEATURE:
<223> OTHER INFORMATION: Primer

<400> SEQUENCE: 633

```
gagccagata aaaagccagc tc                                              22
```

<210> SEQ ID NO 634
<211> LENGTH: 22
<212> TYPE: DNA
<213> ORGANISM: Artificial Sequence
<220> FEATURE:
<223> OTHER INFORMATION: Primer

<400> SEQUENCE: 634

```
ctggtaagca gctctacaac gt                                              22
```

<210> SEQ ID NO 635
<211> LENGTH: 23
<212> TYPE: DNA
<213> ORGANISM: Artificial Sequence
<220> FEATURE:
<223> OTHER INFORMATION: Primer

<400> SEQUENCE: 635

```
ggtgaaggag tacggtaaga gga                                             23
```

<210> SEQ ID NO 636
<211> LENGTH: 23
<212> TYPE: DNA
<213> ORGANISM: Artificial Sequence
<220> FEATURE:
<223> OTHER INFORMATION: Primer

<400> SEQUENCE: 636

```
ggtggattac ggaacaacaa cga                                             23
```

<210> SEQ ID NO 637
<211> LENGTH: 26
<212> TYPE: DNA
<213> ORGANISM: Artificial Sequence
<220> FEATURE:
<223> OTHER INFORMATION: Primer

<400> SEQUENCE: 637

```
gaggagaaga aacactacct catgtg                                          26
```

<210> SEQ ID NO 638
<211> LENGTH: 22
<212> TYPE: DNA
<213> ORGANISM: Artificial Sequence
<220> FEATURE:
<223> OTHER INFORMATION: Primer

<400> SEQUENCE: 638

```
tctaccatcc ggaaaaggag ga                                              22
```

<210> SEQ ID NO 639
<211> LENGTH: 22
<212> TYPE: DNA
<213> ORGANISM: Artificial Sequence

```
<220> FEATURE:
<223> OTHER INFORMATION: Primer

<400> SEQUENCE: 639
cggagtggac taagagctga ga                                          22

<210> SEQ ID NO 640
<211> LENGTH: 23
<212> TYPE: DNA
<213> ORGANISM: Artificial Sequence
<220> FEATURE:
<223> OTHER INFORMATION: Primer

<400> SEQUENCE: 640
gctagggtga tcctaaggac agt                                         23

<210> SEQ ID NO 641
<211> LENGTH: 26
<212> TYPE: DNA
<213> ORGANISM: Artificial Sequence
<220> FEATURE:
<223> OTHER INFORMATION: Primer

<400> SEQUENCE: 641
ccaacctttc tgtctttcca ctctag                                      26

<210> SEQ ID NO 642
<211> LENGTH: 27
<212> TYPE: DNA
<213> ORGANISM: Artificial Sequence
<220> FEATURE:
<223> OTHER INFORMATION: Primer

<400> SEQUENCE: 642
gcactcatga gagtgaaact acagaat                                     27

<210> SEQ ID NO 643
<211> LENGTH: 28
<212> TYPE: DNA
<213> ORGANISM: Artificial Sequence
<220> FEATURE:
<223> OTHER INFORMATION: Primer

<400> SEQUENCE: 643
atgaacagca acaacaataa caaaccaa                                    28

<210> SEQ ID NO 644
<211> LENGTH: 22
<212> TYPE: DNA
<213> ORGANISM: Artificial Sequence
<220> FEATURE:
<223> OTHER INFORMATION: Primer

<400> SEQUENCE: 644
gctgtgcaca catacccTAG ag                                          22

<210> SEQ ID NO 645
<211> LENGTH: 30
<212> TYPE: DNA
<213> ORGANISM: Artificial Sequence
<220> FEATURE:
<223> OTHER INFORMATION: Primer

<400> SEQUENCE: 645
atcggtttaa ccaatttaca agctgaaaaa                                  30
```

<210> SEQ ID NO 646
<211> LENGTH: 28
<212> TYPE: DNA
<213> ORGANISM: Artificial Sequence
<220> FEATURE:
<223> OTHER INFORMATION: Primer

<400> SEQUENCE: 646
ctctccaata agtgaaaatg gatctggt                                28

<210> SEQ ID NO 647
<211> LENGTH: 27
<212> TYPE: DNA
<213> ORGANISM: Artificial Sequence
<220> FEATURE:
<223> OTHER INFORMATION: Primer

<400> SEQUENCE: 647
catcatcacc gtagtggaat atgtacc                                 27

<210> SEQ ID NO 648
<211> LENGTH: 24
<212> TYPE: DNA
<213> ORGANISM: Artificial Sequence
<220> FEATURE:
<223> OTHER INFORMATION: Primer

<400> SEQUENCE: 648
gtggagacca aagtgatgaa ctgt                                    24

<210> SEQ ID NO 649
<211> LENGTH: 24
<212> TYPE: DNA
<213> ORGANISM: Artificial Sequence
<220> FEATURE:
<223> OTHER INFORMATION: Primer

<400> SEQUENCE: 649
tgtgcaacta acaggagaag cttc                                    24

<210> SEQ ID NO 650
<211> LENGTH: 30
<212> TYPE: DNA
<213> ORGANISM: Artificial Sequence
<220> FEATURE:
<223> OTHER INFORMATION: Primer

<400> SEQUENCE: 650
gctacagtag ggttataaat gcaaagtact                              30

<210> SEQ ID NO 651
<211> LENGTH: 30
<212> TYPE: DNA
<213> ORGANISM: Artificial Sequence
<220> FEATURE:
<223> OTHER INFORMATION: Primer

<400> SEQUENCE: 651
agggaaaaat ataaaagtga agtgtcagaa                              30

<210> SEQ ID NO 652
<211> LENGTH: 29
<212> TYPE: DNA
<213> ORGANISM: Artificial Sequence
<220> FEATURE:
<223> OTHER INFORMATION: Primer -continued

<400> SEQUENCE: 652
agggaggata agttttaagg cagaaaatt          29

<210> SEQ ID NO 653
<211> LENGTH: 28
<212> TYPE: DNA
<213> ORGANISM: Artificial Sequence
<220> FEATURE:
<223> OTHER INFORMATION: Primer

<400> SEQUENCE: 653
ccttgaaaaa tggaaggaaa tgtgtgat          28

<210> SEQ ID NO 654
<211> LENGTH: 23
<212> TYPE: DNA
<213> ORGANISM: Artificial Sequence
<220> FEATURE:
<223> OTHER INFORMATION: Primer

<400> SEQUENCE: 654
cccagtatcc gatgttcaga act          23

<210> SEQ ID NO 655
<211> LENGTH: 33
<212> TYPE: DNA
<213> ORGANISM: Artificial Sequence
<220> FEATURE:
<223> OTHER INFORMATION: Primer

<400> SEQUENCE: 655
acaacaacaa aacaacaaca aaacccatat ata          33

<210> SEQ ID NO 656
<211> LENGTH: 30
<212> TYPE: DNA
<213> ORGANISM: Artificial Sequence
<220> FEATURE:
<223> OTHER INFORMATION: Primer

<400> SEQUENCE: 656
ctatctcaaa caatgagtta agcagctttt          30

<210> SEQ ID NO 657
<211> LENGTH: 22
<212> TYPE: DNA
<213> ORGANISM: Artificial Sequence
<220> FEATURE:
<223> OTHER INFORMATION: Primer

<400> SEQUENCE: 657
accttggtgt cattcttgag ca          22

<210> SEQ ID NO 658
<211> LENGTH: 22
<212> TYPE: DNA
<213> ORGANISM: Artificial Sequence
<220> FEATURE:
<223> OTHER INFORMATION: Primer

<400> SEQUENCE: 658
cagccagctc ccttgagata ag          22

<210> SEQ ID NO 659

```
<211> LENGTH: 20
<212> TYPE: DNA
<213> ORGANISM: Artificial Sequence
<220> FEATURE:
<223> OTHER INFORMATION: Primer

<400> SEQUENCE: 659
ggctgccgat gtcatttcct                                              20

<210> SEQ ID NO 660
<211> LENGTH: 22
<212> TYPE: DNA
<213> ORGANISM: Artificial Sequence
<220> FEATURE:
<223> OTHER INFORMATION: Primer

<400> SEQUENCE: 660
ggtgttgtcg cagctgtttt aa                                           22

<210> SEQ ID NO 661
<211> LENGTH: 23
<212> TYPE: DNA
<213> ORGANISM: Artificial Sequence
<220> FEATURE:
<223> OTHER INFORMATION: Primer

<400> SEQUENCE: 661
aggctccagc attaacagtt ctg                                          23

<210> SEQ ID NO 662
<211> LENGTH: 28
<212> TYPE: DNA
<213> ORGANISM: Artificial Sequence
<220> FEATURE:
<223> OTHER INFORMATION: Primer

<400> SEQUENCE: 662
gccatatttc agcttattct tgagcttg                                     28

<210> SEQ ID NO 663
<211> LENGTH: 23
<212> TYPE: DNA
<213> ORGANISM: Artificial Sequence
<220> FEATURE:
<223> OTHER INFORMATION: Primer

<400> SEQUENCE: 663
gaacagaagt ggcttaggaa gga                                          23

<210> SEQ ID NO 664
<211> LENGTH: 22
<212> TYPE: DNA
<213> ORGANISM: Artificial Sequence
<220> FEATURE:
<223> OTHER INFORMATION: Primer

<400> SEQUENCE: 664
agaaggacac acgtactcca gt                                           22

<210> SEQ ID NO 665
<211> LENGTH: 20
<212> TYPE: DNA
<213> ORGANISM: Artificial Sequence
<220> FEATURE:
<223> OTHER INFORMATION: Primer

<400> SEQUENCE: 665
```
cggtaccttc gagtgcatct                                            20

<210> SEQ ID NO 666
<211> LENGTH: 18
<212> TYPE: DNA
<213> ORGANISM: Artificial Sequence
<220> FEATURE:
<223> OTHER INFORMATION: Primer

<400> SEQUENCE: 666
gcagcgctgt gtcaacac                                              18

<210> SEQ ID NO 667
<211> LENGTH: 19
<212> TYPE: DNA
<213> ORGANISM: Artificial Sequence
<220> FEATURE:
<223> OTHER INFORMATION: Primer

<400> SEQUENCE: 667
cgccgtctcg atcacctac                                             19

<210> SEQ ID NO 668
<211> LENGTH: 29
<212> TYPE: DNA
<213> ORGANISM: Artificial Sequence
<220> FEATURE:
<223> OTHER INFORMATION: Primer

<400> SEQUENCE: 668
atggctcttt taacagaaat ttcagttgg                                  29

<210> SEQ ID NO 669
<211> LENGTH: 27
<212> TYPE: DNA
<213> ORGANISM: Artificial Sequence
<220> FEATURE:
<223> OTHER INFORMATION: Primer

<400> SEQUENCE: 669
gcacagcttt ctccaaaatg atcattt                                    27

<210> SEQ ID NO 670
<211> LENGTH: 30
<212> TYPE: DNA
<213> ORGANISM: Artificial Sequence
<220> FEATURE:
<223> OTHER INFORMATION: Primer

<400> SEQUENCE: 670
tgtgtggatt ttatgtaaat gtagaagggt                                 30

<210> SEQ ID NO 671
<211> LENGTH: 27
<212> TYPE: DNA
<213> ORGANISM: Artificial Sequence
<220> FEATURE:
<223> OTHER INFORMATION: Primer

<400> SEQUENCE: 671
ccaattctgt ttgcaaagat tggtgag                                    27

<210> SEQ ID NO 672
<211> LENGTH: 28
<212> TYPE: DNA

<213> ORGANISM: Artificial Sequence
<220> FEATURE:
<223> OTHER INFORMATION: Primer

<400> SEQUENCE: 672
caaattattt tacaggtgaa gggcagaa                28

<210> SEQ ID NO 673
<211> LENGTH: 26
<212> TYPE: DNA
<213> ORGANISM: Artificial Sequence
<220> FEATURE:
<223> OTHER INFORMATION: Primer

<400> SEQUENCE: 673
aagagtgaga agtggaaaag tggaag                  26

<210> SEQ ID NO 674
<211> LENGTH: 28
<212> TYPE: DNA
<213> ORGANISM: Artificial Sequence
<220> FEATURE:
<223> OTHER INFORMATION: Primer

<400> SEQUENCE: 674
tggagcactt caaaatcagc tgatatta                28

<210> SEQ ID NO 675
<211> LENGTH: 29
<212> TYPE: DNA
<213> ORGANISM: Artificial Sequence
<220> FEATURE:
<223> OTHER INFORMATION: Primer

<400> SEQUENCE: 675
ggtgtagagg aagaatgaat tacttcagg               29

<210> SEQ ID NO 676
<211> LENGTH: 25
<212> TYPE: DNA
<213> ORGANISM: Artificial Sequence
<220> FEATURE:
<223> OTHER INFORMATION: Primer

<400> SEQUENCE: 676
ggtagagagc aagagttaca gtgtc                   25

<210> SEQ ID NO 677
<211> LENGTH: 22
<212> TYPE: DNA
<213> ORGANISM: Artificial Sequence
<220> FEATURE:
<223> OTHER INFORMATION: Primer

<400> SEQUENCE: 677
gccctcaagg tagtctcatg ac                      22

<210> SEQ ID NO 678
<211> LENGTH: 29
<212> TYPE: DNA
<213> ORGANISM: Artificial Sequence
<220> FEATURE:
<223> OTHER INFORMATION: Primer

<400> SEQUENCE: 678 cactttagt agaaaggagg tggtatcac                29

<210> SEQ ID NO 679
<211> LENGTH: 28
<212> TYPE: DNA
<213> ORGANISM: Artificial Sequence
<220> FEATURE:
<223> OTHER INFORMATION: Primer

<400> SEQUENCE: 679
acccattttg tgtgcaatga atgtaatc                                    28

<210> SEQ ID NO 680
<211> LENGTH: 30
<212> TYPE: DNA
<213> ORGANISM: Artificial Sequence
<220> FEATURE:
<223> OTHER INFORMATION: Primer

<400> SEQUENCE: 680
cacagttaat atagacaagt ctgagactgt                                  30

<210> SEQ ID NO 681
<211> LENGTH: 27
<212> TYPE: DNA
<213> ORGANISM: Artificial Sequence
<220> FEATURE:
<223> OTHER INFORMATION: Primer

<400> SEQUENCE: 681
atcagactca tcacactgat ttttcca                                     27

<210> SEQ ID NO 682
<211> LENGTH: 27
<212> TYPE: DNA
<213> ORGANISM: Artificial Sequence
<220> FEATURE:
<223> OTHER INFORMATION: Primer

<400> SEQUENCE: 682
ccaaacattt cataagggct cctacat                                     27

<210> SEQ ID NO 683
<211> LENGTH: 30
<212> TYPE: DNA
<213> ORGANISM: Artificial Sequence
<220> FEATURE:
<223> OTHER INFORMATION: Primer

<400> SEQUENCE: 683
tatccttctc tattcactga atgacatcca                                  30

<210> SEQ ID NO 684
<211> LENGTH: 33
<212> TYPE: DNA
<213> ORGANISM: Artificial Sequence
<220> FEATURE:
<223> OTHER INFORMATION: Primer

<400> SEQUENCE: 684
aagtatggtc tacgcgtatt ctcataatat aga                              33

<210> SEQ ID NO 685
<211> LENGTH: 26
<212> TYPE: DNA
<213> ORGANISM: Artificial Sequence
<220> FEATURE:

<223> OTHER INFORMATION: Primer

<400> SEQUENCE: 685
catctcaaag agaggaacga agttga                                          26

<210> SEQ ID NO 686
<211> LENGTH: 30
<212> TYPE: DNA
<213> ORGANISM: Artificial Sequence
<220> FEATURE:
<223> OTHER INFORMATION: Primer

<400> SEQUENCE: 686
catgtaattg atcctgaaga atttccctct                                      30

<210> SEQ ID NO 687
<211> LENGTH: 26
<212> TYPE: DNA
<213> ORGANISM: Artificial Sequence
<220> FEATURE:
<223> OTHER INFORMATION: Primer

<400> SEQUENCE: 687
agaagctatc tttgcaagct ttgaga                                          26

<210> SEQ ID NO 688
<211> LENGTH: 33
<212> TYPE: DNA
<213> ORGANISM: Artificial Sequence
<220> FEATURE:
<223> OTHER INFORMATION: Primer

<400> SEQUENCE: 688
agacatatga agttagatat tacacgaagt tac                                  33

<210> SEQ ID NO 689
<211> LENGTH: 29
<212> TYPE: DNA
<213> ORGANISM: Artificial Sequence
<220> FEATURE:
<223> OTHER INFORMATION: Primer

<400> SEQUENCE: 689
cacttttagt agaaaggagg tggtatcac                                       29

<210> SEQ ID NO 690
<211> LENGTH: 33
<212> TYPE: DNA
<213> ORGANISM: Artificial Sequence
<220> FEATURE:
<223> OTHER INFORMATION: Primer

<400> SEQUENCE: 690
gtactcacct ttcttttcaa ataaaactac atc                                  33

<210> SEQ ID NO 691
<211> LENGTH: 26
<212> TYPE: DNA
<213> ORGANISM: Artificial Sequence
<220> FEATURE:
<223> OTHER INFORMATION: Primer

<400> SEQUENCE: 691
caatgggatt tcacattcca tagcag                                          26

<210> SEQ ID NO 692
<211> LENGTH: 30
<212> TYPE: DNA
<213> ORGANISM: Artificial Sequence
<220> FEATURE:
<223> OTHER INFORMATION: Primer

<400> SEQUENCE: 692
tgtatccaca tgttttcact tgttctaaga                                30

<210> SEQ ID NO 693
<211> LENGTH: 30
<212> TYPE: DNA
<213> ORGANISM: Artificial Sequence
<220> FEATURE:
<223> OTHER INFORMATION: Primer

<400> SEQUENCE: 693
actcaaatga ggactacatg tatatgtaca                                30

<210> SEQ ID NO 694
<211> LENGTH: 26
<212> TYPE: DNA
<213> ORGANISM: Artificial Sequence
<220> FEATURE:
<223> OTHER INFORMATION: Primer

<400> SEQUENCE: 694
tgagaacgtg atgaaagacg atatcc                                    26

<210> SEQ ID NO 695
<211> LENGTH: 30
<212> TYPE: DNA
<213> ORGANISM: Artificial Sequence
<220> FEATURE:
<223> OTHER INFORMATION: Primer

<400> SEQUENCE: 695
ccagaataca aagtgactct atcatgaaca                                30

<210> SEQ ID NO 696
<211> LENGTH: 30
<212> TYPE: DNA
<213> ORGANISM: Artificial Sequence
<220> FEATURE:
<223> OTHER INFORMATION: Primer

<400> SEQUENCE: 696
acaggtactc tcctccacta tgtaaatttt                                30

<210> SEQ ID NO 697
<211> LENGTH: 22
<212> TYPE: DNA
<213> ORGANISM: Artificial Sequence
<220> FEATURE:
<223> OTHER INFORMATION: Primer

<400> SEQUENCE: 697
cgccatccag attcagtgca ta                                        22

<210> SEQ ID NO 698
<211> LENGTH: 31
<212> TYPE: DNA
<213> ORGANISM: Artificial Sequence
<220> FEATURE:
<223> OTHER INFORMATION: Primer

```
<400> SEQUENCE: 698
ccaagaagtg actccttgta aaatgtattt g                              31

<210> SEQ ID NO 699
<211> LENGTH: 29
<212> TYPE: DNA
<213> ORGANISM: Artificial Sequence
<220> FEATURE:
<223> OTHER INFORMATION: Primer

<400> SEQUENCE: 699
tatccatcct tcttttcctc tacatctgt                                 29

<210> SEQ ID NO 700
<211> LENGTH: 22
<212> TYPE: DNA
<213> ORGANISM: Artificial Sequence
<220> FEATURE:
<223> OTHER INFORMATION: Primer

<400> SEQUENCE: 700
ctggactgct gcaactacat ca                                        22

<210> SEQ ID NO 701
<211> LENGTH: 24
<212> TYPE: DNA
<213> ORGANISM: Artificial Sequence
<220> FEATURE:
<223> OTHER INFORMATION: Primer

<400> SEQUENCE: 701
ggatatgttt ggtcagacca ggaa                                      24

<210> SEQ ID NO 702
<211> LENGTH: 30
<212> TYPE: DNA
<213> ORGANISM: Artificial Sequence
<220> FEATURE:
<223> OTHER INFORMATION: Primer

<400> SEQUENCE: 702
caatgggagc ccaaacaaaa ttaataagaa                                30

<210> SEQ ID NO 703
<211> LENGTH: 27
<212> TYPE: DNA
<213> ORGANISM: Artificial Sequence
<220> FEATURE:
<223> OTHER INFORMATION: Primer

<400> SEQUENCE: 703
ccatttatgc agactgtgtg tatccat                                   27

<210> SEQ ID NO 704
<211> LENGTH: 22
<212> TYPE: DNA
<213> ORGANISM: Artificial Sequence
<220> FEATURE:
<223> OTHER INFORMATION: Primer

<400> SEQUENCE: 704
cgtactgctt gtccaaaatg gt                                        22

<210> SEQ ID NO 705
<211> LENGTH: 30
```

```
<212> TYPE: DNA
<213> ORGANISM: Artificial Sequence
<220> FEATURE:
<223> OTHER INFORMATION: Primer

<400> SEQUENCE: 705
tctgtgtcca atcattgtaa atgattctga                                      30

<210> SEQ ID NO 706
<211> LENGTH: 30
<212> TYPE: DNA
<213> ORGANISM: Artificial Sequence
<220> FEATURE:
<223> OTHER INFORMATION: Primer

<400> SEQUENCE: 706
gtattagtcc tgaagattca gaatgaccat                                      30

<210> SEQ ID NO 707
<211> LENGTH: 22
<212> TYPE: DNA
<213> ORGANISM: Artificial Sequence
<220> FEATURE:
<223> OTHER INFORMATION: Primer

<400> SEQUENCE: 707
cagttacaga gccctggagt tt                                              22

<210> SEQ ID NO 708
<211> LENGTH: 30
<212> TYPE: DNA
<213> ORGANISM: Artificial Sequence
<220> FEATURE:
<223> OTHER INFORMATION: Primer

<400> SEQUENCE: 708
aatttttctt gtaaagaagc aacaagatca                                      30

<210> SEQ ID NO 709
<211> LENGTH: 24
<212> TYPE: DNA
<213> ORGANISM: Artificial Sequence
<220> FEATURE:
<223> OTHER INFORMATION: Primer

<400> SEQUENCE: 709
caattcacct cgactgaaac tcca                                            24

<210> SEQ ID NO 710
<211> LENGTH: 30
<212> TYPE: DNA
<213> ORGANISM: Artificial Sequence
<220> FEATURE:
<223> OTHER INFORMATION: Primer

<400> SEQUENCE: 710
ctttgccatt ttaccacttt gtcagattat                                      30

<210> SEQ ID NO 711
<211> LENGTH: 27
<212> TYPE: DNA
<213> ORGANISM: Artificial Sequence
<220> FEATURE:
<223> OTHER INFORMATION: Primer

<400> SEQUENCE: 711
```
atttgtatgc atacacacac acaatca    27

<210> SEQ ID NO 712
<211> LENGTH: 25
<212> TYPE: DNA
<213> ORGANISM: Artificial Sequence
<220> FEATURE:
<223> OTHER INFORMATION: Primer

<400> SEQUENCE: 712
aagagataca caggtgcata tgtgg    25

<210> SEQ ID NO 713
<211> LENGTH: 23
<212> TYPE: DNA
<213> ORGANISM: Artificial Sequence
<220> FEATURE:
<223> OTHER INFORMATION: Primer

<400> SEQUENCE: 713
gggtaacacc tagaagagac tca    23

<210> SEQ ID NO 714
<211> LENGTH: 21
<212> TYPE: DNA
<213> ORGANISM: Artificial Sequence
<220> FEATURE:
<223> OTHER INFORMATION: Primer

<400> SEQUENCE: 714
cacgaggcct ctttgtctct c    21

<210> SEQ ID NO 715
<211> LENGTH: 20
<212> TYPE: DNA
<213> ORGANISM: Artificial Sequence
<220> FEATURE:
<223> OTHER INFORMATION: Primer

<400> SEQUENCE: 715
ccaagtcctc gttgtccgtt    20

<210> SEQ ID NO 716
<211> LENGTH: 30
<212> TYPE: DNA
<213> ORGANISM: Artificial Sequence
<220> FEATURE:
<223> OTHER INFORMATION: Primer

<400> SEQUENCE: 716
gcaatttctc caggaattcc ttatatcttg    30

<210> SEQ ID NO 717
<211> LENGTH: 29
<212> TYPE: DNA
<213> ORGANISM: Artificial Sequence
<220> FEATURE:
<223> OTHER INFORMATION: Primer

<400> SEQUENCE: 717
acttcttctc catactgata actgtctga    29

<210> SEQ ID NO 718
<211> LENGTH: 33
<212> TYPE: DNA
<213> ORGANISM: Artificial Sequence

```
<220> FEATURE:
<223> OTHER INFORMATION: Primer

<400> SEQUENCE: 718
ccatcatagt taaactttca ggtacttgtg tat                                    33

<210> SEQ ID NO 719
<211> LENGTH: 33
<212> TYPE: DNA
<213> ORGANISM: Artificial Sequence
<220> FEATURE:
<223> OTHER INFORMATION: Primer

<400> SEQUENCE: 719
aaataaattt tgaaaattca ccaaagtacc tct                                    33

<210> SEQ ID NO 720
<211> LENGTH: 28
<212> TYPE: DNA
<213> ORGANISM: Artificial Sequence
<220> FEATURE:
<223> OTHER INFORMATION: Primer

<400> SEQUENCE: 720
tcccacatgt aattgatcct gatgtttc                                          28

<210> SEQ ID NO 721
<211> LENGTH: 26
<212> TYPE: DNA
<213> ORGANISM: Artificial Sequence
<220> FEATURE:
<223> OTHER INFORMATION: Primer

<400> SEQUENCE: 721
aactgatgaa gctggagcat atactg                                            26

<210> SEQ ID NO 722
<211> LENGTH: 21
<212> TYPE: DNA
<213> ORGANISM: Artificial Sequence
<220> FEATURE:
<223> OTHER INFORMATION: Primer

<400> SEQUENCE: 722
ggaggctgga acccttttca c                                                 21

<210> SEQ ID NO 723
<211> LENGTH: 22
<212> TYPE: DNA
<213> ORGANISM: Artificial Sequence
<220> FEATURE:
<223> OTHER INFORMATION: Primer

<400> SEQUENCE: 723
ccctctacca ccctgctaga tg                                                22

<210> SEQ ID NO 724
<211> LENGTH: 21
<212> TYPE: DNA
<213> ORGANISM: Artificial Sequence
<220> FEATURE:
<223> OTHER INFORMATION: Primer

<400> SEQUENCE: 724
catcaagtgc agagaagccc t                                                 21
```

```
<210> SEQ ID NO 725
<211> LENGTH: 23
<212> TYPE: DNA
<213> ORGANISM: Artificial Sequence
<220> FEATURE:
<223> OTHER INFORMATION: Primer

<400> SEQUENCE: 725
gtcactgtta ctgtccacga ctt                                              23

<210> SEQ ID NO 726
<211> LENGTH: 23
<212> TYPE: DNA
<213> ORGANISM: Artificial Sequence
<220> FEATURE:
<223> OTHER INFORMATION: Primer

<400> SEQUENCE: 726
cagaggattt ccctgcctga atc                                              23

<210> SEQ ID NO 727
<211> LENGTH: 27
<212> TYPE: DNA
<213> ORGANISM: Artificial Sequence
<220> FEATURE:
<223> OTHER INFORMATION: Primer

<400> SEQUENCE: 727
gcagagaatt gcttcataca aaagtcg                                          27

<210> SEQ ID NO 728
<211> LENGTH: 24
<212> TYPE: DNA
<213> ORGANISM: Artificial Sequence
<220> FEATURE:
<223> OTHER INFORMATION: Primer

<400> SEQUENCE: 728
caagacaccc aagtacttca aacc                                             24

<210> SEQ ID NO 729
<211> LENGTH: 23
<212> TYPE: DNA
<213> ORGANISM: Artificial Sequence
<220> FEATURE:
<223> OTHER INFORMATION: Primer

<400> SEQUENCE: 729
caggagctgg gataagtgga aag                                              23

<210> SEQ ID NO 730
<211> LENGTH: 24
<212> TYPE: DNA
<213> ORGANISM: Artificial Sequence
<220> FEATURE:
<223> OTHER INFORMATION: Primer

<400> SEQUENCE: 730
ctttctgagc tttctctgag ccat                                             24

<210> SEQ ID NO 731
<211> LENGTH: 26
<212> TYPE: DNA
<213> ORGANISM: Artificial Sequence
<220> FEATURE:
<223> OTHER INFORMATION: Primer
```

<400> SEQUENCE: 731
ccatctttct ctcttgtggg ttctag                                            26

<210> SEQ ID NO 732
<211> LENGTH: 24
<212> TYPE: DNA
<213> ORGANISM: Artificial Sequence
<220> FEATURE:
<223> OTHER INFORMATION: Primer

<400> SEQUENCE: 732
caggtcttct ccactgagtt tgag                                              24

<210> SEQ ID NO 733
<211> LENGTH: 24
<212> TYPE: DNA
<213> ORGANISM: Artificial Sequence
<220> FEATURE:
<223> OTHER INFORMATION: Primer

<400> SEQUENCE: 733
gccttatctg tcaccttcct ccta                                              24

<210> SEQ ID NO 734
<211> LENGTH: 28
<212> TYPE: DNA
<213> ORGANISM: Artificial Sequence
<220> FEATURE:
<223> OTHER INFORMATION: Primer

<400> SEQUENCE: 734
gagaatccca aagatcagaa agtagagg                                          28

<210> SEQ ID NO 735
<211> LENGTH: 23
<212> TYPE: DNA
<213> ORGANISM: Artificial Sequence
<220> FEATURE:
<223> OTHER INFORMATION: Primer

<400> SEQUENCE: 735
ctctctcttc tctgcagggt aca                                               23

<210> SEQ ID NO 736
<211> LENGTH: 21
<212> TYPE: DNA
<213> ORGANISM: Artificial Sequence
<220> FEATURE:
<223> OTHER INFORMATION: Primer

<400> SEQUENCE: 736
caaaggtggg agcctttcct a                                                 21

<210> SEQ ID NO 737
<211> LENGTH: 22
<212> TYPE: DNA
<213> ORGANISM: Artificial Sequence
<220> FEATURE:
<223> OTHER INFORMATION: Primer

<400> SEQUENCE: 737
agtgctacgt acagagctca ga                                                22

<210> SEQ ID NO 738

```
<211> LENGTH: 22
<212> TYPE: DNA
<213> ORGANISM: Artificial Sequence
<220> FEATURE:
<223> OTHER INFORMATION: Primer

<400> SEQUENCE: 738
ccgactgagg agagctctag tc                                          22

<210> SEQ ID NO 739
<211> LENGTH: 28
<212> TYPE: DNA
<213> ORGANISM: Artificial Sequence
<220> FEATURE:
<223> OTHER INFORMATION: Primer

<400> SEQUENCE: 739
tttacaggaa tgcttaagaa gagaagca                                    28

<210> SEQ ID NO 740
<211> LENGTH: 25
<212> TYPE: DNA
<213> ORGANISM: Artificial Sequence
<220> FEATURE:
<223> OTHER INFORMATION: Primer

<400> SEQUENCE: 740
ccaacccaaa ctgtcaagta ttcct                                       25

<210> SEQ ID NO 741
<211> LENGTH: 30
<212> TYPE: DNA
<213> ORGANISM: Artificial Sequence
<220> FEATURE:
<223> OTHER INFORMATION: Primer

<400> SEQUENCE: 741
agatagcatg caatacagat tacaaactga                                  30

<210> SEQ ID NO 742
<211> LENGTH: 29
<212> TYPE: DNA
<213> ORGANISM: Artificial Sequence
<220> FEATURE:
<223> OTHER INFORMATION: Primer

<400> SEQUENCE: 742
acctgctttg tttatctgta gatgaaact                                   29

<210> SEQ ID NO 743
<211> LENGTH: 27
<212> TYPE: DNA
<213> ORGANISM: Artificial Sequence
<220> FEATURE:
<223> OTHER INFORMATION: Primer

<400> SEQUENCE: 743
ccgaagaaaa cagaaataag gtgcaat                                     27

<210> SEQ ID NO 744
<211> LENGTH: 28
<212> TYPE: DNA
<213> ORGANISM: Artificial Sequence
<220> FEATURE:
<223> OTHER INFORMATION: Primer

<400> SEQUENCE: 744
```

```
gtcatgccac cactccataa ataaattt                                        28

<210> SEQ ID NO 745
<211> LENGTH: 29
<212> TYPE: DNA
<213> ORGANISM: Artificial Sequence
<220> FEATURE:
<223> OTHER INFORMATION: Primer

<400> SEQUENCE: 745
cttcaaacag gagtctttaa tttgttgct                                       29

<210> SEQ ID NO 746
<211> LENGTH: 27
<212> TYPE: DNA
<213> ORGANISM: Artificial Sequence
<220> FEATURE:
<223> OTHER INFORMATION: Primer

<400> SEQUENCE: 746
acttgtggac caagataaga caatgtt                                         27

<210> SEQ ID NO 747
<211> LENGTH: 30
<212> TYPE: DNA
<213> ORGANISM: Artificial Sequence
<220> FEATURE:
<223> OTHER INFORMATION: Primer

<400> SEQUENCE: 747 acccttcat aatcccaatg gtttaagtta                                       30

<210> SEQ ID NO 748
<211> LENGTH: 25
<212> TYPE: DNA
<213> ORGANISM: Artificial Sequence
<220> FEATURE:
<223> OTHER INFORMATION: Primer

<400> SEQUENCE: 748
gggagtcttg ccatggaaat atctt                                           25

<210> SEQ ID NO 749
<211> LENGTH: 29
<212> TYPE: DNA
<213> ORGANISM: Artificial Sequence
<220> FEATURE:
<223> OTHER INFORMATION: Primer

<400> SEQUENCE: 749
tgatttttac tgtaccttcg gtgataagc                                       29

<210> SEQ ID NO 750
<211> LENGTH: 23
<212> TYPE: DNA
<213> ORGANISM: Artificial Sequence
<220> FEATURE:
<223> OTHER INFORMATION: Primer

<400> SEQUENCE: 750
ttcccagagg caaaactgca act                                             23

<210> SEQ ID NO 751
<211> LENGTH: 26
<212> TYPE: DNA
```

```
<213> ORGANISM: Artificial Sequence
<220> FEATURE:
<223> OTHER INFORMATION: Primer

<400> SEQUENCE: 751
accactctat gaaatcctga ttccca                                              26

<210> SEQ ID NO 752
<211> LENGTH: 19
<212> TYPE: DNA
<213> ORGANISM: Artificial Sequence
<220> FEATURE:
<223> OTHER INFORMATION: Primer

<400> SEQUENCE: 752
cgcctgggta acatgcttg                                                      19

<210> SEQ ID NO 753
<211> LENGTH: 22
<212> TYPE: DNA
<213> ORGANISM: Artificial Sequence
<220> FEATURE:
<223> OTHER INFORMATION: Primer

<400> SEQUENCE: 753
ggatggcagg caacgtctat ag                                                  22

<210> SEQ ID NO 754
<211> LENGTH: 22
<212> TYPE: DNA
<213> ORGANISM: Artificial Sequence
<220> FEATURE:
<223> OTHER INFORMATION: Primer

<400> SEQUENCE: 754
ccctagtgtc acagccagag aa                                                  22

<210> SEQ ID NO 755
<211> LENGTH: 30
<212> TYPE: DNA
<213> ORGANISM: Artificial Sequence
<220> FEATURE:
<223> OTHER INFORMATION: Primer

<400> SEQUENCE: 755 cttttaaca cagttggacc atcaacttaa                                           30

<210> SEQ ID NO 756
<211> LENGTH: 30
<212> TYPE: DNA
<213> ORGANISM: Artificial Sequence
<220> FEATURE:
<223> OTHER INFORMATION: Primer

<400> SEQUENCE: 756
atcaggtgat tagtgacttg aagcattaat                                          30

<210> SEQ ID NO 757
<211> LENGTH: 29
<212> TYPE: DNA
<213> ORGANISM: Artificial Sequence
<220> FEATURE:
<223> OTHER INFORMATION: Primer

<400> SEQUENCE: 757
ctataaagga caaggagaac agcaaacca                                           29
```

<210> SEQ ID NO 758
<211> LENGTH: 26
<212> TYPE: DNA
<213> ORGANISM: Artificial Sequence
<220> FEATURE:
<223> OTHER INFORMATION: Primer

<400> SEQUENCE: 758
agaagctgta gagaaaagga ctgttg                                         26

<210> SEQ ID NO 759
<211> LENGTH: 25
<212> TYPE: DNA
<213> ORGANISM: Artificial Sequence
<220> FEATURE:
<223> OTHER INFORMATION: Primer

<400> SEQUENCE: 759
accaccatct cttatggcca ttttt                                          25

<210> SEQ ID NO 760
<211> LENGTH: 22
<212> TYPE: DNA
<213> ORGANISM: Artificial Sequence
<220> FEATURE:
<223> OTHER INFORMATION: Primer

<400> SEQUENCE: 760
caagtggact taagggccac at                                             22

<210> SEQ ID NO 761
<211> LENGTH: 25
<212> TYPE: DNA
<213> ORGANISM: Artificial Sequence
<220> FEATURE:
<223> OTHER INFORMATION: Primer

<400> SEQUENCE: 761
ctagtctcat cctagtcctg acctt                                          25

<210> SEQ ID NO 762
<211> LENGTH: 23
<212> TYPE: DNA
<213> ORGANISM: Artificial Sequence
<220> FEATURE:
<223> OTHER INFORMATION: Primer

<400> SEQUENCE: 762
gggagctagt cctggaagat cag                                            23

<210> SEQ ID NO 763
<211> LENGTH: 21
<212> TYPE: DNA
<213> ORGANISM: Artificial Sequence
<220> FEATURE:
<223> OTHER INFORMATION: Primer

<400> SEQUENCE: 763
cctggacgac ggtttcatct g                                              21

<210> SEQ ID NO 764
<211> LENGTH: 19
<212> TYPE: DNA
<213> ORGANISM: Artificial Sequence
<220> FEATURE:

```
<223> OTHER INFORMATION: Primer

<400> SEQUENCE: 764
agtcctgcaa cgacctctg                                              19

<210> SEQ ID NO 765
<211> LENGTH: 19
<212> TYPE: DNA
<213> ORGANISM: Artificial Sequence
<220> FEATURE:
<223> OTHER INFORMATION: Primer

<400> SEQUENCE: 765
gcagcagtgc gaagtgaag                                              19

<210> SEQ ID NO 766
<211> LENGTH: 21
<212> TYPE: DNA
<213> ORGANISM: Artificial Sequence
<220> FEATURE:
<223> OTHER INFORMATION: Primer

<400> SEQUENCE: 766
tcgcttctgt tcctgagcat t                                           21

<210> SEQ ID NO 767
<211> LENGTH: 29
<212> TYPE: DNA
<213> ORGANISM: Artificial Sequence
<220> FEATURE:
<223> OTHER INFORMATION: Primer

<400> SEQUENCE: 767
tgccactggt atacaaaaat aaggagaaa                                   29

<210> SEQ ID NO 768
<211> LENGTH: 24
<212> TYPE: DNA
<213> ORGANISM: Artificial Sequence
<220> FEATURE:
<223> OTHER INFORMATION: Primer

<400> SEQUENCE: 768
tcttgatctt tgcttacctg gcaa                                        24

<210> SEQ ID NO 769
<211> LENGTH: 27
<212> TYPE: DNA
<213> ORGANISM: Artificial Sequence
<220> FEATURE:
<223> OTHER INFORMATION: Primer

<400> SEQUENCE: 769
aaatgacagc aaatgtctga tagagct                                     27

<210> SEQ ID NO 770
<211> LENGTH: 33
<212> TYPE: DNA
<213> ORGANISM: Artificial Sequence
<220> FEATURE:
<223> OTHER INFORMATION: Primer

<400> SEQUENCE: 770
aagtttcatg aatcaaaaat taaatgaatt gca                              33
```

<210> SEQ ID NO 771
<211> LENGTH: 28
<212> TYPE: DNA
<213> ORGANISM: Artificial Sequence
<220> FEATURE:
<223> OTHER INFORMATION: Primer

<400> SEQUENCE: 771
agttatttcc agcatgctaa atccctac                                    28

<210> SEQ ID NO 772
<211> LENGTH: 28
<212> TYPE: DNA
<213> ORGANISM: Artificial Sequence
<220> FEATURE:
<223> OTHER INFORMATION: Primer

<400> SEQUENCE: 772
catgtatcta cttgcgtgag gattctat                                    28

<210> SEQ ID NO 773
<211> LENGTH: 22
<212> TYPE: DNA
<213> ORGANISM: Artificial Sequence
<220> FEATURE:
<223> OTHER INFORMATION: Primer

<400> SEQUENCE: 773
ggtaggtgac gctgtcttca ag                                          22

<210> SEQ ID NO 774
<211> LENGTH: 33
<212> TYPE: DNA
<213> ORGANISM: Artificial Sequence
<220> FEATURE:
<223> OTHER INFORMATION: Primer

<400> SEQUENCE: 774
caaacatgta attgatcctg aagaatttcc atc                              33

<210> SEQ ID NO 775
<211> LENGTH: 33
<212> TYPE: DNA
<213> ORGANISM: Artificial Sequence
<220> FEATURE:
<223> OTHER INFORMATION: Primer

<400> SEQUENCE: 775
cacagttcta gggtaataac ccataaaaat tct                              33

<210> SEQ ID NO 776
<211> LENGTH: 32
<212> TYPE: DNA
<213> ORGANISM: Artificial Sequence
<220> FEATURE:
<223> OTHER INFORMATION: Primer

<400> SEQUENCE: 776
agagtaatca attatgtgct ctcctctctt ta                               32

<210> SEQ ID NO 777
<211> LENGTH: 32
<212> TYPE: DNA
<213> ORGANISM: Artificial Sequence
<220> FEATURE:
<223> OTHER INFORMATION: Primer

```
<400> SEQUENCE: 777
tgtccacctt aatgctatgt tataattttc ca                                32

<210> SEQ ID NO 778
<211> LENGTH: 32
<212> TYPE: DNA
<213> ORGANISM: Artificial Sequence
<220> FEATURE:
<223> OTHER INFORMATION: Primer

<400> SEQUENCE: 778
aaaaatatgt aagcatacac acaaaaaccg at                                32

<210> SEQ ID NO 779
<211> LENGTH: 33
<212> TYPE: DNA
<213> ORGANISM: Artificial Sequence
<220> FEATURE:
<223> OTHER INFORMATION: Primer

<400> SEQUENCE: 779
taaatcaaca tattttaacc ctgctatact ccc                               33

<210> SEQ ID NO 780
<211> LENGTH: 26
<212> TYPE: DNA
<213> ORGANISM: Artificial Sequence
<220> FEATURE:
<223> OTHER INFORMATION: Primer

<400> SEQUENCE: 780
tttgtcctga agattcagaa tgacca                                       26

<210> SEQ ID NO 781
<211> LENGTH: 27
<212> TYPE: DNA
<213> ORGANISM: Artificial Sequence
<220> FEATURE:
<223> OTHER INFORMATION: Primer

<400> SEQUENCE: 781
cctcaaagag aggaaagaag ttgacag                                      27

<210> SEQ ID NO 782
<211> LENGTH: 33
<212> TYPE: DNA
<213> ORGANISM: Artificial Sequence
<220> FEATURE:
<223> OTHER INFORMATION: Primer

<400> SEQUENCE: 782
atcctgtcct aactcagaat tcagttttat aac                               33

<210> SEQ ID NO 783
<211> LENGTH: 28
<212> TYPE: DNA
<213> ORGANISM: Artificial Sequence
<220> FEATURE:
<223> OTHER INFORMATION: Primer

<400> SEQUENCE: 783
gggacatcac agtagtcgta aagttttc                                     28

<210> SEQ ID NO 784
<211> LENGTH: 33
```

```
<212> TYPE: DNA
<213> ORGANISM: Artificial Sequence
<220> FEATURE:
<223> OTHER INFORMATION: Primer

<400> SEQUENCE: 784
cacagttcta gggtaataac ccataaaaat tct                          33

<210> SEQ ID NO 785
<211> LENGTH: 23
<212> TYPE: DNA
<213> ORGANISM: Artificial Sequence
<220> FEATURE:
<223> OTHER INFORMATION: Primer

<400> SEQUENCE: 785
ctggtactcg actcttgacc atg                                    23

<210> SEQ ID NO 786
<211> LENGTH: 24
<212> TYPE: DNA
<213> ORGANISM: Artificial Sequence
<220> FEATURE:
<223> OTHER INFORMATION: Primer

<400> SEQUENCE: 786
gtagtccaat gtgtcatgga gctt                                   24

<210> SEQ ID NO 787
<211> LENGTH: 29
<212> TYPE: DNA
<213> ORGANISM: Artificial Sequence
<220> FEATURE:
<223> OTHER INFORMATION: Primer

<400> SEQUENCE: 787
tctctcactc ttttcaagtt ttatgcaca                              29

<210> SEQ ID NO 788
<211> LENGTH: 27
<212> TYPE: DNA
<213> ORGANISM: Artificial Sequence
<220> FEATURE:
<223> OTHER INFORMATION: Primer

<400> SEQUENCE: 788
ctccattctt tgcaagtttt atgcaca                                27

<210> SEQ ID NO 789
<211> LENGTH: 23
<212> TYPE: DNA
<213> ORGANISM: Artificial Sequence
<220> FEATURE:
<223> OTHER INFORMATION: Primer

<400> SEQUENCE: 789
agaccaacca ttgtaaccac aca                                    23

<210> SEQ ID NO 790
<211> LENGTH: 33
<212> TYPE: DNA
<213> ORGANISM: Artificial Sequence
<220> FEATURE:
<223> OTHER INFORMATION: Primer

<400> SEQUENCE: 790
```

```
cggtctcagc ttataattac attttcacaa att                                    33

<210> SEQ ID NO 791
<211> LENGTH: 31
<212> TYPE: DNA
<213> ORGANISM: Artificial Sequence
<220> FEATURE:
<223> OTHER INFORMATION: Primer

<400> SEQUENCE: 791
tgatatagac ctccatgttt aatgtctgga t                                      31

<210> SEQ ID NO 792
<211> LENGTH: 29
<212> TYPE: DNA
<213> ORGANISM: Artificial Sequence
<220> FEATURE:
<223> OTHER INFORMATION: Primer

<400> SEQUENCE: 792
cctcacaagt ataactcaat ttagtccca                                         29

<210> SEQ ID NO 793
<211> LENGTH: 30
<212> TYPE: DNA
<213> ORGANISM: Artificial Sequence
<220> FEATURE:
<223> OTHER INFORMATION: Primer

<400> SEQUENCE: 793
gaaccttgaa cacagaaaat gctatatgtt                                        30

<210> SEQ ID NO 794
<211> LENGTH: 20
<212> TYPE: DNA
<213> ORGANISM: Artificial Sequence
<220> FEATURE:
<223> OTHER INFORMATION: Primer

<400> SEQUENCE: 794
gtggcgtact acacgctgat                                                   20

<210> SEQ ID NO 795
<211> LENGTH: 23
<212> TYPE: DNA
<213> ORGANISM: Artificial Sequence
<220> FEATURE:
<223> OTHER INFORMATION: Primer

<400> SEQUENCE: 795
ctctctcttc tctgcagggt aca                                               23

<210> SEQ ID NO 796
<211> LENGTH: 33
<212> TYPE: DNA
<213> ORGANISM: Artificial Sequence
<220> FEATURE:
<223> OTHER INFORMATION: Primer

<400> SEQUENCE: 796
attagggatt atacaagaga aggtatgtag gtt                                    33

<210> SEQ ID NO 797
<211> LENGTH: 23
<212> TYPE: DNA
<213> ORGANISM: Artificial Sequence
```

```
<220> FEATURE:
<223> OTHER INFORMATION: Primer

<400> SEQUENCE: 797
gctagggtga tcctaaggac agt                                              23

<210> SEQ ID NO 798
<211> LENGTH: 23
<212> TYPE: DNA
<213> ORGANISM: Artificial Sequence
<220> FEATURE:
<223> OTHER INFORMATION: Primer

<400> SEQUENCE: 798
aaaacttaga ggcaggtgct gat                                              23

<210> SEQ ID NO 799
<211> LENGTH: 27
<212> TYPE: DNA
<213> ORGANISM: Artificial Sequence
<220> FEATURE:
<223> OTHER INFORMATION: Primer

<400> SEQUENCE: 799
catcatcacc gtagtggaat atgtacc                                          27

<210> SEQ ID NO 800
<211> LENGTH: 33
<212> TYPE: DNA
<213> ORGANISM: Artificial Sequence
<220> FEATURE:
<223> OTHER INFORMATION: Primer

<400> SEQUENCE: 800
atcctgtcct aactcagaat tcagttttat aac                                   33

<210> SEQ ID NO 801
<211> LENGTH: 21
<212> TYPE: DNA
<213> ORGANISM: Artificial Sequence
<220> FEATURE:
<223> OTHER INFORMATION: Primer

<400> SEQUENCE: 801
cttcagagcc aactgcgagt a                                                21

<210> SEQ ID NO 802
<211> LENGTH: 27
<212> TYPE: DNA
<213> ORGANISM: Artificial Sequence
<220> FEATURE:
<223> OTHER INFORMATION: Primer

<400> SEQUENCE: 802
tttagcaagg caatatcttt tcgtgtg                                          27

<210> SEQ ID NO 803
<211> LENGTH: 30
<212> TYPE: DNA
<213> ORGANISM: Artificial Sequence
<220> FEATURE:
<223> OTHER INFORMATION: Primer

<400> SEQUENCE: 803
gggaaatgaa aaaggttttt aaagggaaa                                        30
```

```
<210> SEQ ID NO 804
<211> LENGTH: 24
<212> TYPE: DNA
<213> ORGANISM: Artificial Sequence
<220> FEATURE:
<223> OTHER INFORMATION: Primer

<400> SEQUENCE: 804
aaaaagagca gtccaggtca gatt                                              24

<210> SEQ ID NO 805
<211> LENGTH: 30
<212> TYPE: DNA
<213> ORGANISM: Artificial Sequence
<220> FEATURE:
<223> OTHER INFORMATION: Primer

<400> SEQUENCE: 805
ctggaaatgt tgaggcatat ctgtaaattt                                        30

<210> SEQ ID NO 806
<211> LENGTH: 33
<212> TYPE: DNA
<213> ORGANISM: Artificial Sequence
<220> FEATURE:
<223> OTHER INFORMATION: Primer

<400> SEQUENCE: 806
ttactcaatt attaataaca tccctgtggg aag                                    33

<210> SEQ ID NO 807
<211> LENGTH: 30
<212> TYPE: DNA
<213> ORGANISM: Artificial Sequence
<220> FEATURE:
<223> OTHER INFORMATION: Primer

<400> SEQUENCE: 807
cgcgtattct cataatatag atgtccatgt                                        30

<210> SEQ ID NO 808
<211> LENGTH: 33
<212> TYPE: DNA
<213> ORGANISM: Artificial Sequence
<220> FEATURE:
<223> OTHER INFORMATION: Primer

<400> SEQUENCE: 808
cctcaatctt atacaagatt ttcaactgga agt                                    33

<210> SEQ ID NO 809
<211> LENGTH: 30
<212> TYPE: DNA
<213> ORGANISM: Artificial Sequence
<220> FEATURE:
<223> OTHER INFORMATION: Primer

<400> SEQUENCE: 809
gactggcaat agtgatataa ttcaggcata                                        30

<210> SEQ ID NO 810
<211> LENGTH: 28
<212> TYPE: DNA
<213> ORGANISM: Artificial Sequence
<220> FEATURE:
<223> OTHER INFORMATION: Primer
```

-continued

```
<210> SEQ ID NO 811
<211> LENGTH: 30
<212> TYPE: DNA
<213> ORGANISM: Artificial Sequence
<220> FEATURE:
<223> OTHER INFORMATION: Primer

<400> SEQUENCE: 811
cccactctcc cataattata ctctatcaga                                    30

<210> SEQ ID NO 812
<211> LENGTH: 30
<212> TYPE: DNA
<213> ORGANISM: Artificial Sequence
<220> FEATURE:
<223> OTHER INFORMATION: Primer

<400> SEQUENCE: 812
acacgctaag gaagagttct caaaaattta                                    30

<210> SEQ ID NO 813
<211> LENGTH: 25
<212> TYPE: DNA
<213> ORGANISM: Artificial Sequence
<220> FEATURE:
<223> OTHER INFORMATION: Primer

<400> SEQUENCE: 813
atccatcttg tgtgcaatga atgtg                                         25

<210> SEQ ID NO 814
<211> LENGTH: 30
<212> TYPE: DNA
<213> ORGANISM: Artificial Sequence
<220> FEATURE:
<223> OTHER INFORMATION: Primer

<400> SEQUENCE: 814
acagagaaag aacttctctc ttgtttacac                                    30

<210> SEQ ID NO 815
<211> LENGTH: 22
<212> TYPE: DNA
<213> ORGANISM: Artificial Sequence
<220> FEATURE:
<223> OTHER INFORMATION: Primer

<400> SEQUENCE: 815
ttacaggcaa tgggagccca aa                                            22

<210> SEQ ID NO 816
<211> LENGTH: 24
<212> TYPE: DNA
<213> ORGANISM: Artificial Sequence
<220> FEATURE:
<223> OTHER INFORMATION: Primer

<400> SEQUENCE: 816
ggtattcccg atctggttcc attg                                          24

<210> SEQ ID NO 817
```

Previous sequence on page:

```
<400> SEQUENCE: 810
cttcgtttga ttactgccag ttatttcc                                      28
```

```
<211> LENGTH: 28
<212> TYPE: DNA
<213> ORGANISM: Artificial Sequence
<220> FEATURE:
<223> OTHER INFORMATION: Primer

<400> SEQUENCE: 817
acatgaacat gctaggattt cagagtag                                            28

<210> SEQ ID NO 818
<211> LENGTH: 27
<212> TYPE: DNA
<213> ORGANISM: Artificial Sequence
<220> FEATURE:
<223> OTHER INFORMATION: Primer

<400> SEQUENCE: 818
ggtaacatta ccttcacatg aaggcaa                                             27

<210> SEQ ID NO 819
<211> LENGTH: 30
<212> TYPE: DNA
<213> ORGANISM: Artificial Sequence
<220> FEATURE:
<223> OTHER INFORMATION: Primer

<400> SEQUENCE: 819
acctgcctta ttcagtagca tttgtaataa                                          30

<210> SEQ ID NO 820
<211> LENGTH: 22
<212> TYPE: DNA
<213> ORGANISM: Artificial Sequence
<220> FEATURE:
<223> OTHER INFORMATION: Primer

<400> SEQUENCE: 820
tctgagactg tcgtccgtgt ta                                                  22

<210> SEQ ID NO 821
<211> LENGTH: 30
<212> TYPE: DNA
<213> ORGANISM: Artificial Sequence
<220> FEATURE:
<223> OTHER INFORMATION: Primer

<400> SEQUENCE: 821
ccagaataca aagtgactct atcatgaaca                                          30

<210> SEQ ID NO 822
<211> LENGTH: 29
<212> TYPE: DNA
<213> ORGANISM: Artificial Sequence
<220> FEATURE:
<223> OTHER INFORMATION: Primer

<400> SEQUENCE: 822
caggaagaat tgaattttaa gcaccatca                                           29

<210> SEQ ID NO 823
<211> LENGTH: 27
<212> TYPE: DNA
<213> ORGANISM: Artificial Sequence
<220> FEATURE:
<223> OTHER INFORMATION: Primer

<400> SEQUENCE: 823
```

```
tcattcagct taaaccatgt gaagtca                                              27

<210> SEQ ID NO 824
<211> LENGTH: 25
<212> TYPE: DNA
<213> ORGANISM: Artificial Sequence
<220> FEATURE:
<223> OTHER INFORMATION: Primer

<400> SEQUENCE: 824
acattccata gcagcagaat gagac                                                25

<210> SEQ ID NO 825
<211> LENGTH: 26
<212> TYPE: DNA
<213> ORGANISM: Artificial Sequence
<220> FEATURE:
<223> OTHER INFORMATION: Primer

<400> SEQUENCE: 825
acaatgtcaa aagccactca attgtc                                               26

<210> SEQ ID NO 826
<211> LENGTH: 33
<212> TYPE: DNA
<213> ORGANISM: Artificial Sequence
<220> FEATURE:
<223> OTHER INFORMATION: Primer

<400> SEQUENCE: 826
taatactaaa gttctgaata aaggtgtgca ctt                                       33

<210> SEQ ID NO 827
<211> LENGTH: 30
<212> TYPE: DNA
<213> ORGANISM: Artificial Sequence
<220> FEATURE:
<223> OTHER INFORMATION: Primer

<400> SEQUENCE: 827
acaggtactc tcctccacta tgtaaatttt                                           30

<210> SEQ ID NO 828
<211> LENGTH: 26
<212> TYPE: DNA
<213> ORGANISM: Artificial Sequence
<220> FEATURE:
<223> OTHER INFORMATION: Primer

<400> SEQUENCE: 828
acattactgg ctccatccat tttgta                                               26

<210> SEQ ID NO 829
<211> LENGTH: 29
<212> TYPE: DNA
<213> ORGANISM: Artificial Sequence
<220> FEATURE:
<223> OTHER INFORMATION: Primer

<400> SEQUENCE: 829
taaattactt actaatgcac gtgggttga                                            29

<210> SEQ ID NO 830
<211> LENGTH: 33
<212> TYPE: DNA
```

<213> ORGANISM: Artificial Sequence
<220> FEATURE:
<223> OTHER INFORMATION: Primer

<400> SEQUENCE: 830
caccatcagt cattttattt gcatttgaaa aat         33

<210> SEQ ID NO 831
<211> LENGTH: 25
<212> TYPE: DNA
<213> ORGANISM: Artificial Sequence
<220> FEATURE:
<223> OTHER INFORMATION: Primer

<400> SEQUENCE: 831
cgtgatttca tctccagttc tgtgt                  25

<210> SEQ ID NO 832
<211> LENGTH: 25
<212> TYPE: DNA
<213> ORGANISM: Artificial Sequence
<220> FEATURE:
<223> OTHER INFORMATION: Primer

<400> SEQUENCE: 832
ggtagagagc aagagttaca gtgtc                  25

<210> SEQ ID NO 833
<211> LENGTH: 22
<212> TYPE: DNA
<213> ORGANISM: Artificial Sequence
<220> FEATURE:
<223> OTHER INFORMATION: Primer

<400> SEQUENCE: 833
acgatcttcc gcttctgttg tt                     22

<210> SEQ ID NO 834
<211> LENGTH: 22
<212> TYPE: DNA
<213> ORGANISM: Artificial Sequence
<220> FEATURE:
<223> OTHER INFORMATION: Primer

<400> SEQUENCE: 834
cttgacacac gcaggcaaga ca                     22

<210> SEQ ID NO 835
<211> LENGTH: 29
<212> TYPE: DNA
<213> ORGANISM: Artificial Sequence
<220> FEATURE:
<223> OTHER INFORMATION: Primer

<400> SEQUENCE: 835
ctataaagga caaggagaac agcaaacca              29

<210> SEQ ID NO 836
<211> LENGTH: 23
<212> TYPE: DNA
<213> ORGANISM: Artificial Sequence
<220> FEATURE:
<223> OTHER INFORMATION: Primer

<400> SEQUENCE: 836
gggcatattg agcatctctc tca                    23

<210> SEQ ID NO 837
<211> LENGTH: 24
<212> TYPE: DNA
<213> ORGANISM: Artificial Sequence
<220> FEATURE:
<223> OTHER INFORMATION: Primer

<400> SEQUENCE: 837
gccaaagcat tgatgttcac ttgg                                          24

<210> SEQ ID NO 838
<211> LENGTH: 22
<212> TYPE: DNA
<213> ORGANISM: Artificial Sequence
<220> FEATURE:
<223> OTHER INFORMATION: Primer

<400> SEQUENCE: 838
cgccctcaag gtagtctcat ga                                            22

<210> SEQ ID NO 839
<211> LENGTH: 24
<212> TYPE: DNA
<213> ORGANISM: Artificial Sequence
<220> FEATURE:
<223> OTHER INFORMATION: Primer

<400> SEQUENCE: 839
acaacagtag agagggaaag ctca                                          24

<210> SEQ ID NO 840
<211> LENGTH: 26
<212> TYPE: DNA
<213> ORGANISM: Artificial Sequence
<220> FEATURE:
<223> OTHER INFORMATION: Primer

<400> SEQUENCE: 840
gtagaagcca gaaggacaca cgtact                                        26

<210> SEQ ID NO 841
<211> LENGTH: 30
<212> TYPE: DNA
<213> ORGANISM: Artificial Sequence
<220> FEATURE:
<223> OTHER INFORMATION: Primer

<400> SEQUENCE: 841
agctagacat cctacaattc aaggtaaatc                                    30

<210> SEQ ID NO 842
<211> LENGTH: 30
<212> TYPE: DNA
<213> ORGANISM: Artificial Sequence
<220> FEATURE:
<223> OTHER INFORMATION: Primer

<400> SEQUENCE: 842
gactccatta tcccaaaaat ctgataagga                                    30

<210> SEQ ID NO 843
<211> LENGTH: 30
<212> TYPE: DNA
<213> ORGANISM: Artificial Sequence
<220> FEATURE:

```
<223> OTHER INFORMATION: Primer

<400> SEQUENCE: 843
caaacaggag tctttaattt gttgctaagt                                     30

<210> SEQ ID NO 844
<211> LENGTH: 30
<212> TYPE: DNA
<213> ORGANISM: Artificial Sequence
<220> FEATURE:
<223> OTHER INFORMATION: Primer

<400> SEQUENCE: 844
gttcaaagct cacttgacat taagtacatt                                     30

<210> SEQ ID NO 845
<211> LENGTH: 29
<212> TYPE: DNA
<213> ORGANISM: Artificial Sequence
<220> FEATURE:
<223> OTHER INFORMATION: Primer

<400> SEQUENCE: 845
aatttactaa tgattccagc ctgtcttgt                                      29

<210> SEQ ID NO 846
<211> LENGTH: 32
<212> TYPE: DNA
<213> ORGANISM: Artificial Sequence
<220> FEATURE:
<223> OTHER INFORMATION: Primer

<400> SEQUENCE: 846
atcaaactta ttactctgat tttctcagga tc                                  32

<210> SEQ ID NO 847
<211> LENGTH: 30
<212> TYPE: DNA
<213> ORGANISM: Artificial Sequence
<220> FEATURE:
<223> OTHER INFORMATION: Primer

<400> SEQUENCE: 847
gagtaatcaa ttatgtgctc tcctctcttt                                     30

<210> SEQ ID NO 848
<211> LENGTH: 33
<212> TYPE: DNA
<213> ORGANISM: Artificial Sequence
<220> FEATURE:
<223> OTHER INFORMATION: Primer

<400> SEQUENCE: 848
ctgctaattg catgttagaa agtatttcca taa                                 33

<210> SEQ ID NO 849
<211> LENGTH: 29
<212> TYPE: DNA
<213> ORGANISM: Artificial Sequence
<220> FEATURE:
<223> OTHER INFORMATION: Primer

<400> SEQUENCE: 849
ctggcatatc cttctctatt cactgaatg                                      29
```

```
<210> SEQ ID NO 850
<211> LENGTH: 33
<212> TYPE: DNA
<213> ORGANISM: Artificial Sequence
<220> FEATURE:
<223> OTHER INFORMATION: Primer

<400> SEQUENCE: 850
ctaaagttct gaataaaggt gtgcatttta tga                                    33

<210> SEQ ID NO 851
<211> LENGTH: 27
<212> TYPE: DNA
<213> ORGANISM: Artificial Sequence
<220> FEATURE:
<223> OTHER INFORMATION: Primer

<400> SEQUENCE: 851
caaagtggcc aattatttg actggat                                            27

<210> SEQ ID NO 852
<211> LENGTH: 24
<212> TYPE: DNA
<213> ORGANISM: Artificial Sequence
<220> FEATURE:
<223> OTHER INFORMATION: Primer

<400> SEQUENCE: 852
gtgtaaaggg tgtaaaggag gcaa                                              24

<210> SEQ ID NO 853
<211> LENGTH: 29
<212> TYPE: DNA
<213> ORGANISM: Artificial Sequence
<220> FEATURE:
<223> OTHER INFORMATION: Primer

<400> SEQUENCE: 853
cctacattca agccacattg caatattag                                         29

<210> SEQ ID NO 854
<211> LENGTH: 26
<212> TYPE: DNA
<213> ORGANISM: Artificial Sequence
<220> FEATURE:
<223> OTHER INFORMATION: Primer

<400> SEQUENCE: 854
atcctatgtt tgggcacctc ataaaa                                            26

<210> SEQ ID NO 855
<211> LENGTH: 22
<212> TYPE: DNA
<213> ORGANISM: Artificial Sequence
<220> FEATURE:
<223> OTHER INFORMATION: Primer

<400> SEQUENCE: 855
ccgactgagg agagctctag tc                                                22

<210> SEQ ID NO 856
<211> LENGTH: 27
<212> TYPE: DNA
<213> ORGANISM: Artificial Sequence
<220> FEATURE:
<223> OTHER INFORMATION: Primer
```

-continued

<400> SEQUENCE: 856
atgaacagca acaacaataa caaacca     27

<210> SEQ ID NO 857
<211> LENGTH: 27
<212> TYPE: DNA
<213> ORGANISM: Artificial Sequence
<220> FEATURE:
<223> OTHER INFORMATION: Primer

<400> SEQUENCE: 857
aatgcaattg gtaggacaaa ctaatgc     27

<210> SEQ ID NO 858
<211> LENGTH: 25
<212> TYPE: DNA
<213> ORGANISM: Artificial Sequence
<220> FEATURE:
<223> OTHER INFORMATION: Primer

<400> SEQUENCE: 858
gctatacaaa tgtcctccct ccttt     25

<210> SEQ ID NO 859
<211> LENGTH: 28
<212> TYPE: DNA
<213> ORGANISM: Artificial Sequence
<220> FEATURE:
<223> OTHER INFORMATION: Primer

<400> SEQUENCE: 859
ctggaaagta tagtctacgc aaactctt     28

<210> SEQ ID NO 860
<211> LENGTH: 32
<212> TYPE: DNA
<213> ORGANISM: Artificial Sequence
<220> FEATURE:
<223> OTHER INFORMATION: Primer

<400> SEQUENCE: 860
aagtaaaaca ctatcatctc aaagagagga ac     32

<210> SEQ ID NO 861
<211> LENGTH: 32
<212> TYPE: DNA
<213> ORGANISM: Artificial Sequence
<220> FEATURE:
<223> OTHER INFORMATION: Primer

<400> SEQUENCE: 861
atcaaactta ttactctgat tttctcagga tc     32

<210> SEQ ID NO 862
<211> LENGTH: 23
<212> TYPE: DNA
<213> ORGANISM: Artificial Sequence
<220> FEATURE:
<223> OTHER INFORMATION: Primer

<400> SEQUENCE: 862
gactcttgac catggcagat aca     23

<210> SEQ ID NO 863
<211> LENGTH: 30

<212> TYPE: DNA
<213> ORGANISM: Artificial Sequence
<220> FEATURE:
<223> OTHER INFORMATION: Primer

<400> SEQUENCE: 863
gtaaaacact atcacctcaa agagaggaaa                                    30

<210> SEQ ID NO 864
<211> LENGTH: 30
<212> TYPE: DNA
<213> ORGANISM: Artificial Sequence
<220> FEATURE:
<223> OTHER INFORMATION: Primer

<400> SEQUENCE: 864
ctatctcaaa caatgagtta agcagctttt                                    30

<210> SEQ ID NO 865
<211> LENGTH: 26
<212> TYPE: DNA
<213> ORGANISM: Artificial Sequence
<220> FEATURE:
<223> OTHER INFORMATION: Primer

<400> SEQUENCE: 865
accactctat gaaatcctga ttccca                                        26

<210> SEQ ID NO 866
<211> LENGTH: 21
<212> TYPE: DNA
<213> ORGANISM: Artificial Sequence
<220> FEATURE:
<223> OTHER INFORMATION: Primer

<400> SEQUENCE: 866
ggaggctgga accctttca c                                              21

<210> SEQ ID NO 867
<211> LENGTH: 22
<212> TYPE: DNA
<213> ORGANISM: Artificial Sequence
<220> FEATURE:
<223> OTHER INFORMATION: Primer

<400> SEQUENCE: 867
cgtctcacat ccgtggaatg ac                                            22

<210> SEQ ID NO 868
<211> LENGTH: 23
<212> TYPE: DNA
<213> ORGANISM: Artificial Sequence
<220> FEATURE:
<223> OTHER INFORMATION: Primer

<400> SEQUENCE: 868
gggtcatttg ggaagagata cac                                           23

<210> SEQ ID NO 869
<211> LENGTH: 22
<212> TYPE: DNA
<213> ORGANISM: Artificial Sequence
<220> FEATURE:
<223> OTHER INFORMATION: Primer

<400> SEQUENCE: 869
caactggcct gctctgttct aa                                          22

<210> SEQ ID NO 870
<211> LENGTH: 23
<212> TYPE: DNA
<213> ORGANISM: Artificial Sequence
<220> FEATURE:
<223> OTHER INFORMATION: Primer

<400> SEQUENCE: 870
tgcgatcaga agaggtacag tca                                         23

<210> SEQ ID NO 871
<211> LENGTH: 23
<212> TYPE: DNA
<213> ORGANISM: Artificial Sequence
<220> FEATURE:
<223> OTHER INFORMATION: Primer

<400> SEQUENCE: 871
caactttctg cttgggagag aga                                         23

<210> SEQ ID NO 872
<211> LENGTH: 23
<212> TYPE: DNA
<213> ORGANISM: Artificial Sequence
<220> FEATURE:
<223> OTHER INFORMATION: Primer

<400> SEQUENCE: 872
aagatccgct actacaccta cct                                         23

<210> SEQ ID NO 873
<211> LENGTH: 22
<212> TYPE: DNA
<213> ORGANISM: Artificial Sequence
<220> FEATURE:
<223> OTHER INFORMATION: Primer

<400> SEQUENCE: 873
gagggaggag gtctaatcct ga                                          22

<210> SEQ ID NO 874
<211> LENGTH: 24
<212> TYPE: DNA
<213> ORGANISM: Artificial Sequence
<220> FEATURE:
<223> OTHER INFORMATION: Primer

<400> SEQUENCE: 874
gatgacctga agcaggtatg aagg                                        24

<210> SEQ ID NO 875
<211> LENGTH: 20
<212> TYPE: DNA
<213> ORGANISM: Artificial Sequence
<220> FEATURE:
<223> OTHER INFORMATION: Primer

<400> SEQUENCE: 875
acctgaagcc ctccttgtct                                             20

<210> SEQ ID NO 876
<211> LENGTH: 25
<212> TYPE: DNA
<213> ORGANISM: Artificial Sequence
<220> FEATURE:
<223> OTHER INFORMATION: Primer

<400> SEQUENCE: 876
gcatgcatct ctttctgagc tttct                                      25

<210> SEQ ID NO 877
<211> LENGTH: 27
<212> TYPE: DNA
<213> ORGANISM: Artificial Sequence
<220> FEATURE:
<223> OTHER INFORMATION: Primer

<400> SEQUENCE: 877
actaagaagt ttgaccttcc tagggta                                    27

<210> SEQ ID NO 878
<211> LENGTH: 22
<212> TYPE: DNA
<213> ORGANISM: Artificial Sequence
<220> FEATURE:
<223> OTHER INFORMATION: Primer

<400> SEQUENCE: 878
cttgtcttgg gacattccgg aa                                         22

<210> SEQ ID NO 879
<211> LENGTH: 24
<212> TYPE: DNA
<213> ORGANISM: Artificial Sequence
<220> FEATURE:
<223> OTHER INFORMATION: Primer

<400> SEQUENCE: 879
tcgacctcaa ggtcaccata aaac                                       24

<210> SEQ ID NO 880
<211> LENGTH: 22
<212> TYPE: DNA
<213> ORGANISM: Artificial Sequence
<220> FEATURE:
<223> OTHER INFORMATION: Primer

<400> SEQUENCE: 880
acatcatcgg gaaggacact tg                                         22

<210> SEQ ID NO 881
<211> LENGTH: 22
<212> TYPE: DNA
<213> ORGANISM: Artificial Sequence
<220> FEATURE:
<223> OTHER INFORMATION: Primer

<400> SEQUENCE: 881
cgggtacctc ttcatccaga ca                                         22

<210> SEQ ID NO 882
<211> LENGTH: 22
<212> TYPE: DNA
<213> ORGANISM: Artificial Sequence
<220> FEATURE:
<223> OTHER INFORMATION: Primer

<400> SEQUENCE: 882
gggaggccct tatcctctca tc                                         22

<210> SEQ ID NO 883
<211> LENGTH: 22
<212> TYPE: DNA
<213> ORGANISM: Artificial Sequence
<220> FEATURE:
<223> OTHER INFORMATION: Primer

<400> SEQUENCE: 883
cggagtggac taagagctga ga                                          22

<210> SEQ ID NO 884
<211> LENGTH: 20
<212> TYPE: DNA
<213> ORGANISM: Artificial Sequence
<220> FEATURE:
<223> OTHER INFORMATION: Primer

<400> SEQUENCE: 884
agctcacgga gaagcgaatg                                             20

<210> SEQ ID NO 885
<211> LENGTH: 23
<212> TYPE: DNA
<213> ORGANISM: Artificial Sequence
<220> FEATURE:
<223> OTHER INFORMATION: Primer

<400> SEQUENCE: 885
caattcccag gtctcaggga ttc                                         23

<210> SEQ ID NO 886
<211> LENGTH: 26
<212> TYPE: DNA
<213> ORGANISM: Artificial Sequence
<220> FEATURE:
<223> OTHER INFORMATION: Primer

<400> SEQUENCE: 886
ccaacctttc tgtctttcca ctctag                                      26

<210> SEQ ID NO 887
<211> LENGTH: 30
<212> TYPE: DNA
<213> ORGANISM: Artificial Sequence
<220> FEATURE:
<223> OTHER INFORMATION: Primer

<400> SEQUENCE: 887
cttagacaca attggaaccg aaaatcaaat                                  30

<210> SEQ ID NO 888
<211> LENGTH: 29
<212> TYPE: DNA
<213> ORGANISM: Artificial Sequence
<220> FEATURE:
<223> OTHER INFORMATION: Primer

<400> SEQUENCE: 888
ggtggtatct ccattgttaa tagatggag                                   29

<210> SEQ ID NO 889
<211> LENGTH: 30
<212> TYPE: DNA
<213> ORGANISM: Artificial Sequence
<220> FEATURE:
<223> OTHER INFORMATION: Primer -continued

```
<400> SEQUENCE: 889
gctaattgca tgttggaaaa tatttccaga                                      30

<210> SEQ ID NO 890
<211> LENGTH: 30
<212> TYPE: DNA
<213> ORGANISM: Artificial Sequence
<220> FEATURE:
<223> OTHER INFORMATION: Primer

<400> SEQUENCE: 890
tccatcgttt ctccatttta actgtatgtt                                      30

<210> SEQ ID NO 891
<211> LENGTH: 30
<212> TYPE: DNA
<213> ORGANISM: Artificial Sequence
<220> FEATURE:
<223> OTHER INFORMATION: Primer

<400> SEQUENCE: 891
cccttgtgat tatcaagacc ttatgatctt                                      30

<210> SEQ ID NO 892
<211> LENGTH: 30
<212> TYPE: DNA
<213> ORGANISM: Artificial Sequence
<220> FEATURE:
<223> OTHER INFORMATION: Primer

<400> SEQUENCE: 892
cttgtggaag gaagagtcag tatcaataaa                                      30

<210> SEQ ID NO 893
<211> LENGTH: 30
<212> TYPE: DNA
<213> ORGANISM: Artificial Sequence
<220> FEATURE:
<223> OTHER INFORMATION: Primer

<400> SEQUENCE: 893
gccaaggctt ttaaagaata acatttgtct                                      30

<210> SEQ ID NO 894
<211> LENGTH: 28
<212> TYPE: DNA
<213> ORGANISM: Artificial Sequence
<220> FEATURE:
<223> OTHER INFORMATION: Primer

<400> SEQUENCE: 894
aagtgcaaag taatagtaac tgtcctgt                                        28

<210> SEQ ID NO 895
<211> LENGTH: 22
<212> TYPE: DNA
<213> ORGANISM: Artificial Sequence
<220> FEATURE:
<223> OTHER INFORMATION: Primer

<400> SEQUENCE: 895
gcttgctcat aggcatctcc at                                              22

<210> SEQ ID NO 896
```

```
<211> LENGTH: 19
<212> TYPE: DNA
<213> ORGANISM: Artificial Sequence
<220> FEATURE:
<223> OTHER INFORMATION: Primer

<400> SEQUENCE: 896
cgccgtctcg atcacctac                                                        19

<210> SEQ ID NO 897
<211> LENGTH: 23
<212> TYPE: DNA
<213> ORGANISM: Artificial Sequence
<220> FEATURE:
<223> OTHER INFORMATION: Primer

<400> SEQUENCE: 897
ttcctcaatg ccagtcagat ctg                                                   23

<210> SEQ ID NO 898
<211> LENGTH: 24
<212> TYPE: DNA
<213> ORGANISM: Artificial Sequence
<220> FEATURE:
<223> OTHER INFORMATION: Primer

<400> SEQUENCE: 898
gtccagcttg tgaggtaagc atat                                                  24

<210> SEQ ID NO 899
<211> LENGTH: 29
<212> TYPE: DNA
<213> ORGANISM: Artificial Sequence
<220> FEATURE:
<223> OTHER INFORMATION: Primer

<400> SEQUENCE: 899
agaagtcctt ctgtagtagt tcttaaaga                                             29

<210> SEQ ID NO 900
<211> LENGTH: 24
<212> TYPE: DNA
<213> ORGANISM: Artificial Sequence
<220> FEATURE:
<223> OTHER INFORMATION: Primer

<400> SEQUENCE: 900
caaagtgcct ggcacacaaa taaa                                                  24

<210> SEQ ID NO 901
<211> LENGTH: 24
<212> TYPE: DNA
<213> ORGANISM: Artificial Sequence
<220> FEATURE:
<223> OTHER INFORMATION: Primer

<400> SEQUENCE: 901
gagcataatc tccttgcact ggaa                                                  24

<210> SEQ ID NO 902
<211> LENGTH: 25
<212> TYPE: DNA
<213> ORGANISM: Artificial Sequence
<220> FEATURE:
<223> OTHER INFORMATION: Primer

<400> SEQUENCE: 902
```
ctgtttcttc ctcatcccac tctag                                                25

<210> SEQ ID NO 903
<211> LENGTH: 30
<212> TYPE: DNA
<213> ORGANISM: Artificial Sequence
<220> FEATURE:
<223> OTHER INFORMATION: Primer

<400> SEQUENCE: 903
gtctaagaga aatttggtcc taggaagttg                                           30

<210> SEQ ID NO 904
<211> LENGTH: 29
<212> TYPE: DNA
<213> ORGANISM: Artificial Sequence
<220> FEATURE:
<223> OTHER INFORMATION: Primer

<400> SEQUENCE: 904
cttgaagact gattaagaca tagacaggt                                            29

<210> SEQ ID NO 905
<211> LENGTH: 24
<212> TYPE: DNA
<213> ORGANISM: Artificial Sequence
<220> FEATURE:
<223> OTHER INFORMATION: Primer

<400> SEQUENCE: 905
atcccatagg acttgtaggt cact                                                 24

<210> SEQ ID NO 906
<211> LENGTH: 23
<212> TYPE: DNA
<213> ORGANISM: Artificial Sequence
<220> FEATURE:
<223> OTHER INFORMATION: Primer

<400> SEQUENCE: 906
ggtgaaggag tacggtaaga gga                                                  23

<210> SEQ ID NO 907
<211> LENGTH: 29
<212> TYPE: DNA
<213> ORGANISM: Artificial Sequence
<220> FEATURE:
<223> OTHER INFORMATION: Primer

<400> SEQUENCE: 907
agaatgtcgc agtagtcata tctcttttc                                            29

<210> SEQ ID NO 908
<211> LENGTH: 30
<212> TYPE: DNA
<213> ORGANISM: Artificial Sequence
<220> FEATURE:
<223> OTHER INFORMATION: Primer

<400> SEQUENCE: 908
atcggtttaa ccaatttaca agctgaaaaa                                           30

<210> SEQ ID NO 909
<211> LENGTH: 21
<212> TYPE: DNA

```
<213> ORGANISM: Artificial Sequence
<220> FEATURE:
<223> OTHER INFORMATION: Primer

<400> SEQUENCE: 909
tggtaggtgg gaccagaaga t                                          21

<210> SEQ ID NO 910
<211> LENGTH: 25
<212> TYPE: DNA
<213> ORGANISM: Artificial Sequence
<220> FEATURE:
<223> OTHER INFORMATION: Primer

<400> SEQUENCE: 910
ctagtctcat cctagtcctg acctt                                      25

<210> SEQ ID NO 911
<211> LENGTH: 28
<212> TYPE: DNA
<213> ORGANISM: Artificial Sequence
<220> FEATURE:
<223> OTHER INFORMATION: Primer

<400> SEQUENCE: 911
ctagaaaaat caggaattgg gtgaccta                                   28

<210> SEQ ID NO 912
<211> LENGTH: 30
<212> TYPE: DNA
<213> ORGANISM: Artificial Sequence
<220> FEATURE:
<223> OTHER INFORMATION: Primer

<400> SEQUENCE: 912
tgctgatatt ccttagaatg aacgatgttt                                 30

<210> SEQ ID NO 913
<211> LENGTH: 22
<212> TYPE: DNA
<213> ORGANISM: Artificial Sequence
<220> FEATURE:
<223> OTHER INFORMATION: Primer

<400> SEQUENCE: 913
ctctgtgctg ctatgtggga at                                         22

<210> SEQ ID NO 914
<211> LENGTH: 30
<212> TYPE: DNA
<213> ORGANISM: Artificial Sequence
<220> FEATURE:
<223> OTHER INFORMATION: Primer

<400> SEQUENCE: 914
gaaccttgaa cacagaaaat gctatatgtt                                 30

<210> SEQ ID NO 915
<211> LENGTH: 22
<212> TYPE: DNA
<213> ORGANISM: Artificial Sequence
<220> FEATURE:
<223> OTHER INFORMATION: Primer

<400> SEQUENCE: 915
gtcccagctc tgatttgaac ct                                         22
```

```
<210> SEQ ID NO 916
<211> LENGTH: 30
<212> TYPE: DNA
<213> ORGANISM: Artificial Sequence
<220> FEATURE:
<223> OTHER INFORMATION: Primer

<400> SEQUENCE: 916
gaaggaaatg tgtgattttc tctttcacat                                        30

<210> SEQ ID NO 917
<211> LENGTH: 25
<212> TYPE: DNA
<213> ORGANISM: Artificial Sequence
<220> FEATURE:
<223> OTHER INFORMATION: Primer

<400> SEQUENCE: 917
tgaatccctt gtcctcttga gaact                                             25

<210> SEQ ID NO 918
<211> LENGTH: 30
<212> TYPE: DNA
<213> ORGANISM: Artificial Sequence
<220> FEATURE:
<223> OTHER INFORMATION: Primer

<400> SEQUENCE: 918
tctttgcaag ttttatgcac atattgttgt                                        30

<210> SEQ ID NO 919
<211> LENGTH: 28
<212> TYPE: DNA
<213> ORGANISM: Artificial Sequence
<220> FEATURE:
<223> OTHER INFORMATION: Primer

<400> SEQUENCE: 919
tgggaggagg ttagctttga aattaaaa                                          28

<210> SEQ ID NO 920
<211> LENGTH: 30
<212> TYPE: DNA
<213> ORGANISM: Artificial Sequence
<220> FEATURE:
<223> OTHER INFORMATION: Primer

<400> SEQUENCE: 920
tctctcactc ttttcaagtt ttatgcacat                                        30

<210> SEQ ID NO 921
<211> LENGTH: 26
<212> TYPE: DNA
<213> ORGANISM: Artificial Sequence
<220> FEATURE:
<223> OTHER INFORMATION: Primer

<400> SEQUENCE: 921
cagaatagga cctggagatt ttcctg                                            26

<210> SEQ ID NO 922
<211> LENGTH: 26
<212> TYPE: DNA
<213> ORGANISM: Artificial Sequence
<220> FEATURE:
```

```
<223> OTHER INFORMATION: Primer

<400> SEQUENCE: 922
ccattctggc tggaataata cacaca                                         26

<210> SEQ ID NO 923
<211> LENGTH: 23
<212> TYPE: DNA
<213> ORGANISM: Artificial Sequence
<220> FEATURE:
<223> OTHER INFORMATION: Primer

<400> SEQUENCE: 923
cagagcggtg tacttactga cac                                            23

<210> SEQ ID NO 924
<211> LENGTH: 24
<212> TYPE: DNA
<213> ORGANISM: Artificial Sequence
<220> FEATURE:
<223> OTHER INFORMATION: Primer

<400> SEQUENCE: 924
agaccaggaa cctgtcagaa tttc                                           24

<210> SEQ ID NO 925
<211> LENGTH: 32
<212> TYPE: DNA
<213> ORGANISM: Artificial Sequence
<220> FEATURE:
<223> OTHER INFORMATION: Primer

<400> SEQUENCE: 925
aagtaaaaca ctatcatctc aaagagagga ac                                  32

<210> SEQ ID NO 926
<211> LENGTH: 29
<212> TYPE: DNA
<213> ORGANISM: Artificial Sequence
<220> FEATURE:
<223> OTHER INFORMATION: Primer

<400> SEQUENCE: 926
attggtacca cttacacttt gaatgaaga                                      29

<210> SEQ ID NO 927
<211> LENGTH: 29
<212> TYPE: DNA
<213> ORGANISM: Artificial Sequence
<220> FEATURE:
<223> OTHER INFORMATION: Primer

<400> SEQUENCE: 927
tttttgtctt tacgcatctg attaatgga                                      29

<210> SEQ ID NO 928
<211> LENGTH: 28
<212> TYPE: DNA
<213> ORGANISM: Artificial Sequence
<220> FEATURE:
<223> OTHER INFORMATION: Primer

<400> SEQUENCE: 928
ggttgtcata ttgtgagaat tgggaatc                                       28
```

```
<210> SEQ ID NO 929
<211> LENGTH: 31
<212> TYPE: DNA
<213> ORGANISM: Artificial Sequence
<220> FEATURE:
<223> OTHER INFORMATION: Primer

<400> SEQUENCE: 929
cacctgcttt gtttatctgt agatgaaact a                              31

<210> SEQ ID NO 930
<211> LENGTH: 30
<212> TYPE: DNA
<213> ORGANISM: Artificial Sequence
<220> FEATURE:
<223> OTHER INFORMATION: Primer

<400> SEQUENCE: 930
actagattcc cactctacat tgtatgagaa                                30

<210> SEQ ID NO 931
<211> LENGTH: 30
<212> TYPE: DNA
<213> ORGANISM: Artificial Sequence
<220> FEATURE:
<223> OTHER INFORMATION: Primer

<400> SEQUENCE: 931
ggcaagagga ggtatataga agtatccttt                                30

<210> SEQ ID NO 932
<211> LENGTH: 27
<212> TYPE: DNA
<213> ORGANISM: Artificial Sequence
<220> FEATURE:
<223> OTHER INFORMATION: Primer

<400> SEQUENCE: 932
cctgtaaggg taaaagtacc aaaagga                                   27

<210> SEQ ID NO 933
<211> LENGTH: 33
<212> TYPE: DNA
<213> ORGANISM: Artificial Sequence
<220> FEATURE:
<223> OTHER INFORMATION: Primer

<400> SEQUENCE: 933
tctcctttct tcgatctttg aaagttttat aca                            33

<210> SEQ ID NO 934
<211> LENGTH: 26
<212> TYPE: DNA
<213> ORGANISM: Artificial Sequence
<220> FEATURE:
<223> OTHER INFORMATION: Primer

<400> SEQUENCE: 934
gatcccatct tccatttatg cagact                                    26

<210> SEQ ID NO 935
<211> LENGTH: 30
<212> TYPE: DNA
<213> ORGANISM: Artificial Sequence
<220> FEATURE:
<223> OTHER INFORMATION: Primer
```

```
<400> SEQUENCE: 935
cctcacaagt ataactcaat ttagtcccat                                     30

<210> SEQ ID NO 936
<211> LENGTH: 30
<212> TYPE: DNA
<213> ORGANISM: Artificial Sequence
<220> FEATURE:
<223> OTHER INFORMATION: Primer

<400> SEQUENCE: 936
cccagtttat gtcaaatcag gagatatctt                                     30

<210> SEQ ID NO 937
<211> LENGTH: 28
<212> TYPE: DNA
<213> ORGANISM: Artificial Sequence
<220> FEATURE:
<223> OTHER INFORMATION: Primer

<400> SEQUENCE: 937
tttttcctta acattcccat tgaggagt                                       28

<210> SEQ ID NO 938
<211> LENGTH: 24
<212> TYPE: DNA
<213> ORGANISM: Artificial Sequence
<220> FEATURE:
<223> OTHER INFORMATION: Primer

<400> SEQUENCE: 938
cccacttcaa tcttcatctc cctg                                           24

<210> SEQ ID NO 939
<211> LENGTH: 23
<212> TYPE: DNA
<213> ORGANISM: Artificial Sequence
<220> FEATURE:
<223> OTHER INFORMATION: Primer

<400> SEQUENCE: 939
ctgctttgtt cctgcaggtt ttt                                            23

<210> SEQ ID NO 940
<211> LENGTH: 30
<212> TYPE: DNA
<213> ORGANISM: Artificial Sequence
<220> FEATURE:
<223> OTHER INFORMATION: Primer

<400> SEQUENCE: 940
ctgtgtccaa tcattgtaaa tgattctgag                                     30

<210> SEQ ID NO 941
<211> LENGTH: 30
<212> TYPE: DNA
<213> ORGANISM: Artificial Sequence
<220> FEATURE:
<223> OTHER INFORMATION: Primer

<400> SEQUENCE: 941
caaacagtga aatatcagac tcatcacaga                                     30

<210> SEQ ID NO 942
<211> LENGTH: 30
```

```
<212> TYPE: DNA
<213> ORGANISM: Artificial Sequence
<220> FEATURE:
<223> OTHER INFORMATION: Primer

<400> SEQUENCE: 942
gcttccaaca gccttacttt gtatatacaa                                    30

<210> SEQ ID NO 943
<211> LENGTH: 23
<212> TYPE: DNA
<213> ORGANISM: Artificial Sequence
<220> FEATURE:
<223> OTHER INFORMATION: Primer

<400> SEQUENCE: 943
ccaaaaggat ctggaacaca ggt                                           23

<210> SEQ ID NO 944
<211> LENGTH: 22
<212> TYPE: DNA
<213> ORGANISM: Artificial Sequence
<220> FEATURE:
<223> OTHER INFORMATION: Primer

<400> SEQUENCE: 944
cattgaggat gggtggagtg ta                                            22

<210> SEQ ID NO 945
<211> LENGTH: 25
<212> TYPE: DNA
<213> ORGANISM: Artificial Sequence
<220> FEATURE:
<223> OTHER INFORMATION: Primer

<400> SEQUENCE: 945
gagaaggagg aatgaagaag gcttt                                         25

<210> SEQ ID NO 946
<211> LENGTH: 23
<212> TYPE: DNA
<213> ORGANISM: Artificial Sequence
<220> FEATURE:
<223> OTHER INFORMATION: Primer

<400> SEQUENCE: 946
cctaagccct tctagagcta ggt                                           23

<210> SEQ ID NO 947
<211> LENGTH: 27
<212> TYPE: DNA
<213> ORGANISM: Artificial Sequence
<220> FEATURE:
<223> OTHER INFORMATION: Primer

<400> SEQUENCE: 947
aacgacttct cttgtgaact atcaagg                                       27

<210> SEQ ID NO 948
<211> LENGTH: 24
<212> TYPE: DNA
<213> ORGANISM: Artificial Sequence
<220> FEATURE:
<223> OTHER INFORMATION: Primer

<400> SEQUENCE: 948
```

| | |
|---|---|
| cccaaccatg ggtatagtgt taca | 24 |

<210> SEQ ID NO 949
<211> LENGTH: 27
<212> TYPE: DNA
<213> ORGANISM: Artificial Sequence
<220> FEATURE:
<223> OTHER INFORMATION: Primer

<400> SEQUENCE: 949

| | |
|---|---|
| aggtttaaac aaagtgagga aagagca | 27 |

<210> SEQ ID NO 950
<211> LENGTH: 30
<212> TYPE: DNA
<213> ORGANISM: Artificial Sequence
<220> FEATURE:
<223> OTHER INFORMATION: Primer

<400> SEQUENCE: 950

| | |
|---|---|
| agggacaaag tttttaaata acggaacatg | 30 |

<210> SEQ ID NO 951
<211> LENGTH: 30
<212> TYPE: DNA
<213> ORGANISM: Artificial Sequence
<220> FEATURE:
<223> OTHER INFORMATION: Primer

<400> SEQUENCE: 951

| | |
|---|---|
| agagaatgag aggacattac tctagtttct | 30 |

<210> SEQ ID NO 952
<211> LENGTH: 30
<212> TYPE: DNA
<213> ORGANISM: Artificial Sequence
<220> FEATURE:
<223> OTHER INFORMATION: Primer

<400> SEQUENCE: 952

| | |
|---|---|
| gtgttgtaaa ggtagacata aatctagcct | 30 |

<210> SEQ ID NO 953
<211> LENGTH: 30
<212> TYPE: DNA
<213> ORGANISM: Artificial Sequence
<220> FEATURE:
<223> OTHER INFORMATION: Primer

<400> SEQUENCE: 953

| | |
|---|---|
| ctgttataga gccagtaaaa ctcatcgtta | 30 |

<210> SEQ ID NO 954
<211> LENGTH: 27
<212> TYPE: DNA
<213> ORGANISM: Artificial Sequence
<220> FEATURE:
<223> OTHER INFORMATION: Primer

<400> SEQUENCE: 954

| | |
|---|---|
| gggcaggagg atgatgtaat tataaga | 27 |

<210> SEQ ID NO 955
<211> LENGTH: 29
<212> TYPE: DNA
<213> ORGANISM: Artificial Sequence
<220> FEATURE:
<223> OTHER INFORMATION: Primer

<400> SEQUENCE: 955
aagggaggat aagttttaag gcagaaaat                29

<210> SEQ ID NO 956
<211> LENGTH: 30
<212> TYPE: DNA
<213> ORGANISM: Artificial Sequence
<220> FEATURE:
<223> OTHER INFORMATION: Primer

<400> SEQUENCE: 956
tgccttttac actgtagaac ttagaaaaca                30

<210> SEQ ID NO 957
<211> LENGTH: 27
<212> TYPE: DNA
<213> ORGANISM: Artificial Sequence
<220> FEATURE:
<223> OTHER INFORMATION: Primer

<400> SEQUENCE: 957
gaccataaga gtgagaagtg gaaaagt                27

<210> SEQ ID NO 958
<211> LENGTH: 30
<212> TYPE: DNA
<213> ORGANISM: Artificial Sequence
<220> FEATURE:
<223> OTHER INFORMATION: Primer

<400> SEQUENCE: 958
attttgttac caacagcaaa atatcagact                30

<210> SEQ ID NO 959
<211> LENGTH: 32
<212> TYPE: DNA
<213> ORGANISM: Artificial Sequence
<220> FEATURE:
<223> OTHER INFORMATION: Primer

<400> SEQUENCE: 959
ttccatggtt tatttttgga aaatcacaaa at                32

<210> SEQ ID NO 960
<211> LENGTH: 30
<212> TYPE: DNA
<213> ORGANISM: Artificial Sequence
<220> FEATURE:
<223> OTHER INFORMATION: Primer

<400> SEQUENCE: 960
ggacacaatt ggaactgaaa atcaaatgaa                30

<210> SEQ ID NO 961
<211> LENGTH: 30
<212> TYPE: DNA
<213> ORGANISM: Artificial Sequence
<220> FEATURE:
<223> OTHER INFORMATION: Primer

<400> SEQUENCE: 961
gccaaattct ttcagagttc aaaagtacaa                30

```
<210> SEQ ID NO 962
<211> LENGTH: 30
<212> TYPE: DNA
<213> ORGANISM: Artificial Sequence
<220> FEATURE:
<223> OTHER INFORMATION: Primer

<400> SEQUENCE: 962
cctatctcca taaaacatcc aagagttgtt                                    30

<210> SEQ ID NO 963
<211> LENGTH: 24
<212> TYPE: DNA
<213> ORGANISM: Artificial Sequence
<220> FEATURE:
<223> OTHER INFORMATION: Primer

<400> SEQUENCE: 963
tgccaatatc tctttgctca ggtt                                          24

<210> SEQ ID NO 964
<211> LENGTH: 22
<212> TYPE: DNA
<213> ORGANISM: Artificial Sequence
<220> FEATURE:
<223> OTHER INFORMATION: Primer

<400> SEQUENCE: 964
gctgtgcaca cataccctag ag                                            22

<210> SEQ ID NO 965
<211> LENGTH: 22
<212> TYPE: DNA
<213> ORGANISM: Artificial Sequence
<220> FEATURE:
<223> OTHER INFORMATION: Primer

<400> SEQUENCE: 965
gtggaagaag tcgacactgg aa                                            22

<210> SEQ ID NO 966
<211> LENGTH: 33
<212> TYPE: DNA
<213> ORGANISM: Artificial Sequence
<220> FEATURE:
<223> OTHER INFORMATION: Primer

<400> SEQUENCE: 966
cacactcata ggaggactac atatatatgt aca                                33

<210> SEQ ID NO 967
<211> LENGTH: 26
<212> TYPE: DNA
<213> ORGANISM: Artificial Sequence
<220> FEATURE:
<223> OTHER INFORMATION: Primer

<400> SEQUENCE: 967
agaccataag agtgagaagt ggaagt                                        26

<210> SEQ ID NO 968
<211> LENGTH: 29
<212> TYPE: DNA
<213> ORGANISM: Artificial Sequence
<220> FEATURE:
<223> OTHER INFORMATION: Primer
```

-continued

```
<400> SEQUENCE: 968
actctcacaa aatatgctac ttctgctag                                29

<210> SEQ ID NO 969
<211> LENGTH: 30
<212> TYPE: DNA
<213> ORGANISM: Artificial Sequence
<220> FEATURE:
<223> OTHER INFORMATION: Primer

<400> SEQUENCE: 969
gtctctgaac attcctgttt ttaaaaggaa                               30

<210> SEQ ID NO 970
<211> LENGTH: 30
<212> TYPE: DNA
<213> ORGANISM: Artificial Sequence
<220> FEATURE:
<223> OTHER INFORMATION: Primer

<400> SEQUENCE: 970
cacactcaaa tgaggactac atgtatatgt                               30

<210> SEQ ID NO 971
<211> LENGTH: 23
<212> TYPE: DNA
<213> ORGANISM: Artificial Sequence
<220> FEATURE:
<223> OTHER INFORMATION: Primer

<400> SEQUENCE: 971
ggtgcctcat ccatcttctt ctc                                      23

<210> SEQ ID NO 972
<211> LENGTH: 30
<212> TYPE: DNA
<213> ORGANISM: Artificial Sequence
<220> FEATURE:
<223> OTHER INFORMATION: Primer

<400> SEQUENCE: 972 gctacttttta gcatagatgg atgtttgaag                              30

<210> SEQ ID NO 973
<211> LENGTH: 22
<212> TYPE: DNA
<213> ORGANISM: Artificial Sequence
<220> FEATURE:
<223> OTHER INFORMATION: Primer

<400> SEQUENCE: 973
tcaagagcac agctagcatg tg                                       22

<210> SEQ ID NO 974
<211> LENGTH: 22
<212> TYPE: DNA
<213> ORGANISM: Artificial Sequence
<220> FEATURE:
<223> OTHER INFORMATION: Primer

<400> SEQUENCE: 974
aggaatgccc tttgacctca tg                                       22

<210> SEQ ID NO 975
```

```
<211> LENGTH: 22
<212> TYPE: DNA
<213> ORGANISM: Artificial Sequence
<220> FEATURE:
<223> OTHER INFORMATION: Primer

<400> SEQUENCE: 975
gcaccttgtc ggtaaggaac ag                                              22

<210> SEQ ID NO 976
<211> LENGTH: 22
<212> TYPE: DNA
<213> ORGANISM: Artificial Sequence
<220> FEATURE:
<223> OTHER INFORMATION: Primer

<400> SEQUENCE: 976
cacctgggtc cctgttctta ac                                              22

<210> SEQ ID NO 977
<211> LENGTH: 24
<212> TYPE: DNA
<213> ORGANISM: Artificial Sequence
<220> FEATURE:
<223> OTHER INFORMATION: Primer

<400> SEQUENCE: 977
acagggagtt caagtcagaa aagg                                            24

<210> SEQ ID NO 978
<211> LENGTH: 21
<212> TYPE: DNA
<213> ORGANISM: Artificial Sequence
<220> FEATURE:
<223> OTHER INFORMATION: Primer

<400> SEQUENCE: 978
acgactcagc ttcttccctc t                                               21

<210> SEQ ID NO 979
<211> LENGTH: 25
<212> TYPE: DNA
<213> ORGANISM: Artificial Sequence
<220> FEATURE:
<223> OTHER INFORMATION: Primer

<400> SEQUENCE: 979
tgctgaattg ctcattcatc tttgc                                           25

<210> SEQ ID NO 980
<211> LENGTH: 23
<212> TYPE: DNA
<213> ORGANISM: Artificial Sequence
<220> FEATURE:
<223> OTHER INFORMATION: Primer

<400> SEQUENCE: 980
cagaggattt ccctgcctga atc                                             23

<210> SEQ ID NO 981
<211> LENGTH: 23
<212> TYPE: DNA
<213> ORGANISM: Artificial Sequence
<220> FEATURE:
<223> OTHER INFORMATION: Primer

<400> SEQUENCE: 981
```
cagaaatccc tgatgctcag gaa                                              23

<210> SEQ ID NO 982
<211> LENGTH: 22
<212> TYPE: DNA
<213> ORGANISM: Artificial Sequence
<220> FEATURE:
<223> OTHER INFORMATION: Primer

<400> SEQUENCE: 982
ggtctgagca agccacactt ac                                               22

<210> SEQ ID NO 983
<211> LENGTH: 21
<212> TYPE: DNA
<213> ORGANISM: Artificial Sequence
<220> FEATURE:
<223> OTHER INFORMATION: Primer

<400> SEQUENCE: 983
caccgacttc atcccttcct t                                                21

<210> SEQ ID NO 984
<211> LENGTH: 22
<212> TYPE: DNA
<213> ORGANISM: Artificial Sequence
<220> FEATURE:
<223> OTHER INFORMATION: Primer

<400> SEQUENCE: 984
gttgacatgg cagtctctgg at                                               22

<210> SEQ ID NO 985
<211> LENGTH: 29
<212> TYPE: DNA
<213> ORGANISM: Artificial Sequence
<220> FEATURE:
<223> OTHER INFORMATION: Primer

<400> SEQUENCE: 985
agcttaggaa atggtattga gaaatctgg                                        29

<210> SEQ ID NO 986
<211> LENGTH: 25
<212> TYPE: DNA
<213> ORGANISM: Artificial Sequence
<220> FEATURE:
<223> OTHER INFORMATION: Primer

<400> SEQUENCE: 986
cagaatgaac aaaactgtgg ctgtt                                            25

<210> SEQ ID NO 987
<211> LENGTH: 24
<212> TYPE: DNA
<213> ORGANISM: Artificial Sequence
<220> FEATURE:
<223> OTHER INFORMATION: Primer

<400> SEQUENCE: 987
ttaccggcag aaccaagagc tcaa                                             24

<210> SEQ ID NO 988
<211> LENGTH: 22
<212> TYPE: DNA

```
<213> ORGANISM: Artificial Sequence
<220> FEATURE:
<223> OTHER INFORMATION: Primer

<400> SEQUENCE: 988
cgtgggcaac tccaacaatt ac                                              22

<210> SEQ ID NO 989
<211> LENGTH: 19
<212> TYPE: DNA
<213> ORGANISM: Artificial Sequence
<220> FEATURE:
<223> OTHER INFORMATION: Primer

<400> SEQUENCE: 989
gaggcgtgca agaaggtct                                                  19

<210> SEQ ID NO 990
<211> LENGTH: 25
<212> TYPE: DNA
<213> ORGANISM: Artificial Sequence
<220> FEATURE:
<223> OTHER INFORMATION: Primer

<400> SEQUENCE: 990
gtgttcgtgc tgaataagaa gaaca                                           25

<210> SEQ ID NO 991
<211> LENGTH: 30
<212> TYPE: DNA
<213> ORGANISM: Artificial Sequence
<220> FEATURE:
<223> OTHER INFORMATION: Primer

<400> SEQUENCE: 991
ctttgccatt ttaccacttt gtcagattat                                      30

<210> SEQ ID NO 992
<211> LENGTH: 30
<212> TYPE: DNA
<213> ORGANISM: Artificial Sequence
<220> FEATURE:
<223> OTHER INFORMATION: Primer

<400> SEQUENCE: 992
gtattagtcc tgaagattca gaatgaccat                                      30

<210> SEQ ID NO 993
<211> LENGTH: 30
<212> TYPE: DNA
<213> ORGANISM: Artificial Sequence
<220> FEATURE:
<223> OTHER INFORMATION: Primer

<400> SEQUENCE: 993
gtgcaacaga ttagtcataa gttcttgttt                                      30

<210> SEQ ID NO 994
<211> LENGTH: 30
<212> TYPE: DNA
<213> ORGANISM: Artificial Sequence
<220> FEATURE:
<223> OTHER INFORMATION: Primer

<400> SEQUENCE: 994
gacaggaaag attttgactg aatgaaactt                                      30
```

<210> SEQ ID NO 995
<211> LENGTH: 28
<212> TYPE: DNA
<213> ORGANISM: Artificial Sequence
<220> FEATURE:
<223> OTHER INFORMATION: Primer

<400> SEQUENCE: 995
acagaaatcc atggtgtatt tttggaaa                                28

<210> SEQ ID NO 996
<211> LENGTH: 24
<212> TYPE: DNA
<213> ORGANISM: Artificial Sequence
<220> FEATURE:
<223> OTHER INFORMATION: Primer

<400> SEQUENCE: 996
gctgaacata accgtactcg agtt                                    24

<210> SEQ ID NO 997
<211> LENGTH: 30
<212> TYPE: DNA
<213> ORGANISM: Artificial Sequence
<220> FEATURE:
<223> OTHER INFORMATION: Primer

<400> SEQUENCE: 997
tctttcccag atagcttgag taatgttttt                              30

<210> SEQ ID NO 998
<211> LENGTH: 21
<212> TYPE: DNA
<213> ORGANISM: Artificial Sequence
<220> FEATURE:
<223> OTHER INFORMATION: Primer

<400> SEQUENCE: 998
ctacatcctg gacgacggtt t                                       21

<210> SEQ ID NO 999
<211> LENGTH: 18
<212> TYPE: DNA
<213> ORGANISM: Artificial Sequence
<220> FEATURE:
<223> OTHER INFORMATION: Primer

<400> SEQUENCE: 999
tgcgagcact tctgcgtt                                           18

<210> SEQ ID NO 1000
<211> LENGTH: 20
<212> TYPE: DNA
<213> ORGANISM: Artificial Sequence
<220> FEATURE:
<223> OTHER INFORMATION: Primer

<400> SEQUENCE: 1000
cagtgggtta cgggagacaa                                         20

<210> SEQ ID NO 1001
<211> LENGTH: 19
<212> TYPE: DNA
<213> ORGANISM: Artificial Sequence
<220> FEATURE:

<223> OTHER INFORMATION: Primer

<400> SEQUENCE: 1001
cagcggcaag aagtgtctg                                         19

<210> SEQ ID NO 1002
<211> LENGTH: 30
<212> TYPE: DNA
<213> ORGANISM: Artificial Sequence
<220> FEATURE:
<223> OTHER INFORMATION: Primer

<400> SEQUENCE: 1002
cctacacaaa acagagcagg taaatatttc                             30

<210> SEQ ID NO 1003
<211> LENGTH: 30
<212> TYPE: DNA
<213> ORGANISM: Artificial Sequence
<220> FEATURE:
<223> OTHER INFORMATION: Primer

<400> SEQUENCE: 1003 cttttaaca cagttggacc atcaacttaa                              30

<210> SEQ ID NO 1004
<211> LENGTH: 29
<212> TYPE: DNA
<213> ORGANISM: Artificial Sequence
<220> FEATURE:
<223> OTHER INFORMATION: Primer

<400> SEQUENCE: 1004
cacatttcat ctacacaagt cttcacttg                              29

<210> SEQ ID NO 1005
<211> LENGTH: 27
<212> TYPE: DNA
<213> ORGANISM: Artificial Sequence
<220> FEATURE:
<223> OTHER INFORMATION: Primer

<400> SEQUENCE: 1005
tttggatgaa catgtatcta cttgcgt                                27

<210> SEQ ID NO 1006
<211> LENGTH: 22
<212> TYPE: DNA
<213> ORGANISM: Artificial Sequence
<220> FEATURE:
<223> OTHER INFORMATION: Primer

<400> SEQUENCE: 1006
gtaatcgcaa agcttgggtt ga                                     22

<210> SEQ ID NO 1007
<211> LENGTH: 29
<212> TYPE: DNA
<213> ORGANISM: Artificial Sequence
<220> FEATURE:
<223> OTHER INFORMATION: Primer

<400> SEQUENCE: 1007
tcctatgatc aggtgattag tgacttgaa                              29

```
<210> SEQ ID NO 1008
<211> LENGTH: 23
<212> TYPE: DNA
<213> ORGANISM: Artificial Sequence
<220> FEATURE:
<223> OTHER INFORMATION: Primer

<400> SEQUENCE: 1008
atggaaggtt tctgcatcag tga                                          23

<210> SEQ ID NO 1009
<211> LENGTH: 33
<212> TYPE: DNA
<213> ORGANISM: Artificial Sequence
<220> FEATURE:
<223> OTHER INFORMATION: Primer

<400> SEQUENCE: 1009
gctccataaa tttctctttc ctcttaaatc att                               33

<210> SEQ ID NO 1010
<211> LENGTH: 25
<212> TYPE: DNA
<213> ORGANISM: Artificial Sequence
<220> FEATURE:
<223> OTHER INFORMATION: Primer

<400> SEQUENCE: 1010
aagggaatgt cttacctagg tctgt                                        25

<210> SEQ ID NO 1011
<211> LENGTH: 26
<212> TYPE: DNA
<213> ORGANISM: Artificial Sequence
<220> FEATURE:
<223> OTHER INFORMATION: Primer

<400> SEQUENCE: 1011
ccttcccttc tctcttatcc aattgc                                       26

<210> SEQ ID NO 1012
<211> LENGTH: 24
<212> TYPE: DNA
<213> ORGANISM: Artificial Sequence
<220> FEATURE:
<223> OTHER INFORMATION: Primer

<400> SEQUENCE: 1012
tcaagatgcc catgatgaag agtg                                         24

<210> SEQ ID NO 1013
<211> LENGTH: 29
<212> TYPE: DNA
<213> ORGANISM: Artificial Sequence
<220> FEATURE:
<223> OTHER INFORMATION: Primer

<400> SEQUENCE: 1013
gaccacaata gcattaaact tacaaagct                                    29

<210> SEQ ID NO 1014
<211> LENGTH: 25
<212> TYPE: DNA
```

```
<213> ORGANISM: Artificial Sequence
<220> FEATURE:
<223> OTHER INFORMATION: Primer

<400> SEQUENCE: 1014
cggttgaaaa tccttgaatt tgcca                                              25
```

METHOD OF DIAGNOSIS OF COMPLEMENT-MEDIATED THROMBOTIC MICROANGIOPATHIES

CROSS-REFERENCE TO RELATED APPLICATIONS

The present application claims the benefit of U.S. Provisional Patent Application No. 61/972,568 titled "Method for Diagnosis of Complement-Mediated Thrombotic Microangiopathies," filed on Mar. 31, 2014, the contents of which are incorporated in this disclosure by reference in their entirety.

BACKGROUND

Thrombotic microangiopathy (TMA) is a disease that is caused by injury to endothelial cells that results in thrombosis in capillaries and arterioles. One of the categories of thrombotic microangiopathy is complement-mediated. Complement-mediated thrombotic microangiopathy (CMTM) is also known as atypical hemolytic-uremic syndrome (aHUS), complement-mediated hemolytic uremic syndrome and thrombotic microangiopathies of unknown etiologies. aHUS occurs when the body's overactive complement system attacks the cells that line blood vessels in the kidneys, causing inflammation and the formation of abnormal clots. aHUS is a life threatening, progressive, genetic disease that is characterized by three major features: microangiopatic hemolytic anemia (MAHA), thrombocytopenia and kidney injury, which can lead to kidney damage, kidney failure and end-stage renal disease. In addition, a patient's central nervous system may become involved, and gastrointestinal symptoms may also be present.

Fifty percent of patients diagnosed with aHUS will die, develop end-stage renal disease or suffer permanent kidney injury within one year after diagnosis despite plasma exchange or plasma infusion therapy. aHUS is considered a rare disease (1 in 500,000 in the general population of the United States). However, some reports have cited a prevalence as high as 1 in 150,000 in certain pediatric populations.

Development of aHUS occurs through a combination of environmental and genetic factors. aHUS most frequently occurs following a triggering event such as organ transplantation, pregnancy, malignant hypertension, autoimmune disorders, sepsis, or malignancy. The genes associated with aHUS regulate the complement system, which provides the instructions for making proteins involved in the body's immune response. The proteins destroy bacteria and viruses, trigger inflammation, and remove debris from cells and tissues. The complement system must be carefully regulated so that it only targets unwanted material and does not attack the body's healthy cells. The regulatory proteins associated with aHUS protect healthy cells by preventing activation of the complement system when it is not needed.

Mutations in at least seven genes appear to be associated with an increase in the risk of developing aHUS. The most common genetic mutation is found in the complement factor H (CFH) gene. Other genes involved include the Membrane cofactor protein (CD46), Complement factor 1 (CF1), Complement component 3 (C3), Complement factor B (CFB), Complement factor H-related proteins including CFHR1, CFHR3, CFHR4, CFHR5, Thrombomodulin (THBD), Plasminogen (PLG), and Diacyl glycerol kinase (DGKE).

As a thrombotic microangiopathy, aHUS presents with clinical features that are nearly identical to thrombotic thrombocytopenic purpura and hemolytic uremic syndrome, making immediate laboratory differentiation essential.

Current genetic methods for confirming a clinical diagnoses of CMTM or aHUS takes at least 28 days. However, since aHUS is a progressive disease, a faster turnaround time is required for faster patient diagnosis and management.

Therefore, there is a need for an improved method to rapidly identify mutations, polymorphisms and other variants of genes involved with CMTM in order to identify, diagnosis, and assess the risk of an individual in developing CMTM.

SUMMARY

According to one embodiment of the present invention, there is provided a method of identifying a patient's risk for developing complement-mediated thrombic microangiopathy, where the method contains the steps of: obtaining a sample of genetic material from a patient; amplification of the sample of genetic material using primers specific for complement-mediated thrombic microangiopathy; determining the genetic sequence of the amplified genetic material of step (b); comparing the sequence of the amplified genetic material with a normal reference sequence; and identifying variations between the sample amplified genetic material and the normal reference sequence. A variation between the sample amplified genetic material and the normal reference sequence is indicative of a risk for the patient for developing complement-mediated thrombic microangiopathy. The variation between the sample amplified genetic material and the normal reference sequence can be a mutation, a polymorphism, a deletion or the like. It is contemplated that at least twelve genes are amplified in the sample of genetic material. The twelve genes can include Membrane cofactor protein (CD46), Complement factor 1 (CF1), Complement component 3 (C3), Complement factor B (CFB), Complement factor H-related proteins including CFHR1, CFHR3, CFHR4, CFHR5, Thrombomodulin (THBD), Plasminogen (PLG), and Diacyl glycerol kinase (DGKE). The method can indicate a risk of the patent's developing aHUS. The method can be performed so that the risk for the patient for developing complement-mediated thrombic microangiopathy is identified within 48 hours or 5 days from receipt of the sample of genetic material from the patient.

According to another embodiment, a method for diagnosing complement-mediated thrombic microangiopathy in a patient by analyzing a patient's DNA sample for the presence or absence of variations in the patient's DNA sample is described. The method includes analysis of the DNA sequence of the genes comprising CFH, MCP, CFI, C3, CFB, CFHR1, CFHR3, CFHR4, CFHR5, THBD, PLG, and DGKE. If one or more variations in the genes comprising CFH, MCP, CFI, C3, CFB, CFHR1, CFHR3, CFHR4, CFHR5, THBD, PLG, and DGKE is detected, the patient is diagnosed with complement-mediated thrombic microangiopathy. The variation in the patient's DNA sample can be a mutation, a polymorphism or a deletion. The diagnosis is made within 48 hours or 5 days from receipt of the sample of genetic material from the patient.

In another embodiment, a method for determining the risk of complement-mediated thrombic microangiopathy is described. The method includes assessing a DNA sequence from 12 genes consisting of CFH, CD46, CFI, C3, CFB, CFHR1, CFHR3, CFHR4, CFHR5, THBD, PLG, and DGKE in the patient's DNA sample by amplifying the DNA sequences. The DNA sequences are selected from the group comprising SEQ ID NO. 1 through SEQ ID NO. 1014. The method also includes comparing the amplified DNA sequences with DNA sequences from a normal control subject. Any variations in the patient's DNA sequence as compared to the normal control subject indicates that the subject has a risk of complement-mediated thrombic microangiopathy. The variation in the subject's DNA sample can be a mutation, a polymorphism, or a deletion. The determination can be made within 48 hours, or 5 days, from receipt of the sample of genetic material from the patient.

DESCRIPTION

According to one embodiment of the present invention, there is provided a method for rapid detection of mutations, deletions and polymorphisms that have been previously reported as associated with complement-mediated TMAs. The time for diagnosing or determining the patient's risk of developing a complement-mediated TMA using the method of the present invention can be as early as 48 hours after receipt of the patient's sample. The method of the present invention can also be used to diagnose or determine complement-mediated TMA within 5 days after receipt of the patient's sample. The method involves analysis of 12 genes, including: Complement factor H (CFH), Membrane cofactor protein (CD46), Complement factor 1 (CF1), Complement component 3 (C3), Complement factor B (CFB), Complement factor H-related proteins including CFHR1, CFHR3, CFHR4, CFHR5, Thrombomodulin (THBD), Plasminogen (PLG), and Diacyl glycerol kinase (DGKE), referred to herein as the "genes of interest."

As used in this disclosure, except where the context requires otherwise, the term "comprise" and variations of the term, such as "comprising," "comprises" and "comprised" are not intended to exclude other additives, components, integers or steps. Thus, throughout this specification, unless the context requires otherwise, the words "comprise," "comprising" and the like, are to be construed in an inclusive sense as opposed to an exclusive sense, that is to say, in the sense of "including, but not limited to."

As used in this disclosure, except where the context requires otherwise, the method steps disclosed and shown are not intended to be limiting nor are they intended to indicate that each step is essential to the method or that each step must occur in the order disclosed.

As used herein, "sample" refers to any sample that can be from or derived a human patient, e.g., bodily fluids (blood, saliva, urine etc.), biopsy, tissue, and/or waste from the patient. Thus, tissue biopsies, stool, sputum, saliva, blood, lymph, tears, sweat, urine, vaginal secretions, or the like can be used in the method, as can essentially any tissue of interest that contains the appropriate nucleic acids. The sample may be in a form taken directly from the patient. Preferably, the sample may be at least partially purified to remove at least some non-nucleic acid material.

The term "DNA sequence" as used herein refers to chromosomal sequence as well as to cDNA sequence.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An "amplicon" is an amplified nucleic acid, e.g., a nucleic acid that is produced by amplifying a template nucleic acid by any available amplification method (e.g., PCR, LCR, transcription, or the like).

A "gene" is one or more sequence(s) of nucleotides in a genome that together encode one or more expressed molecules, e.g., an RNA. The gene can include coding sequences that are transcribed into RNA which may then be translated into a polypeptide sequence, and can include associated structural or regulatory sequences that aid in replication or expression of the gene.

A "set" or "pool" of primers or amplicons refers to a collection or group of primers or amplicons, or the data derived therefrom, used for a common purpose, e.g., identifying an individual with a specified genotype (e.g., risk of developing aHUS). Frequently, data corresponding to the primers or amplicons, or derived from their use, is stored in an electronic medium.

A set of oligonucleotide nucleic acid sequences, or primers, have been identified that facilitates the rapid identification of mutations, polymorphisms, and other variants of Complement-mediated thrombotic microangiopathy (CMTM). This set of oligonucleotides detects sequences that are indicative of the risk that an individual has for developing CMTM.

The primers are used to amplify certain genes involved with CMTM, including CFH, CD46, CF1, C3, CFB, CFHR1, CFHR3, CFHR4, CFHR5, THBD, PLG, and DGKE. The list of primers is set forth in Appendix A.

The DNA used in the method of the invention can be extracted from whole blood, extracted from a buccal swab, or it can be from previously extracted genomic DNA samples. Preferably, the DNA is extracted from whole blood using known techniques. Prior to analysis, extracted DNA can be stored for one month at room temperature or 2-8° C. For longer storage of up to 2 years, DNA can be stored frozen at <−20° C. to minimize the degradation of nucleic acid.

After extraction, the DNA sample is measured and assessed for purity. 30 ng of genomic DNA, at a minimum concentration of 1.7 ng/µL, is required for analysis. The concentration of purified DNA should preferably be adjusted to 2 ng/µL to 25 ng/µL prior to analysis. Optimal DNA purity is an absorbance ratio ($A_{260}/A_{280}$) of 1.80 or greater (typical range is 1.60 to 2.00).

The extracted sample DNA is then amplified. A well-known amplification method is the polymerase chain reaction (PCR). In PCR, a characteristic piece of the particular nucleotide sequence of interest is amplified with specific primers. If the primer finds its target site, a sequence of the genetic material undergoes a million-fold proliferation.

During the PCR process, the DNA generated is used as a template for replication. This sets in motion a chain reaction in which the DNA template is exponentially amplified. PCR can amplify a single or few copies of a piece of DNA by several orders of magnitude, generating millions or more copies of the DNA piece. PCR can be extensively modified to perform a wide array of genetic manipulations, as known by one of skill in the art.

In the method described herein, one primer pool aliquot is used per sample. The primer pool aliquot contains a minimum of 93 primer sets directed towards the 12 genes of interest, as listed in Appendix A.

Following standard techniques, the amplified sequences, or amplicons, are purified and a library is made with the purified amplicons. The library contains multiple sequences from different areas of the 12 genes of interest. The library made from the amplicons is then amplified and sequenced.

The DNA sequence of the library may be determined by any suitable method, such as multiplex sequencing, as is known by one of skill in the art. For example, the DNA sequence may be determined by available method, including Sanger sequencing (chain termination), pH sequencing, pyrosequencing, sequencing-by-hybridization, sequencing-by-ligation, etc. Exemplary sequencing systems include 454 pyrosequencing (454 Life Sciences), Illumina (Solexa) sequencing, SOLiD (Applied Biosystems), and Ion Torrent Systems' pH sequencing system.

After sequencing, the DNA sequence of the library is mapped with one or more reference sequences to identify sequence variants. For example, the base reads are mapped against a reference sequence, which in various embodiments is presumed to be a "normal" non-disease sequence. The Human genome (Hg19) sequence is generally used as the reference sequence. A number of computerized mapping applications are known, and include GSMAPPER, ELAND, MOSAIK, and MAQ. Various other alignment tools are known, and could also be implemented to map the DNA sequence of the amplicon library.

Based on the sequence alignments and mapping results, sequence variants are identified based upon available information including for example, information from human mutational databases and other reference databases. Furthermore, any sequence variations, including aHUS-associated mutations, disease-associated polymorphisms, benign polymorphisms and other known variants of undetermined significance can be determined to be homozygous or heterozygous. Any variations in the gene analyzed as compared to the normal control gene can be classified as pathogenic, predicted pathogenic, uncertain, predicted benign or benign, as recommended by the American College of Medical Genetics (ACMG).

EXAMPLES

Example 1

The DNA was extracted from the whole blood of Patient 1 using known procedures. The extracted sample DNA was then amplified. One primer pool aliquot was used per sample. The primer pool aliquot contained 95 sets of forward and reverse primers as set forth in Appendix A. In the present example, the twelve target genes were amplified and analyzed.

Following standard techniques, the sample DNA was amplified, and the amplicons were purified. A library was then made with the purified amplicons. The library was amplified and sequenced. After sequencing, the sequence of the amplicon from the sample was compared to a reference sequence comprising the Human genome (Hg19) sequence.

In this example, a heterozygous mutation in the CFH gene was identified. The mutation was a nonsense mutation, Try957Stop, which created a premature stop codon that prevents the rest of the protein from being translated and will likely result in a functional defect. Additionally, the mutation falls within the SCR domain, which is considered to be a hotspot region for aHUS-associated mutations. Mutations in the SCR domain generally result in a failure to regulate complement at cell surfaces. Renal and/or liver transplantation may have an increased failure rate in this patient.

Example 2

The DNA was extracted from the whole blood of Patient 2 using known procedures. The extracted sample DNA was then amplified. One primer pool aliquot was used per sample. In the present example, the twelve target genes were amplified and analyzed.

Following standard techniques, the sample DNA was amplified using forward and reverse primers as set forth in Appendix A, and the amplicons were purified. A library was then made with the purified amplicons. The library was amplified and sequenced. After sequencing, the sequence of the amplicon from the sample was compared to a reference sequence comprising the Hg19 sequence.

In this example, a common polymorphism (c.184G>A, p.Val62Ile, rs800292) was detected in the CFH gene from Patient 2. This polymorphism is present in about 43% of the general population. The polymorphism was detected in detected in 48% of the total reads, indicating this donor is heterozygous for this variant. This polymorphism does not correlate with aHUS disease.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

APPENDIX A

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 1 | CTCCAAGAAGAAATACAGAAATTCTGACAG | 508 | GACTGGCAATAGTGATATAATTCAGGCATA | CFH | chr1 | 196642122 | 1.97E+08 | 1.97E+08 | 1.97E+08 |
| 2 | CCATGTTCACACCACCTCAGA | 509 | TAACCTTCACACTGAGGTGAGAA | CFH-896-900del5aa | chr1 | 196706612 | 1.97E+08 | 1.97E+08 | 1.97E+08 |
| 3 | TCTCATGGTGTGTTAGCTCACATG | 510 | TTGGTACCACTTACACTTTGAATGAAGAA | CFH | chr1 | 196709777 | 1.97E+08 | 1.97E+08 | 1.97E+08 |
| 4 | CATAAGGTACAGATGTAGAGGAAAAGAAGG | 511 | ACCTGCCTTATTCAGTAGCATTTGTAATAA | CFH | chr1 | 196697566 | 1.97E+08 | 1.97E+08 | 1.97E+08 |
| 5 | GCAATGAACCAGATCGGAAT | 512 | TGCTGATATATTCCTTAGAATGAACGATGTTT | CFH | chr1 | 196646658 | 1.97E+08 | 1.97E+08 | 1.97E+08 |
| 6 | ATTTGTAACTGTTATCAGTTGATTTGCTACT | 513 | GGCTCCTACACATTGATAACGTACTCTC | CFH | chr1 | 196712506 | 1.97E+08 | 1.97E+08 | 1.97E+08 |
| 7 | CTATGGAGATTCAGTGGAATTCAATGC | 514 | CTGGAAATGTTGAGGCATATCGTAAATTT | CFH | chr1 | 196695963 | 1.97E+08 | 1.97E+08 | 1.97E+08 |
| 8 | ATGCTAAGGACAAATAAATAACACCCACT | 515 | CGTGATTTCATCTCCAGTTCTGTGTTTAA | CFH | chr1 | 196654088 | 1.97E+08 | 1.97E+08 | 1.97E+08 |
| 9 | GTACCGTTGCCAGTCCTTCTAT | 516 | GACAGGAAAGATTTTGACTGAATGAAACTT | CFHR5 | chr1 | 196973884 | 1.97E+08 | 1.97E+08 | 1.97E+08 |
| 10 | CGTCTGTTGCCCCTATCAACA | 517 | CTTGTGGAAGGAAGATTCAGTAGTTAGTAAACTTTT | CFHR5 | chr1 | 196965205 | 1.97E+08 | 1.97E+08 | 1.97E+08 |
| 11 | CAAACTAGGATATGTAACAGCAGATGT | 518 | CCCACAAAAAGACTAAAGTTAGTAAACTTTT | CFH | chr1 | 196682958 | 1.97E+08 | 1.97E+08 | 1.97E+08 |
| 12 | GCCCAATCTTTGCAAAGGGAAT | 519 | GCCCGTTGATACCACCAAGAAATG | CPAMD1 | chr19 | 6692813 | 6692835 | 6692937 | 6692959 |
| 13 | GTAGGAAAGGCTCCCACCTTT | 520 | GAACCGAGGACCACCTAGTAGT | CPAMD1 | chr19 | 6707459 | 6707480 | 6707586 | 6707608 |
| 14 | GTCTGCTCCGATCTCTGCTTT | 521 | TCGTGCTGAATAAGAGAACAAACTGA | CPAMD1 | chr19 | 6709566 | 6709587 | 6709705 | 6709732 |
| 15 | TTTTTAACATCTTGCATTCCATTCCTTGT | 522 | CCATTTTCGACTACTGGAAATCGACAT | CD46 | chr1 | 207940240 | 2.08E+08 | 2.08E+08 | 2.08E+08 |
| 16 | AGAGGAAGAAGATTAATGTCTTAGAGAACG | 523 | TGTGTCACATTCACGGTAATTAATCTCA | CFH | chr1 | 196644895 | 1.97E+08 | 1.97E+08 | 1.97E+08 |
| 17 | TTTTTAAAATTTTTATTGCAAGTGAAACCTTGT | 524 | CCATCCATTCTTGTGTCAATGAATG | CFH | chr1 | 196658527 | 1.97E+08 | 1.97E+08 | 1.97E+08 |
| 18 | AGGAAAAATGTTATTTTCCTTATTGGAAAATGG | 525 | TCATCTATGTTACTTAGAAAGACATGAACATGC | CFH | chr1 | 196659190 | 1.97E+08 | 1.97E+08 | 1.97E+08 |
| 19 | GGGACATTACTTCATTCCCGTTGT | 526 | AAATATCAGACTCATCACACAGAGATTTTTCCA | CFH | chr1 | 196714988 | 1.97E+08 | 1.97E+08 | 1.97E+08 |
| 20 | AGAGAAAGATGGGAGAGGGTATACC | 527 | AGAGGGACCATCTCCTCTTGTC | CPAMD1 | chr19 | 6684465 | 6684490 | 6684716 | 6684738 |
| 21 | CTCCTCCTCTTACCGTACTCCTT | 528 | CTTGTCTTGGGACATTCCGAA | CPAMD1 | chr19 | 6714163 | 6714186 | 6714370 | 6714392 |
| 22 | GCTTGTGGTTGACGGTGAAGAT | 529 | ACAGGGAGTTCAAGTCAGAAAAGG | CPAMD1 | chr19 | 6718142 | 6718164 | 6718389 | 6718413 |
| 23 | TTCTCACTGGACAGCACTAGTTTTT | 530 | TCTCACATCCGTGGAATGACAAG | CPAMD1 | chr19 | 6719270 | 6719295 | 6719440 | 6719463 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 24 | CCTCAGAACCTCAGAACCTCAAC | TGTCTAGCTTTCAAAGTTCACCAATAACTTT | CPAMD1 | chr19 | 6679981 | 6680004 | 6680223 | 6680253 |
| 25 | GGGTTGCACTGTGATTCCAGA | CAACTGCCTGCTCTGTTCTA | CPAMD1 | chr19 | 6702380 | 6702401 | 6702614 | 6702635 |
| 26 | CCCACATGAGGTAGTGTTTCTTCT | AGCTGTCCAATGACTTTGACGA | CPAMD1 | chr19 | 6678196 | 6678220 | 6678417 | 6678439 |
| 27 | CCTGAACTTCAGCATGCCATCT | TGATCCTTACTAACGTGACAGCAATG | CPAMD1 | chr19 | 6686706 | 6686728 | 6686950 | 6686976 |
| 28 | CTTCCAGGGTGACCTTGTCATC | GGTCTGAGCAAGCCACACTTAC | CPAMD1 | chr19 | 6679174 | 6679196 | 6679367 | 6679389 |
| 29 | CCACGCAGGAGTCCTTGAC | CCCAGATCATGAACAAGGGCA | CPAMD1 | chr19 | 6710654 | 6710673 | 6710840 | 6710861 |
| 30 | CATGAGGTCAAAGGGCATTCCT | GAGGGAGGAGGTCTAATCCTGAG | CPAMD1 | chr19 | 6712518 | 6712540 | 6712674 | 6712697 |
| 31 | TCCAGTAGATGATGAGGGTGTT | AGGATGCCACTATGTCTATATTGGACAT | CPAMD1 | chr19 | 6681955 | 6681978 | 6682198 | 6682226 |
| 32 | CCCGAGCCATCCTCAATCT | GGGAGATCCCATTCTCCAGG | CPAMD1 | chr19 | 6713309 | 6713328 | 6713557 | 6713577 |
| 33 | CAAGGCTTGAACACCATGAAG | CTCTAGTAGGTTCTAGGCCACATTTTG | CPAMD1 | chr19 | 6685130 | 6685152 | 6685254 | 6685281 |
| 34 | GAACAGGTGAGGTTTCAAGTAGGA | ACATCATCGGGAAGGACACTTG | CPAMD1 | chr19 | 6677751 | 6677775 | 6678004 | 6678026 |
| 35 | TCTTTAGCGCACGATGACATAT | GGAAATCCGAGCCGTTCTCTAC | CPAMD1 | chr19 | 6697437 | 6697460 | 6697689 | 6697711 |
| 36 | GGTTGTCTGAAGGCCAGCT | CACCTCCTCGTTCTGATCCC | CPAMD1 | chr19 | 6693467 | 6693486 | 6693659 | 6693679 |
| 37 | GGAAGAGAAAGTGCGGGTTAA | GGGTAAATGACCTGGGTTTAGTGA | CPAMD1 | chr19 | 6696288 | 6696310 | 6696532 | 6696556 |
| 38 | GCAGGAGGAAGTTGACGTTGAG | CAATTCCCAGGTCTCAGGGATTC | CPAMD1 | chr19 | 6711044 | 6711066 | 6711261 | 6711284 |
| 39 | CCCTCAAACTACTGTAGTGTAGAAAAGA | GTGTAAAGGGTGTAAAGGAGGCAA | CD46 | chr1 | 207932873 | 2.08E+08 | 2.08E+08 | 2.08E+08 |
| 40 | ATTTTATCCCACTTGTTATGCTACTCGT | GCCAATATCTCTTTGCTCCAGGTTATTGATA | CD46 | chr1 | 207963513 | 2.08E+08 | 2.08E+08 | 2.08E+08 |
| 41 | TTTTTCCTAGGATATCCTAAACCTGAGGA | CCCTACCAAGGATCCTATGTTTGG | CD46 | chr1 | 207956626 | 2.08E+08 | 2.08E+08 | 2.08E+08 |
| 42 | GTCATTCAGGTTTAGTAGCTTCTTCCT | TAAGTGAACATTCACCAGAAATTTGAAGGA | CD46 | chr1 | 207940987 | 2.08E+08 | 2.08E+08 | 2.08E+08 |
| 43 | GCCAAGGGCCTTTCTGTTTT | GGCAAGAGGAGTATATAGAAGTATCCTTT | CD46 | chr1 | 207930248 | 2.08E+08 | 2.08E+08 | 2.08E+08 |
| 44 | GCTTCCAGCTGCTTTGCATATG | GTTCAAAGCTCACTTGACATTAAGTACATT | CFI | chr4 | 110685736 | 1.11E+08 | 1.11E+08 | 1.11E+08 |
| 45 | GACAGAATCTATATTGCCTCTGTGACT | CGCTGATGTGGTTTGTTGTTATACACAGA | CFI | chr4 | 110682548 | 1.11E+08 | 1.11E+08 | 1.11E+08 |
| 46 | TAGCGGATGAAAATATGAGGAGAATGAAC | CATTCCAAGCCAGTATCAATGCA | CFI | chr4 | 110681252 | 1.11E+08 | 1.11E+08 | 1.11E+08 |
| 47 | GTGCTAGGAAAATTAGCTCCTATACATTTCT | ACTACAATGCAGGCACTTACCAAAA | CFI | chr4 | 110667292 | 1.11E+08 | 1.11E+08 | 1.11E+08 |
| 48 | TTTAGGCTGTTTCTCGGCAGTT | TGTGGCATAGATAATCAAGAGTGTGTT | CFI | chr4 | 110670605 | 1.11E+08 | 1.11E+08 | 1.11E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 49 | ATTTGTTGCTGACTATAGAGTGGCAT | TTTCAAAAGAATACCTGGAGTGGAAAAGA | CFI | chr4 | 110722925 | 1.11E+08 | 1.11E+08 | 1.11E+08 |
| 50 | CCGTTTTATTTCCATTAAATGGAACTCTT | GTGTTTACACCAAAGTGGCCAATTAT | CFI | chr4 | 110661981 | 1.11E+08 | 1.11E+08 | 1.11E+08 |
| 51 | GGAATGTGTTCCTTCCTTTTGTGAAAA | TCTTTAAATAATTAGCAAAACTGAGAGAGTGT | CFHR5 | chr1 | 196953089 | 1.97E+08 | 1.97E+08 | 1.97E+08 |
| 52 | TTTTAAGTGATGGTCCAACTGTGTT | ATCAACAGCTTAGAATTGGATTGGGA | DGKE | chr17 | 54939400 | 54939427 | 54939645 | 54939671 |
| 53 | CTTTTCATCAGCATCTAGTCTACCATAAGG | AAGTCTTCATATAATCCAGAGACCACCTA | DGKE | chr17 | 54935814 | 54935844 | 54936060 | 54936087 |
| 54 | CTAGGGACAAGAAAAGTACATTCCACA | AGTCTTCACTTGTTAACCAATTATGGCTAA | DGKE | chr17 | 54926052 | 54926079 | 54926252 | 54926282 |
| 55 | AGGGTGCCTGGCATATTGTTAAA | GTACAGAGTTGTAGGGCTTTGATAGG | DGKE | chr17 | 54925142 | 54925165 | 54925306 | 54925332 |
| 56 | TGCATATATTTTATTTGCCAAATGTTATGGT | TTCTCCAAAATCACATTTTCATTCTTTAAACT | DGKE | chr17 | 54921239 | 54921270 | 54921425 | 54921458 |
| 57 | ACCAGGTCTAGGTCTCTGGAGTTT | GGTGGTCACACCTGAAGAGAAA | CFB | chr6 | 31913885 | 31913907 | 31914138 | 31914160 |
| 58 | AAATGGCCATAAGAGATGGTGTGTT | GATCTGTAGAAAGTGGGAGGTGTT | CFB | chr6 | 31917997 | 31918021 | 31918227 | 31918251 |
| 59 | TATCAGTCAGTGAGAGCGTCCAGAT | GCCAGGCATCATCTCTTCCTATT | CFB | chr6 | 31918543 | 31918565 | 31918790 | 31918813 |
| 60 | GAGGAGTGAGTCCCTATGCTGA | AGGCTCTGCCTACCTCGAATTA | CFB | chr6 | 31919211 | 31919233 | 31919464 | 31919486 |
| 61 | GTTTTCGCACTCGTCGATGT | CTTCAGAGCCAACTGCGAGTA | THBD | chr20 | 23028800 | 23028820 | 23029014 | 23029035 |
| 62 | GGGTTGGGAACGCAGAAGT | TCGGCTTACAGCTAATGTGCA | THBD | chr20 | 23029242 | 23029261 | 23029468 | 23029489 |
| 63 | GAAGTGGAACTCGCAGAGGAA | GTTACGGGAGACAACAACACA | THBD | chr20 | 23029628 | 23029649 | 23029789 | 23029811 |
| 64 | AGAGTCCAATCACCGAACTCT | CGGTTGAAAATCCTTGAATTTGCCA | PLG | chr6 | 161173232 | 1.61E+08 | 1.61E+08 | 1.61E+08 |
| 65 | AATCTGTCTGCTAATACAGAAAAGAGAACA | GGTAGCTCTGTTCCATCACCATG | PLG | chr6 | 161143306 | 1.61E+08 | 1.61E+08 | 1.61E+08 |
| 66 | CTCAATGTTTGCTCTTGAAAAAGAGTCT | ACTGACACATGTTTCTTTTGATTTCAAGA | PLG | chr6 | 161137596 | 1.61E+08 | 1.61E+08 | 1.61E+08 |
| 67 | GTCATGACAATTAGACATTGACATTGATTT | AAAATTTGTGAGTAAATTACTTGCCATCTGAATT | PLG | chr6 | 161127371 | 1.61E+08 | 1.61E+08 | 1.61E+08 |
| 68 | GACTATGCTGTGCAGACCTTCA | CTCACAGACACAGAGGGACAACTT | PLG | chr6 | 161132038 | 1.61E+08 | 1.61E+08 | 1.61E+08 |
| 69 | ATGGCACAGAGGTTACCTGAAG | CCCATAAAAACCCAGACATAAAGCAAA | PLG | chr6 | 161160034 | 1.61E+08 | 1.61E+08 | 1.61E+08 |
| 70 | TGTAAACCAGGATATGCAACAGCA | CATCTCAAAGAGAGGAACGAAGTTGA | CFHR3 | chr1 | 196757437 | 1.97E+08 | 1.97E+08 | 1.97E+08 |
| 71 | GTGCACCGCCTGTTTCTT | CTTGCTCTTGCGGAAGATGTC | DGKE | chr17 | 54912110 | 54912129 | 54912312 | 54912333 |
| 72 | GTATCCCTGCCTTAGCCAGTTTA | CCAAACACATAGACTCTGAGGGATA | CFB | chr6 | 31916953 | 31916977 | 31917186 | 31917212 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 73 | GGAATGCGCTGTTTCTCAGTGA | GCAGTGGAAAGAGATCTCATCACTC | CFB | chr6 | 31914680 | 31914702 | 31914853 | 31914878 |
| 74 | CCCAGGAAAATCTCCAGGTCCTA | CATATGTCACTAGACCATATCTTGGCTT | CFB | chr6 | 31915954 | 31915977 | 31916168 | 31916196 |
| 75 | GCTTCAGTGCTTACCTCGATGT | GTAGGATGGAAGACCAGGATCTGA | CFB | chr6 | 31915087 | 31915109 | 31915323 | 31915347 |
| 76 | CCCTAGCTTCATGGTAGTGCA | AGACATACAAAGCTAGATATTACATGAAGTTAC | CFHR3 | chr1 | 196743893 | 1.97E+08 | 1.97E+08 | 1.97E+08 |
| 77 | GGATGCATTTTATTTGCTCATGAAAGAGA | CCGACACACTCTTGAAATGATAGAAT | CFHR3 | chr1 | 196762381 | 1.97E+08 | 1.97E+08 | 1.97E+08 |
| 78 | GTACATTATTTTTGGATGTTTATGCGATCT | CTTTCTCCGTACATGTAACTGTGGT | CFHR3 | chr1 | 196748803 | 1.97E+08 | 1.97E+08 | 1.97E+08 |
| 79 | AAAGTGCTGTGTTTGTTTGTATTGCCTTAT | AACTGATGAAGCTGGAGCATATACTG | CFHR1 | chr1 | 196799542 | 1.97E+08 | 1.97E+08 | 1.97E+08 |
| 80 | GTAATTCTTCAGTTTTATGTTATTTCCCAGCA | GTCCAAAATGATTTTGAAGGAGACACAAA | CFHR1 | chr1 | 196794575 | 1.97E+08 | 1.97E+08 | 1.97E+08 |
| 81 | GATCCGTGTGTAATATCCCGAGAAATTA | CTAAAGTTCTGAATAAAGGTGCATTTTATGA | CFHR1 | chr1 | 196800925 | 1.97E+08 | 1.97E+08 | 1.97E+08 |
| 82 | GACTGTGTTTCTTTCCTTTGTGGAAAA | AGTATGTGGCAAAACCTATATTTAACCTGTAAA | CFHR1 | chr1 | 196795958 | 1.97E+08 | 1.97E+08 | 1.97E+08 |
| 83 | CAAGAGTAATGGCATGCGTTT | CACACTGCATAGGAGGACTACATATATGTACA | CFHR1 | chr1 | 196883661 | 1.97E+08 | 1.97E+08 | 1.97E+08 |
| 84 | GCATTTTATTTGCTCATGAAAGGCAA | GGTATTCCACTATGCCTTCCCTACA | CFHR4 | chr1 | 196887276 | 1.97E+08 | 1.97E+08 | 1.97E+08 |
| 85 | AATTCATTAACAAATGTTTCATTGTTTTGCC | AAACATGTAATTGAACCTGAAGAATTTCCATC | CFHR4 | chr1 | 196881754 | 1.97E+08 | 1.97E+08 | 1.97E+08 |
| 86 | TTTATTCCTACAATGGGACTTTCTTAGTCG | TCTGTGTTGTTCCATAACTGCTTT | CFHR4 | chr1 | 196875907 | 1.97E+08 | 1.97E+08 | 1.97E+08 |
| 87 | GCCAGCTAAGGTGCTTTGGTA | CATTCGGGCTTTGCTCATAGG | THBD | chr20 | 23028329 | 23028350 | 23028582 | 23028602 |
| 88 | TCAATTCATTAACAGATGTTTCATTGTTTCA | GAGGAGGATTCAGAAATGAATCCATTTTCAATT | CFHR4 | chr1 | 196874120 | 1.97E+08 | 1.97E+08 | 1.97E+08 |
| 89 | GGTGCTGATTGTGAAAACATTGC | CAATTCTCACTGCACTCCCACTA | CFH-C-257T polymorphism | chr1 | 196620770 | 1.97E+08 | 1.97E+08 | 1.97E+08 |
| 90 | GTGGGAGTACTGCAACCTGAAAA | GTTTCTGTCATCAGTGAGATTTTCCATG | PLG | chr6 | 161152160 | 1.61E+08 | 1.61E+08 | 1.61E+08 |
| 91 | TGGTGCTACACGACAAATCCAA | CCAGAAGCAGTCTGCTCAGAAG | PLG | chr6 | 161155062 | 1.61E+08 | 1.61E+08 | 1.61E+08 |
| 92 | TAGAGAGACATAGTGTGTGTGTGTCA | TCACTGTGGTTGTGTCATATTCTGAGC | CFHR5 | chr1 | 196971494 | 1.97E+08 | 1.97E+08 | 1.97E+08 |
| 93 | AGCTGAATGAAAACAAAACTATAAATGAGATG | AACTTGGGAAAAGGGTTATAATCTTCTTCA | CFHR5 | chr1 | 196951909 | 1.97E+08 | 1.97E+08 | 1.97E+08 |
| 94 | CCAAAAATAGAGAGTGCAATATAAAGGCAA | GCCCGTTTATTATAAAATTAGGATTGCAAT | CFHR5 | chr1 | 196964729 | 1.97E+08 | 1.97E+08 | 1.97E+08 |
| 95 | CTTCCCGCAAAAAGTGTATCTGC | AAACAGTTCTAGGGTAATAACCCATAAAAATT | CFHR4 | chr1 | 196876500 | 1.97E+08 | 1.97E+08 | 1.97E+08 |
| 96 | ACACCATTCTTGATTGTTTAGGATGCT | GTCCCCTTCATTAGAGAAATCTAGGATTGCA | C630W | chr1 | 196695453 | 1.97E+08 | 1.97E+08 | 1.97E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 97 | TGACTTCACATGGTTAAGCTGAATGA | CCCAGTTTATGTCAAATCAGGAGATATCTT | CFH-C564P | chr1 | 196684765 | 1.97E+08 | 1.97E+08 | 1.97E+08 |
| 98 | ACTCAGGGAACTCTTCTTGTTTGG | AAAACAGATACTAGTCACCATACTCAGGA | CFH | chr1 | 196670332 | 1.97E+08 | 1.97E+08 | 1.97E+08 |
| 99 | TTTTTAGTGGCACAAATACAATTATGCC | GCACAAGAGAATATTAACCTCATTTGAAAGAAT | CFH | chr1 | 196705946 | 1.97E+08 | 1.97E+08 | 1.97E+08 |
| 100 | CAATTCTTGGAAGAGGAGAACTGGA | GCCACTCAATTGTCAAGTTACAGAATACTT | CFH | chr1 | 196621173 | 1.97E+08 | 1.97E+08 | 1.97E+08 |
| 101 | CAAATGTGACTACTCACCTTTAAGGA | GCTTCCAACAGCCTTACTTTGTATATACAA | CFH | chr1 | 196654220 | 1.97E+08 | 1.97E+08 | 1.97E+08 |
| 102 | ACCATTTCTTCTTTCAGATCCATGTGT | GCTACTTTTAGCATAGATGGATGTTTGAAG | CFHR5 | chr1 | 196977599 | 1.97E+08 | 1.97E+08 | 1.97E+08 |
| 103 | AGTTTTGTGATGTTGCTTAAAAGCATCA | TCTTTCCCAGATAGCTTGAGTAATGTTTTT | CFHR5 | chr1 | 196967151 | 1.97E+08 | 1.97E+08 | 1.97E+08 |
| 104 | CCCTTGCATCTTATTTTATATAGCACACA | GGTGACCACCCAAATTGGTAACAT | CFHR5 | chr1 | 196963124 | 1.97E+08 | 1.97E+08 | 1.97E+08 |
| 105 | CCAAAATACACCATGGATTTCTGTATGA | CCCTTGTGATTATCAAGACCTTATGATCTT | CFHR5 | chr1 | 196952031 | 1.97E+08 | 1.97E+08 | 1.97E+08 |
| 106 | ACCGCCACCTCAGATACCTAAT | GTGCAACAGATTAGTACATAAGTTCTTGTTT | CFHR5 | chr1 | 196971633 | 1.97E+08 | 1.97E+08 | 1.97E+08 |
| 107 | ATCGCTATTTTAGAATCCATTACATGTATTGT | ATCCTTCTTCTCTCCCATGGTAT | CFH | chr1 | 196710918 | 1.97E+08 | 1.97E+08 | 1.97E+08 |
| 108 | CTCAAGAACCTGACATACTTGACGA | CTCCGAAGAGCCACTTTATCCTC | CPAMD1 | chr19 | 6714344 | 6714369 | 6714482 | 6714505 |
| 109 | CACGGTCACGAACTTGTTGC | ATAATGGGCAGGCAAGGAGGA | CPAMD1 | chr19 | 6718366 | 6718386 | 6718502 | 6718524 |
| 110 | AGCAAAGCCAGTCATCATGGAT | AGAAGTCTCAGTGCCTGATCAGA | CPAMD1 | chr19 | 6682176 | 6682198 | 6682315 | 6682338 |
| 111 | TTTTTGGTTTTCAGTTATCAATTGCTAGG | ACTAGAATTCCCACTCTACATTGTATGAGAA | CFH | chr1 | 196645104 | 1.97E+08 | 1.97E+08 | 1.97E+08 |
| 112 | CCCACTCCTACATAAAATATATTCCTTGCT | ACAGCTTTTACACCATATATTCAAACACATTT | CFH | chr1 | 196642919 | 1.97E+08 | 1.97E+08 | 1.97E+08 |
| 113 | CGTCAGGAAGTTACTGGGATCA | GGTGTAATCACTTATGTCTCTCCTT | CFH | chr1 | 196658675 | 1.97E+08 | 1.97E+08 | 1.97E+08 |
| 114 | CCCTCTGTATGACCCAATATCAACC | GCGATCAGGAACTAAGTGTACATCTATTTT | CFH | chr1 | 196694143 | 1.97E+08 | 1.97E+08 | 1.97E+08 |
| 115 | AATCAATAAAGCTTTTTCTTCTTAGAATGGG | GCTTAAACCATGTGAAGTCATTTTTAGTTCT | CFH | chr1 | 196684629 | 1.97E+08 | 1.97E+08 | 1.97E+08 |
| 116 | AGACAGATGAGTAAATATCCATCTGGTGA | CCATCAGTCATTTATTTGCATTTGAAAAATCT | CFH | chr1 | 196712631 | 1.97E+08 | 1.97E+08 | 1.97E+08 |
| 117 | TCTTGAGATGAGGTGGGATCTTAGG | CGGTCATCGCTGTGCATTAC | CPAMD1 | chr19 | 6694359 | 6694384 | 6694514 | 6694534 |
| 118 | GCGCAGGAGAGAACCTTCTCTAT | GCAGTTCTAACCCAGGAGAT | CPAMD1 | chr19 | 6712138 | 6712160 | 6712324 | 6712346 |
| 119 | TCCAGGCTGGATAAGCTCTACATT | CTCCTTGATCCTTCAGTTTCTTCCA | CPAMD1 | chr19 | 6680199 | 6680223 | 6680352 | 6680376 |
| 120 | GGGTGTTCCTGCTCCCATTT | GGGCAGTGGGAAGGATTACG | CPAMD1 | chr19 | 6707632 | 6707652 | 6707879 | 6707899 |
| 121 | TGGGAGGAGACACAATGTCA | CAGGGTTTACTGGGAAGCAAGA | CPAMD1 | chr19 | 6684670 | 6684692 | 6684922 | 6684944 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 122 | TCTGCTCAATGGCCATGATGTAC | CAACTTTCTGCTTGGGAGAGAGA | CPAMD1 | chr19 | 6678394 | 6678417 | 6678553 | 6678576 |
| 123 | CACTCTGAGCCTCCCTCCTTA | CCGAGCAGAAGACCTGGTG | CPAMD1 | chr19 | 6713092 | 6713113 | 6713242 | 6713261 |
| 124 | GGGATGAAGTCGGTGGTGAT | AAGATCCGCTACTACCTACCT | CPAMD1 | chr19 | 6710755 | 6710775 | 6710998 | 6711021 |
| 125 | CCCTAAATCCCAGCCTCTTACAAT | TCTCTGGATCTCAGAGCCGATT | CPAMD1 | chr19 | 6692913 | 6692937 | 6693119 | 6693141 |
| 126 | ACACCCAAATGCACCCTGAAT | GAGCCAGATAAAAAGCCAGCTC | CPAMD1 | chr19 | 6720425 | 6720446 | 6720676 | 6720698 |
| 127 | GGCCTCCAGTGTCTTCTCTAGGA | CTGGTAAGCAGCTCTACAACGT | CPAMD1 | chr19 | 6686051 | 6686073 | 6686255 | 6686277 |
| 128 | CCCTCACTGGCTCTTACCT | GGTGAAGGAGTACGGTAAGAGA | CPAMD1 | chr19 | 6713960 | 6713980 | 6714167 | 6714190 |
| 129 | GATGAGTTAAGTGCTCAAAAGATGTTAGC | GGTGGATTACGGAACAACAACCA | CPAMD1 | chr19 | 6690472 | 6690501 | 6690715 | 6690738 |
| 130 | TTCTCTTCGTCTTGGCATTCGT | GAGGAAGAAGAACAACACTACCTCATGTG | CPAMD1 | chr19 | 6677959 | 6677981 | 6678198 | 6678224 |
| 131 | CAGGGTCTAAGTCCCACTCCTT | TCTACCATCCGAAAAGGAGGA | CPAMD1 | chr19 | 6679238 | 6679260 | 6679467 | 6679489 |
| 132 | GCTCTCTTGGTTCTGCCGGTAATT | CGGAGTTGGACTAAGAGCTGAGA | CPAMD1 | chr19 | 6697667 | 6697689 | 6697870 | 6697892 |
| 133 | CGCCTATCCTACCTCACTAAAC | GCTAGGGTGATCCTAAGGACAGT | CPAMD1 | chr19 | 6696518 | 6696541 | 6696745 | 6696768 |
| 134 | CACTGGCCCTTACCTACTCTG | CCAACCTTTCTGTCTTTCCACTCTAG | CPAMD1 | chr19 | 6709681 | 6709703 | 6709928 | 6709954 |
| 135 | TGTTCATTTTCTGAATAGGCTTCTGAA | GCACTCATGAGAGTGAAACTACAGAAT | CD46 | chr1 | 207966775 | 2.08E+08 | 2.08E+08 | 2.08E+08 |
| 136 | GAGGTTTCTCTAATTTTCCAGTGGTCAA | ATGAACAGCAACAATAACAAACAA | CD46 | chr1 | 207940336 | 2.08E+08 | 2.08E+08 | 2.08E+08 |
| 137 | AAATTCTAAGATGTGGAATTGCAAAGTTTGT | GCTGTGCACACATACCCTAGAG | CD46 | chr1 | 207943522 | 2.08E+08 | 2.08E+08 | 2.08E+08 |
| 138 | ACAGCCAAACATATCAAGTGTTTAGAT | ATCGGTTTAACCAATTTACAAGCTGAAAAA | CD46 | chr1 | 207958318 | 2.08E+08 | 2.08E+08 | 2.08E+08 |
| 139 | TGAAGACACAGAAATTTACTAATGCTGTCT | CTCTCCAATAAGTGAAAATGGATCTGT | CD46 | chr1 | 207934520 | 2.08E+08 | 2.08E+08 | 2.08E+08 |
| 140 | CCTACTATGAGATTGGTGAACGAGTAGATT | CATCATCACCGTAGTGGAATATGTACC | CD46 | chr1 | 207930415 | 2.08E+08 | 2.08E+08 | 2.08E+08 |
| 141 | GTAATGGTCCACCTCACCAT | GTGGAGCCAAAGTGATGAACTGT | CFI | chr4 | 110681451 | 1.11E+08 | 1.11E+08 | 1.11E+08 |
| 142 | CTGATAGAAAGTATGCATACAAATACCCT | TGTGCAACTAACAGAGAGAAGCTTC | CFI | chr4 | 110687639 | 1.11E+08 | 1.11E+08 | 1.11E+08 |
| 143 | GCAAATACTCCACCAACCTGCTT | GCTACAGTAGGGTTATAAATGCAAAGTACT | CFI | chr4 | 110682655 | 1.11E+08 | 1.11E+08 | 1.11E+08 |
| 144 | TTTTTCATTTCAATCAAAGCGATGTCA | AGGGAAAAATATAAAAGTGAAGTGTCAGAA | CFI | chr4 | 110667496 | 1.11E+08 | 1.11E+08 | 1.11E+08 |
| 145 | TTGATACCAAAACTACTTGTTGCTTGAAT | AGGGAGGATAAGTTTTAAGGCAGAAATT | CFI | chr4 | 110673514 | 1.11E+08 | 1.11E+08 | 1.11E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 146 | TCCTACATGGTAGCTAATCCAGTCAAA | CCTTGAAAAATGGAAGGAAATGTGTGAT | CFI | chr4 | 110662078 | 1.11E+08 | 1.11E+08 | 1.11E+08 |
| 147 | CTGAAGAGATAGAAAGGGCAGATGA | CCCAGTATCCGATGTTCAGAACT | DGKE | chr17 | 54938979 | 54939005 | 54939201 | 54939224 |
| 148 | TGTTTCTAGGTTTTTGATGTAACTAAAACTCCT | AACAACAACAAAACACAACAAAACCCATATAT | DGKE | chr17 | 54925273 | 54925306 | 54925489 | 54925522 |
| 149 | AAAACAGTACATGATGAGTGCATGAAAAAT | CTATCTCAAACAATGAGTTAAGCAGCTTTT | DGKE | chr17 | 54921395 | 54921425 | 54921577 | 54921607 |
| 150 | GGTGTCATCACCTTCTGGTGTAG | ACCTTGGTGTCATTCTTGAGCA | DGKE | chr17 | 54912254 | 54912278 | 54912490 | 54912512 |
| 151 | ACGTGTCGGTTACTTTTGTAGATGGTATT | CAGCCAGCTCCCTTGAGATAAG | DGKE | chr17 | 54926427 | 54926455 | 54926679 | 54926701 |
| 152 | CGTGCCCACCTGCTATAGC | GGCTGCCGATGTCATTTCCT | THBD | chr20 | 23029770 | 23029789 | 23029924 | 23029944 |
| 153 | GCCATGCTTCCAGGATTAGGAA | GGTGTTGTCGCAGCTGTTTTAA | CFB | chr6 | 31919590 | 31919612 | 31919841 | 31919863 |
| 154 | CCTTTTATACCCTGGAAACCATGA | AGGCTCCAGCATTAACAGTTCTG | CFB | chr6 | 31915424 | 31915449 | 31915676 | 31915699 |
| 155 | GGGAAGACGTGAAGTTAGGAATGA | GCCATATTTCAGCTTATTCTTGAGCTTG | CFB | chr6 | 31918312 | 31918336 | 31918510 | 31918538 |
| 156 | GGCCCAGAACCTAGCTCTAGAA | GAACAGAAGACACGTGGCTTAGGAAGGA | CFB | chr6 | 31918810 | 31918832 | 31919061 | 31919084 |
| 157 | TGCCTGATGCCCTTTATCTTGG | AGAAGGACACACGTACTCCAGT | CFB | chr6 | 31914025 | 31914047 | 31914255 | 31914277 |
| 158 | CAGGGCTCGCGATGGAGAT | CGGTACCTTCGAGTGCATCT | THBD | chr20 | 23028563 | 23028581 | 23028745 | 23028765 |
| 159 | GCAGAGGTAGCTAGTTGGTTCAG | GCAGCGCTGTGTCAACAC | THBD | chr20 | 23028977 | 23029001 | 23029113 | 23029131 |
| 160 | CCCAGGGATCGCATTGCA | CGCCGTCTCGATCACCTAC | THBD | chr20 | 23029358 | 23029376 | 23029562 | 23029581 |
| 161 | AATTTCAGCACCACCTGAGCTAA | ATGGCTCTTTTTAACAGAAATTTCAGTTGG | PLG | chr6 | 161143431 | 1.61E+08 | 1.61E+08 | 1.61E+08 |
| 162 | CTCAAGACAGGGATGACTGGTT | GCACAGCTTCTCCAAAATGATCATTT | PLG | chr6 | 161162261 | 1.61E+08 | 1.61E+08 | 1.61E+08 |
| 163 | TGTCTCGAATTACACCACAAAATTGC | TGTGTGGATTTTATGTAAATGTAGAAGGGT | PLG | chr6 | 161157849 | 1.61E+08 | 1.61E+08 | 1.61E+08 |
| 164 | TTCCATATCATCCTGGGTCTCTGT | CCAATTCTGTTTGCAAAGATTGGTGAG | PLG | chr6 | 161152717 | 1.61E+08 | 1.61E+08 | 1.61E+08 |
| 165 | GCATCTCCTTCTGCCTTGCTAA | CAAATTATTTTACAGGTGAAGGGCAGAA | PLG | chr6 | 161133941 | 1.61E+08 | 1.61E+08 | 1.61E+08 |
| 166 | ATGTGTAAATTGGGATATAATGCAAATACATCA | AAGAGTGAGAAGTGGAAAAGTGGAAG | CFHR3 | chr1 | 196762550 | 1.97E+08 | 1.97E+08 | 1.97E+08 |
| 167 | GGCTAGAGTGGGATGAGGAAGAA | TGGAGCACTTCAAAATCAGCTGATATTA | DGKE | chr17 | 54939745 | 54939768 | 54939963 | 54939991 |
| 168 | CTTTGGACCCTCATCCTTCCTTTT | GGTGTAGAGGAAGAAATGAATTACTTCAGG | CFB | chr6 | 31917163 | 31917186 | 31917380 | 31917409 |
| 169 | CCCGGTCTCCCTACTACAATGT | GGTAGAGAGCAAGAGTTACAGTGTC | CFB | chr6 | 31914831 | 31914853 | 31915044 | 31915069 |
| 170 | ACAGGTGGCAAGTTATGGTGTG | GCCCTCAAGGTAGTCTCATGAC | CFB | chr6 | 31916146 | 31916168 | 31916350 | 31916372 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 171 | CAGATGTCTTCCTAAGAAATCAAATAAGATACA | CACTTTTAGTAGAAAGGAGGTGGTATCAC | CFHR3 | chr1 | 196759057 | 1.97E+08 | 1.97E+08 | 1.97E+08 |
| 172 | TCCACAAGAAAATGTTTGAGAGAAGGT | ACCCATTTTGTGTGCAATGAATGATAATC | CFHR3 | chr1 | 196748187 | 1.97E+08 | 1.97E+08 | 1.97E+08 |
| 173 | AGGGTAACTCTACAGAAGTTGCCT | CACAGTTAATATAGACAAGTCTGAGACTGT | CFHR3 | chr1 | 196748989 | 1.97E+08 | 1.97E+08 | 1.97E+08 |
| 174 | GGGACATTACTTCATTCCGTTGT | ATCGAGACTCATCACACTGATTTTTCCA | CFHR1 | chr1 | 196799671 | 1.97E+08 | 1.97E+08 | 1.97E+08 |
| 175 | GTATTAGTTGATTGCTACTCAAAATGAACA | CCAAACATTTCATAAGGGCTCCTACAT | CFHR1 | chr1 | 196797135 | 1.97E+08 | 1.97E+08 | 1.97E+08 |
| 176 | GGGAAGTTTTCTATTACTCCTGTGAATATAAT | TATCCTTCTCTATTCACTGAATGACATCCA | CFHR1 | chr1 | 196794690 | 1.97E+08 | 1.97E+08 | 1.97E+08 |
| 177 | TTGGAAGGTAACATAATCAAAACAGTCATCT | AAGTATGGTCTACGCCTATTCTCATAATATAGA | CFHR4 | chr1 | 196879318 | 1.97E+08 | 1.97E+08 | 1.97E+08 |
| 178 | TGTAAACCAGGATATGCAACAGCA | CATCTCAAAGAGAGGAACGAAGTTGA | CFHR4 | chr1 | 196881961 | 1.97E+08 | 1.97E+08 | 1.97E+08 |
| 179 | CTATTTTAGGACACATGCTCAAAATCAGATGTAG | CATGTAATTGATCCTGAAGAATTTCCCTCT | CFHR4 | chr1 | 196874228 | 1.97E+08 | 1.97E+08 | 1.97E+08 |
| 180 | CGAATACATCAGTTCTATCATTTCAAGCAGT | AGAAGCTATCTTTGCAAGCTTTGAGA | CFHR4 | chr1 | 196887465 | 1.97E+08 | 1.97E+08 | 1.97E+08 |
| 181 | CTAAGTGACCTTAAAGCCCTAGCTTT | AGACATATGAAGTTAGAATATTACACGAAGTTAC | CFHR4 | chr1 | 196857141 | 1.97E+08 | 1.97E+08 | 1.97E+08 |
| 182 | ATGTACATATATAGTAGTCCTCCTATGAGTG | CACTTTTAGTAGAAAGGAGGTGGTATCATG | CFHR4 | chr1 | 196883890 | 1.97E+08 | 1.97E+08 | 1.97E+08 |
| 183 | TCCCTCAAGATATTCATGATCTTTAGCAG | GTACTCACCTTTCTTTTCAAATAAAACATC | PLG | chr6 | 161128625 | 1.61E+08 | 1.61E+08 | 1.61E+08 |
| 184 | ATTCATTGTAACTTATTTTGCCATTCAA | CAATGGGATTCACATTCCATAGCAG | PLG | chr6 | 161139295 | 1.61E+08 | 1.61E+08 | 1.61E+08 |
| 185 | GGAATATGGACACACAATGAAGTAGTGGAATA | TGTATCCACATGTTTTCACTGTTCTAAGA | CFHR5 | chr1 | 196964913 | 1.97E+08 | 1.97E+08 | 1.97E+08 |
| 186 | CACATTGGACTATGAATGCTATGATGATA | ACTCAAATGAGACTACATGTATATGTACA | CFHR4 | chr1 | 196876060 | 1.97E+08 | 1.97E+08 | 1.97E+08 |
| 187 | GTGTTTGAGAATAATTCCTGAACCATCA | TGAGAACGTGATGAAGAGACGATATCC | CFH-V1168X | chr1 | 196716126 | 1.97E+08 | 1.97E+08 | 1.97E+08 |
| 188 | AGGATATCTGAAGAAAATGAAACACATGC | CCAGAATACAAAGTGACTCATCATGAACA | CFH-C926F | chr1 | 196706723 | 1.97E+08 | 1.97E+08 | 1.97E+08 |
| 189 | AAACGAAGAAGAAGAATATGGACACAGTGA | ACAGGTACTCTCCTCCACTATGTAAATTTT | CFH-E635D | chr1 | 196695656 | 1.97E+08 | 1.97E+08 | 1.97E+08 |
| 190 | GAACTTTTGTTTGGTTGACTGATTACCT | CGCCATCCAGATTCAGTGCATA | CFH-G218E | chr1 | 196648628 | 1.97E+08 | 1.97E+08 | 1.97E+08 |
| 191 | CTTGAGTAAATGCTCATAAGTTCCTTTCT | CCAAGAAGTGACTCCTTGTAAAATGTATTTG | PLG | chr6 | 161173793 | 1.61E+08 | 1.61E+08 | 1.61E+08 |
| 192 | GATCAGGAATAACTTGGTTGGTGAAATTT | TATCCATCCTTCTTTTCCTCACATCTGT | Frameshift 774Stop | chr1 | 196697328 | 1.97E+08 | 1.97E+08 | 1.97E+08 |
| 193 | GGTTTCCTCCCTCCTCAGACA | CTGGACTGCTGCAACTACATCA | C3-R735W | chr19 | 6706884 | 6706905 | 6707137 | 6707159 |
| 194 | ATAGACCTGTGACTGTCTAGGCAT | GGATATGTTTGTCAGACCAGGAA | CFH | chr1 | 196642002 | 1.97E+08 | 1.97E+08 | 1.97E+08 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 195 | TCAAGAAGAGAATGCGAACTTCCT | 702 | CAATGGGAGCCCAAACAAAATTAATAAGAA | CFH | chr1 | 196694245 | 1.97E+08 | 1.97E+08 | 1.97E+08 |
| 196 | AGTTGGTTTGATTCCTATCATTTGATTTTC | 703 | CCATTTATGCAGACTGTGTGTATCCAT | CFH | chr1 | 196697421 | 1.97E+08 | 1.97E+08 | 1.97E+08 |
| 197 | TTCCTCCAATCTTATCCTGAGGATGA | 704 | CGTACTGCTTGTCCAAAATGT | CFH | chr1 | 196646505 | 1.97E+08 | 1.97E+08 | 1.97E+08 |
| 198 | TTGAGTGGAGAGTGGACAACTTTACC | 705 | TCTGTGTCCAATCATTGTAAATGATTCTGA | CFH | chr1 | 196695746 | 1.97E+08 | 1.97E+08 | 1.97E+08 |
| 199 | TACACATGATGTCAGTTTTCAAAGTTTTCC | 706 | GTATTAGTCCTGAAGATTCAGAATGACCAT | CFHR5 | chr1 | 196952984 | 1.97E+08 | 1.97E+08 | 1.97E+08 |
| 200 | ACATAATGTCTCAACAAATAAATGCTCTTT | 707 | CAGTTACAGAGCCCTGGAGTTT | CFHR5 | chr1 | 196973755 | 1.97E+08 | 1.97E+08 | 1.97E+08 |
| 201 | AAGAGAGTGCAAAATGCAGGAGTTAATAT | 708 | AATTTTCTTGTAAAGAAGCAACAAGATCA | CFHR5 | chr1 | 196967271 | 1.97E+08 | 1.97E+08 | 1.97E+08 |
| 202 | GAAAATACAATGTGTGATGGAGAATGG | 709 | CAATTCACCTCGACTGAAACTTCA | CFHR5 | chr1 | 196964979 | 1.97E+08 | 1.97E+08 | 1.97E+08 |
| 203 | TCTTATAAGAGTTGGATCGAGACTCAGTTCA | 710 | CTTTGCCATTTTACCACTTTGTCAGATTAT | CFHR5 | chr1 | 196963312 | 1.97E+08 | 1.97E+08 | 1.97E+08 |
| 204 | CCCTTAGTACATTGAAATTCAAAGTCATGC | 711 | ATTTGTATGCATACACACACAAGTCATGC | CFHR5 | chr1 | 196946680 | 1.97E+08 | 1.97E+08 | 1.97E+08 |
| 205 | CCTGCGTCGGAGAAGACA | 712 | AAGAGATACACAGGTGCATATGTGG | CPAMD1 | chr19 | 6707857 | 6707875 | 6707998 | 6708023 |
| 206 | CCGTGAGGGCCATGTCTTTC | 713 | GGGTAACACCTAGAAGAGACTCA | CPAMD1 | chr19 | 6690695 | 6690715 | 6690838 | 6690861 |
| 207 | CTTTGCCTCTCTAAGCCTGT | 714 | CACGAGCTCTTTGTCTCTC | CPAMD1 | chr19 | 6718047 | 6718068 | 6718180 | 6718201 |
| 208 | GAGCCCTCTCTGAAGGACAAG | 715 | CCAAGTCCTCGTGTCCGTT | CPAMD1 | chr19 | 6697307 | 6697328 | 6697462 | 6697482 |
| 209 | GAGAGCAATACTCCCAAGTGTT | 716 | GCAATTTCTCCAGGAATTCCTATATCTTG | CD46 | chr1 | 207940899 | 2.08E+08 | 2.08E+08 | 2.08E+08 |
| 210 | TTCTCTGTGATGTCATAGTAGCTCCT | 717 | ACTTCTTCTCCATACTGATAACTGTCTGA | CFH | chr1 | 196709623 | 1.97E+08 | 1.97E+08 | 1.97E+08 |
| 211 | TTTTGGTACTTTTACCCTTACAGGAGG | 718 | CCATACATAGTAAACTTTCAGGTACTTGTGTAT | CFH | chr1 | 196643017 | 1.97E+08 | 1.97E+08 | 1.97E+08 |
| 212 | CTCAGTTTACCTAGCTTTGAAAATGCC | 719 | AAATAATTTTGAAAATTCACCAAAGTACCTCT | CFH | chr1 | 196711015 | 1.97E+08 | 1.97E+08 | 1.97E+08 |
| 213 | TTATCCAGGTTTTCAGTTACAAATGACTCA | 720 | TCCCACATGTAATTGATCCTGATGTTTC | CFH | chr1 | 196682747 | 1.97E+08 | 1.97E+08 | 1.97E+08 |
| 214 | AAAACTGTTGATATTATATACAGTGTGTGT | 721 | AACTGATGAAGCTGGAGCATATACTG | CFH | chr1 | 196714840 | 1.97E+08 | 1.97E+08 | 1.97E+08 |
| 215 | CCACTGCTCCGTTTCATCCAG | 722 | GGAGGCTGGAACCCTTTTCAC | CPAMD1 | chr19 | 6694493 | 6694514 | 6694705 | 6694726 |
| 216 | AGGGTTGATTGAGTTTGGATAAAATGAGA | 723 | CCCTCTACCACCCTGCTAGATG | CPAMD1 | chr19 | 6702049 | 6702078 | 6702258 | 6702280 |
| 217 | GGGCGTGACAATGGTGTG | 724 | CATCAAGTGCAGAGAAGCCCT | CPAMD1 | chr19 | 6678086 | 6678104 | 6678231 | 6678252 |
| 218 | AGGGCTTAGAAGGGAGGAAGACA | 725 | GTCACTGTTGTACTGTCCACGACTT | CPAMD1 | chr19 | 6719118 | 6719141 | 6719303 | 6719326 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 219 | GCAGACACGTACAAAGACTTCC | CAGAGGATTTCCCTGCCTGAATC | CPAMD1 | chr19 | 6713219 | 6713241 | 6713433 | 6713456 |
| 220 | TACCTAGGCCACTCACAGTCAT | GCAGAGAATTGCTTCATACAAAAGTCG | CPAMD1 | chr19 | 6678948 | 6678970 | 6679196 | 6679223 |
| 221 | GGGTGTGTTGATGCTGAGTT | CAAGCACCCAAGTACTTCAAACC | CPAMD1 | chr19 | 6712292 | 6712314 | 6712540 | 6712564 |
| 222 | CTGAAAGGAAAAGAAAGAAGACCAGCCAGATA | CAGGAGCTGGGATAAGTGGAAAG | CPAMD1 | chr19 | 6681871 | 6681900 | 6682117 | 6682140 |
| 223 | GTAGGGCCAAGAGGGCATAGGAT | CTTTCTGAGCTTTCTCTGAGCCAT | CPAMD1 | chr19 | 6686223 | 6686246 | 6686350 | 6686374 |
| 224 | CTCCCCTTGCTTCCCAGTAAA | CCATCTTTCTCTCTTGTGGGTTCTAG | CPAMD1 | chr19 | 6684917 | 6684939 | 6685157 | 6685183 |
| 225 | CCTCCAGGCCCTTCTTCGTTATA | CAGGTCTTCTCCACTGAGTTTGAG | CPAMD1 | chr19 | 6714018 | 6714040 | 6714189 | 6714213 |
| 226 | ACAGTATCAGATACACAGTGTACTTGGA | GCCTTATCTGTCACCTTCCTCCTA | C3-T1383N | chr19 | 6684280 | 6684308 | 6684531 | 6684555 |
| 227 | GCAGAGCTTGTTCAGCTTCCA | GAGAATCCCAAAGATCAGAAGATAGAGG | CPAMD1 | chr19 | 6679445 | 6679467 | 6679652 | 6679680 |
| 228 | GGTCCGTGCTTAAGATGCTTA | CTCTCTCTTCTCTGCAGGGTACA | CPAMD1 | chr19 | 6693241 | 6693263 | 6693492 | 6693515 |
| 229 | GCTGGCACGAGAACTTCATG | CAAAGTGGGAGCCTTTCCTA | CPAMD1 | chr19 | 6707206 | 6707226 | 6707460 | 6707481 |
| 230 | AGCCTGCCCTTGTTCATGATC | AGTGCTACGTACAGAGCTCAGA | CPAMD1 | chr19 | 6710836 | 6710857 | 6711078 | 6711100 |
| 231 | GGGATTGTTGCGTCCCATATCT | CCGACTGAGGAGAGCTCTAGTC | CD46 | chr1 | 207925450 | 2.08E+08 | 2.08E+08 | 2.08E+08 |
| 232 | CCATTCAAAAGAGCACTGCAGAA | TTTCACAGGAATGCTTAAGAAGGAAGCA | CD46 | chr1 | 207930796 | 2.08E+08 | 2.08E+08 | 2.08E+08 |
| 233 | GGGAGGAAGAAAGAGATTATGACATT | CCAACCCAAACTGTCAAGTATTCCT | CD46 | chr1 | 207956417 | 2.08E+08 | 2.08E+08 | 2.08E+08 |
| 234 | AACATTTGACCACTGAAAATGTAACCAA | AGATAGCATGCAATACAGATTACAAACTGA | CD46 | chr1 | 207958855 | 2.08E+08 | 2.08E+08 | 2.08E+08 |
| 235 | CTTGATGCAGTAACTTATAGTTGTGATCCT | ACCTGCTTGTTTATCTGTAGATGAAACT | CD46 | chr1 | 207934667 | 2.08E+08 | 2.08E+08 | 2.08E+08 |
| 236 | ATGTTCAGGCTGGGTTATTACTAAAATGT | CCGAAGAAAACAGAAATAAGGTGCAAT | CFI | chr4 | 110678786 | 1.11E+08 | 1.11E+08 | 1.11E+08 |
| 237 | AGAGGCTAGATTTATGTCTACCTTTACAAC | GTCATGCCACCACTCCATAAATAAATTT | CFI | chr4 | 110681657 | 1.11E+08 | 1.11E+08 | 1.11E+08 |
| 238 | CCAAATCTTTTTGTTGTGACATGTGG | CTTCAAACAGGAGTCTTTAATTTGTTGCT | CFI | chr4 | 110687763 | 1.11E+08 | 1.11E+08 | 1.11E+08 |
| 239 | TCATCCTCATAACAATGCTATGATGCA | ACTTGTGGACCAAGATAAGACAATGTT | CFI | chr4 | 110685546 | 1.11E+08 | 1.11E+08 | 1.11E+08 |
| 240 | GTGGTGGGAGGAGATGTTTGATAG | ACCCTTTCATAATCCCAATGGTTTAAGTTA | CFI | chr4 | 110663574 | 1.11E+08 | 1.11E+08 | 1.11E+08 |
| 241 | TCAGATATGCTTTATCATCTGCCACAAT | GGGAGTCTTGCCATGAAAATATCTT | CFI | chr4 | 110670286 | 1.11E+08 | 1.11E+08 | 1.11E+08 |
| 242 | GCATCTCCATTGTCAAAGAACACA | TGATTTTACTGTACCTTCGGTGATAAGC | DGKE | chr17 | 54933767 | 54933792 | 54934012 | 54934041 |
| 243 | CAATTAGCACAAGCTTTAGCAAAACAA | TTCCCAGAGGCAAAACTGCAACT | DGKE | chr17 | 54925914 | 54925941 | 54926079 | 54926102 |

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 244 | CGCTTCCAGTGCAAGGAGATTA | 751 | ACCACTCTATGAAATCCTGATTCCCA | DGKE | chr17 | 54912468 | 54912490 | 54912660 | 54912686 |
| 245 | CGTGCCGTTCAGTAGCA | 752 | CGCCTGGGTAACATGCTTG | THBD-D34E | chr20 | 23029906 | 23029924 | 23030134 | 23030153 |
| 246 | TGCAAACCTTTGTTAGTAACTTTAGTTCG | 753 | GGATGGCAGGCAACGTCTATAG | Q400K | chr1 | 196659029 | 1.97E+08 | 1.97E+08 | 1.97E+08 |
| 247 | GTCTTTCTGGCTTTCTGTACAATGG | 754 | CCCTAGTGTCACAGCCAGAGAA | PLG | chr6 | 161159492 | 1.61E+08 | 1.61E+08 | 1.61E+08 |
| 248 | CTGCCCAGCTTGGAAGGTATTAT | 755 | CTTAACACAGTTGGACCATCAACTTAA | DGKE | chr17 | 54939178 | 54939201 | 54939403 | 54939433 |
| 249 | GCATGGAAAATGTGCTTTTCATCTTTAAG | 756 | ATCAGGTGATTAGTGACTTGAAGCATTAAT | DGKE | chr17 | 54922985 | 54923014 | 54923230 | 54923260 |
| 250 | ATTTTATGACTATGACTTGCCCTGAT | 757 | CTATAAAGGACAAGGAGAACAGCAAACCA | CFB | chr6 | 31918483 | 31918510 | 31918615 | 31918644 |
| 251 | CCCAATCCTTCCTAAGCACTT | 758 | AGAAGCTGTAGAGAAAAGGACTGTTG | CFB | chr6 | 31919056 | 31919078 | 31919292 | 31919318 |
| 252 | CCATAGACTCCTACCCAAAAGCT | 759 | ACCACCATCCTTATGCCATTTT | CFB | chr6 | 31917745 | 31917769 | 31917995 | 31918020 |
| 253 | GGTTAAAGATGGCTTGAAGACCA | 760 | CAAGTGGACTTAAGGCCACAT | CFB | chr6 | 31916550 | 31916575 | 31916789 | 31916811 |
| 254 | CTCCTTCCGACTTCTCCAAGAG | 761 | CTAGTCTCATCCTAGTCCTGACCTT | CFB | chr6 | 31914225 | 31914247 | 31914440 | 31914465 |
| 255 | GGAAAATGGAGAAGGGACAGAACTG | 762 | GGGAGCTAGTCCTGGAAGATCAG | CFB | chr6 | 31915659 | 31915684 | 31915900 | 31915923 |
| 256 | GAGTCACAGTCGGTGCCAAT | 763 | CCTGGACGACGTTTCATCTG | THBD | chr20 | 23028696 | 23028716 | 23028825 | 23028846 |
| 257 | CACTCGAAGCCACCCTGT | 764 | AGTCCTGCAACGACCCTG | THBD | chr20 | 23029095 | 23029113 | 23029266 | 23029285 |
| 258 | CGCGGGTGCACATTAGCTG | 765 | GCAGCAGTGCGAAGTGAAG | THBD | chr20 | 23029463 | 23029481 | 23029658 | 23029677 |
| 259 | CCCTGAATATTCTCCACCTCTT | 766 | TCGCTTCTGTTCCTGAGCATT | PLG | chr6 | 161152031 | 1.61E+08 | 1.61E+08 | 1.61E+08 |
| 260 | AAGCGTGGTTCCCTAGACTTTT | 767 | TGCCACTGGTATACAAAAATAAGGAGAAA | PLG | chr6 | 161139661 | 1.61E+08 | 1.61E+08 | 1.61E+08 |
| 261 | CCGCTGCTGTCTGTTCTGAATAT | 768 | TCTTGATCTTTTGCTTACCTGCAA | PLG | chr6 | 161173069 | 1.61E+08 | 1.61E+08 | 1.61E+08 |
| 262 | ACTCTCTTATTTTGCTTCATCCATTCAGT | 769 | AAATGACAGACAAATGTCTGATAGAGCT | PLG | chr6 | 161135756 | 1.61E+08 | 1.61E+08 | 1.61E+08 |
| 263 | TCATTAACTTAATTGACTACTGGTTTGTGA | 770 | AAGTTTCATGAATCAAAATAAATGAATTGCA | PLG | chr6 | 161123227 | 1.61E+08 | 1.61E+08 | 1.61E+08 |
| 264 | CTCTGGTTTGCTTGCTGAGAAGA | 771 | AGTTATTTCCAGCATGCTAAATCCCTAC | PLG | chr6 | 161173947 | 1.61E+08 | 1.61E+08 | 1.61E+08 |
| 265 | GGGACTACTTTTAAACATTATTGTTCCC | 772 | CATGTATCTACTTGCGTGAGGATTCTAT | DGKE | chr17 | 54939933 | 54939963 | 54940177 | 54940205 |
| 266 | GTGACAACGGAGGTGAGAAGCA | 773 | GGTAGGTGACCGTGTCTTCAAG | CFB | chr6 | 31914957 | 31914979 | 31915186 | 31915208 |
| 267 | CATATATTGCCATGTTTTTACTTGTTCCCT | 774 | CAAACATGTAATTGATCCTGAAGAATTTCCATC | CFHR3 | chr1 | 196757260 | 1.97E+08 | 1.97E+08 | 1.97E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 268 | GCCTCCTCCACCTATTAGCAATG | CACAGTTCTAGGGTAATAACCCATAAAAATTCT | CFHR3 | chr1 | 196759193 | 1.97E+08 | 1.97E+08 | 1.97E+08 |
| 269 | TGAGACTCCTTCAGGAAGTTACTGG | AGAGTAATCAATTATGTGCTCTCCTCTTTA | CFHR3 | chr1 | 196748409 | 1.97E+08 | 1.97E+08 | 1.97E+08 |
| 270 | TCCTGAACCATCATATAACATTCTACTTGA | TGTCCACCTTAATGCTATGTTATAATTTCCA | CFHR1 | chr1 | 196800829 | 1.97E+08 | 1.97E+08 | 1.97E+08 |
| 271 | AGGACTTTACTAAACTAGCTTCCAGTTAGT | AAAAATATGTAAGCATACACACAAAAACCGAT | CFHR1 | chr1 | 196788838 | 1.97E+08 | 1.97E+08 | 1.97E+08 |
| 272 | AATATCCATCTGGTGAGAGTACGTTAT | TAAATCAACATATTTAACCCTGCTATACTCCC | CFHR1 | chr1 | 196797262 | 1.97E+08 | 1.97E+08 | 1.97E+08 |
| 273 | AGCCACTTCACCCGGTTTATTAA | TTTGTCCTGAAGATTCAGAATGACCA | CFHR1 | chr1 | 196795862 | 1.97E+08 | 1.97E+08 | 1.97E+08 |
| 274 | CACAATATAATTGTAAACCAGGATATGCAACAG | CCTCAAAGAGGAAAGAAGTTGACAG | CFHR4 | chr1 | 196874318 | 1.97E+08 | 1.97E+08 | 1.97E+08 |
| 275 | GGAAGTCCTCCATAATCATTAGGATGAGA | ATCCTGTCCTAACTCAGAATTCAGTTTTATAAC | PLG | chr6 | 161128784 | 1.61E+08 | 1.61E+08 | 1.61E+08 |
| 276 | AGAAGGAAGGAAAAAGAAAACTCCTT | GGGACATCACAGTAGTCGTAAAGTTTTC | PLG | chr6 | 161154899 | 1.61E+08 | 1.61E+08 | 1.61E+08 |
| 277 | GCCTCCTCCACCTATTAGCAATG | CACAGTTCTAGGGTAATAACCCATAAAAATTCT | CFHR4 | chr1 | 196884104 | 1.97E+08 | 1.97E+08 | 1.97E+08 |
| 278 | TTCAGAAAGTTTCCAATAAAACTGTTGATT | CTGGTACTCGACTCTTGACCATG | CFHR4 | chr1 | 196876386 | 1.97E+08 | 1.97E+08 | 1.97E+08 |
| 279 | AATAGTACTCAATTTATTAGCACACACTGA | GTAGTCCAAATGTCATGGAGCTT | CFHR4 | chr1 | 196883502 | 1.97E+08 | 1.97E+08 | 1.97E+08 |
| 280 | TTTATTACAAGAAGTGAAACCTTGTGATTTTCC | TCTCTCACTCTTTTCAAGTTTTATGCACA | CFHR4 | chr1 | 196871536 | 1.97E+08 | 1.97E+08 | 1.97E+08 |
| 281 | TGAGTTTCCAGAAATTCAACATGGACA | CTCCATTCTTTTGCAAGTTTTATGCACA | CFHR4 | chr1 | 196879423 | 1.97E+08 | 1.97E+08 | 1.97E+08 |
| 282 | TATGCACTAGAAATCTTGTGATATCCCAGT | AGACCAACCATTGTAACCACACA | CFHR4 | chr1 | 196684712 | 1.97E+08 | 1.97E+08 | 1.97E+08 |
| 283 | ATTCGAACAGGTGAATCAGTTGAA | CGGTCTCCAGCTTATAATTACATTTTCACAAATT | 3768-71 delAGAA | chr1 | 196716315 | 1.97E+08 | 1.97E+08 | 1.97E+08 |
| 284 | ACGCATCATGTGATCCACAAGA | TGATATAGACCTCCATGTTTAATGTCTGGAT | CFH-C325Y | chr1 | 196658322 | 1.97E+08 | 1.97E+08 | 1.97E+08 |
| 285 | GGTGGAGGAATATATCTTTGCGAGT | CCTCACAAGTATAACTCAATTTAGTCCCA | I881L | chr1 | 196706440 | 1.97E+08 | 1.97E+08 | 1.97E+08 |
| 286 | CATGGGTTATGAATACAGTGAAAGAGA | GAACCTTGACACACAGAAAATGCTATATGTT | P258L | chr1 | 196648846 | 1.97E+08 | 1.97E+08 | 1.97E+08 |
| 287 | AGATAAAAGAGAGACAGTTGAGAGACAGA | GTGGCGTACTACACGCTGAT | C3-S562L | chr19 | 6710468 | 6710498 | 6710722 | 6710742 |
| 288 | GGTCCGTGCTTAAGGATGCTTA | CTCTCTCTTCTCTGCAGGGGTACA | CPAMD1 | chr19 | 6693242 | 6693264 | 6693492 | 6693515 |
| 289 | GTGGACTTCCCTTCCCTTCAGTGTATCTC | ATTAGGGATTATACAAGAGAAGGTATGTAGGTT | PLG | chr6 | 161132093 | 1.61E+08 | 1.61E+08 | 1.61E+08 |
| 290 | CGGCCCATCCTACCCTCACTAAAC | GCTAGGGTGATCCTAAGGACAGT | CPAMD1 | chr19 | 6696519 | 6696542 | 6696745 | 6696768 |
| 291 | ATTTAGTTCGGCCTTTAAGATGTCAAAAC | AAAACTTAGAGGCCAGGTGCTGAT | PLG | chr6 | 161157805 | 1.61E+08 | 1.61E+08 | 1.61E+08 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 292 | CCTACTATGAGATTGGTGAACGAGTAGATT | 799 | CATCATCACCGTAGTGAATATGTACC | CD46 | chr1 | 207930416 | 2.08E+08 | 2.08E+08 | 2.08E+08 |
| 293 | TCCCTCAAGATATTCAATGATCTTTAGCATG | 800 | ATCCTGTCCTAACTCAGAATTCAGTTTTATAAC | PLG | chr6 | 161128626 | 1.61E+08 | 1.61E+08 | 1.61E+08 |
| 294 | GTTTTGCACTCGTCGATGT | 801 | CTTCAGAGCCAACTGCGAGTA | THBD | chr20 | 23028801 | 23028821 | 23029014 | 23029035 |
| 295 | CCTGAATAAACTGCAGAACAGAGCT | 802 | TTTAGCAAGGCAATATCTTTCGTGTG | PLG | chr6 | 161159857 | 1.61E+08 | 1.61E+08 | 1.61E+08 |
| 296 | GGGTGTATCCAGTCTACTACTGTTG | 803 | GGGAAATGAAAAAGGTTTTTAAAAGGGAAA | CFI | chr4 | 110667602 | 1.11E+08 | 1.11E+08 | 1.11E+08 |
| 297 | CCCTGATTCTGTCATCCTAGAGAAAC | 804 | AAAAAGAGACAGTCCAGTCAGATT | PLG | chr6 | 161152674 | 1.61E+08 | 1.61E+08 | 1.61E+08 |
| 298 | CCCTCCTTATTACTATGGAGATTCAGTG | 805 | CTGGAAATGTTGAGGCATATCCTGTAAATTT | CFH | chr1 | 196695952 | 1.97E+08 | 1.97E+08 | 1.97E+08 |
| 299 | TGCAGGAATCCAGACAACGATC | 806 | TTACTCAATTATTAATAACATCCCTGTGGAAG | PLG | chr6 | 161134064 | 1.61E+08 | 1.61E+08 | 1.61E+08 |
| 300 | GGGAGACAGAGCGAAATTTCATCTA | 807 | CGCGTATTCTCATAATATAGATGTCCATGT | CFHR4 | chr1 | 196879257 | 1.97E+08 | 1.97E+08 | 1.97E+08 |
| 301 | AACATGTGTAAGGACTCTTTATTCAAGGT | 808 | CCTCAATCTTATACAGATTTTCAACTGGAAGT | PLG | chr6 | 161123153 | 1.61E+08 | 1.61E+08 | 1.61E+08 |
| 302 | TGTAGATTGCAATGAACTTCCTCCAA | 809 | GACTGGCAATAGTGATATAATTCAGGCATA | CFH | chr1 | 196642103 | 1.97E+08 | 1.97E+08 | 1.97E+08 |
| 303 | CCTTTCTGATTTCAATTACTGGGAAAATGT | 810 | CTTCGTTTGATTCAATTACTGCCAGTTATTCC | PLG | chr6 | 161173817 | 1.61E+08 | 1.61E+08 | 1.61E+08 |
| 304 | TTTTAGAAAGGCCCTGTGGACAT | 811 | CCCACTCCTCCCATAATTATACTCTATCAGA | CFH | chr1 | 196642981 | 1.97E+08 | 1.97E+08 | 1.97E+08 |
| 305 | CTACAGCCAGAAGGCCAAATGGA | 812 | ACACGCTAAGGAAGAAGAGTTCTCAAAATTTA | CFI | chr4 | 110663521 | 1.11E+08 | 1.11E+08 | 1.11E+08 |
| 306 | CAAAGACCTTCTTGTTACATATCTCAGTCA | 813 | ATCCATCTTGTGTGCAATGAATGTG | CFH | chr1 | 196658365 | 1.97E+08 | 1.97E+08 | 1.97E+08 |
| 307 | TAGTGGCACAAATACAATTATCAACCTCACTT | 814 | ACAGAGAAAGAACTTCTCTCTTGTTTTACAC | CFH | chr1 | 196705951 | 1.97E+08 | 1.97E+08 | 1.97E+08 |
| 308 | CTGTATGACCCAATATGCAAACCTCCCAAA | 815 | TTACAGGCAATGGGAGCCCAAA | CFH | chr1 | 196694148 | 1.97E+08 | 1.97E+08 | 1.97E+08 |
| 309 | TCATTGTCCACTCCCATAGAAAAGAATC | 816 | GGTATTCCCGATCTGGTTCCATTG | CFH | chr1 | 196646388 | 1.97E+08 | 1.97E+08 | 1.97E+08 |
| 310 | CAAACCTTTGTTAGTAACTTTAGTTCCTCT | 817 | ACATGAACATGCTAGGATTTCAGAGTAG | CFH | chr1 | 196659032 | 1.97E+08 | 1.97E+08 | 1.97E+08 |
| 311 | GGTCAAGTCAAAACAGAACTTTTGTTTG | 818 | GGTAACATTACCTTCACAGAAGGCAA | CFH | chr1 | 196648614 | 1.97E+08 | 1.97E+08 | 1.97E+08 |
| 312 | ATAAGGTACAGATGTAGAGGAAAAGAAGGA | 819 | ACCTGCCTTATTCAGTTAGCATTTGTAATAA | CFH | chr1 | 196697568 | 1.97E+08 | 1.97E+08 | 1.97E+08 |
| 313 | ACCACAGTACATGTACGGAGAAAG | 820 | TCTGAGACTGTCGTCCGTGTTA | CFHR3 | chr1 | 196749046 | 1.97E+08 | 1.97E+08 | 1.97E+08 |
| 314 | CCATTAATTCATCCAGTCTTCACAAGA | 821 | CCAGAATACAAAGTGACTCTATCATGAACA | CFH | chr1 | 196706647 | 1.97E+08 | 1.97E+08 | 1.97E+08 |
| 315 | GCTACTCAAAATGAACACTAGGTGGAA | 822 | CAGGAAGAATTGAATTTTAAGCACCATCA | CFHR1 | chr1 | 196797150 | 1.97E+08 | 1.97E+08 | 1.97E+08 |
| 316 | CTGTAATGGCCTGTTTATTACTAGCATTG | 823 | TCATTCAGCTTAAACCATGTGAAGTCA | CFH | chr1 | 196684418 | 1.97E+08 | 1.97E+08 | 1.97E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 317 | ATTGTAACTTATTTTGCCCATTCAAGCA | ACATTCCATAGCAGCAGAATGAGAC | PLG | chr6 | 161139300 | 1.61E+08 | 1.61E+08 | 1.61E+08 |
| 318 | AGTTTCTGATAGGCGGAGCATCTA | ACAATGTCAAAAGCCACTCAATTGTC | CFH | chr1 | 196621107 | 1.97E+08 | 1.97E+08 | 1.97E+08 |
| 319 | GTGTTTGAGAATAATTCCTGAACCATCA | TAATACTAAAGTTCTGAATAAAGGTGTGCACTT | CFH | chr1 | 196716127 | 1.97E+08 | 1.97E+08 | 1.97E+08 |
| 320 | TCTACTATAGAGCAAGTACAATCATGTGGT | ACAGGTACTCTCCTCCCACTATGTAAATTTT | CFH | chr1 | 196695590 | 1.97E+08 | 1.97E+08 | 1.97E+08 |
| 321 | TGCTACGGCTACCAATATTTCTTCAG | ACATTACTGGCTCCATCCATTTTGTA | CFH | chr1 | 196710764 | 1.97E+08 | 1.97E+08 | 1.97E+08 |
| 322 | ATGTCTTTGGCAACTCTGAGCT | TAAATTACTTACTCACGTGGGTTGA | CFH | chr1 | 196682691 | 1.97E+08 | 1.97E+08 | 1.97E+08 |
| 323 | TTGTAACTGTTATCAGTTGATTTGCTACTCA | CACCATCAGTCATTTTATTGCATTGAAAAAT | CFH | chr1 | 196712509 | 1.97E+08 | 1.97E+08 | 1.97E+08 |
| 324 | TGAAGTTATATGTGATGAGAACATTGCCA | CGTGATTTCATCTCCAGTTCTGT | CFH | chr1 | 196653903 | 1.97E+08 | 1.97E+08 | 1.97E+08 |
| 325 | CTCCGAGACCAGGAGGATACA | GGTAGAGAGCAAGAGTTACAGTGTC | CFB | chr6 | 31914709 | 31913903 | 31915044 | 31915069 |
| 326 | TGCTCTTTCCTCACTTTGTTTAAACCT | ACGATCTTCCGCTTCTTGTGTT | CFB | chr6 | 31915372 | 31915399 | 31915724 | 31915746 |
| 327 | AGGCTATGACAAAGTCAAGGACATC | CTTGACACACGCAGGCAAGA | CFB | chr6 | 31919153 | 31919178 | 31919505 | 31919527 |
| 328 | GGGAAGACGTGAAGTTAGGAATGA | CTATAAAGGACAAGGAGAGCAACCA | CFB | chr6 | 31918313 | 31918337 | 31918615 | 31918644 |
| 329 | TGAGAGGGAGGTGCAATAGGAA | GGGCATATTGAGCATCTCTCA | CFB | chr6 | 31918777 | 31918799 | 31919128 | 31919151 |
| 330 | GGAATTCTTCCTAAGCCCTGTGAT | GCCAAAGCATTGATGTTCACTTGG | CFB | chr6 | 31916887 | 31916911 | 31917230 | 31917254 |
| 331 | GACTGTGTAATTCCTCATGAACCT | CGCCCTCAAGGTAGTCTCATGA | CFB | chr6 | 31916015 | 31916039 | 31916351 | 31916373 |
| 332 | TTCTCCTAACACGAGGAAACAAATACC | ACAACAGTAGAGAGGGAAAGCTCA | CFB | chr6 | 31917682 | 31917709 | 31918030 | 31918054 |
| 333 | TTTGGACACTGAGCCAAGCAGACA | GTAGAAGCCAGAAGGACACACGTACT | CFB | chr6 | 31913912 | 31913935 | 31914260 | 31914286 |
| 334 | AGAGTGAAAGTTTATCACACTGAGAAAGG | AGCTAGACATCCTACAATTCAAGGTAAATC | CFI | chr4 | 110678740 | 1.11E+08 | 1.11E+08 | 1.11E+08 |
| 335 | CTTGGCATGCTGTGCAAACATA | GACTTCCATTATCCCAAAAATCTGATAAGGA | CFI | chr4 | 110681528 | 1.11E+08 | 1.11E+08 | 1.11E+08 |
| 336 | AGAATGACTTGAAAACTGAAAACAGTAGTGTCTTGCTAC | CAAACAGGAGTCTTTAATTGTTGCTAAGT | CFI | chr4 | 110687680 | 1.11E+08 | 1.11E+08 | 1.11E+08 |
| 337 | TACACAGAAAGGTTAGGTAATCAAAAGCA | GTTCAAAGCTCACTTGACATTAAGTACATT | CFI | chr4 | 110685612 | 1.11E+08 | 1.11E+08 | 1.11E+08 |
| 338 | TAGCGATACAAACAGCCCTAAGATATTTC | AATTTACTAATGATTCCAGCCTGTCTGT | CFI | chr4 | 110670518 | 1.11E+08 | 1.11E+08 | 1.11E+08 |
| 339 | AAAAACAACGTTGAAAATGCAGATGT | ATCAAAACTTATTACTCTGATTTTCTCAGGATC | CFHR3 | chr1 | 196759039 | 1.97E+08 | 1.97E+08 | 1.97E+08 |
| 340 | CACAAGAAAATGTTTGAGAGAAGGTGA | GAGTAATCAATTATGTGCTCTCCTCTTT | CFHR3 | chr1 | 196748190 | 1.97E+08 | 1.97E+08 | 1.97E+08 |

| SEQ ID NO | Reverse Primer |
|---|---|
| 824 | ACATTCCATAGCAGCAGAATGAGAC |
| 825 | ACAATGTCAAAAGCCACTCAATTGTC |
| 826 | TAATACTAAAGTTCTGAATAAAGGTGTGCACTT |
| 827 | ACAGGTACTCTCCTCCCACTATGTAAATTTT |
| 828 | ACATTACTGGCTCCATCCATTTTGTA |
| 829 | TAAATTACTTACTCACGTGGGTTGA |
| 830 | CACCATCAGTCATTTTATTGCATTGAAAAAT |
| 831 | CGTGATTTCATCTCCAGTTCTGT |
| 832 | GGTAGAGAGCAAGAGTTACAGTGTC |
| 833 | ACGATCTTCCGCTTCTTGTGTT |
| 834 | CTTGACACACGCAGGCAAGA |
| 835 | CTATAAAGGACAAGGAGAGCAACCA |
| 836 | GGGCATATTGAGCATCTCTCA |
| 837 | GCCAAAGCATTGATGTTCACTTGG |
| 838 | CGCCCTCAAGGTAGTCTCATGA |
| 839 | ACAACAGTAGAGAGGGAAAGCTCA |
| 840 | GTAGAAGCCAGAAGGACACACGTACT |
| 841 | AGCTAGACATCCTACAATTCAAGGTAAATC |
| 842 | GACTTCCATTATCCCAAAAATCTGATAAGGA |
| 843 | CAAACAGGAGTCTTTAATTGTTGCTAAGT |
| 844 | GTTCAAAGCTCACTTGACATTAAGTACATT |
| 845 | AATTTACTAATGATTCCAGCCTGTCTGT |
| 846 | ATCAAAACTTATTACTCTGATTTTCTCAGGATC |
| 847 | GAGTAATCAATTATGTGCTCTCCTCTTT |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 341 | TGATGTTTACCACAAAGGACTTTACTAAACT | 848 | CTGCTAATTGCATGTTAGAAAGTATTTCCATAA | CFHR1 | chr1 | 196788824 | 1.97E+08 | 1.97E+08 | 1.97E+08 |
| 342 | TTCTTCAGTTTTATGTTATTTCCCAGCAAC | 849 | CTGGCATATCCTTCTCTATTCACTGAATG | CFHR1 | chr1 | 196794580 | 1.97E+08 | 1.97E+08 | 1.97E+08 |
| 343 | ACATAGTCGGTTTGGACAGTGTTT | 850 | CTAAAGTTCTGAATAAAGGTGTGCATTTTATGA | CFHR1 | chr1 | 196800795 | 1.97E+08 | 1.97E+08 | 1.97E+08 |
| 344 | TCAGTCAATAAATCACTCCCGCATT | 851 | CAAAGTGGCCAATTATATTTGACTGGAT | CFI | chr4 | 110661788 | 1.11E+08 | 1.11E+08 | 1.11E+08 |
| 345 | GCTCTTGGCCATATATATTCAAATGGG | 852 | GTGTAAAGGGTGTAAAGGAGGCAA | CD46 | chr1 | 207932774 | 2.08E+08 | 2.08E+08 | 2.08E+08 |
| 346 | CCAGGTTGGTGCTCATTACTA | 853 | CCTACATTCAAGCACCATTGCAATATTAG | CD46 | chr1 | 207966742 | 2.08E+08 | 2.08E+08 | 2.08E+08 |
| 347 | CAGAAATGTTGTCACAGAAAATGTGAGT | 854 | ATCCTATGTTTGGGCACCTCATAAAA | CD46 | chr1 | 207956390 | 2.08E+08 | 2.08E+08 | 2.08E+08 |
| 348 | AGCACTGGATGCTTTGTGAGTT | 855 | CCGACTGAGGAGAGCTCTAGTC | CD46 | chr1 | 207925428 | 2.08E+08 | 2.08E+08 | 2.08E+08 |
| 349 | TGTTTTTAAACATCTTGCATTCCATTCCTTG | 856 | ATGAACAGCACAACAATAACAAACCA | CD46 | chr1 | 207940239 | 2.08E+08 | 2.08E+08 | 2.08E+08 |
| 350 | GATTTAGATAGCAAAGAGTGTCTGATGA | 857 | AATGCATTGGTAGGACAAACTAATGC | CD46 | chr1 | 207958804 | 2.08E+08 | 2.08E+08 | 2.08E+08 |
| 351 | TCCTAGTGCTGCCTCATCTAG | 858 | GCTATACAAATGTCCTCCCTCCTTT | CD46 | chr1 | 207940946 | 2.08E+08 | 2.08E+08 | 2.08E+08 |
| 352 | CTGAATGCTAAAATAAGCGCCTTCAT | 859 | CTGGAAAGTATAGTCTCACGCAAACTCTT | CFHR4 | chr1 | 196871251 | 1.97E+08 | 1.97E+08 | 1.97E+08 |
| 353 | AATTCATTAACACAAATGTTTCATTGTTTTGCC | 860 | AAGTAAAACACTATCATCTCAAAGAGAGGAAC | CFHR4 | chr1 | 196881755 | 1.97E+08 | 1.97E+08 | 1.97E+08 |
| 354 | AAAACAACGTTGAAAATGCAGATGT | 861 | ATCAAACTTATTACTCTGATTTTCTCAGGATC | CFHR4 | chr1 | 196883950 | 1.97E+08 | 1.97E+08 | 1.97E+08 |
| 355 | ACATGTAGTCCTCATTTGAGTGTGAATT | 862 | GACTCTTGACCATGGCAGAATACA | CFHR4 | chr1 | 196876270 | 1.97E+08 | 1.97E+08 | 1.97E+08 |
| 356 | GTTTCATTGTTTCACCATACTGCCAT | 863 | GTAAAACATACTCACCTCAAAGAGAGAAA | CFHR4 | chr1 | 196874138 | 1.97E+08 | 1.97E+08 | 1.97E+08 |
| 357 | GAGAATTCAAAACTAATCATTCCACCAA | 864 | CTATCTCAAACAATGAGTTAAGCAGCTTTT | DGKE | chr17 | 54921454 | 54921484 | 54921577 | 54921607 |
| 358 | CAGTTACTACTGTATGGTTGCAAGCA | 865 | ACCACTTCTATGAAATCCTGATTCCCA | DGKE | chr17 | 54912561 | 54912585 | 54912660 | 54912686 |
| 359 | GCGTGGTCTTGAGATGAGGT | 866 | GGAGGCTTGGAACCCTTTTCAC | CPAMD1 | chr19 | 6694354 | 6694374 | 6694705 | 6694726 |
| 360 | AGGGCTTAGAAAGGGAGAAGACA | 867 | CGTCTCACATCCGTGAATGAC | CPAMD1 | chr19 | 6719119 | 6719142 | 6719443 | 6719465 |
| 361 | GGGAGGGATTTACTAGGTGGT | 868 | GGGTCATTGGGAAGAGATACAC | CPAMD1 | chr19 | 6707680 | 6707701 | 6708012 | 6708035 |
| 362 | CCTTCCATGTAGGTCACCAATT | 869 | CAACTGGCCTCTCTGTTCTAA | CPAMD1 | chr19 | 6702334 | 6702356 | 6702613 | 6702635 |
| 363 | GGTACATTGTCACCACCTGGTA | 870 | TGCGATCAGAGAGAGGTACAGTCA | CPAMD1 | chr19 | 6684646 | 6684668 | 6684989 | 6685012 |
| 364 | GTAGTGTTTCTTCTTCCTCCAGCTT | 871 | CAACTTTCTGCTTGGGAGAGAGA | CPAMD1 | chr19 | 6678207 | 6678231 | 6678553 | 6678576 |
| 365 | GCACCGATCAGGTGTAGTAC | 872 | AAGATCCGACTACTAACCTACCT | CPAMD1 | chr19 | 6710717 | 6710738 | 6710998 | 6711021 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 366 | CCATCTCCCTGGGTTAGAGACT | 873 | GAGGGAGGAGGTCTAATCCTGA | CPAMD1 | chr19 | 6712323 | 6712345 | 6712675 | 6712697 |
| 367 | GGGTTAGTCTGACCCAGAGACA | 874 | GATGACCTGAAGCAGTATGAAGG | CPAMD1 | chr19 | 6681846 | 6681868 | 6682143 | 6682167 |
| 368 | GCCTCACCTGAGTGCAAGAT | 875 | ACCTGAAGCCCTCCTTGTCT | CPAMD1 | chr19 | 6713193 | 6713213 | 6713529 | 6713549 |
| 369 | GGCCTCAGTGTCTTCTCTAGGA | 876 | GCATGCATCTCTTTCTGAGCTTCT | CPAMD1 | chr19 | 6686052 | 6686074 | 6686359 | 6686384 |
| 370 | GGAGAGCTGCAAATTCCCTGAA | 877 | ACTAAGAAGTTTGACCTTCCTAGGGTA | CPAMD1 | chr19 | 6690539 | 6690561 | 6690864 | 6690891 |
| 371 | CCTCCAGGCCCTTCTCTCTTATA | 878 | CTTGTCTTGGGACATTCCGAA | CPAMD1 | chr19 | 6714019 | 6714041 | 6714370 | 6714392 |
| 372 | AGCAAGGACTGTCTGTGTTGTC | 879 | TCGACCTCAAGGTCACCATAAAAC | CPAMD1 | chr19 | 6684237 | 6684259 | 6684585 | 6684609 |
| 373 | GGTCCATGCTCCTTGGCTAAAG | 880 | ACATCATCGGGAAGGACACTTG | CPAMD1 | chr19 | 6677686 | 6677708 | 6678004 | 6678026 |
| 374 | GGGTGTGTGTCTGCATATCTCTT | 881 | CGGGTACCTCTTCATCCAGACA | CPAMD1 | chr19 | 6717964 | 6717987 | 6718288 | 6718310 |
| 375 | GGTGACCTTGTCATCCGACTTT | 882 | GGGAGGCCCTTATCCTCCATC | CPAMD1 | chr19 | 6679182 | 6679204 | 6679529 | 6679551 |
| 376 | CAGAAGGCTGGATTGTGTGAGTA | 883 | CGGAGTGGACTAAGAAGCTGAGA | CPAMD1 | chr19 | 6697533 | 6697555 | 6697870 | 6697892 |
| 377 | GCAGCTCTGTGATGTAGTTGC | 884 | AGCTCACGGAGAAGCGAATG | CPAMD1 | chr19 | 6707129 | 6707150 | 6707483 | 6707503 |
| 378 | TCTGAGCTCTACGTAGCACT | 885 | CAATTCCCAGGTCTCAGGGATTC | CPAMD1 | chr19 | 6711079 | 6711101 | 6711261 | 6711284 |
| 379 | GGTCACTGGCCCTTACCTTACT | 886 | CCAACCTTTCTGTCTTTCCACTCTAG | CPAMD1 | chr19 | 6709679 | 6709701 | 6709928 | 6709954 |
| 380 | TGTTCTTAGGAATGTGTTCCTTTCC | 887 | CTTAGACACAATTGGAACCGAAAATCAAAT | CFHR5 | chr1 | 196953081 | 1.97E+08 | 1.97E+08 | 1.97E+08 |
| 381 | GTGGAGGAGGAACCTAGACCAGA | 888 | GGTGGGTATCTCCATTGTTGAAAATAGATGAG | CFHR5 | chr1 | 196973530 | 1.97E+08 | 1.97E+08 | 1.97E+08 |
| 382 | GTTTTCCACAAAGGGCTTTACTAAACT | 889 | GCTAAATTGCATGTTGGAAAATATTTCCAGA | CFHR5 | chr1 | 196946648 | 1.97E+08 | 1.97E+08 | 1.97E+08 |
| 383 | GTATAGCAATTAAGAGCTCAGGTTCTGA | 890 | TCCATCGTTCTCCATTTTAACTGTATGTT | CFHR5 | chr1 | 196977316 | 1.97E+08 | 1.97E+08 | 1.97E+08 |
| 384 | CTTCAGTTTTGTGTTATTTTCCCAGAA | 891 | CCCTTGTGATTATCAAGACCTTATGATCTT | CFHR5 | chr1 | 196951989 | 1.97E+08 | 1.97E+08 | 1.97E+08 |
| 385 | CATTTCTTAGAACAAGTGAAAACATGTGG | 892 | CTTGTGGAAGGAGAGTCAGTATCAATAAA | CFHR5 | chr1 | 196965141 | 1.97E+08 | 1.97E+08 | 1.97E+08 |
| 386 | ACCAACTTAAGAGGTGCAAATAGCA | 893 | GCCAAGGCTTTTAAAGAATAACATTTGTCT | CFHR5 | chr1 | 196967264 | 1.97E+08 | 1.97E+08 | 1.97E+08 |
| 387 | CCCAAAAATAGAAGTAATGCAATATAAAGCA | 894 | AAGTGCAAAGTAATAGTAACTGTCCTGT | CFHR5 | chr1 | 196964729 | 1.97E+08 | 1.97E+08 | 1.97E+08 |
| 388 | GAGGCTCATTCTCCTCCCTCTA | 895 | GCTTGCTCATAGGCATCTCCAT | THBD | chr20 | 23028230 | 23028252 | 23028573 | 23028595 |
| 389 | CGCACATGCACGAGTAGGA | 896 | CGCCGTCGATCACCTTAC | THBD | chr20 | 23029211 | 23029230 | 23029562 | 23029581 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 390 | CGTGCCCACCTGCTATAGC | 897 | TTCCTCAATGCCAGTCAGATCTG | THBD | chr20 | 23029771 | 23029790 | 23029986 | 23030009 |
| 391 | GAGCCGAAGTAATAAGTTACACTGAGT | 898 | GTCCAGCTTGTGAGGTAAGCATAT | DGKE | chr17 | 54926373 | 54926400 | 54926720 | 54926744 |
| 392 | GGGATAGAGCTACAATGAATAATAAAGAGTC | 899 | AGAAGTCCTTCTGTAGTAGTTCTTAAAGA | DGKE | chr17 | 54925110 | 54925139 | 54925433 | 54925462 |
| 393 | CCTTTGTTGCCCTTCTTTTCAT | 900 | CAAAGTGCCTGCACACAAATAAA | DGKE | chr17 | 54935800 | 54935823 | 54936141 | 54936165 |
| 394 | GTTTCTTTTTCTTGGTTAGGTATCGTCTT | 901 | GAGCATAAATCTCCTTGCACTGGAA | DGKE | chr17 | 54912122 | 54912150 | 54912471 | 54912495 |
| 395 | TTTTTAAGTTGATGGTCCAACTGTGT | 902 | CTGTTTCTTCCTCATCCCACTCTAG | DGKE | chr17 | 54939401 | 54939428 | 54939747 | 54939772 |
| 396 | AGTCATAATTCTCAGAGGGCTACCGTA | 903 | GTCTAAGAGAAATTTGGTCCTAGGAAGTTG | PLG | chr6 | 161143336 | 1.61E+08 | 1.61E+08 | 1.61E+08 |
| 397 | CTCAAGACAGGGATGACTGGTT | 904 | CTTGAAGACTGATTAAGACATAGACAGGT | PLG | chr6 | 161162262 | 1.61E+08 | 1.61E+08 | 1.61E+08 |
| 398 | GCCTTCATCTGATTACCTCCTCCAT | 905 | ATCCCATAGGACTTGTAGGTCACT | PLG | chr6 | 161137543 | 1.61E+08 | 1.61E+08 | 1.61E+08 |
| 399 | CCCTCACCTGGCTCTTACCT | 906 | GGTGAAGGAGTACGGTAAGAGGA | CPAMD1 | chr19 | 6713961 | 6713981 | 6714167 | 6714190 |
| 400 | AAATATTTTGGCTCTCTAAGACTTGGCT | 907 | AGAATGTCGCAGTAGTCATATCTCTTTC | PLG | chr6 | 161133778 | 1.61E+08 | 1.61E+08 | 1.61E+08 |
| 401 | ACAGCCAAACCATATCAAGTGTTTAGAT | 908 | ATCGGTTTAACCAATTTACAAGCTGAAAAA | CD46 | chr1 | 207958319 | 2.08E+08 | 2.08E+08 | 2.08E+08 |
| 402 | AATTATTCATTGTAGGGCTGGGCA | 909 | TGGTAGGTGGGACCAGAAGAT | PLG | chr6 | 161138987 | 1.61E+08 | 1.61E+08 | 1.61E+08 |
| 403 | CTCCCTTCCGACTTCTCCAAGAG | 910 | CTAGTCTCATCCTAGTCCTGACCTT | CFB | chr6 | 31914226 | 31914248 | 31914440 | 31914465 |
| 404 | CTGGTAACAACACCCTCTGTGTA | 911 | CTAGAAAAATCAGGAATTGGTGACCTA | CPAMD1 | chr19 | 6701995 | 6702018 | 6702341 | 6702369 |
| 405 | GTGACAGCACCAGAGAGAATGGAAAAT | 912 | TGCTGATATTCCTTAGAATGAACGATGTTT | CFH | chr1 | 196646623 | 1.97E+08 | 1.97E+08 | 1.97E+08 |
| 406 | GCTTTGTCCAGCTCATACTTGG | 913 | CTCTGTGCTGCTATGTCGGAAT | CPAMD1 | chr19 | 6681992 | 6682014 | 6682339 | 6682361 |
| 407 | GGAGATGCTGTATGCACTGAATCTG | 914 | GAACCTTGAACACAGAAAATGCTATATGTT | CFH | chr1 | 196648872 | 1.97E+08 | 1.97E+08 | 1.97E+08 |
| 408 | CTCCCCTTCTTGCTTCCCAGTAA | 915 | GTCCCAGCTCTGATTTGAACCT | CPAMD1 | chr19 | 6684918 | 6684940 | 6685230 | 6685252 |
| 409 | CATTGTACTGAGAGAAATAAAAGGCCTTCCTA | 916 | GAAGGAAATGTGTGATTTTCTC111CACAT | CFI | chr4 | 110662054 | 1.11E+08 | 1.11E+08 | 1.11E+08 |
| 410 | GGTGCCCGTTTCACGAAG | 917 | TGAATCCCTGTCCTCTTGAGAACT | CPAMD1 | chr19 | 6693432 | 6693450 | 6693683 | 6693708 |
| 411 | GTTACAAGCAATGAATGAACCTTGTGAGTTT | 918 | TCTTTGCAAGTTTATGCACATATTGTTGT | CFH | chr1 | 196879403 | 1.97E+08 | 1.97E+08 | 1.97E+08 |
| 412 | GAATGAGAGGCAAGTCCACTTA | 919 | TGGGAGGAGGTTAGCTTTGAAATTAAAA | PLG | chr6 | 161135712 | 1.61E+08 | 1.61E+08 | 1.61E+08 |
| 413 | TTGTGATTTTCCAGAAATTCAACATGAG | 920 | TCTCTCACTCTTTTCAAGTTTTTATGCACAT | CFHR4 | chr1 | 196871558 | 1.97E+08 | 1.97E+08 | 1.97E+08 |
| 414 | GCCCAGTTTGAAGACAGAGAA | 921 | CAGAATAGGACCTGGAGATTTCCTG | CFB | chr6 | 31915615 | 31915637 | 31915956 | 31915982 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 415 | GAAAGGTCTTTTGTTTGTTCTTTGTCTTGT | 922 | CCATTCTGGCTGGAATAATACACACA | CFH | chr1 | 196670243 | 1.97E+08 | 1.97E+08 | 1.97E+08 |
| 416 | TGACATTTCCTCTGTACAACCTTTGT | 923 | CAGAGCGGTGTACTTACTGACAC | CFHR3 | chr1 | 196748752 | 1.97E+08 | 1.97E+08 | 1.97E+08 |
| 417 | GTAGAATGCTCTCCAGCAATTAAGAGT | 924 | AGACCAGGAACCTGTCAGAATTTC | CFH | chr1 | 196641789 | 1.97E+08 | 1.97E+08 | 1.97E+08 |
| 418 | GCCATATTGCCATGTTTTACTTGTTC | 925 | AAGTAAAACACTATCATCTCAAAGAGAGGAAC | CFHR3 | chr1 | 196757259 | 1.97E+08 | 1.97E+08 | 1.97E+08 |
| 419 | GTGTTACTTCTCTGTGATGTCATAGTAGC | 926 | ATTGGTACCACTTACACTTTGAATGAAGA | CFH | chr1 | 196709617 | 1.97E+08 | 1.97E+08 | 1.97E+08 |
| 420 | AAAAAGTGCTGTTAGATTAAAACTGCCA | 927 | TTTTTGTCTTTACGCATCTGATTAATGA | DGKE | chr17 | 54921171 | 54921198 | 54921494 | 54921523 |
| 421 | CTACAAGAAAGTCTATGAGAATACAAGCCA | 928 | GGTTGTCATATTGTGAGAATTGGGAATC | CFH | chr1 | 196705704 | 1.97E+08 | 1.97E+08 | 1.97E+08 |
| 422 | TGAAGACACAGAAATTTTACTAATGCTGTCT | 929 | CACCTGCTTGTTTATCTGTAGATGAAACTA | CD46 | chr1 | 207934521 | 2.08E+08 | 2.08E+08 | 2.08E+08 |
| 423 | AGAAACAAGAAACAAGAAACATGAATG | 930 | ACTAGATTCCCACTCTACATTGTATGAGAA | CFH | chr1 | 196644982 | 1.97E+08 | 1.97E+08 | 1.97E+08 |
| 424 | CTATGACCACTCAGGTAAAAGCATG | 931 | GGCAAGAGGAGGTATATAGAAGTATCCTTT | CD46 | chr1 | 207930204 | 2.08E+08 | 2.08E+08 | 2.08E+08 |
| 425 | TGCCCAGCCAATACAATCATCAT | 932 | CCTGTAAGGGTAAAGTACCAAAAGGA | CFH | chr1 | 196642757 | 1.97E+08 | 1.97E+08 | 1.97E+08 |
| 426 | TTTTTAAAATTTTATTGCAAGTGAAACCTTGT | 933 | TCTCCTTTCTTCGATCTTTGAAAGTTTTATACA | CFH | chr1 | 196658528 | 1.97E+08 | 1.97E+08 | 1.97E+08 |
| 427 | ACATAATAGCATTTTGATGCAATGTGATCA | 934 | GATCCCATCTTCCATTTATGCAGACT | CFH | chr1 | 196697304 | 1.97E+08 | 1.97E+08 | 1.97E+08 |
| 428 | AATCCTTGTGATGAACAAGACATGAATG | 935 | CCTCACAAGTATAACTCAAATTTAGTCCCAT | CFH | chr1 | 196706375 | 1.97E+08 | 1.97E+08 | 1.97E+08 |
| 429 | TCTTGTGATATCCCAGTATTTATGAATGCC | 936 | CCCAGTTTATGTCAAATCAGGAGATATCTT | CFH | chr1 | 196684725 | 1.97E+08 | 1.97E+08 | 1.97E+08 |
| 430 | CCACATTTGCTAATTGTTTTCTTGC | 937 | TTTTTCCTTAACATTCCCATTGAGGAGT | CFH | chr1 | 196695341 | 1.97E+08 | 1.97E+08 | 1.97E+08 |
| 431 | GGGTGAGCAAGTGACTTACACTT | 938 | CCCACTTCAATCTTCATCTCCCTG | CFH | chr1 | 196711078 | 1.97E+08 | 1.97E+08 | 1.97E+08 |
| 432 | CATCAGGATCAATTACATGTGGGAAAGAT | 939 | CTGCTTTTGTTCCTGCAGGTTTTT | CFH | chr1 | 196682991 | 1.97E+08 | 1.97E+08 | 1.97E+08 |
| 433 | AAACGAAAGAAGAATATGGACACAGTGA | 940 | CTGTGTCCAATCATTGTAAATGATTCTGAG | CFH | chr1 | 196695657 | 1.97E+08 | 1.97E+08 | 1.97E+08 |
| 434 | TGATATTATATACAGTGCTGTGTTTGCGT | 941 | CAAACAGTGAAATATCAGGACTCATCACAGA | CFH | chr1 | 196714849 | 1.97E+08 | 1.97E+08 | 1.97E+08 |
| 435 | CTTTATTCCAAATGTGACTACTCACCT | 942 | GCTTCCAACAGCCTTACTTTGTATATACAA | CFH | chr1 | 196654212 | 1.97E+08 | 1.97E+08 | 1.97E+08 |
| 436 | AGCTGGGTCCCTAGTCTGATTC | 943 | CCAAAAGGATCTGGAACACAGGT | CFB | chr6 | 31919538 | 31919560 | 31919860 | 31919883 |
| 437 | GCAGGCCAAGATCTCAGTCATT | 944 | CATTGAGGATGGGTGGAGTGTA | CFB | chr6 | 31917903 | 31917925 | 31918252 | 31918274 |
| 438 | TACATTGGCAAGGATCGCAAAAAC | 945 | GAGAGGAGGAATGAATGAAGAAGGCTTT | CFB | chr6 | 31917079 | 31917103 | 31917428 | 31917453 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 439 | GCAGGAATTCCTGAATTTTATGACTATGAC | 946 | CCTAAGCCCTTCTAGAGCTAGT | CFB | chr6 | 31918470 | 31918500 | 31918818 | 31918841 |
| 440 | GGTGAGAAACGGGCATCCTAAG | 947 | AACGACTTCTCTTGTGAACTATCAAGG | CFB | chr6 | 31919021 | 31919043 | 31919346 | 31919373 |
| 441 | GCCACTTTGTGTCAAAGGAA | 948 | CCCAACCATGGGTATAGTGTTACA | CFB | chr6 | 31916461 | 31916483 | 31916809 | 31916833 |
| 442 | GCTCCGACACTGTAACTCTTG | 949 | AGGTTAAACAAAGTGAGGAAAGAGCA | CFB | chr6 | 31915039 | 31915061 | 31915371 | 31915398 |
| 443 | TGGGTTCTGACCAACTCAATGG | 950 | AGGGACAAAGTTTTAAATAACGGACCATG | CFI | chr4 | 110687377 | 1.11E+08 | 1.11E+08 | 1.11E+08 |
| 444 | GGCAACAGGCATCAATCATT | 951 | AGAGAATGAGGAGGACATTACTTCTAGTTTCT | CFI | chr4 | 110682579 | 1.11E+08 | 1.11E+08 | 1.11E+08 |
| 445 | CCTAAAGAAAAGTTTCAGAATCCCTGAT | 952 | GTGTTGTGAAGGTAGACATAAATCTAGCCT | CFI | chr4 | 110681358 | 1.11E+08 | 1.11E+08 | 1.11E+08 |
| 446 | GTGCTAGGAAATTAGCTCCTATACATTTCT | 953 | CTGTTATAGAGCCAGTAAAACTCATCGTTA | CFI | chr4 | 110667293 | 1.11E+08 | 1.11E+08 | 1.11E+08 |
| 447 | GGAATTCCAGTCGCGAATACA | 954 | GGGCAGGAGGATGATGTAATTATAAGA | CFI | chr4 | 110670220 | 1.11E+08 | 1.11E+08 | 1.11E+08 |
| 448 | AGCAATTCTCAAGAATCATTAAGCTTGC | 955 | AAGGAGGATAAGTTTTAAGGCAGAAAAT | CFI | chr4 | 110673430 | 1.11E+08 | 1.11E+08 | 1.11E+08 |
| 449 | CAAAGTGCAACTGAACTTTGTATTAG | 956 | TGCCTTTTACACTGTGAACTTAGAAAACA | CFHR3 | chr1 | 196743965 | 1.97E+08 | 1.97E+08 | 1.97E+08 |
| 450 | GGATGCATTTATTTGCTCATGAAAGAGA | 957 | GACCATAAGAGTGAGAAGTGGAAAGT | CFHR3 | chr1 | 196762382 | 1.97E+08 | 1.97E+08 | 1.97E+08 |
| 451 | AAAGTGCTGTGTTGTATTGCCTTAT | 958 | ATTTGTTACCAACAGCAAAATACAGACT | CFHR1 | chr1 | 196799543 | 1.97E+08 | 1.97E+08 | 1.97E+08 |
| 452 | ACTATGTAGATCAGGAAGAGATTTGCTACTCT | 959 | TTCCATGGTTTATTTTGGAAAATCACAAAT | CFHR1 | chr1 | 196794268 | 1.97E+08 | 1.97E+08 | 1.97E+08 |
| 453 | TGCTACTTCCATCTTGTACATTAATCCG | 960 | GGACACAATTGGAACTGAAAATCAAATGAA | CFHR1 | chr1 | 196795917 | 1.97E+08 | 1.97E+08 | 1.97E+08 |
| 454 | ATTTGTTGCTGACTATAGAGTGGCAT | 961 | GCCAAATTCTTTCAGAGTTCAAAAGTACAA | CFI | chr4 | 110722926 | 1.11E+08 | 1.11E+08 | 1.11E+08 |
| 455 | ATTATATTCCCACCCATTCAAAGAGCA | 962 | CCTATCTCCATAAAACATCCAAGAGTTGTT | CD46 | chr1 | 207930784 | 2.08E+08 | 2.08E+08 | 2.08E+08 |
| 456 | CTTCCTAGCACAAAATTCATGTTTCCAGT | 963 | TGCCAATAATCTCTTTGCTCAGTT | CD46 | chr1 | 207963414 | 2.08E+08 | 2.08E+08 | 2.08E+08 |
| 457 | CCATTATAAAAATACAGAGTGTGTGAGCA | 964 | GCTGTGCACACATACCCTAGAG | CD46 | chr1 | 207943447 | 2.08E+08 | 2.08E+08 | 2.08E+08 |
| 458 | GTTATGTACATTGCATGGGTATATGCTTT | 965 | GTGGAAGAAGTCGACACTGGAA | CD46 | chr1 | 207940765 | 2.08E+08 | 2.08E+08 | 2.08E+08 |
| 459 | ACAATGGGACTTTCTTAGTTGAGTTGT | 966 | CACACTCATAGGAGACTACATATATATGTACA | CFHR4 | chr1 | 196883551 | 1.97E+08 | 1.97E+08 | 1.97E+08 |
| 460 | GCATTTTATTTGCTCATGAAAGGCAA | 967 | AGACCATAAGAGTGAGAAGTGGAAGT | CFHR4 | chr1 | 196887277 | 1.97E+08 | 1.97E+08 | 1.97E+08 |
| 461 | CTAAGTGACCCTTAAAGCCTAGCTTT | 968 | ACTCTCACAAAATATGCTACTTCTGCTAG | CFHR4 | chr1 | 196857142 | 1.97E+08 | 1.97E+08 | 1.97E+08 |
| 462 | GCAATGAGAGATACCACGTCCTT | 969 | GTCTCTGAACATTCCTGTTTTTAAAGGAA | CFHR4 | chr1 | 196876482 | 1.97E+08 | 1.97E+08 | 1.97E+08 |
| 463 | AATGGGACTTTCTTAGTGCGAGTTGTAC | 970 | CACACTCAAATGAGGACTACATGTATATGT | CFHR4 | chr1 | 196875919 | 1.97E+08 | 1.97E+08 | 1.97E+08 |

APPENDIX A-continued

| SEQ ID NO | Forward Primer | Reverse Primer | Gene Symbol | Chromosome | Amplicon Start | Insert Start | Insert Stop | Amplicon Stop |
|---|---|---|---|---|---|---|---|---|
| 464 | GTAGGAAAGGCTCCCACCTTT | GGTGCCTCATCCATCTTCTTCTC | CPAMD1 | chr19 | 6707460 | 6707481 | 6707566 | 6707589 |
| 465 | ATCCATGTGTGGTATCTGAAGAAAACA | GCTACTTTTAGCATAGATGATGTTTGAAG | CFHR5 | chr1 | 196977617 | 1.97E+08 | 1.97E+08 | 1.97E+08 |
| 466 | CCGCATGTTCAGGAAATAGAAGTGT | TCAAGAGCACAGCTAGCATGTG | PLG | chr6 | 161160161 | 1.61E+08 | 1.61E+08 | 1.61E+08 |
| 467 | CTGTACCGTCTTTCCCAGTGATG | AGGAATGCCCTTTGACCTCATG | CPAMD1 | chr19 | 6712219 | 6712241 | 6712518 | 6712540 |
| 468 | GCATCCTGAGGCCTCTTTTCTAG | GCACCTTGTCGGTAAGGAACAG | CPAMD1 | chr19 | 6684432 | 6684455 | 6684774 | 6684796 |
| 469 | GAGTTTTCATAGTAGGCTCGGATCTT | CACCTGGGTCCCTGTTCTTAAC | CPAMD1 | chr19 | 6714221 | 6714247 | 6714573 | 6714595 |
| 470 | GGCACCTCAATGTTGACCATGA | ACAGGGAGTTCAAGTCAGAAAAGG | CPAMD1 | chr19 | 6718100 | 6718122 | 6718389 | 6718413 |
| 471 | TTCTCTTCGTCTTGGCATTCGT | ACGACTCAGCTTCTTCCCCT | CPAMD1 | chr19 | 6677960 | 6677982 | 6678312 | 6678333 |
| 472 | TGGGACCTTCATACTACGAATGC | TGCTGAATTGCTCATTCATCTTTGC | CPAMD1 | chr19 | 6680033 | 6680056 | 6680382 | 6680407 |
| 473 | CTGAGCCTCCCTCCTTAGACTA | CAGAGGATTTCCCTGCCTGAATC | CPAMD1 | chr19 | 6713097 | 6713119 | 6713433 | 6713456 |
| 474 | CTCAGCTTTGGGCTTTAGGTCATC | CAGAAATCCCTGATGCTCAGGAA | CPAMD1 | chr19 | 6686637 | 6686659 | 6686988 | 6687011 |
| 475 | CTGAAGCCACACATGACAACCA | GGTCTGAGCAAGCCACACTTAC | CPAMD1 | chr19 | 6679042 | 6679065 | 6679367 | 6679389 |
| 476 | AAAGAGAGAGGGAAAGAGAGATGTAGAG | CACCGACTTCATCCTCTCCTT | CPAMD1 | chr19 | 6710429 | 6710457 | 6710749 | 6710770 |
| 477 | GCCCAATCTTTGCAAAGGGAAT | GTTGACATGGCAGTCTCTGGAT | CPAMD1 | chr19 | 6692814 | 6692836 | 6693132 | 6693154 |
| 478 | TGAATCCACAACACCCAAATGC | AGCTTAGGAAATGGTATTGAGAAATCTGG | CPAMD1 | chr19 | 6720415 | 6720438 | 6720758 | 6720787 |
| 479 | GGAAGAGAAAGTGCGGGTTAA | CAGAAGATGAACAAAACTGTGGCTGTT | CPAMD1 | chr19 | 6696289 | 6696311 | 6696634 | 6696659 |
| 480 | CTCTCTGAAGGACAAGGTTTGT | TTACCGGCAGAACCAAGAGTCAA | CPAMD1 | chr19 | 6697313 | 6697336 | 6697663 | 6697687 |
| 481 | AGCCTGCCCTTGTTCATGATC | CGTGGGCAACTCCAACAATTAC | CPAMD1 | chr19 | 6710837 | 6710858 | 6711111 | 6711133 |
| 482 | CCCTCCTCAGACGGAGGTTT | GAGGCGTGCAAGAAGGTCT | CPAMD1 | chr19 | 6706870 | 6706890 | 6707161 | 6707180 |
| 483 | CCCAATTGGAACCCATGTCCAA | GTGTTCGTGCTGAATAAGAAGAACA | CPAMD1 | chr19 | 6709506 | 6709528 | 6709711 | 6709736 |
| 484 | TAGCACACATTAAATTTGTTTCTGCAATGA | CTTTGCCATTTTACCACTTTGTCAGATTAT | CFHR5 | chr1 | 196963146 | 1.97E+08 | 1.97E+08 | 1.97E+08 |
| 485 | TGAAGATATTGTTGTGGTGCTAGAAGAGTT | GTATTAGTCCTGAAGATTCAGAATGACCAT | CFHR5 | chr1 | 196952818 | 1.97E+08 | 1.97E+08 | 1.97E+08 |
| 486 | GAATCTTCCATTTTCCTGAAACACTACC | GTGCAACAGATTAGTCATAAGTTCTTGTTT | CFHR5 | chr1 | 196971523 | 1.97E+08 | 1.97E+08 | 1.97E+08 |
| 487 | GCTGTTTTCCAGAGTCTACTGCATA | GACAGGAAAGATTTGACTGAATGAACTT | CFHR5 | chr1 | 196973779 | 1.97E+08 | 1.97E+08 | 1.97E+08 |

APPENDIX A-continued

| SEQ ID NO | Forward Primer | SEQ ID NO | Reverse Primer | Gene Symbol | Chromosome | Amplicon Start | Insert Start | Insert Stop | Amplicon Stop |
|---|---|---|---|---|---|---|---|---|---|
| 488 | AGTGAGCCAAGATTTGCGTGAT | 995 | ACAGAAATCCATGGTGTATTTTGGAAA | CFHR5 | chr1 | 196951740 | 1.97E+08 | 1.97E+08 | 1.97E+08 |
| 489 | ACCTCCTCAACTCTCCAATGGT | 996 | GCTGAACATAACCGTACTCGAGTT | CFHR5 | chr1 | 196964869 | 1.97E+08 | 1.97E+08 | 1.97E+08 |
| 490 | TGTAGCTTCCTAAGAACTATCTTTCAGTCA | 997 | TCTTTCCCAGATAGCTTGAGTAATGTTTTT | CFHR5 | chr1 | 196966970 | 1.97E+08 | 1.97E+08 | 1.97E+08 |
| 491 | GCGCACTTGTACTCCATCTTG | 998 | CTACATCCTGGACGACGGTTT | THBD | chr20 | 23028478 | 23028499 | 23028831 | 23028852 |
| 492 | GCAGAGGTAGCTAGTTTGGTTCAG | 999 | TGCGAGCACTTCTGCGTT | THBD | chr20 | 23028978 | 23029002 | 23029250 | 23029268 |
| 493 | CGCGGTGCACATTAGCTG | 1000 | CAGTGGGTTACGGGAGACAA | THBD | chr20 | 23029464 | 23029482 | 23029797 | 23029817 |
| 494 | GAGCGCACTGTCATTAGGTG | 1001 | CAGCGGCAAGAAGTGTCTG | THBD | chr20 | 23029951 | 23029971 | 23030259 | 23030278 |
| 495 | GAAAAGTAAAATGCAGAAAGCATCTCCA | 1002 | CCTACACAAAACAGAGCAGGTAAATATTTC | DGKE | chr17 | 54933750 | 54933777 | 54934091 | 54934121 |
| 496 | TGTGAATTCTAAATGATGTGTGTGGA | 1003 | CTTTTTAACACAGTTGGACCATCAACTTAA | DGKE | chr17 | 54939081 | 54939108 | 54939403 | 54939433 |
| 497 | AAGCTTTAGCAAAACAACATACAGTTGT | 1004 | CACATTTCATCTACACAAGTCTTCACTTG | DGKE | chr17 | 54925925 | 54925953 | 54926270 | 54926299 |
| 498 | AAAATGAAATGCATAAGGGTTAAGGATTG | 1005 | TTTGGATGAACATGTATCTACTTGCGT | DGKE | chr17 | 54939866 | 54939896 | 54940188 | 54940215 |
| 499 | GGTGTTCATCACCTTCTGGTGT | 1006 | GTAATCGCAAAGCTTGGGTTGA | DGKE | chr17 | 54912255 | 54912277 | 54912596 | 54912618 |
| 500 | ATTTCAGCAAATTATAGCACCATTGTTCTC | 1007 | TCCTATGATCAGGTGATTAGTGACTTGAA | DGKE | chr17 | 54922953 | 54922983 | 54923238 | 54923267 |
| 501 | TTCAAAGTCCACTTGTTAACCACTTTGTTAG | 1008 | ATGGAAGGTTTCTGCATCAGTGA | PLG | chr6 | 161151977 | 1.61E+08 | 1.61E+08 | 1.61E+08 |
| 502 | TTGGTTAATGCTAACCAAATAGATTAAAAGGA | 1009 | GCTCCATAAATTTCTCTTTCCTCTTAAATCATT | PLG | chr6 | 161127339 | 1.61E+08 | 1.61E+08 | 1.61E+08 |
| 503 | GCATTTGAATACATGAATCAAGAATGGCT | 1010 | AAGGGAATGTCTTACCTAGGTCTGT | PLG | chr6 | 161131918 | 1.61E+08 | 1.61E+08 | 1.61E+08 |
| 504 | TTGCAGTCCTTTCCTTTGGAA | 1011 | CCTTCCCTTCTCTCTTATCCAATTGC | PLG | chr6 | 161159442 | 1.61E+08 | 1.61E+08 | 1.61E+08 |
| 505 | AGAAGGAAGGAAAAAGAAACTCCTT | 1012 | TCAAGATGCCCATGATGAAGAGTG | PLG | chr6 | 161154900 | 1.61E+08 | 1.61E+08 | 1.61E+08 |
| 506 | TTTTTCCCGTAACGGTTGTTCTC | 1013 | GACCACAATAGCATTAAACTTACAAAGCT | PLG | chr6 | 161139638 | 1.61E+08 | 1.61E+08 | 1.61E+08 |
| 507 | CCGCTGCTCTGTTCTGGAATAT | 1014 | CGGTTGAAAATCCTTGAATTTGCCA | PLG | chr6 | 161173070 | 1.61E+08 | 1.61E+08 | 1.61E+08 |

What is claimed is:

1. A method for determining a patient's risk for developing atypical hemolytic uremic syndrome (aHUS), the method comprising:
   (a) detecting a DNA sequence alteration in a group of aHUS genes, the group consisting of: Complement factor H (CFH), Membrane cofactor protein (CD46), Complement factor 1 (CF1), Complement component 3 (C3), Complement factor B (CFB), Complement factor H-related protein 1 (CDHR1), Complement factor H-related protein 3 (CFHR3), Complement factor H-related protein 4 (CFHR4), Complement factor H-related protein 5 (CFHR5), Thrombomodulin (THBD), Plasminogen (PLG), and Diacyl glycerol kinase (DGKE), wherein the DNA sequence alteration is detected by analyzing the DNA sequence of the twelve aHUS genes in a sample, wherein the aHUS genes are analyzed by amplifying the twelve aHUS genes in the sample using a minimum of twenty four sequences selected from the group comprising SEQ ID NO. 1 through SEQ ID NO. 1014;
   (b) comparing the amplified aHUS genes from step (a) with amplified aHUS sequences from a normal control subject; and
   (c) determining the patient's risk for developing aHUS, wherein one or more DNA sequence alterations of CFH, CD46, CFI, C3, CFB, CFHR1, CFHR3, CFHR4, CFHR5, THBD, PLG, and DGKE in the sample that are not present in the normal control has a risk of developing aHUS.

2. The method of claim 1 wherein the aHUS genes comprise aHUS RNA from a sample or aHUS CDNA made from mRNA from the sample.

3. The method of claim 1, wherein the DNA sequence alteration in the aHUS gene is a mutation.

4. The method of claim 1, wherein the DNA sequence alteration in the aHUS gene is a deletion.

5. The method of claim 1, wherein determining the patient's risk for developing aHUS is made within 48 hours of receipt of the sample from the patient.

6. The method of claim 1, wherein determining the patient's risk for developing aHUS is made within 5 days of receipt of the sample from the patient.

* * * * *